(12) United States Patent
Mahalingam et al.

(10) Patent No.: US 11,399,721 B2
(45) Date of Patent: Aug. 2, 2022

(54) SYSTEMS AND METHODS FOR REMOTE AND HOST MONITORING COMMUNICATIONS

(71) Applicant: DexCom, Inc., San Diego, CA (US)

(72) Inventors: Aarthi Mahalingam, San Diego, CA (US); Esteban Cabrera, Jr., San Diego, CA (US); Basab Dattaray, San Diego, CA (US); Rian Draeger, San Diego, CA (US); Laura J. Dunn, San Diego, CA (US); Derek James Escobar, Escondido, CA (US); Thomas Hall, San Diego, CA (US); Hari Hampapuram, Carlsbad, CA (US); Apurv Ullas Kamath, San Diego, CA (US); Katherine Yerre Koehler, Solana Beach, CA (US); Phil Mayou, San Diego, CA (US); Michael Robert Mensinger, San Diego, CA (US); Michael Levozier Moore, Poway, CA (US); Andrew Attila Pal, San Diego, CA (US); Nicholas Polytaridis, San Diego, CA (US); Eli Reihman, San Diego, CA (US); Brian Christopher Smith, San Marcos, CA (US)

(73) Assignee: Dexcom, Inc., San Diego, CA (US)

( * ) Notice: Subject to any disclaimer, the term of this patent is extended or adjusted under 35 U.S.C. 154(b) by 333 days.

(21) Appl. No.: 15/377,821

(22) Filed: Dec. 13, 2016

(65) Prior Publication Data

US 2017/0181629 A1    Jun. 29, 2017

Related U.S. Application Data

(63) Continuation of application No. 15/377,216, filed on Dec. 13, 2016.

(Continued)

(51) Int. Cl.
*A61B 5/00* (2006.01)
*G16H 40/67* (2018.01)
(Continued)

(52) U.S. Cl.
CPC .......... *A61B 5/0205* (2013.01); *A61B 5/0004* (2013.01); *A61B 5/0022* (2013.01);
(Continued)

(58) Field of Classification Search
CPC ..... A61B 5/0205; A61B 5/004; A61B 5/0022; A61B 5/14532; A61B 5/4806; A61B 5/74;
(Continued)

(56) References Cited

U.S. PATENT DOCUMENTS 612,939 A    10/1898  Willson, Jr.
4,757,022 A   7/1988  Shults et al.
(Continued)

FOREIGN PATENT DOCUMENTS

CN    1244104 A    2/2000
CN    1432166 A    7/2003
(Continued)

OTHER PUBLICATIONS

Blood Sugar & Stress, Jul. 27, 2013, Diabetes Education Online (Year: 2013).*

(Continued)

*Primary Examiner* — Evangeline Barr
*Assistant Examiner* — Karen A Hranek
(74) *Attorney, Agent, or Firm* — Patterson + Sheridan, LLP

(57) ABSTRACT

Systems and methods for remote and host monitoring communication are disclosed. In some implementations, monitoring systems can comprise a host monitoring device associated with a Host communicatively coupled to one or more (Continued)

remote monitoring devices associated with Remote Monitors. The host monitoring device can send communications based at least in part on analyte measurements of a Host sensor and/or other contextual data giving such measurements context. Different remote monitoring devices can receive different communications based at least in part on the role of the respective Remote Monitors relative to the Host. These roles can be reflected in classifications of Remote Monitors.

11 Claims, 35 Drawing Sheets

Related U.S. Application Data

(60) Provisional application No. 62/271,840, filed on Dec. 28, 2015.

(51) Int. Cl.
| | |
|---|---|
| *A61B 5/145* | (2006.01) |
| *A61B 5/0205* | (2006.01) |
| *G16H 10/60* | (2018.01) |
| *G09B 5/02* | (2006.01) |
| *A63B 24/00* | (2006.01) |
| *G09B 5/08* | (2006.01) |
| *A61B 5/024* | (2006.01) |

(52) U.S. Cl.
CPC ........ *A61B 5/14532* (2013.01); *A61B 5/4806* (2013.01); *A61B 5/74* (2013.01); *A61B 5/746* (2013.01); *A63B 24/0062* (2013.01); *G09B 5/02* (2013.01); *G16H 10/60* (2018.01); *G16H 40/67* (2018.01); *A61B 5/024* (2013.01); *A61B 5/6802* (2013.01); *A61B 2505/07* (2013.01); *A61B 2560/0242* (2013.01); *G09B 5/08* (2013.01)

(58) Field of Classification Search
CPC ....... A61B 5/76; A63B 24/0062; G06F 10/00; G06F 10/34; G06Q 50/24; G09B 5/02
USPC .......................................................... 705/2
See application file for complete search history.

(56) References Cited

U.S. PATENT DOCUMENTS

| | | | |
|---|---|---|---|
| 4,994,167 | A | 2/1991 | Shults et al. |
| 5,572,999 | A | 11/1996 | Funda et al. |
| 5,590,648 | A | 1/1997 | Mitchell et al. |
| 5,832,448 | A | 11/1998 | Brown |
| 5,897,493 | A | 4/1999 | Brown |
| 5,970,457 | A | 10/1999 | Brant et al. |
| 6,001,067 | A | 12/1999 | Shults et al. |
| 6,053,887 | A | 4/2000 | Levitas et al. |
| 6,101,478 | A | 8/2000 | Brown |
| 6,168,563 | B1 | 1/2001 | Brown |
| 6,224,542 | B1 | 5/2001 | Chang et al. |
| 6,234,964 | B1 | 5/2001 | Iliff |
| 6,270,455 | B1 | 8/2001 | Brown |
| 6,278,975 | B1 | 8/2001 | Brant et al. |
| 6,334,778 | B1 | 1/2002 | Brown |
| 6,364,834 | B1 | 4/2002 | Reuss et al. |
| 6,366,871 | B1 | 4/2002 | Geva |
| 6,368,273 | B1 | 4/2002 | Brown |
| 6,415,166 | B1 | 7/2002 | Van Hoy et al. |
| 6,416,471 | B1 | 7/2002 | Kumar et al. |
| 6,424,847 | B1 | 7/2002 | Mastrototaro et al. |
| 6,442,432 | B2 | 8/2002 | Lee |
| 6,447,424 | B1 | 9/2002 | Ashby et al. |
| 6,463,361 | B1 | 10/2002 | Wang et al. |
| 6,477,395 | B2 | 11/2002 | Schulman et al. |
| 6,477,424 | B1 | 11/2002 | Thompson et al. |
| 6,484,046 | B1 | 11/2002 | Say et al. |
| 6,492,901 | B1 | 12/2002 | Ridolfo |
| 6,544,174 | B2 | 4/2003 | West et al. |
| 6,558,320 | B1 | 5/2003 | Causey, III et al. |
| 6,558,321 | B1 | 5/2003 | Burd et al. |
| 6,564,104 | B2 | 5/2003 | Nelson et al. |
| 6,565,509 | B1 | 5/2003 | Say et al. |
| 6,579,690 | B1 | 6/2003 | Bonnecaze et al. |
| 6,585,644 | B2 | 7/2003 | Lebel et al. |
| 6,592,528 | B2 | 7/2003 | Amano |
| 6,602,191 | B2 | 8/2003 | Quy |
| 6,638,223 | B2 | 10/2003 | Lifshitz et al. |
| 6,641,533 | B2 | 11/2003 | Causey, III et al. |
| 6,645,142 | B2 | 11/2003 | Braig et al. |
| 6,669,631 | B2 | 12/2003 | Norris et al. |
| 6,702,857 | B2 | 3/2004 | Brauker et al. |
| 6,735,479 | B2 | 5/2004 | Fabian et al. |
| 6,741,877 | B1 | 5/2004 | Shults et al. |
| 6,775,577 | B2 | 8/2004 | Crnkovich et al. |
| 6,816,241 | B2 | 11/2004 | Grubisic |
| 6,862,465 | B2 | 3/2005 | Shults et al. |
| 6,931,327 | B2 | 8/2005 | Goode, Jr. et al. |
| 6,943,787 | B2 | 9/2005 | Webb |
| 6,950,708 | B2 | 9/2005 | Bowman IV et al. |
| 6,957,102 | B2 | 10/2005 | Silver et al. |
| 6,958,705 | B2 | 10/2005 | Lebel et al. |
| 7,026,929 | B1 | 4/2006 | Wallace |
| 7,074,307 | B2 | 7/2006 | Simpson et al. |
| 7,081,195 | B2 | 7/2006 | Simpson et al. |
| 7,088,233 | B2 | 8/2006 | Menard |
| 7,103,578 | B2 | 9/2006 | Beck et al. |
| 7,108,778 | B2 | 9/2006 | Simpson et al. |
| 7,110,803 | B2 | 9/2006 | Shults et al. |
| 7,134,994 | B2 | 11/2006 | Alpert et al. |
| 7,134,999 | B2 | 11/2006 | Brauker et al. |
| 7,136,689 | B2 | 11/2006 | Shults et al. |
| 7,171,274 | B2 | 1/2007 | Starkweather et al. |
| 7,192,450 | B2 | 3/2007 | Brauker et al. |
| 7,219,303 | B2 | 5/2007 | Fish |
| 7,226,978 | B2 | 6/2007 | Tapsak et al. |
| 7,256,708 | B2 | 8/2007 | Rosenfeld et al. |
| 7,276,029 | B2 | 10/2007 | Goode, Jr. et al. |
| 7,278,983 | B2 | 10/2007 | Ireland et al. |
| 7,294,105 | B1 | 11/2007 | Islam |
| 7,301,451 | B2 | 11/2007 | Hastings |
| 7,310,544 | B2 | 12/2007 | Brister et al. |
| 7,364,592 | B2 | 4/2008 | Carr-Brendel et al. |
| 7,366,556 | B2 | 4/2008 | Brister et al. |
| 7,379,765 | B2 | 5/2008 | Petisce et al. |
| 7,399,277 | B2 | 7/2008 | Saidara et al. |
| 7,424,318 | B2 | 9/2008 | Brister et al. |
| 7,448,996 | B2 | 11/2008 | Khanuja et al. |
| 7,460,898 | B2 | 12/2008 | Brister et al. |
| 7,467,003 | B2 | 12/2008 | Brister et al. |
| 7,471,972 | B2 | 12/2008 | Rhodes et al. |
| 7,494,465 | B2 | 2/2009 | Brister et al. |
| 7,497,827 | B2 | 3/2009 | Brister et al. |
| 7,519,408 | B2 | 4/2009 | Rasdal et al. |
| 7,519,430 | B2 | 4/2009 | Von Arx et al. |
| 7,565,197 | B2 | 7/2009 | Haubrich et al. |
| 7,583,990 | B2 | 9/2009 | Goode, Jr. et al. |
| 7,591,801 | B2 | 9/2009 | Brauker et al. |
| 7,599,726 | B2 | 10/2009 | Goode, Jr. et al. |
| 7,613,491 | B2 | 11/2009 | Boock et al. |
| 7,615,007 | B2 | 11/2009 | Shults et al. |
| 7,618,368 | B2 | 11/2009 | Brown |
| 7,632,228 | B2 | 12/2009 | Brauker et al. |
| 7,637,868 | B2 | 12/2009 | Saint et al. |
| 7,640,048 | B2 | 12/2009 | Dobbles et al. |
| 7,643,798 | B2 | 1/2010 | Ljung |
| 7,651,596 | B2 | 1/2010 | Petisce et al. |
| 7,654,956 | B2 | 2/2010 | Brister et al. |
| 7,657,297 | B2 | 2/2010 | Simpson et al. |
| 7,685,005 | B2 | 3/2010 | Riff et al. |
| 7,711,402 | B2 | 5/2010 | Shults et al. |
| 7,713,574 | B2 | 5/2010 | Brister et al. |
| 7,715,893 | B2 | 5/2010 | Kamath et al. |
| 7,761,130 | B2 | 7/2010 | Simpson et al. |

(56) References Cited

U.S. PATENT DOCUMENTS

| | | |
|---|---|---|
| 7,771,352 B2 | 8/2010 | Shults et al. |
| 7,774,145 B2 | 8/2010 | Brauker et al. |
| 7,775,975 B2 | 8/2010 | Brister et al. |
| 7,778,680 B2 | 8/2010 | Goode, Jr. et al. |
| 7,783,333 B2 | 8/2010 | Brister et al. |
| 7,792,562 B2 | 9/2010 | Shults et al. |
| 7,797,028 B2 | 9/2010 | Goode, Jr. et al. |
| 7,811,231 B2 | 10/2010 | Jin et al. |
| 7,826,981 B2 | 11/2010 | Goode, Jr. et al. |
| 7,828,728 B2 | 11/2010 | Boock et al. |
| 7,831,287 B2 | 11/2010 | Brister et al. |
| 7,835,777 B2 | 11/2010 | Shults et al. |
| 7,857,760 B2 | 12/2010 | Brister et al. |
| 7,860,545 B2 | 12/2010 | Shults et al. |
| 7,875,293 B2 | 1/2011 | Shults et al. |
| 7,881,763 B2 | 2/2011 | Brauker et al. |
| 7,885,697 B2 | 2/2011 | Brister et al. |
| 7,896,809 B2 | 3/2011 | Simpson et al. |
| 7,899,511 B2 | 3/2011 | Shults et al. |
| 7,901,354 B2 | 3/2011 | Shults et al. |
| 7,905,833 B2 | 3/2011 | Brister et al. |
| 7,914,450 B2 | 3/2011 | Goode, Jr. et al. |
| 7,917,186 B2 | 3/2011 | Kamath et al. |
| 7,920,906 B2 | 4/2011 | Goode, Jr. et al. |
| 7,925,321 B2 | 4/2011 | Goode et al. |
| 7,927,274 B2 | 4/2011 | Rasdal et al. |
| 7,933,639 B2 | 4/2011 | Goode et al. |
| 7,933,781 B2 | 4/2011 | Bjorlin et al. |
| 7,935,057 B2 | 5/2011 | Goode, Jr. et al. |
| 7,946,984 B2 | 5/2011 | Brister et al. |
| 7,946,995 B1 | 5/2011 | Koh et al. |
| 7,949,381 B2 | 5/2011 | Brister et al. |
| 7,955,261 B2 | 6/2011 | Goode et al. |
| 7,959,569 B2 | 6/2011 | Goode et al. |
| 7,970,448 B2 | 6/2011 | Shults et al. |
| 7,974,672 B2 | 7/2011 | Shults et al. |
| 7,976,492 B2 | 7/2011 | Brauker et al. |
| 7,979,104 B2 | 7/2011 | Kamath et al. |
| 7,981,034 B2 | 7/2011 | Jennewine et al. |
| 7,986,986 B2 | 7/2011 | Goode et al. |
| 7,998,071 B2 | 8/2011 | Goode, Jr. et al. |
| 8,000,901 B2 | 8/2011 | Brauker et al. |
| 8,005,524 B2 | 8/2011 | Brauker et al. |
| 8,005,525 B2 | 8/2011 | Goode, Jr. et al. |
| 8,010,174 B2 | 8/2011 | Goode, Jr. et al. |
| 8,050,731 B2 | 11/2011 | Tapsak et al. |
| 8,052,601 B2 | 11/2011 | Goode, Jr. et al. |
| 8,053,018 B2 | 11/2011 | Tapsak et al. |
| 8,060,173 B2 | 11/2011 | Goode, Jr. et al. |
| 8,060,174 B2 | 11/2011 | Simpson et al. |
| 8,064,977 B2 | 11/2011 | Boock et al. |
| 8,073,008 B2 | 12/2011 | Mehta et al. |
| 8,073,519 B2 | 12/2011 | Goode, Jr. et al. |
| 8,073,520 B2 | 12/2011 | Kamath et al. |
| 8,085,151 B2 | 12/2011 | Jennewine |
| 8,086,292 B2 | 12/2011 | Peyser |
| 8,095,692 B2 | 1/2012 | Mehta et al. |
| 8,112,240 B2 | 2/2012 | Fennell |
| 8,118,877 B2 | 2/2012 | Brauker et al. |
| 8,121,857 B2 | 2/2012 | Galasso et al. |
| 8,128,562 B2 | 3/2012 | Goode, Jr. et al. |
| 8,131,566 B2 | 3/2012 | Dicks et al. |
| 8,133,178 B2 | 3/2012 | Brauker et al. |
| 8,150,488 B2 | 4/2012 | Goode, Jr. et al. |
| 8,155,723 B2 | 4/2012 | Shults et al. |
| 8,160,669 B2 | 4/2012 | Brauker et al. |
| 8,160,671 B2 | 4/2012 | Kamath et al. |
| 8,167,801 B2 | 5/2012 | Goode, Jr. et al. |
| 8,170,803 B2 | 5/2012 | Kamath et al. |
| 8,180,591 B2 | 5/2012 | Yuen et al. |
| 8,195,265 B2 | 6/2012 | Goode, Jr. et al. |
| 8,206,297 B2 | 6/2012 | Kamath et al. |
| 8,208,973 B2 | 6/2012 | Mehta |
| 8,216,139 B2 | 7/2012 | Brauker et al. |
| 8,229,534 B2 | 7/2012 | Brister et al. |
| 8,229,535 B2 | 7/2012 | Mensinger et al. |
| 8,229,536 B2 | 7/2012 | Goode, Jr. et al. |
| 8,231,531 B2 | 7/2012 | Brister et al. |
| 8,233,958 B2 | 7/2012 | Brauker et al. |
| 8,233,959 B2 | 7/2012 | Kamath et al. |
| 8,249,684 B2 | 8/2012 | Kamath et al. |
| 8,251,906 B2 | 8/2012 | Brauker et al. |
| 8,255,030 B2 | 8/2012 | Petisce et al. |
| 8,255,032 B2 | 8/2012 | Petisce et al. |
| 8,255,033 B2 | 8/2012 | Petisce et al. |
| 8,257,259 B2 | 9/2012 | Brauker et al. |
| 8,260,393 B2 | 9/2012 | Kamath et al. |
| 8,265,725 B2 | 9/2012 | Brauker et al. |
| 8,275,437 B2 | 9/2012 | Brauker et al. |
| 8,275,438 B2 | 9/2012 | Simpson et al. |
| 8,277,713 B2 | 10/2012 | Petisce et al. |
| 8,280,475 B2 | 10/2012 | Brister et al. |
| 8,282,549 B2 | 10/2012 | Brauker et al. |
| 8,282,550 B2 | 10/2012 | Rasdal et al. |
| 8,285,354 B2 | 10/2012 | Goode et al. |
| 8,287,453 B2 | 10/2012 | Li et al. |
| 8,290,559 B2 | 10/2012 | Shariati et al. |
| 8,290,560 B2 | 10/2012 | Kamath et al. |
| 8,290,561 B2 | 10/2012 | Brauker et al. |
| 8,290,562 B2 | 10/2012 | Goode, Jr. et al. |
| 8,292,810 B2 | 10/2012 | Goode, Jr. et al. |
| 8,298,142 B2 | 10/2012 | Simpson et al. |
| 8,311,749 B2 | 11/2012 | Brauker et al. |
| 8,313,434 B2 | 11/2012 | Brister et al. |
| 8,321,149 B2 | 11/2012 | Brauker et al. |
| 8,323,189 B2 | 12/2012 | Tran et al. |
| 8,332,008 B2 | 12/2012 | Goode et al. |
| 8,346,338 B2 | 1/2013 | Goode, Jr. et al. |
| 8,355,320 B1 | 1/2013 | Dhiman et al. |
| 8,364,229 B2 | 1/2013 | Simpson et al. |
| 8,369,919 B2 | 2/2013 | Kamath et al. |
| 8,374,667 B2 | 2/2013 | Brauker et al. |
| 8,381,268 B2 | 2/2013 | Winget et al. |
| 8,386,004 B2 | 2/2013 | Kamath et al. |
| 8,394,021 B2 | 3/2013 | Goode et al. |
| 8,409,093 B2 | 4/2013 | Bugler |
| 8,412,185 B2 | 4/2013 | Cader et al. |
| 8,416,085 B2 | 4/2013 | Gawlick |
| 8,432,260 B2 | 4/2013 | Talty et al. |
| 8,472,108 B2 | 6/2013 | Islam |
| 8,515,777 B1 * | 8/2013 | Rajasenan ............ G16H 40/20 705/2 |
| 8,527,025 B1 | 9/2013 | Shults et al. |
| 8,527,449 B2 | 9/2013 | Gajic et al. |
| 8,549,600 B2 | 10/2013 | Shedrinsky |
| 8,638,397 B2 | 1/2014 | Ueno et al. |
| 8,704,656 B2 | 4/2014 | Abedi |
| 8,784,271 B2 | 7/2014 | Brumback et al. |
| 8,786,425 B1 | 7/2014 | Hutz |
| 8,789,156 B2 | 7/2014 | Fisk et al. |
| 8,821,622 B2 | 9/2014 | Manahan et al. |
| 8,912,897 B2 | 12/2014 | Carnes |
| 8,926,509 B2 | 1/2015 | Magar et al. |
| 8,968,198 B2 | 3/2015 | Brauker et al. |
| 9,011,332 B2 | 4/2015 | Heller et al. |
| 9,028,410 B2 | 5/2015 | San Vicente et al. |
| 9,035,744 B2 | 5/2015 | Waniss |
| 9,079,033 B2 | 7/2015 | Kuenzler et al. |
| 9,198,623 B2 | 12/2015 | Fern et al. |
| 9,232,916 B2 | 1/2016 | Mao et al. |
| 9,363,337 B2 | 6/2016 | Chor |
| 9,445,445 B2 | 9/2016 | Miller et al. |
| 9,451,910 B2 | 9/2016 | Brister et al. |
| 9,503,526 B2 | 11/2016 | Daoud et al. |
| 9,532,737 B2 | 1/2017 | Karan et al. |
| 9,579,053 B2 | 2/2017 | Brister et al. |
| 9,585,563 B2 | 3/2017 | Mensinger et al. |
| 9,655,518 B2 | 5/2017 | Lin |
| 9,662,438 B2 | 5/2017 | Kamen et al. |
| 9,668,682 B2 | 6/2017 | Brister et al. |
| 9,681,807 B2 | 6/2017 | Miller et al. |
| 9,724,028 B2 | 8/2017 | Brauker et al. |
| 9,730,620 B2 | 8/2017 | Cohen et al. |
| 9,730,621 B2 | 8/2017 | Cohen et al. |

(56) References Cited

U.S. PATENT DOCUMENTS

| | | |
|---|---|---|
| 9,788,354 B2 | 10/2017 | Miller et al. |
| 9,788,766 B2 | 10/2017 | Simpson et al. |
| 9,801,541 B2 | 10/2017 | Mensinger et al. |
| 9,839,353 B2 | 12/2017 | Mensinger et al. |
| 9,854,972 B2 | 1/2018 | Mensinger et al. |
| 9,931,036 B2 | 4/2018 | Miller et al. |
| 9,931,037 B2 | 4/2018 | Miller et al. |
| 9,962,081 B2 | 5/2018 | Mensinger et al. |
| 9,980,646 B2 | 5/2018 | Mensinger et al. |
| 10,376,188 B2 | 8/2019 | Simpson et al. |
| 10,499,811 B2 | 12/2019 | Mensinger et al. |
| 10,667,686 B2 | 6/2020 | Mensinger et al. |
| 10,856,736 B2 | 12/2020 | Mensinger et al. |
| 10,860,687 B2 | 12/2020 | Cohen et al. |
| 10,869,599 B2 | 12/2020 | Mensinger et al. |
| 11,043,300 B2 | 6/2021 | Reggiardo et al. |
| 11,152,112 B2 | 10/2021 | Nekoomaram et al. |
| 2001/0023360 A1* | 9/2001 | Nelson ............... A61B 5/0031 607/60 |
| 2002/0016719 A1* | 2/2002 | Nemeth ............... G16H 40/67 705/2 |
| 2002/0019584 A1 | 2/2002 | Schulze et al. |
| 2002/0045808 A1 | 4/2002 | Ford et al. |
| 2002/0061092 A1 | 5/2002 | Maropis et al. |
| 2002/0065453 A1 | 5/2002 | Lesho et al. |
| 2002/0068858 A1* | 6/2002 | Braig ............... A61B 5/0002 600/316 |
| 2002/0169584 A1 | 11/2002 | Fu et al. |
| 2002/0169587 A1 | 11/2002 | Emek et al. |
| 2002/0195997 A1 | 12/2002 | Peek et al. |
| 2003/0028184 A1 | 2/2003 | Lebel et al. |
| 2003/0032874 A1 | 2/2003 | Rhodes et al. |
| 2003/0060692 A1 | 3/2003 | L. Ruchti et al. |
| 2003/0149526 A1 | 8/2003 | Zhou et al. |
| 2003/0208465 A1 | 11/2003 | Yurko et al. |
| 2004/0015132 A1 | 1/2004 | Brown |
| 2004/0030753 A1* | 2/2004 | Horvitz ............... H04W 4/02 709/206 |
| 2004/0044272 A1 | 3/2004 | Moerman et al. |
| 2004/0102683 A1 | 5/2004 | Khanuja et al. |
| 2004/0236189 A1 | 11/2004 | Hawthorne et al. |
| 2004/0243941 A1 | 12/2004 | Fish |
| 2005/0027182 A1 | 2/2005 | Siddiqui et al. |
| 2005/0027462 A1 | 2/2005 | Goode, Jr. et al. |
| 2005/0027463 A1 | 2/2005 | Goode, Jr. et al. |
| 2005/0033132 A1 | 2/2005 | Shults et al. |
| 2005/0038332 A1 | 2/2005 | Saidara et al. |
| 2005/0043598 A1 | 2/2005 | Goode, Jr. et al. |
| 2005/0051427 A1 | 3/2005 | Brauker et al. |
| 2005/0056552 A1 | 3/2005 | Simpson et al. |
| 2005/0090607 A1 | 4/2005 | Tapsak et al. |
| 2005/0097200 A1 | 5/2005 | Denning, Jr. et al. |
| 2005/0143671 A1 | 6/2005 | Hastings et al. |
| 2005/0148890 A1 | 7/2005 | Hastings |
| 2005/0151640 A1* | 7/2005 | Hastings ............... A61B 5/411 340/539.11 |
| 2005/0154271 A1 | 7/2005 | Rasdal et al. |
| 2005/0165627 A1 | 7/2005 | Fotsch et al. |
| 2005/0176136 A1 | 8/2005 | Burd et al. |
| 2005/0182451 A1 | 8/2005 | Griffin et al. |
| 2005/0192557 A1 | 9/2005 | Brauker et al. |
| 2005/0193191 A1 | 9/2005 | Sturgis |
| 2005/0203360 A1 | 9/2005 | Brauker et al. |
| 2005/0207379 A1 | 9/2005 | Shen et al. |
| 2005/0245799 A1 | 11/2005 | Brauker et al. |
| 2005/0261062 A1 | 11/2005 | Lewin et al. |
| 2005/0261562 A1 | 11/2005 | Zhou et al. |
| 2005/0283198 A1* | 12/2005 | Haubrich ............. G06F 19/3418 607/30 |
| 2005/0283208 A1 | 12/2005 | Von Arx et al. |
| 2006/0010098 A1 | 1/2006 | Goodnow et al. |
| 2006/0015020 A1 | 1/2006 | Neale et al. |
| 2006/0016700 A1 | 1/2006 | Brister et al. |
| 2006/0019613 A1 | 1/2006 | Lim |
| 2006/0020187 A1 | 1/2006 | Brister et al. |
| 2006/0020188 A1 | 1/2006 | Kamath et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036140 A1 | 2/2006 | Brister et al. |
| 2006/0036143 A1 | 2/2006 | Brister et al. |
| 2006/0036144 A1 | 2/2006 | Brister et al. |
| 2006/0040402 A1 | 2/2006 | Brauker et al. |
| 2006/0047538 A1 | 3/2006 | Condurso et al. |
| 2006/0068208 A1 | 3/2006 | Tapsak et al. |
| 2006/0071797 A1* | 4/2006 | Rosenfeld ............. G16H 50/20 340/573.1 |
| 2006/0089452 A1 | 4/2006 | Schneider et al. |
| 2006/0089542 A1 | 4/2006 | Sands |
| 2006/0142651 A1 | 6/2006 | Brister et al. |
| 2006/0155180 A1 | 7/2006 | Brister et al. |
| 2006/0168592 A1* | 7/2006 | Andrews ............... G06Q 10/10 719/318 |
| 2006/0198864 A1 | 9/2006 | Shults et al. |
| 2006/0200020 A1 | 9/2006 | Brister et al. |
| 2006/0200022 A1 | 9/2006 | Brauker et al. |
| 2006/0200970 A1 | 9/2006 | Brister et al. |
| 2006/0204536 A1 | 9/2006 | Shults et al. |
| 2006/0222566 A1 | 10/2006 | Brauker et al. |
| 2006/0224108 A1 | 10/2006 | Brauker et al. |
| 2006/0235285 A1 | 10/2006 | Brister et al. |
| 2006/0249381 A1 | 11/2006 | Petisce et al. |
| 2006/0252027 A1 | 11/2006 | Petisce et al. |
| 2006/0253012 A1 | 11/2006 | Petisce et al. |
| 2006/0257995 A1 | 11/2006 | Simpson et al. |
| 2006/0258761 A1 | 11/2006 | Boock et al. |
| 2006/0263763 A1 | 11/2006 | Simpson et al. |
| 2006/0270922 A1 | 11/2006 | Brauker et al. |
| 2006/0270923 A1 | 11/2006 | Brauker et al. |
| 2007/0016381 A1 | 1/2007 | Kamath et al. |
| 2007/0027370 A1 | 2/2007 | Brauker et al. |
| 2007/0027385 A1 | 2/2007 | Brister et al. |
| 2007/0032706 A1 | 2/2007 | Kamath et al. |
| 2007/0032718 A1 | 2/2007 | Shults et al. |
| 2007/0045902 A1 | 3/2007 | Brauker et al. |
| 2007/0059196 A1 | 3/2007 | Brister et al. |
| 2007/0060093 A1 | 3/2007 | Kerth et al. |
| 2007/0060132 A1 | 3/2007 | Wilhelmsson et al. |
| 2007/0066873 A1 | 3/2007 | Kamath et al. |
| 2007/0088223 A1 | 4/2007 | Mann et al. |
| 2007/0118187 A1 | 5/2007 | Denker et al. |
| 2007/0153993 A1 | 7/2007 | Cohen |
| 2007/0163880 A1 | 7/2007 | Woo et al. |
| 2007/0173709 A1 | 7/2007 | Petisce et al. |
| 2007/0173710 A1 | 7/2007 | Petisce et al. |
| 2007/0185390 A1 | 8/2007 | Perkins et al. |
| 2007/0192137 A1 | 8/2007 | Ombrellaro |
| 2007/0203966 A1 | 8/2007 | Brauker et al. |
| 2007/0208245 A1 | 9/2007 | Brauker et al. |
| 2007/0208246 A1 | 9/2007 | Brauker et al. |
| 2007/0231846 A1 | 10/2007 | Cosentino et al. |
| 2007/0232879 A1 | 10/2007 | Brister et al. |
| 2007/0242666 A1 | 10/2007 | Barrett |
| 2007/0253021 A1 | 11/2007 | Mehta et al. |
| 2007/0255116 A1 | 11/2007 | Mehta et al. |
| 2007/0293742 A1 | 12/2007 | Simonsen et al. |
| 2008/0015422 A1 | 1/2008 | Wessel |
| 2008/0033254 A1 | 2/2008 | Kamath et al. |
| 2008/0034438 A1 | 2/2008 | Mireku |
| 2008/0045824 A1 | 2/2008 | Tapsak et al. |
| 2008/0083617 A1 | 4/2008 | Simpson et al. |
| 2008/0086044 A1 | 4/2008 | Brister et al. |
| 2008/0098038 A1 | 4/2008 | Motoyama |
| 2008/0108942 A1 | 5/2008 | Brister et al. |
| 2008/0119703 A1 | 5/2008 | Brister et al. |
| 2008/0119705 A1 | 5/2008 | Brister et al. |
| 2008/0119706 A1 | 5/2008 | Brister et al. |
| 2008/0148148 A1* | 6/2008 | Ramanathan ......... H04M 1/72563 715/700 |
| 2008/0172737 A1* | 7/2008 | Shen ..................... G16H 10/60 726/21 |
| 2008/0183061 A1 | 7/2008 | Goode et al. |
| 2008/0183399 A1 | 7/2008 | Goode et al. |

(56) References Cited

U.S. PATENT DOCUMENTS

| | | |
|---|---|---|
| 2008/0188731 A1 | 8/2008 | Brister et al. |
| 2008/0189051 A1 | 8/2008 | Goode et al. |
| 2008/0194938 A1 | 8/2008 | Brister et al. |
| 2008/0197024 A1 | 8/2008 | Simpson et al. |
| 2008/0199894 A1 | 8/2008 | Galasso |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0214915 A1 | 9/2008 | Brister et al. |
| 2008/0228054 A1 | 9/2008 | Shults et al. |
| 2008/0242961 A1 | 10/2008 | Brister et al. |
| 2008/0250482 A1 | 10/2008 | Ahtisaari |
| 2008/0262469 A1 | 10/2008 | Brister et al. |
| 2008/0263100 A1 | 10/2008 | Van Engelshoven et al. |
| 2008/0275313 A1 | 11/2008 | Brister et al. |
| 2008/0287765 A1 | 11/2008 | Rasdal et al. |
| 2008/0300572 A1 | 12/2008 | Rankers et al. |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0316015 A1 | 12/2008 | Naedele et al. |
| 2008/0319294 A1 | 12/2008 | Taub |
| 2008/0319295 A1 | 12/2008 | Bernstein et al. |
| 2008/0319296 A1 | 12/2008 | Bernstein et al. |
| 2009/0005703 A1 | 1/2009 | Fasciano |
| 2009/0018424 A1 | 1/2009 | Kamath et al. |
| 2009/0025063 A1 | 1/2009 | Thomas |
| 2009/0030294 A1 | 1/2009 | Petisce et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0045055 A1 | 2/2009 | Rhodes et al. |
| 2009/0054737 A1 | 2/2009 | Magar et al. |
| 2009/0062633 A1 | 3/2009 | Brauker et al. |
| 2009/0062635 A1 | 3/2009 | Brauker et al. |
| 2009/0076360 A1 | 3/2009 | Brister et al. |
| 2009/0085768 A1 | 4/2009 | Patel et al. |
| 2009/0097623 A1 | 4/2009 | Bharadwaj |
| 2009/0099436 A1 | 4/2009 | Brister et al. |
| 2009/0118596 A1 | 5/2009 | Khanuja et al. |
| 2009/0124877 A1 | 5/2009 | Goode, Jr. et al. |
| 2009/0124879 A1 | 5/2009 | Brister et al. |
| 2009/0124964 A1 | 5/2009 | Leach et al. |
| 2009/0131769 A1 | 5/2009 | Leach et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0147940 A1* | 6/2009 | Graves .............. H04M 3/42365 379/208.01 |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0171180 A1 | 7/2009 | Pering et al. |
| 2009/0178459 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192751 A1 | 7/2009 | Kamath et al. |
| 2009/0203973 A1 | 8/2009 | Donoghue et al. |
| 2009/0203981 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0270705 A1 | 10/2009 | Enegren et al. |
| 2009/0287074 A1 | 11/2009 | Shults et al. |
| 2009/0289507 A1 | 11/2009 | Shiu |
| 2009/0291634 A1 | 11/2009 | Saarisalo |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0026250 A1 | 2/2010 | Petty |
| 2010/0030484 A1 | 2/2010 | Brauker et al. |
| 2010/0030596 A1 | 2/2010 | Johari |
| 2010/0036215 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0082364 A1 | 4/2010 | Taub et al. |
| 2010/0087724 A1 | 4/2010 | Brauker et al. |
| 2010/0088387 A1 | 4/2010 | Calamera |
| 2010/0096259 A1 | 4/2010 | Zhang et al. |
| 2010/0121169 A1 | 5/2010 | Petisce et al. |
| 2010/0131294 A1 | 5/2010 | Venon et al. |
| 2010/0161269 A1 | 6/2010 | Kamath et al. |
| 2010/0168540 A1 | 7/2010 | Kamath et al. |
| 2010/0168541 A1 | 7/2010 | Kamath et al. |
| 2010/0168542 A1 | 7/2010 | Kamath et al. |
| 2010/0168543 A1 | 7/2010 | Kamath et al. |
| 2010/0168544 A1 | 7/2010 | Kamath et al. |
| 2010/0168545 A1 | 7/2010 | Kamath et al. |
| 2010/0168546 A1 | 7/2010 | Kamath et al. |
| 2010/0168657 A1 | 7/2010 | Kamath et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0179401 A1 | 7/2010 | Rasdal et al. |
| 2010/0179402 A1 | 7/2010 | Goode, Jr. et al. |
| 2010/0179404 A1 | 7/2010 | Kamath et al. |
| 2010/0179408 A1 | 7/2010 | Kamath et al. |
| 2010/0179409 A1 | 7/2010 | Kamath et al. |
| 2010/0185065 A1 | 7/2010 | Goode, Jr. et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185075 A1 | 7/2010 | Brister et al. |
| 2010/0191075 A1 | 7/2010 | Angelides |
| 2010/0191082 A1 | 7/2010 | Brister et al. |
| 2010/0198034 A1 | 8/2010 | Thomas et al. |
| 2010/0198035 A1 | 8/2010 | Kamath et al. |
| 2010/0198036 A1 | 8/2010 | Kamath et al. |
| 2010/0198142 A1 | 8/2010 | Sloan et al. |
| 2010/0212583 A1 | 8/2010 | Brister et al. |
| 2010/0216507 A1 | 8/2010 | Maeda |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228497 A1 | 9/2010 | Kamath et al. |
| 2010/0240975 A1 | 9/2010 | Goode, Jr. et al. |
| 2010/0240976 A1 | 9/2010 | Goode, Jr. et al. |
| 2010/0249625 A1 | 9/2010 | Lin |
| 2010/0261987 A1 | 10/2010 | Kamath et al. |
| 2010/0265073 A1 | 10/2010 | Harper |
| 2010/0274107 A1 | 10/2010 | Boock et al. |
| 2010/0280341 A1 | 11/2010 | Boock et al. |
| 2010/0281409 A1 | 11/2010 | Rainisto et al. |
| 2010/0283917 A1 | 11/2010 | Ueno et al. |
| 2010/0286496 A1 | 11/2010 | Simpson et al. |
| 2010/0292556 A1 | 11/2010 | Golden |

(56) References Cited

U.S. PATENT DOCUMENTS

| | | |
|---|---|---|
| 2010/0298684 A1 | 11/2010 | Leach et al. |
| 2010/0305965 A1 | 12/2010 | Benjamin et al. |
| 2010/0313105 A1 | 12/2010 | Nekoomaram et al. |
| 2010/0323431 A1 | 12/2010 | Rutkowski et al. |
| 2010/0324403 A1 | 12/2010 | Brister et al. |
| 2010/0331644 A1 | 12/2010 | Neale et al. |
| 2010/0331656 A1 | 12/2010 | Mensinger et al. |
| 2010/0331657 A1 | 12/2010 | Mensinger et al. |
| 2011/0001605 A1 | 1/2011 | Kiani et al. |
| 2011/0004085 A1 | 1/2011 | Mensinger et al. |
| 2011/0009727 A1 | 1/2011 | Mensinger et al. |
| 2011/0016064 A1* | 1/2011 | Barton ............... G06F 19/3418 706/11 |
| 2011/0019824 A1 | 1/2011 | Satti et al. |
| 2011/0022411 A1 | 1/2011 | Hjelm et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0046467 A1 | 2/2011 | Simpson et al. |
| 2011/0054282 A1 | 3/2011 | Nekoomaram et al. |
| 2011/0058485 A1 | 3/2011 | Sloan |
| 2011/0060530 A1 | 3/2011 | Fennell |
| 2011/0065384 A1 | 3/2011 | Cader et al. |
| 2011/0077490 A1 | 3/2011 | Simpson et al. |
| 2011/0081888 A1* | 4/2011 | Waniss ............... H04M 1/72527 455/411 |
| 2011/0105854 A1 | 5/2011 | Kiani et al. |
| 2011/0112908 A1 | 5/2011 | Rowley et al. |
| 2011/0118579 A1 | 5/2011 | Goode, Jr. et al. |
| 2011/0119080 A1 | 5/2011 | Hayter et al. |
| 2011/0124992 A1 | 5/2011 | Brauker et al. |
| 2011/0124996 A1 | 5/2011 | Reinke et al. |
| 2011/0125410 A1 | 5/2011 | Goode, Jr. et al. |
| 2011/0130970 A1 | 6/2011 | Goode, Jr. et al. |
| 2011/0130971 A1 | 6/2011 | Goode, Jr. et al. |
| 2011/0130998 A1 | 6/2011 | Goode, Jr. et al. |
| 2011/0144465 A1 | 6/2011 | Shults et al. |
| 2011/0149759 A1 | 6/2011 | Jollota |
| 2011/0152970 A1 | 6/2011 | Jollota et al. |
| 2011/0160544 A1 | 6/2011 | Hayter |
| 2011/0161111 A1 | 6/2011 | Dicks et al. |
| 2011/0178378 A1 | 7/2011 | Brister et al. |
| 2011/0184268 A1 | 7/2011 | Taub |
| 2011/0190614 A1 | 8/2011 | Brister et al. |
| 2011/0199214 A1 | 8/2011 | Gawlick |
| 2011/0201910 A1 | 8/2011 | Rasdal et al. |
| 2011/0201911 A1 | 8/2011 | Johnson et al. |
| 2011/0210830 A1 | 9/2011 | Talty et al. |
| 2011/0213225 A1 | 9/2011 | Bernstein et al. |
| 2011/0218414 A1 | 9/2011 | Kamath et al. |
| 2011/0231140 A1 | 9/2011 | Goode, Jr. et al. |
| 2011/0231141 A1 | 9/2011 | Goode, Jr. et al. |
| 2011/0231142 A1 | 9/2011 | Goode, Jr. et al. |
| 2011/0234406 A1 | 9/2011 | Young et al. |
| 2011/0253533 A1 | 10/2011 | Shults et al. |
| 2011/0263958 A1 | 10/2011 | Brauker et al. |
| 2011/0264035 A1 | 10/2011 | Yodfat et al. |
| 2011/0270062 A1 | 11/2011 | Goode, Jr. et al. |
| 2011/0270158 A1 | 11/2011 | Brauker et al. |
| 2011/0275919 A1 | 11/2011 | Petisce et al. |
| 2011/0287528 A1 | 11/2011 | Fern et al. |
| 2011/0289497 A1 | 11/2011 | Kiaie et al. |
| 2011/0290645 A1 | 12/2011 | Brister et al. |
| 2011/0313543 A1 | 12/2011 | Brauker et al. |
| 2011/0320130 A1 | 12/2011 | Valdes et al. |
| 2012/0016305 A1 | 1/2012 | Jollota et al. |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0075103 A1 | 3/2012 | Powell et al. |
| 2012/0078071 A1 | 3/2012 | Bohm et al. |
| 2012/0084053 A1 | 4/2012 | Yuen et al. |
| 2012/0108934 A1 | 5/2012 | Valdes et al. |
| 2012/0130214 A1 | 5/2012 | Brister et al. |
| 2012/0136221 A1 | 5/2012 | Killen et al. |
| 2012/0157127 A1* | 6/2012 | Ferren ............... G06F 21/32 455/566 |
| 2012/0172691 A1 | 7/2012 | Brauker et al. |
| 2012/0179014 A1 | 7/2012 | Shults et al. |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0203467 A1 | 8/2012 | Kamath et al. |
| 2012/0209098 A1 | 8/2012 | Goode, Jr. et al. |
| 2012/0215086 A1 | 8/2012 | Kamath et al. |
| 2012/0215087 A1 | 8/2012 | Cobelli et al. |
| 2012/0215201 A1 | 8/2012 | Brauker et al. |
| 2012/0215461 A1 | 8/2012 | Goode, Jr. et al. |
| 2012/0215462 A1 | 8/2012 | Goode, Jr. et al. |
| 2012/0215496 A1 | 8/2012 | Kamath et al. |
| 2012/0216297 A1 | 8/2012 | Cohen et al. |
| 2012/0216507 A1 | 8/2012 | Nieuwstadt |
| 2012/0220266 A1 | 8/2012 | Lau et al. |
| 2012/0220979 A1 | 8/2012 | Brauker et al. |
| 2012/0226121 A1 | 9/2012 | Kamath et al. |
| 2012/0228134 A1 | 9/2012 | Simpson et al. |
| 2012/0233679 A1 | 9/2012 | Shedrinsky |
| 2012/0235823 A1 | 9/2012 | Trock et al. |
| 2012/0238851 A1 | 9/2012 | Kamen et al. |
| 2012/0238852 A1 | 9/2012 | Brauker et al. |
| 2012/0242501 A1* | 9/2012 | Tran ............... A61B 5/0024 340/870.02 |
| 2012/0245447 A1 | 9/2012 | Karan et al. |
| 2012/0245448 A1 | 9/2012 | Shariati et al. |
| 2012/0245855 A1 | 9/2012 | Kamath et al. |
| 2012/0255875 A1 | 10/2012 | Vicente et al. |
| 2012/0258748 A1 | 10/2012 | San Vicente et al. |
| 2012/0259191 A1 | 10/2012 | Shariati et al. |
| 2012/0260323 A1 | 10/2012 | San Vicente et al. |
| 2012/0262298 A1 | 10/2012 | Bohm et al. |
| 2012/0265035 A1 | 10/2012 | Bohm et al. |
| 2012/0265036 A1 | 10/2012 | Estes et al. |
| 2012/0265037 A1 | 10/2012 | Bohm et al. |
| 2012/0277562 A1 | 11/2012 | Brister et al. |
| 2012/0277566 A1 | 11/2012 | Kamath et al. |
| 2012/0283541 A1 | 11/2012 | Kamath et al. |
| 2012/0283543 A1 | 11/2012 | Brauker et al. |
| 2012/0296311 A1 | 11/2012 | Brauker et al. |
| 2012/0296988 A1 | 11/2012 | Rao |
| 2012/0302854 A1 | 11/2012 | Kamath et al. |
| 2012/0302855 A1 | 11/2012 | Kamath et al. |
| 2012/0309302 A1 | 12/2012 | Buhot |
| 2012/0323100 A1 | 12/2012 | Kamath et al. |
| 2013/0012798 A1 | 1/2013 | Brister et al. |
| 2013/0030273 A1 | 1/2013 | Tapsak et al. |
| 2013/0030494 A1 | 1/2013 | Meredith et al. |
| 2013/0035575 A1 | 2/2013 | Mayou et al. |
| 2013/0035865 A1 | 2/2013 | Mayou et al. |
| 2013/0035871 A1 | 2/2013 | Mayou et al. |
| 2013/0047233 A1* | 2/2013 | Fisk ............... G06F 21/6245 726/7 |
| 2013/0053666 A1 | 2/2013 | Hughes et al. |
| 2013/0059541 A1 | 3/2013 | Sloan et al. |
| 2013/0116526 A1 | 5/2013 | Javitt et al. |
| 2013/0117696 A1 | 5/2013 | Robertson et al. |
| 2013/0117797 A1 | 5/2013 | Lam |
| 2013/0132416 A1 | 5/2013 | Hayter et al. |
| 2013/0136221 A1 | 5/2013 | Nishikata et al. |
| 2013/0137946 A1 | 5/2013 | Geske et al. |
| 2013/0151708 A1 | 6/2013 | Shelby et al. |
| 2013/0159456 A1 | 6/2013 | Daoud et al. |
| 2013/0172709 A1 | 7/2013 | Mears et al. |
| 2013/0173742 A1 | 7/2013 | Thomas et al. |
| 2013/0203351 A1 | 8/2013 | Hillan et al. |
| 2013/0276144 A1* | 10/2013 | Hansen ............... G06F 21/60 726/29 |
| 2013/0285835 A1 | 10/2013 | Kim et al. |
| 2013/0321425 A1 | 12/2013 | Greene et al. |
| 2014/0088392 A1 | 3/2014 | Bernstein et al. |
| 2014/0104058 A1 | 4/2014 | Sheleheda et al. |

(56) References Cited

U.S. PATENT DOCUMENTS

| | | | |
|---|---|---|---|
| 2014/0118104 A1 | 5/2014 | Sicurello et al. | |
| 2014/0176346 A1* | 6/2014 | Brumback | A61B 5/0015 340/870.16 |
| 2014/0184422 A1* | 7/2014 | Mensinger | A61B 5/0004 340/870.02 |
| 2014/0184423 A1 | 7/2014 | Mensinger et al. | |
| 2014/0187889 A1 | 7/2014 | Cohen et al. | |
| 2014/0187890 A1 | 7/2014 | Mensinger et al. | |
| 2014/0188398 A1 | 7/2014 | Cohen et al. | |
| 2014/0207486 A1* | 7/2014 | Carty | G16H 50/20 705/2 |
| 2014/0235166 A1 | 8/2014 | Molettiere et al. | |
| 2014/0244301 A1 | 8/2014 | Lee et al. | |
| 2014/0266776 A1 | 9/2014 | Miller et al. | |
| 2014/0288402 A1 | 9/2014 | Brister et al. | |
| 2015/0032826 A1* | 1/2015 | Gunaratnam | H04L 51/14 709/206 |
| 2015/0172096 A1 | 6/2015 | Sadovsky et al. | |
| 2015/0195286 A1 | 7/2015 | Doppler et al. | |
| 2015/0347711 A1* | 12/2015 | Soli | G16H 40/67 705/3 |
| 2015/0365818 A1* | 12/2015 | Mese | H04W 4/12 370/252 |
| 2015/0371350 A1* | 12/2015 | Zebarjadi | G06Q 10/10 705/2 |
| 2015/0371516 A1* | 12/2015 | Petersen | G16H 40/67 340/539.12 |
| 2016/0066866 A1 | 3/2016 | Mensinger et al. | |
| 2016/0066867 A1 | 3/2016 | Mensinger et al. | |
| 2016/0066868 A1 | 3/2016 | Mensinger et al. | |
| 2016/0073879 A1 | 3/2016 | Mensinger et al. | |
| 2016/0073880 A1 | 3/2016 | Mensinger et al. | |
| 2016/0081586 A1 | 3/2016 | Miller et al. | |
| 2016/0239619 A1* | 8/2016 | Abou-Hawi | G06Q 50/22 |
| 2017/0034649 A1* | 2/2017 | Dotan-Cohen | H04M 1/72454 |
| 2017/0034682 A1 | 2/2017 | Matsumasa et al. | |
| 2017/0135041 A1 | 5/2017 | Miller et al. | |
| 2017/0181630 A1 | 6/2017 | Mahalingam et al. | |
| 2017/0181645 A1 | 6/2017 | Mahalingam et al. | |
| 2017/0229006 A1* | 8/2017 | Tonna | G16H 40/20 |
| 2017/0231497 A1 | 8/2017 | Brister et al. | |
| 2017/0293732 A1 | 10/2017 | Cohen et al. | |
| 2017/0303785 A1 | 10/2017 | Mensinger et al. | |
| 2018/0132720 A1 | 5/2018 | Miller et al. | |
| 2018/0160949 A1 | 6/2018 | Brister et al. | |
| 2019/0059730 A1 | 2/2019 | Brister et al. | |
| 2019/0069817 A1 | 3/2019 | Brister et al. | |
| 2019/0354674 A1 | 11/2019 | Berman et al. | |
| 2019/0380163 A1 | 12/2019 | Miller et al. | |
| 2020/0221949 A1 | 7/2020 | Mensinger et al. | |
| 2020/0221950 A1 | 7/2020 | Mensinger et al. | |
| 2021/0398663 A1 | 12/2021 | Reggiardo et al. | |
| 2022/0013224 A1 | 1/2022 | Reggiardo et al. | |
| 2022/0037007 A1 | 2/2022 | Nekoomaram et al. | |

FOREIGN PATENT DOCUMENTS

| | | |
|---|---|---|
| CN | 1989733 A | 6/2007 |
| CN | 101278847 A | 10/2008 |
| CN | 201282481 Y | 7/2009 |
| CN | 101589393 A | 11/2009 |
| CN | 101601040 A | 12/2009 |
| CN | 101677770 A | 3/2010 |
| CN | 101742981 A | 6/2010 |
| CN | 101969836 A | 2/2011 |
| CN | 201732454 U | 2/2011 |
| CN | 102036718 A | 4/2011 |
| CN | 102065385 A | 5/2011 |
| CN | 102068310 A | 5/2011 |
| CN | 102724913 A | 10/2012 |
| EP | 2227062 A1 | 9/2010 |
| EP | 2453398 A1 | 5/2012 |
| EP | 2498196 A2 | 9/2012 |
| JP | 2000316819 A | 11/2000 |
| JP | 2004282541 A | 10/2004 |
| JP | 2005538794 A | 12/2005 |
| JP | 2006021031 A | 1/2006 |
| JP | 2006026270 A | 2/2006 |
| JP | 2006239084 A | 9/2006 |
| JP | 2006520657 A | 9/2006 |
| JP | 2008098744 A | 4/2008 |
| JP | 2008516303 A | 5/2008 |
| JP | 2008216057 A | 9/2008 |
| JP | 2011028765 A | 2/2011 |
| JP | 2016035699 A | 3/2016 |
| WO | WO-9718639 A1 | 5/1997 |
| WO | WO-03094074 A1 | 11/2003 |
| WO | WO-2004027676 A2 | 4/2004 |
| WO | WO-2004084720 A2 | 10/2004 |
| WO | WO-2005041131 A2 | 5/2005 |
| WO | WO-2006109072 A2 | 10/2006 |
| WO | WO-2008057951 A2 | 5/2008 |
| WO | WO-2008057952 A2 | 5/2008 |
| WO | 2008157701 A2 | 12/2008 |
| WO | WO-2010040092 A1 | 4/2010 |
| WO | WO-2011021118 A1 | 2/2011 |
| WO | WO-2011124993 A2 | 10/2011 |
| WO | WO-2012108935 A1 | 8/2012 |
| WO | WO-2012108936 A1 | 8/2012 |
| WO | WO-2012108939 A1 | 8/2012 |
| WO | WO-2012108940 A1 | 8/2012 |
| WO | WO-2013019225 A1 | 2/2013 |
| WO | WO-2014105631 A2 | 7/2014 |

OTHER PUBLICATIONS

American Diabetes Association, "Position Statement: Standards of Medical Care in Diabetes," Diabetes Care, vol. 32, Supplement 01, Jan. 2009, pp. S13-S61.

Anonymous, "Near Field Communication—Wikipedia, The Free Encyclopedia," Retrieved from https://en.wikipedia.org/w/index.php?title=Near_field_communication%20oldid=543740757, Jun. 27, 2014, 15 pages.

Dassau et al., "Enhanced 911/Global Position System Wizard: A Telemedicine Application for the Prevention of Sever Hypoglycemia-M," Journal of Diabetes, vol. 3(6), 2009, pp. 1501-1506.

Extended European Search Report for Application No. 16882308.6 dated Jul. 23, 2019, 07 pages.

Extended European Search Report for Application No. 18175412.8 dated Oct. 17, 2018, 11 pages.

File History of European Application No. 14708172.3 filed on Jun. 16, 2015, including Opposition documents for Patent No. 2973082 (Appl. No. EP14708172.3), 1179 pages.

Garg S., et al. "Improvement in Glycemic Excursions with a Transcutaneous, Real-Time Continuous Glucose Sensor: A Randomized Controlled Trial," Diabetes Care, vol. 29(1), 2006, pp. 44-50.

Garg S.K., et al., "Improved Glucose Excursions Using an Implantable Real-Time Continuous Glucose Sensor in Adults With Type 1 Diabetes," Emerging Treatments and Technologies, Diabetes Care, vol. 27 (3), 2004, pp. 734-738.

Hirsch, Irl B., et al., "Should Minimal Blood Glucose Variability Become the Gold Standard of Glycemic Control?," Journal of Diabetes and Its Complications 19, 2005, pp. 178-181.

International Preliminary Reporton Patentability for Application No. PCT/US2013/076544 dated Jul. 9, 2015, 12 pages.

International Preliminary Reporton Patentability for Application No. PCT/US2014/016111 dated Sep. 24, 2015, 10 pages.

International Preliminary Reporton Patentability for Application No. PCT/US2016/066399 dated Jul. 12, 2018, 14 pages.

International Search Report and Written Opinion for Application No. PCT/US2013/076544 dated Oct. 14, 2014, 16 pages.

International Search Report and Written Opinion for Application No. PCT/US2014/016111 dated Dec. 22, 2014, 13 pages.

International Search Report and Written Opinion for Application No. PCT/US2016/066399 dated Mar. 30, 2017, 15 pages.

Kovatchev, et al., "Algorithmic Evaluation of Metabolic Control and Risk of Sever Hypoglycemia in Type 1 and Type 2 Diabetes

(56) References Cited

OTHER PUBLICATIONS

Using Self-Monitoring Blood Glucose Data", 2003, Diabetes Technology & Therapeutics, vol. 5(5), pp. 817-828.
Marling et al., "Characterizing Blood Glucose Variability Using New Metrics with Continuous Glucose Monitoring", Journal of Diabetes Science & Technology, vol. 5(4), Jul. 2011, 871-878.
Mirano Systems Inc, "Green Receipt," Retrieved from https://web.archive.org/web/20121224003730/http://mirano.ca/, 2012, 1 page.
NFC Forum, "NFC Data Exchange Format (NDEF)," NFCForum-TS-NDEF 1.0, Technical Specification, NFC Forum™, NDEF 1.0, Jul. 24, 2006, 25 pages.
NFCForum, NFCForum-TS-DigitalProtocol-1.0, 2010; 194 pages.
Office Action from Australian Patent Application No. 2019257401, dated Jun. 24, 2020, 7 pages.
Penckofer et al., "Does Glycemic Variability Impact Mood and Quality of Life?", Diabetes Technology & Therapeutics, 2012,vol. 14(4), pp. 303-310.
Wikipedia, "Near-Field Communication," downloaded from https://en.wikipedia.org/wiki/Near-field_commucation on Jan. 3, 2019, pp. 1-14.
Wiley et al., "Automatic Detection of Excessive Glycemic Variability for Diabetes Management", 10th International Conference on Machine Learning and Applications, IEEE Computer Society, 2011, pp. 148-154.
Office Action for Chinese Application No. 201810549393.X, dated Sep. 2, 2020, 11 pages.
Office Action for Canadian Application No. 2,886,791, dated Nov. 4, 2020, 4 pages.
Office Action for Chinese Application No. 201810548292.0, dated Sep. 22, 2020, 35 pages.
Office Action from Japanese Patent Application No. 2019-211605, dated Nov. 9, 2020, 10 pages.
Examination Report No. 2 from Australian Patent Application No. 2019200545, dated Jan. 14, 2021, 4 pages.
Office Action for Canadian Application No. 3002096, dated Jan. 27, 2021, 3 pages.
Office Action for Australian Application No. 2019200545, dated Feb. 16, 2021, 3 pages.
Office Action from European Patent Application No. 13821308.7, dated Feb. 3, 2021, 11 pages.
Office Action from Australian Patent Application No. 2019257401, dated May 4, 2021, 3 pages.
Response to the first office action for Chinese Application No. 201810548292.0, dated Feb. 8, 2021, 19 pages.

* cited by examiner

SYSTEMS AND METHODS FOR REMOTE AND HOST MONITORING COMMUNICATIONS

CROSS-REFERENCE TO RELATED APPLICATIONS

Any and all priority claims identified in the Application Data Sheet, or any correction thereto, are hereby incorporated by reference under 37 C.F.R. § 1.57. This application is a continuation of U.S. application Ser. No. 15/377,216, filed Dec. 13, 2016, which claims the benefit of U.S. Provisional Application No. 62/271,840, filed Dec. 28, 2015. Each of the aforementioned applications is incorporated by reference herein in its entirety, and each is hereby expressly made a part of this specification.

BACKGROUND

Field

The present application relates generally to remote monitoring, and more specifically to systems and methods for remote and host monitoring communication.

Description of the Related Art

Analyte monitors can be configured to mount on tissue to detect analytes in a sensing area. For example, analyte monitors can include sensors that measure the concentration of glucose, lactate, cholesterol, hemoglobin, and/or other blood or bodily fluid constituents.

In some cases, persons with diabetes mellitus (also known as diabetes) can use an analyte monitor. Diabetes is a disorder in which the pancreas of a person may not create sufficient insulin, such as in the case of Type I diabetes, and/or in which insulin may not be effective for a person, such as is in the case of Type II diabetes. In a diabetic state, the patient can suffer from high blood sugar, which can cause an array of physiological derangements, such as kidney failure, skin ulcers, or bleeding into the vitreous of the eye, which can be associated with the deterioration of small blood vessels. A hypoglycemic reaction, such as low blood sugar, can be induced by an inadvertent overdose of insulin, or after a normal dose of insulin or glucose-lowering agent accompanied by extraordinary exercise or insufficient food intake.

A diabetic can carry an analyte monitor such as a self-monitoring blood glucose ("SMBG") monitor, which typically requires uncomfortable finger pricking methods. Due to the lack of comfort and convenience, a diabetic typically measures his or her glucose level only two to four times per day. Unfortunately, these time intervals can be spread so far apart that the diabetic would likely find out too late that he/she has a hyperglycemic or hypoglycemic condition, which can sometimes cause dangerous side effects. In fact, it is not only unlikely that a diabetic would take a timely SMBG value, but additionally, the diabetic would likely not know if his/her blood glucose value is rising or falling based on conventional methods.

Consequently, a variety of non-invasive, transdermal (e.g., transcutaneous) and/or implantable electrochemical sensors have been and are being developed for detecting and/or quantifying glucose values from such sensor measurements having accuracy corresponding to direct blood glucose measurements. These, as well as other types of devices, generally transmit raw or processed data to remote devices, which can include a display, to allow presentation of information to a user hosting the sensor. For example, the DEXCOM G4® PLATINUM SYSTEM WITH SHARE™ continuous glucose monitoring ("CGM") system and the DEXCOM G5™ Mobile CGM system available from DEXCOM, INC. are continuous glucose monitoring systems that can allow a user to monitor glucose levels. Some systems and methods that relate to CGM are described in U.S. Publication No. 2014/0184422 to Mensinger et al., which is incorporated herein by reference.

SUMMARY

Example implementations described herein have innovative features, no single one of which is indispensable or solely responsible for their desirable attributes. Without limiting the scope of the claims, some of the advantageous features will now be summarized.

Disclosed are techniques, systems, and devices for providing enhanced engagement and remote monitoring experience for a Remote Monitor or group of Remote Monitors with a Host or Hosts and/or other Remote Monitor(s). In some implementations, the disclosed techniques, systems, and devices provide intelligent alerting and/or actionable information to Remote Monitor(s). In some implementations, one or more remote monitoring devices and host monitoring devices can be configured (e.g., through hardware and/or software) to communicate with one another. Each remote monitoring device can receive data indicative at least in part of an analyte state (e.g., glucose level) of Host(s) as well as other desired information. Host may be using a host monitoring device of an analyte sensor system (e.g., a continuous glucose monitoring system). In some cases, a remote monitoring device can communicate with a host monitoring device or a server that stores the data of the Host (e.g., analyte data and other data as described herein).

In some implementations, remote monitoring devices can receive and/or display communications with data that may be cumulative with data collected by a host monitoring device. In some implementations, remote monitoring devices and/or host monitoring devices can present data to contextualize the analyte state of Host(s). Such data can be used at least in part to further understand the reasons for measurements and also to perform pattern recognition and/or predictive calculations. In some implementations, remote monitoring devices and/or host monitoring devices can transmit data about Remote Monitor(s) (e.g., Remote Monitor's level of stress or worry, heart rate, blood pressure, overall condition, etc.) or transmit Remote Monitor-observed data about Host or transmit Remote Monitor-observed data that affects Host (e.g., observed mood, current weather, amount of homework, etc.) to contextualize at least in part the analyte state of the host.

In some implementations, remote monitoring devices and/or host monitoring devices can classify Remote Monitors. These classifications can have associated notification settings (e.g., predetermined default settings or user determined settings) based at least in part on the needs of the host and/or Remote Monitor.

In some implementations, remote monitoring devices and/or host monitoring devices can provide intelligent communications representative at least in part of an event associated with the analyte state of the host. For example, when an event is triggered, the event can cause a communication (e.g., alert, notification, message, or other communication) to be sent to one or more remote monitoring devices to inform the remote monitoring devices of the event.

In some implementations, a remote monitoring device and/or host monitoring device can autonomously manage the communications between themselves based at least in part on treatment information provided by the host (e.g., whether the host has already administered medicaments). In other embodiments, the communications between remote monitoring devices and/or host monitoring devices may be triggered based on predetermined rule settings.

In some embodiments, a method for remote monitoring of a subject's health data by authorized monitors includes receiving, at a secure server, data associated with an analyte state of a host that is provided by a host device operable to receive sensor data generated by a continuous analyte sensor worn by the host, in which one or more remote monitoring devices are authorized by the secure server to access permissible data of the received data stored on the secure server based on a set of permissions pre-selected and modifiable by the host for each remote monitoring device, in which the permissions are associated with what data is available to a remote monitoring device once authorized; generating, at the server, a plurality of classifications including a first classification and a second classification of the remote monitoring devices authorized to access permissible data, in which a classification of the remote monitoring devices designates a hierarchy to provide communications based on notifications rules to inform an authorized remote monitoring device about the host's analyte state; and assigning, at the server, each of the remote monitoring devices to one of the plurality of classifications, in which the second classification includes one or both of (i) greater restrictions to the permissible data than that of the first classification, and (ii) more restrictive notification rules than the first classification.

In some embodiments, a method for remote monitoring of a subject's health data by authorized monitors includes receiving, at a secure server, data associated with an analyte state of a host that is provided by a host device operable to receive sensor data generated by a continuous analyte sensor worn by the host, in which a plurality of remote monitoring devices are authorized by the secure server to access permissible data of the received data stored on the secure server based on a set of permissions pre-selected and modifiable by the host for each remote monitoring device, in which the permissions are associated with what data is available to a remote monitoring device once authorized; providing, by the server, an alert informative of an event associated with the analyte state of the host to selected remote monitoring devices based on notification rules that define circumstances to send the alert to a respective remote monitoring device, in which the notification rules are modifiable by the authorized remote monitoring devices within a scope of the set of permissions to the data associated with the respective remote monitoring device; receiving, at the server, a response from one or more of the selected remote monitoring device; and processing, by the server, the received response to determine the ability or inability of the selected remote monitoring device corresponding to the received response to react to the alert.

In some embodiments, a method for remote monitoring of a subject's health data by authorized monitors includes receiving, at a secure server, data associated with an analyte state of a host that is provided by a host device operable to receive sensor data generated by a continuous analyte sensor worn by the host, in which a plurality of host-designated remote monitoring devices are authorized by the secure server to access permissible data of the received data stored on the secure server based on a set of permissions pre-selected and modifiable by the host for each host-designated remote monitoring device, in which the permissions are associated with what data is available to a remote monitoring device once authorized; receiving, by the server, location information of the host-designated remote monitoring devices and the host device; determining, by the server, the ability or inability of each of the host-designated selected remote monitoring devices to react to an alert informative of a dangerous event associated with the analyte state of the host based on a proximity of a host-designated selected remote monitoring device to the host device within a predetermined distance; upon the determining the inability of all of the host-designated selected remote monitoring devices to react to an alert, assigning, by the server, a universal remote monitoring device not among the host-designated selected remote monitoring devices, in which the assigning includes generating a set of notifications rules pertaining to circumstances to send a message to the universal remote monitoring device informative of the dangerous event associated with the analyte state of the host.

In some embodiments, a method for remote monitoring of a subject's health data by authorized monitors includes receiving, at a secure server, data associated with an analyte state of a host that is provided by a host device operable to receive sensor data generated by a continuous analyte sensor worn by the host, in which one or more remote monitoring devices are authorized by the secure server to access permissible data of the received data stored on the secure server based on a set of permissions pre-selected and modifiable by the host for each remote monitoring device, in which the permissions are associated with what data is available to a remote monitoring device once authorized, and in which the one or more remote monitoring devices are assigned notification rules that define circumstances to send a message to a respective remote monitoring device informative of an event associated with the analyte state of the host, in which the notification rules are modifiable by the authorized remote monitoring devices within a scope of the set of permissions to the data associated with the respective remote monitoring device; processing, by the server, an alert informative of a dangerous event associated with the analyte state of the host, in which the processed alert is within a set of notification rules associated with at least one of the authorized remote monitoring devices; receiving, by the server, an instruction to suppress sending the message associated with the alert to the at least one of the authorized remote monitoring devices; and suppressing, by the server, the sending of the message to the at least one of the authorized remote monitoring devices.

In some embodiments of the present technology, a method for remote monitoring of a subject's health data by authorized monitors includes receiving, at a secure server, data associated with an analyte state of a host that is provided by a host device operable to receive sensor data generated by a continuous analyte sensor worn by the host, in which one or more remote monitoring devices are authorized by the secure server to access permissible data of the received data stored on the secure server based on a set of permissions pre-selected and modifiable by the host for each remote monitoring device, in which the permissions are associated with what data is available to a remote monitoring device once authorized; providing, by the server, a notification informative of an event associated with the analyte state of the host to selected remote monitoring devices based on notification rules that define circumstances to send the notification to a respective remote monitoring device, in which the notification rules are modifiable by the authorized remote monitoring devices within a scope of the set of permissions to the data associated with the respective remote monitoring device; and providing, by the server, contextual information with the notification, the contextual information including a time, an amount, and/or a type of (i) a medicament taken by the host, (ii) a food or drink ingested by the host, (iii) an exercise or activity undertaken by the host, (iv) a level of stress experienced by the host, or (v) an environmental condition experienced by the host, or a combination of (i)-(vi) thereof.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

Figure 1A:
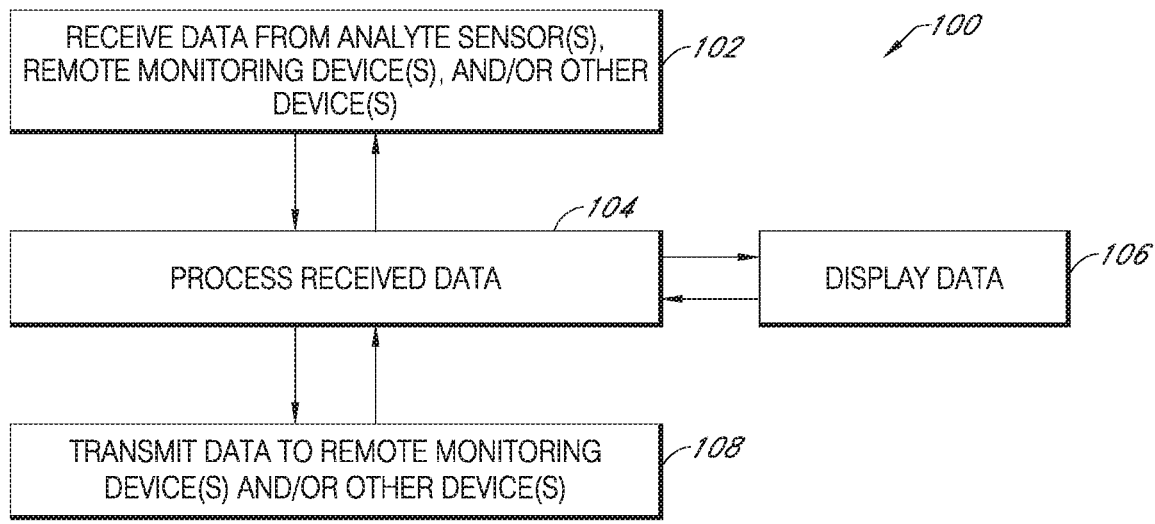
FIGS. 1A and 1B illustrate flow charts describing example processes where a host monitoring device and a remote monitoring device receive, process, and transmit data, respectively.

Various aspects of the systems, apparatuses, and methods disclosed herein are described more fully hereinafter with reference to the accompanying drawings. This disclosure can, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein, one skilled in the art should appreciate that the scope of the disclosure is intended to cover any aspect of the systems, apparatuses, and methods disclosed herein, whether implemented independently of, or combined with, any other aspect of the disclosure. For example, an apparatus can be implemented or a method can be practiced using any number of the aspects set forth herein. In addition, the scope of the disclosure is intended to cover such an apparatus or method that is practiced using other structure, functionality, or structure and functionality in addition to or other than the various aspects of the disclosure set forth herein. It should be understood that any aspect disclosed herein can be implemented by one or more elements of a claim.

Although particular aspects are described herein, many variations and permutations of these aspects fall within the scope of the disclosure. Although some benefits and advantages of the preferred aspects are mentioned, the scope of the disclosure is not intended to be limited to particular benefits, uses, and/or objectives. The detailed description and drawings are merely illustrative of the disclosure rather than limiting, the scope of the disclosure being defined by the appended claims and equivalents thereof.

Data from sensor devices, such as analyte monitors like CGM, can provide desirable information to caregivers, clinicians, and/or others who care about a diabetic person or individual monitoring characteristics of a health-related condition, which is sometimes referred to in this specification as the "Host." Typically, a Host monitors such characteristics using a host monitoring device, also referred to as a "host device," such as a computing device including a smartphone or the like as part of a larger monitoring system, such as an analyte monitoring system (e.g., CGM). However, many existing analyte monitoring systems presently suffer from constricting limitations on the amount and types of information and engagement shared between a Host and other individuals or groups that can remotely monitor characteristics of the Host, which are referred to in this specification as "Remote Monitors." Remote Monitors remotely monitor the characteristics of the Host using a remote monitoring device, such as a computing device including a smartphone having a software application operating thereon to provide the remote monitoring functionality for the remote monitor user.

In one example, a continuous analyte monitoring system of the Host can include one or more body-worn medical devices that can each generate data and provide the data to a mobile electronics device, such as a smartphone, tablet, smartwatch, or other wearable and/or mobile computing device. A smartphone is used in the following example and other examples described. The smartphone can include a dedicated application that configures the smartphone to receive and process the data provided (e.g., wirelessly transmitted) by the body-worn medical device(s). For example, the data provided by the body-worn medical device(s) can include glucose measurements, insulin delivery amounts, diagnostic information about the medical devices and timestamps associated with each. The smartphone, using the dedicated application, can then perform various functions based on the received data, such as generate charts and user perceptible-alarms using the data. Similarly, for example, the smartphone, using the dedicated application, can receive formatted or partially formatted data to produce charts, alarms, and other features based on the acquired data of the continuous analyte sensor device. The smartphone, using the dedicated application, may also receive and generate other data, such as data from a user of the smartphone (e.g., user identifying information), user interactions with the dedicated application, dedicated application diagnostic information, and the like. In some embodiments of the present technology, the continuous analyte monitoring system may include a suite of dedicated applications operable on one or more computing devices of the Host and on one or more computing devices of Remote Monitors to monitor the Host's analyte state and/or manage access to the Host's data acquired by the medical device(s).

As engaging platforms expand and incorporate a plurality of Remote Monitors, additional challenges arise. Present technology does not provide the desired communication channels and/or functionality to accommodate sophisticated networks of people (e.g., groups of Host(s) and/or Remote Monitor(s)). For example, different Remote Monitor(s) can have different roles and responsibilities as to Host(s) and, consequently, desire different information and/or privileges as to Host's health data (e.g., including analyte data) and sensor device(s) (e.g., including an analyte monitor, such as CGM). Remote Monitor(s) for the same Host can also desire to communicate with each other regarding the Host and/or each other.

Moreover, while alerts about Host's glucose concentration in some current technologies can inform Remote Monitor(s) of a concerning event about the Host's condition, some minimally informative alerts can cause increased stress and worry by the Remote Monitor(s) that is detrimental to both Remote Monitor(s) and the Host alike, or worse, these alerts may affect the chances of latent action or inaction by the Remote Monitor(s) that might have otherwise been different had the Remote Monitor(s) received more comprehensive and contextual information. For example, Remote Monitor(s) can desire only certain kinds and amounts of information and become irritated by too many or too few kinds and/or too much or too little amounts of information. Too much information, for some Remote Monitor(s), may cause certain desirable information to get lost or ignored. Too little information can cause Remote Monitor(s) not to receive desired information or distrust the integrity of communication systems and/or monitoring systems. As a result, many existing analyte monitoring systems fail to create an engaging platform that enable and/or encourage efficient, communicative interactions between Host(s) and Remote Monitor(s) that can enhance the role of Remote Monitor(s) in a Host's health management while reducing interruptions and/or interferences in that Host's life. These current technologies also do not provide the desired level of communication customizability and/or management to accommodate expanded networks of Host(s) and/or Remote Monitor(s). Accordingly, there is a need for improved systems and methods for remote and host monitoring communication.

Additionally, many conventional monitoring systems can be burdened by large amounts of communication traffic (e.g., between host monitoring devices, remote monitoring devices, and/or servers) across their networks. In some cases, these networks can become overloaded with untimely and/or unwanted communications that drain network resources. In some cases, such drains can slow down the networks, cause network failures, and/or increase the cost of running the networks. Accordingly, there is a need for improved communications that effectively utilize network resources. For example, by selectively and/or contextually transmitting communications, as will be described in this disclosure, monitoring systems can reduce the number of transmissions and/or utilize network resources where they are effective and/or desired. In some implementations, contextual communications may include slightly larger datasizes per transmission, but can also reduce the number of transmissions that may otherwise bog down networks.

In some cases, selective and/or contextual communications that focus on relevant data can enhance processing at remote and/or host monitoring devices. Such communications can also facilitate display of and/or user interaction with communications. For example, by reducing the number of communications to a remote monitoring device, the remote monitoring device can have fewer items to process, and can thereby utilize its resources more effectively, and sometimes more quickly. Furthermore, with fewer items to display, remote monitoring devices and/or host monitoring devices can more effectively engage users by not over-stimulating them with notifications, alerts, and/or other displays.

Moreover, many conventional monitoring systems are no more than passive displays of Host's present and/or historical health measurements. Therefore, it would be beneficial to provide Hosts, and/or those who interact and/or care for Hosts (e.g., Remote Monitors), useful information that can facilitate Host care. For example, as will be described herein, methods that can recognize patterns in Hosts' behavior (and/or the behavior of those who impact Host, such as Remote Monitors) can allow for enhanced care of Host by giving context to Host's health measurements, such as Host's estimated glucose levels. In some cases, predictive calculations can further help Hosts, Remote Monitors, and/or other users understand and anticipate changes in Hosts' health.

In some cases, as networks of host monitoring devices and/or remote monitoring devices become larger, it can become difficult to organize the data and/or communications between them in a way that is administrable. As a result, many conventional monitoring systems are not user-friendly, and/or provide copious amounts of data without a workable operative framework. Accordingly, there is a need for ways to organize communications and/or data from host monitoring devices and/or remote monitoring devices. For example, as will be described in this disclosure, classifications, interfaces, data logs, discussion logs, and/or other structures can assist in organizing data in a framework that can be controlled, segmented, and/or searched.

In some cases, it can be difficult for a Host to observe and/or monitor certain characteristics of him/herself. Such characteristics may not be readily observable by the Host's perception, and/or may be continuously changing and/or too difficult (and/or onerous) to repeatedly observe. In some cases, a Host may be under the care of others due to health conditions, age, competency, convenience, and/or other reasons. These Caretakers may desire to be able to observe and/or monitor characteristics of the Host.

Implementations described herein can include systems and methods for one or more Remote Monitors to remotely monitor characteristics (e.g., health characteristics) of one or more Hosts. Hosts can include any entity whose one or more characteristics (e.g., a health characteristic) can be measured using a sensing device, for example, an analyte monitor, like a continuous glucose monitor. These Hosts can include, children (e.g., babies, infants, toddlers, and/or small children), teenagers, young adults, adults, middle-aged person, elderly, and/or any other person. In some cases, Hosts can also include non-humans, such as pets, animals, organics, experimental environments (electronic or physical), and/or any system in which measuring an analyte state is desirable. Hosts can be identified (e.g., by name, username, identification number, nickname, etc.) or anonymous with respect to Remote Monitors.

Embodiments in accordance with aspects of the disclosed remote monitoring technology are perceived to improve operations of the systems and devices that implement the remote monitoring technology, for example, by reducing complexities in data processing and data transmissions between devices, reducing the amount of data and processing algorithms to be stored and operated, and thereby speeding up the performance of the systems as described herein. Moreover, implementations in accordance with such aspects of the present technology are envisioned to improve the ability of users to manage their diabetes or other disorders with continuous analyte monitoring.

Remote Monitors can include any entity that can remotely monitor on its devices characteristics of a Host measured by Host device(s). Remote Monitors can include any of the aforementioned example entities described with respect to Hosts. Remote Monitors can also include electronic systems configured to monitor a person's health, such as hospital computer systems, medical databases, hospital beds, medical robots, personal health monitors, automated health systems, and the like. Remote Monitors can also be Hosts, where Remote Monitors themselves have host monitoring devices which can measure their characteristics using an analyte monitor, such as a CGM.

Generally, Remote Monitors can have a particular role with respect to a Host. For example, Remote Monitors can include Caretakers of the Host, such as parents, spouses, relatives, guardians, significant others, teachers, health practitioners, etc. These Caretakers can take certain responsibilities in the health and well-being of monitored Hosts. In some cases, Caretakers can be those who actively take care of the Host and assist the Host when the Host is in need. As another non-limiting example, Remote Monitors can include Social Associates of Host(s), including friends, acquaintances, persons in the same social network, persons in the same geographic area, and/or persons connected by one or more degrees of separation from any of the aforementioned Social Associates. These Social Associates may have some interest in the activities and/or health characteristics of a Host, but ultimately may not take on the kinds of responsibilities a Caretaker might. As another non-limiting example, Remote Monitors can also be Strangers and otherwise personally unknown to a particular Host. Such Strangers could include emergency healthcare professionals, concerned citizens, researchers, and/or others who may desire to learn about and/or assist Hosts, even those who could be personally unknown to them. As another non-limiting example, Remote Monitors can include Watchers of Host(s). In a non-limiting example, Watchers can include any interested person temporarily watching a Host in the same or similar manner as a Caretaker, but may not be a Caretaker. Watchers can be contextual (e.g., based at least in part on proximity and/or activity), such as co-workers, other students, teachers, school program operators, administrators, friends, etc. As another non-limiting example, Assigned Remote Monitors can include any one assigned, for whatever reason, to be a Remote Monitor of a Host. As another non-limiting example, Universal Remote Monitors can be persons who provide assistance when there are no other Remote Monitors available or other Remote Monitors are too far to assist in a timely manner. These can be concerned citizens and/or any persons who desire to be of assistance.

For example, when the analyte state of a host drops to a dangerous level or other health issues arise and no designated Remote Monitor are in close proximity to provide assistance, the host remote monitoring device can emit a beacon to devices in the vicinity of Host, which may be capable of receiving the beacon. The beacon can be transmitted via a Bluetooth or other wireless signal as described herein. In addition or alternatively, the beacon can be transmitted by a server or other computing device using a cloud-based system with GPS coordinates. In some embodiments, the cloud-based system can map a distance radius around the GPS coordinates of the Host to determine proximity of devices and presumably owners of those devices who may be in a position to assist the Host. Individuals receiving this beacon on their respective receiver devices can receive an alert that someone physically close to them may need urgent assistance. A map of the area can be provided to the receivers identifying the location of the individual in need of assistance. For example, if the receiver device is a smart-glasses device, a heads-up-display (HUD), or other smart device, an augmented reality may be presented to the individual receiver to assist them in locating the patient in need of help. The receiver individual can scan the horizon with their augmented reality display and see a virtual identifier at or near the location of the person in need of assistance. For example, a red blinking dot can be displayed in the augmented reality through a HUD.

In some environments, individuals near or around a Host may not know how to assist an unresponsive diabetic patient. For example, in an airplane, the flight attendants may lack the training to assist a diabetic patient generally or may lack the data to assist a diabetic individual in need. In one embodiment, passive monitoring of wireless signals (e.g., Bluetooth or other wireless communication as described herein) can be implemented to listen for emergency calls. A CGM system can send a special Bluetooth (or other wireless communication) call in case of a health emergency (e.g., low glucose value). The passive monitoring system can alert the individuals nearby (e.g., flight attendants) and provide them with data and information to handle the emergency.

In some cases, Universal Remote Monitors can also be designated Remote Monitors who are qualified people to treat diabetic conditions, and/or any other conditions relevant to the Host and/or Universal Remote Monitor. As will be described in this disclosure, in some cases, Hosts and/or Remote Monitors can classify Remote Monitors based on the Remote Monitors' roles. Such classifications (also called classes) can be used to define the Remote Monitor's rights, privileges, and/or frequency of communication with Hosts and with other Remote Monitors.

In some cases, it can be desirable for a Host to be able to transmit data (e.g., raw and/or processed) to one or more Remote Monitor(s) based on data measured by an analyte sensor and/or other devices of the Host and/or Remote Monitor. Advantageously, transmitting such information can allow a level of communication and/or coordination that may not be achievable in present systems.

As used throughout this disclosure, normal glucose levels can be determined for each individual by consultation with his/her doctor or otherwise, and can be dependent on factors such as whether the individual has eaten or not, the individual's activity, and/or the time of day. By way of illustrative example, typical glucose levels of a healthy adult can be between 72 mg/dL and 108 mg/dL (4 to 6 mmol/L). The normal concentration of glucose in the blood of an adult in the morning on an empty stomach can be between 68 mg/dL and 108 mg/dL (3.8 and 6.0 mmol/L). Two hours after consuming foods or drinks rich in carbohydrates, the normal concentration of glucose in the blood of a healthy adult can be between 120 and 140 mg/dL (6.7 and 7.8 mmol/L). For children up to 6 years of age, normal glucose levels before eating can be between 100 mg/dL (5.5 mmol/L) and 180 mg/dL (10 mmol/L). Before sleep, normal glucose concentration can be between 110 mg/dL (6.1 mmol/L) and 200 mg/dL (11.1 mmol/L). For children between the age of 6 and 12, before eating, normal glucose concentration can be between 90 mg/dL (5 mmol/L) and 180 mg/dL (10 mmol/L). Before sleep, normal glucose concentration can be between 100 mg/dL (5.5 mmol/L) and 180 mg/dL (10 mmol/L).

As used herein, remote monitoring devices can be devices used by Remote Monitors to remotely monitor characteristics of a Host. Throughout this disclosure, reference will be made to the functionality and/or structure of remote monitoring devices. Such functionality and/or structure can be instantiated in hardware and/or software. For example, such functionality and structure can represent physical hardware that is hardcoded to perform such functionality. As another example, remote monitoring devices can run software that performs such functionality and/or has such structure. In some implementations, such software can run computer-implemented methods to create functionality. In some cases, remote monitoring devices can run a software application, such as a mobile application, also referred to as an "app," (e.g., a mobile application downloaded from an entity that created and/or owns and/or licenses the app, and/or an app store such as from APPLE, INC. or GOOGLE INC., or other), that performs the functionality and/or has the structure described.

Similarly, as used herein, host monitoring devices are devices used by Hosts to monitor characteristics of the Host. Throughout this disclosure, reference will be made to the functionality and/or structure of host monitoring devices. Such functionality and/or structure can be instantiated in hardware and/or software. For example, such functionality and structure can represent physical hardware that is hardcoded to perform such functionality. As another example, host monitoring devices can run software that performs such functionality and/or has such structure. In some implementations, such software can run computer-implemented methods to create functionality. In some cases, host monitoring devices can run a software application, such as a mobile application (e.g., a mobile application downloaded from an entity that created and/or owns and/or licenses the app, and/or an app store such as from APPLE, INC. or GOOGLE INC., or other), that performs the functionality and/or has the structure described.

Figure 1B:
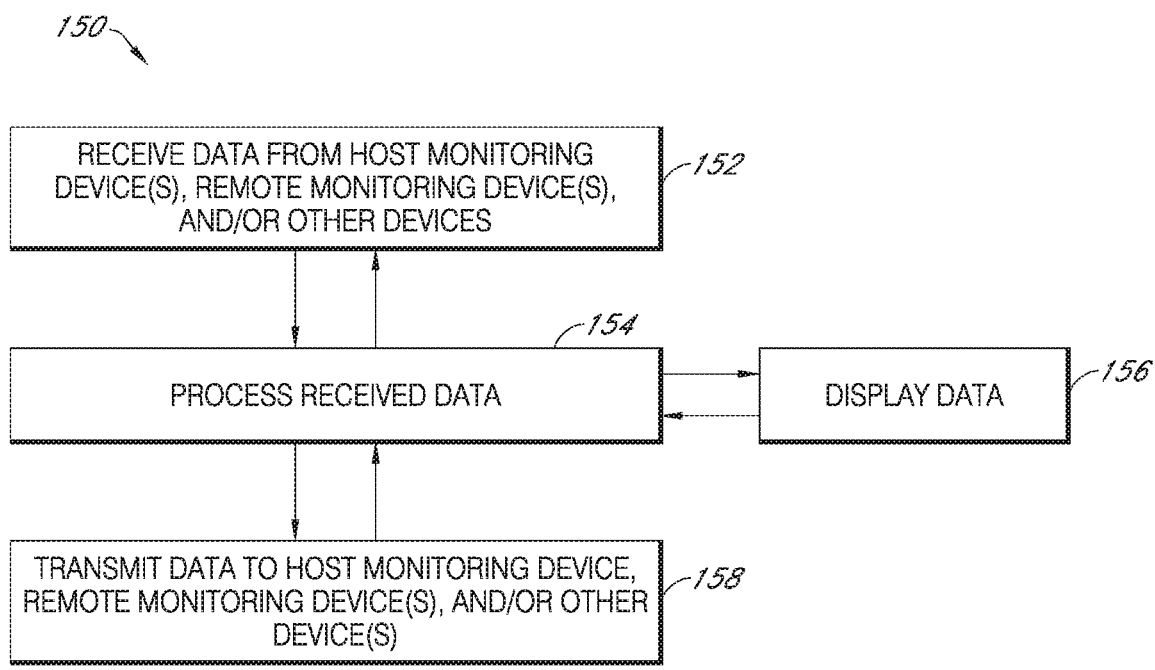

FIGS. 1A-B illustrate flow charts describing example processes where a host monitoring device and a remote monitoring device receive, process, and/or transmit data, respectively. In some implementations, the processes (e.g., Processes 100, 150) described with respect to a host monitoring device and/or a remote monitoring device can be performed by a server (e.g., a secure server) in communication with one or both of the host monitoring device and remote monitoring device.

FIG. 1A illustrates example Process 100 where a host monitoring device and/or server can receive, process, and/or transmit data, e.g., information, symbols, measurements, communications, and/or any data described in this disclosure. In some cases, a host monitoring device substantially similar to Host Monitoring Device 200 (FIG. 2) and/or any host monitoring devices described in this disclosure can perform Process 100. In some embodiments, Process 100 can be performed by a server (e.g., Secure Server 504), in the alternative or in addition to a host monitoring device. In some embodiments of Block 102, the host monitoring device can receive data from analyte sensor(s), remote monitoring device(s), and/or other device(s). In some embodiments of Block 102, the server can receive data from a transmitter unit of the analyte sensor device(s), the host monitoring device (e.g., smartphone of Host, which may initially receive the data from the analyte sensor device(s)), the remote monitoring device(s), and/or other device(s). By way of illustrative example, the analyte sensors can be part of a CGM that measures a Host's glucose levels (e.g., an estimated glucose value ("EGV")). The analyte sensor can be a component of a host monitoring device, or a separate component that is not a component of a host monitoring device. Advantageously, a CGM can allow a Host to measure the glucose concentration of his/her blood. In some cases, the CGM can transmit data to a secure server.

Data received in Block 102 can include communications from sensor(s), remote monitoring device(s), and/or other devices. Such communications can include notifications, alerts, alarms, messages, and/or any other sort of communication desirable. Data can be received through wired and/or wireless connections. By way of illustrative example, a processor can receive data through wired and/or wireless connections. For example, wireless connections can include a transmission protocol such as Bluetooth, ZigBee, Wi-Fi, induction wireless data transmission, radio frequencies, radio-frequency identification ("RFID"), near-field communication ("NFC"), global system for mobile communications ("GSM"), infrared, and/or any other form of wireless data transmission. Wired connections can include any wire with a signal line. For example, such wires with signal lines can include cables, such as Ethernet cables, coaxial cables, Universal Serial Bus ("USB"), firewire, datalines, wire, and/or any wired connection known in the art. Wired and/or wireless connections can also include combinations of any of the aforementioned. Such wired and/or wireless connections can be received by a receiver and/or a transceiver. For example, a host monitoring device can have a receiver and/or transceiver. As another non-limiting example, a server (e.g., secure server) can have a receiver and/or transceiver.

However, in some cases, more information than just an analyte measurement may be desirable. For example, in the case of measuring glucose levels, many current technologies do not put such glucose measurements into a contextual framework that allows for greater analysis. Advantageously, having such an analysis can reveal more about a Host's conditions, treatments, and responses that can allow for improved response predictions and enhanced therapies. The received information in Block 102 can include Contextual Data relevant to the Host, such as data from remote monitoring device(s) and/or other devices.

Contextual data can be provided with alarms or notifications to Hosts and/or Remote Monitors. For example, as described herein, a server can relay or generate a notifications based on notification rules that define circumstances under which notifications are sent to remote monitoring devices. The notification can include information, data or circumstances associated with the analyte state of Host. The server can provide the notifications with the contextual information. The server can also provide notifications to Host along with contextual data about one or more Remote Monitors.

In the case of a diabetic host, received data can include Contextual Data such as data and/or information that may be associated with "why" a measured analyte, such as glucose levels, occurs and/or behaves as it does (e.g., why the glucose levels are, or are trending, in a certain way). Such received information can be measured by the aforementioned analyte sensor(s), measured by other devices internal or external to the Host, manually inputted by the Host, received by remote monitoring device(s), or otherwise inputted into the host monitoring device. Contextual Data can also be inputted by a Remote Monitor on a remote monitoring device and/or host monitoring device. For example, Contextual Data can include data inputted by Remote Monitor(s) about a Host. In addition to being able to be received by Remote Monitor(s), Contextual Data can also be about the Remote Monitor(s). Contextual Data can also include information about the Remote Monitor(s) that can be indicative of the health, awareness, availability, etc. of Remote Monitor(s) to assist a Host.

In some implementations, this Contextual Data can include, (i) time/amount/type of medicament taken (e.g., insulin, sulfonylureas, biguanids, meglitinides, thiazolidinediones, DPP-4 inhibitors, SGLT2 inhibitors, alpha-glucosidase inhibitors, bile acid sequestrants, and/or other drugs or treatments), (ii) time/amount/type of food ingested (e.g., carbohydrates, protein, dairy, fat, fruits, vegetables, candy, dessert, sugars, calories, quantities, preparations, etc.), (iii) time/amount/type of exercise or physical activity undertaken (e.g., engaging in sports, running, walking, swimming, skiing, snowboarding, skateboarding, biking, weight lifting, sitting, sleeping, being idle, resting, etc.), (iv) level of stress felt (e.g., acute, episodic acute, emotional, chronic, high stress, medium stress, low stress, no stress, anxiety, panic attack, etc.), (v) environmental conditions (e.g., weather, humidity, pressure, temperature, scenery, location or situation including being at work, at school, on break or on vacation, etc.), (vi) time of day, and/or (vii) other measurements, and/or patterns and/or combinations of any of the aforementioned. Accordingly, notifications can be provided with contextual data as described herein.

As described herein, notification rules, sets of permissible data, access and authorization rules can be generated or assigned based on Remote Monitor's classification. Some classification entail higher privileges, priorities, and responsibilities than other classifications and accordingly receive greater access, more notifications and other privileges and duties as described herein. Other classifications may entail fewer privileges, priorities and responsibilities and accordingly receive greater restrictions to the permissible data than higher priority classifications and/or more restrictive notification rules than the higher priority classifications. In some embodiments, prior to providing contextual data, the classification of Remote Monitor may be determined. If a Remote Monitor's respective remote monitoring device is assigned to a higher priority classification, then notifications, alerts or communications are provided with contextual data. If the respective remote monitoring device is assigned to a lower priority classification, then notifications, alerts or communications are provided with limited or no amount of contextual data.

Additionally, there can be different categories of Contextual Data. In many conventional devices, such information can be difficult to identify, locate, communicate, and/or analyze. Advantageously, some implementations of the present disclosure can categorize Contextual Data in advantageous and/or non-intuitive ways. Some categories may be of more interest to some Remote Monitor(s), Host(s), and/or others, whereas some categories may be of less interest. These categories can be used to sort and/or identify data for Remote Monitor(s), Host(s), and/or others in some implementations. In some implementations, the data for such categories can be viewed by itself as a category, and/or viewed with other categories together. In some implementations, no categories may be used to sort data. By way of illustrative example, some categories of received Contextual Data can include Health Data, System Data, Treatment Data, User Data, and Sensor Data. Accordingly, in some embodiments, the scope and amount of providing the contextual data can depend on predetermined categorizations, which may be determined by a Host or a host monitoring device, automatically by the device, or as pre-designated input by a Host.

Health Data can include, insulin intake and administration (e.g., basal or bolus), type of insulin, exercise, stress, illness (e.g., those that can affect insulin/carbohydrate ratios), form of diabetes, other chronic conditions, and/or other characteristics (e.g., permanent or temporary) of a Host and/or Remote Monitor. In some implementations, Health Data can include data generated by a bolus calculator that makes suggestions on bolus administration. The bolus calculator can estimate the bolus desired to cover any carbohydrates eaten or drank in order to correct high glucose. Such data can be estimated for a Host and/or Remote Monitor to determine bolus administration, if any, which could be therapeutically beneficial.

System Data can include, system errors, alerts, statuses, warnings, and/or other information related to a host monitoring device, another device of the Host, server (e.g., secure servers and/or servers such as those implementing notification services), workstation, remote monitoring device, and/or another device of Remote Monitor(s). Non-limiting examples of System Information can include statuses, reservoir levels of sensors, battery statuses, calibrations, occlusion detection, use logs, histories, power on/off, failures, etc.

Treatment Data can include, prepopulated and/or user-inputted information about a treatment administered and/or that will be administered. This prepopulated and/or user-inputted information can include a statement of acknowledgement of condition (e.g., acknowledging glucose level, future glucose levels, activities, communications, and/or any information that might be available to a Host and/or Remote Monitor, including, but not limited to, those from the host monitoring device, remote monitoring device(s), and other devices), a future or past treatment, and any other information the Host might desire to add for himself/herself or a Remote Monitor. By way of illustrative example, Treatment Information can include a statement such as, "I responded to my low alert. Ate 15 grams of carbs. No need to panic."

User Data can include data based on data from a Host and/or Remote Monitor(s). User Data can include, user-inputted information, such as descriptions of treatments, activities, observations, schedules, reactions, emotions, thoughts, notes, etc. User Data can also include data based on information and/or data in a Host's and/or Remote Monitor's calendars, messages, email, social media, Global Positioning Systems ("GPS"), and/or any other program or application used by Host(s) and/or Remote Monitor(s). User data can also include data that can be configured to be used with other applications of Hosts and/or Remote Monitor(s), including, calendars, messages, email, social media, GPS, and/or any other program or application used by Host(s) and/or Remote Monitor(s). As a non-limiting example, user data can include calendar information instructing a viewer to look at the Host's information at a particular day and/or time.

In some cases, a Remote Monitor can input information about a Host, and/or the Host about the Remote Monitor, as User Data. For example, the Remote Monitor can be a Caretaker of a Host, who may be unable and/or unwilling to input data (e.g., when the Host is a child or elderly person). In other situations, the Host and/or Remote Monitor can observe information about the other and input that information into either a host monitoring device or a remote monitoring device, or both. In some implementations, the Remote Monitor can input ancillary data to a Host to be included on the display (e.g., on the display graph or other form of data display, of a host monitoring device). The Host can add events (e.g., ate, exercise, insulin dose) to a trend display, such as a graph/reflection view (e.g., a display shown in Block 106). The Remote Monitor can also be able to add events to make the Host's display contextually richer. For example, a Remote Monitor can add observed mood, weather, meeting schedule, homework stress, etc. Other examples include changed basal rate, blood pressure high, started on another prescription for another issue, etc. In some cases, a Host can push insights to a Remote Monitor about a Host, such as calendar information (e.g., a calendar message saying "Let's look at your Host's day today" and other events). Such inputs can be made using a user interface, such as any user interface described in this disclosure.

User Data can also include insights about a Host's and/or Remote Monitor's activities. For example, and without limitation a Host and/or Remote Monitor can input teachable moments, such as insights, notes, feelings, etc. that are written, recorded, and/or selected from prepopulated options. In some cases, User Data can also include processed information from inputted data. For example, a processor (e.g., a processor communicatively coupled to a host monitoring device or a remote monitoring device) can learn teachable moments from the activities of a Host and/or Remote Monitor. By way of illustrative example, the processor can recognize that after taking insulin, the Host's insulin levels go low after eating. A processor can learn this pattern and/or make recommendations to a Host to change the timing of insulin, give an alert, or modify, ignore, or elevate any alerts regarding such insulin drops when such happens. By way of another illustrative example, after a Host exercises, his/her glucose levels can go low. A processor can learn this pattern and/or make recommendations to eat before exercising.

Sensor Data can include data based on data collected by sensors associated with a Host or Remote Monitor(s). This Sensor Data can include, data from health rate monitors, activity trackers, pulse oximeters, wearables (e.g., smart watches, smart rings, workout monitors, electrocardiographs, bioimpedance sensors, breathing monitors, sleep monitors, posture monitors, habit detectors, temperature trackers, fabrics embedded with sensors, moisture detectors, etc.), accelerometers, gyroscopes, speedometers, pedometers, blood pressure readers, pump data for administration of other drugs, drug sensors (e.g., breathalyzers and sensors configured to measure intoxication or presence of drugs), medical devices, and/or other devices that measure a characteristic of the Host and/or Remote Monitor(s). In some cases, such sensor data can be indicative of a Host's and/or Remote Monitor(s)' health. As a non-limiting example, data from an accelerometer can indicate whether a Host and/or Remote Monitor is sleeping, exercising, and/or any other activity. In some cases alerting of Hosts and/or Remote Monitors can be modified based on such data.

Any of the data mentioned in this disclosure (e.g., analyte measurements, communications, Processed Data, Contextual Data, Health Data, System Data, Treatment Data, User Data, Sensor Data, Summary Data, and/or other data mentioned in this disclosure) can be retrospective and/or actionable. Retrospective Data can include data that is no longer Actionable Data. That is, Actionable Data can be data that can be used with timeliness sufficient to allow effective action to prevent and/or respond to a change (e.g., an adverse change) in physiological state of a Host, Remote Monitor, and/or other user. Actionable Data can be so-called real-time continuous glucose measurements and can also include predicted continuous glucose measurements (e.g., glucose values predicted for a future period in time, such as 5 minutes or an hour into the future). To illustrate with an example of glucose data, actionable continuous glucose measurement data can be glucose measurement data that can be used to treat a current clinical diabetic state of a Host, Remote Monitor, and/or other user, such as impending or actual hypoglycemia, or impending or actual hyperglycemia. In contrast, retrospective continuous glucose data can be data that would not be used for treating a current clinical state of a Host, Remote Monitor, and/or other user because the data can be likely too old to provide value for formulating decisions on how to treat the Host, Remote Monitor, and/or other user. While possibly not useful for treating a current clinical state, Retrospective Data can be still very useful for extrapolating insights into the health of a Host, Remote Monitor, and/or other user. Examples include comparing glucose levels of a patient over time to carbohydrates ("carbs") and/or medication ingested by the Host, Remote Monitor, and/or other user to gain insights as to how the carbs and/or medication have been affecting the glucose levels of the Host, Remote Monitor, and/or other user. In some cases, the insights gained from the retrospective data can be used to modify a treatment plan associated with the Host, Remote Monitor, and/or other user.

It is understood that what constitutes Actionable Data can depend upon various factors. For instance, what constitutes Actionable Data can depend upon how quickly a clinical state of a health condition associated with one or more monitored health characteristics can change from a non-adverse physiological state to an adverse physiological state. To illustrate, although diabetic clinical states can change relatively quickly—for example, from being in safe range of glucose concentration to an unhealthy range of glucose concentration—the timeframe for such a change can be typically in the order of longer than about 30 minutes. In contrast, a monitored health condition associated with a heart condition can change much quicker, in the order of minutes or even seconds. Thus, Actionable Data associated with monitoring a diabetic condition (e.g., continuous glucose data) may extend along a longer timeframe than data associated with monitoring a heart condition (e.g., Electrocardiogram ("EKG") and heart rate data).

The data received in Block 102 can be Raw Data or Processed Data, or both. For example, Raw Data can be impedances, currents, voltages, capacitances, bits, impulses, switches, and/or other electrical or mechanical measurements from a sensor that can be processed (e.g., correlated) to determine a characteristic (e.g., glucose concentration or any of the aforementioned information). Processed Data can include characteristics, measurements, conclusions, communications, descriptions, observations, parameters, statistics, etc. In some cases, data received in Block 102 can be passed directly to Block 108 for transmission.

In some implementations, Processed Data can include Summary Data, which can be derived from received data, including analyte measurements, received communications, Contextual Data, Health Data, System Data, Treatment Data, User Data, Sensor Data, and/or any data described in this disclosure. By way of illustrative example, Summary Data can include a summary number on a scale, such as a health scale. In the example of Summary Data for Host data, a Host's overall health can be rated on a health scale from zero (0) to ten (10), or any other scaled range as desired. By factoring data received in Block 102, such as one or more of glucose level, activity, pulse, time of day, etc., Summary Data can give a summary to a viewer (e.g., a Host or Remote Monitor) indicative of the overall health of a Host.

In some cases, it can be desirable to know a Remote Monitor's condition. For example, contextual data about a Remote Monitor may be received at a server. The contextual data about the Remote Monitor operating a remote monitoring device can include, for example, time, amount, and/or type of (i) an activity undertaken by the remote monitor user, (ii) a level of stress experienced by the remote monitor user, or (iii) an environmental condition experienced by the remote monitor user, or a combination of (i)-(iii). The emotions, activities, and stresses that the Remote Monitor experiences may be informative, especially when it can be perceived by a Host and/or can affect the Host's health. In such a case, the Remote Monitor's condition can be a factor that affects an analyte measurement such as the Host's glucose levels. The condition of the Remote Monitor can also roll back to the health of the Host. The Remote Monitor's condition can be used to gauge the engagement of the Remote Monitor as well as predict whether the Remote Monitor is suffering from alarm fatigue, is likely to assist the Host effectively and timely, etc. As a result, it can be desirable to collect data on the condition of the Remote Monitor, process it, and provide it as Summary Data to the Host, Remote Monitor, or other Remote Monitors. Accordingly, if processing a Remote Monitor's contextual data indicates an inability of the Remote Monitor to react to alarms or notifications, Host and/or other Remote Monitors can be provided with Summary Data including at least some of Remote Monitor's contextual data to alert them.

For example, such Summary Data can include a worry scale of a Remote Monitor, which can be based on processing Remote Monitor data (e.g., analyte measurements, communications, Processed Data, Contextual Data, Health Data, System Data, Treatment Data, User Data, Sensor Data, Summary Data, and/or any data described in this disclosure). In some embodiments, the worry scare can include scales from "not scared" to "scared." In some implementations, the worry scale can account for data relating to how the Remote Monitor's physiological condition may affect the health of the Host. Such a worry scale can also analyze the Remote Monitor's response time and/or behaviors in relation to communications (e.g., does the Remote Monitor close an alert or view an EGV because of the alert?). In some cases, the worry scale can range from zero (0) to ten (10), or any other scaled range as desired. In this example, a zero (0) on the worry scale can be indicative of little or no worries and a ten (10) can be indicative of high or the most worried. Other ways of scaling the worry scale can also be used (e.g., zero (0) is the most worried and five (5) is the least worried, and/or any other format and/or scaling). In some cases an upper threshold can be used with the worry scale where if the Remote Monitor has a rating on the scale greater than or equal to a predetermined value, communication settings (e.g., communication frequency, privileges, notifications, alerts, etc.) can be changed. In some cases, a lower threshold can be used where if the Remote Monitor has a rating on the scale less than or equal to a predetermined value, communication settings can be changed. By way of example, a worry scale where zero (0) is not worried and ten (10) is very worried can have an upper threshold of eight (8). If a Remote Monitor is measured to have a nine (9) on the worry scale, he/she may receive additional notifications (e.g., for even non-critical events). In some cases, the Remote Monitor's classification can change so that the Remote Monitor can be elevated to a classification with more responsibilities and/or communications. In some implementations, the opposite may be true where an over-worried Remote Monitor is seen as not being fit to take care of a Host. In such a case, the Remote Monitor's communication settings may be changed so that he/she receives fewer communications (e.g., only important notifications and/or none at all), and/or the Remote Monitor can be moved in classification so that he/she has fewer responsibilities and/or communications.

In Block 104, the received data from Block 102 can be processed. Block 104 can also receive other data from Blocks 106, 108, as will later be described. In implementations of the process in Block 104, the received data can be processed by the host monitoring device and/or the secure server. In some embodiments, the data received from the analyte sensor(s), remote monitoring device(s), and/or other device(s) can be received by the host monitoring device, and transmitted to the secure server to implement the processing of the received data in Block 104. By way of illustrative example, a processor can receive data through wired and/or wireless connections, such as any wired and/or wireless connections described in this disclosure. Such processor can be communicatively coupled to the aforementioned analyte sensor(s), remote monitoring device(s), and/or other device(s) internal or external to a Host, so that data and/or information can be sent between them. In some implementations, for example, the processor can be included in a server. Sent data can include, any of the data described in this disclosure (e.g., analyte measurements, communications, Processed Data, Contextual Data, Health Data, System Data, Treatment Data, User Data, Sensor Data, Summary Data, etc.). Signals can also be sent (e.g., received and transmitted) between such processor and the aforementioned analyte sensor(s), remote monitoring device(s), and/or other devices(s), including any device described with respect to Blocks 102, 106, 108. Non-limiting examples of such signals include interrogative signals, status signals, synchronization signals, timer signals, data, and the like.

In some implementations, Block 104 can perform signal processing, pattern recognition, and/or any other analysis on the data received from Blocks 102, 106, 108. In some cases, data can be generated based on received data. For example, in the case of a continuous glucose monitor, Block 104 can analyze measurements taken by the continuous glucose monitor to determine glucose concentration, generate communications (e.g., messages, notifications, alerts, interrogative signals, status signals, synchronization signals, timer signals, data, information, etc.) based on the measurements and/or received data. Similarly, in the cases of continuous glucose monitor, Block 104 can detect upward or downward trends in glucose levels, make recommendations, and/or any other desired information that may be relevant about the Host.

In Block 106, the data (e.g., data generated in Block 104) can be displayed. For example, a display can be used, including liquid-crystal displays ("LCDs"), light-emitting diode ("LED") displays, LED LCD displays, in-plane switching panels ("IPSs"), cathode ray tubes, plasma displays, ultra-high definition ("HD") panels, 4K displays, retina displays, organic LED displays, touchscreens, surfaces, canvases, and/or any displays, televisions, monitors, panels, and/or devices known in the art for visual presentation. The display may be a component of a host monitoring device and/or communicatively coupled to a host monitoring device. Similarly, the display can be a component of a server and/or communicatively coupled to the server.

In some implementations, a user interface can be communicatively coupled to the display (e.g., on a host monitoring device and/or server). In this way, a user can input data related to the Host and/or Remote Monitors. In some implementations, the display and/or user interface can display data from Blocks 102, 104, 108 directly or indirectly. Such data can include, data related to communications, analyte measurements, Processed Data, Health Data, System Data, Treatment Data, User Data, Sensor Data, Summary Data, and/or any other data received in Block 102, processed in Block 104, and/or sent in Block 108. In this way, if desirable, a user can input other data (e.g., any additional data), including, but not limited to, reactions to what is displayed on the display. Such inputted data can fall under the category of User Data. This data can be sent to Block 104 for processing. In some implementations, the information can be sent directly to Block 108 for transmitting, or sent to Block 102 to inquire more data.

In some implementations, Block 106 can provide adaptive and/or contextual communication (e.g., alerting, notification, messages, etc.) to a Host. For example, the host monitoring device can use data (e.g., analyte measurements, Processed Data, Health Data, System Data, Treatment Data, User Data, Sensor Data, Summary Data, and/or any other data described in this disclosure) to determine a characteristic of the Host and/or modify alerting behavior accordingly. Similarly, for example, the determination of a characteristic of the Host and/or identification of alerting behavior can be processed by the secure server (e.g., in Block 104) and provided to the host monitoring device to present the adaptive and/or contextual communication to the Host. By way of illustrative example, a host monitoring device can be communicatively coupled to an accelerometer. Data from the accelerometer can be indicative of movement of the Host, which can allow a host monitoring device to determine the activity of a Host, such as whether a Host is sleeping, exercising, and/or any other activity as desired. The host monitoring device can then modify the alerting as desired based on that activity. For example, the Host using the host monitoring device can turn down the frequency of communications (e.g., via the dedicated application on the host monitoring device) while the Host is asleep if the Host desires to not be disturbed while sleeping. As another non-limiting example, data from the accelerometer can be sent to a server, which can determine the activity of a host. The server can modify the alerting as desired based on the activity, such as turning down the frequency of communications while the Host is sleeping. In some cases, the host monitoring device and/or server can turn off non-urgent communications. In some cases, the host monitoring device and/or server can elevate urgent communications and/or increase alert volumes in order to wake up a Host. As mentioned, other data described in this disclosure can be used, including, data from calendars, messages, email, social media, GPS, smart watches, applications (e.g., mobile applications), heart rate monitors, activity trackers, pulse oximeters, wearables, accelerometers, gyroscopes, speedometers, pedometers, blood pressure readers, drug administration data (e.g., pump data), or data from other medical devices, etc.

In Block 108, data can be transmitted. Such data can be data aforementioned with respect to Blocks 102, 104, 106, and/or data and/or information based on such data. A transmitter, receiver, and/or transceiver can be used for the transmittal from a host monitoring device and/or server. This transmitter, receiver, and/or transceiver can use a transmission protocol across any wired or wireless connection mentioned in this disclosure. In some implementations, such data can be transmitted to one or more remote monitoring device(s) either directly or through a network. Also either directly or through a network, Block 108 can transmit data to other device(s), such as other sensor(s), host monitoring device(s), mobile devices (e.g., tablets, cellphones, smartphones, e-readers, phablets, and the like), wearables (e.g., smart watches, smart rings, workout monitors, electrocardiographs, bioimpedence sensors, breathing monitors, sleep monitors, posture monitors, habit detectors, temperature trackers, fabrics embedded with sensors, moisture detectors, etc.), medical devices, set-top boxes, internet streaming devices, gaming consoles, smart appliances, any device with access to the internet and/or any network protocol, computers (e.g., laptops, desktops, personal computers, etc.), and/or any desirable device. In some cases, any of the aforementioned other device(s) may also be remote monitoring devices, servers, and/or host monitoring devices.

In some cases, it may be desirable for Remote Monitor(s) to view data from Host monitoring device(s), servers, other remote monitoring device(s), and/or other device(s). Such information can be desirable for the Remote Monitor(s) to fulfill a particular role, such as Caretaker, Social Associate, Stranger, Watcher, Assigned Remote Monitor, Universal Remote Monitor, and/or any other role. FIG. 1B illustrates example Process 150 where a remote monitoring device and/or server can receive, process, and transmit data. In some cases, a remote monitoring device substantially similar to Remote Monitoring Device 300 of FIG. 3, and/or any remote monitoring devices described in this disclosure can perform Process 150. Process 150 can be performed by a server (e.g., Secure Server 504 of FIG. 5), in the alternative or in addition to a remote monitoring device. In some cases, such a server can be a separate server than a server that performs Process 100. In some cases, the same server can perform Process 100 and Process 150.

In Block 152, the remote monitoring device and/or server can receive data from host monitoring device(s), remote monitoring device(s), servers, and/or other devices directly or indirectly (e.g., via a server). The sent or received data can include data related to analyte concentrations (e.g., glucose levels), communications, Processed Data, Contextual Data (e.g., Health Data, System Data, Treatment Data, User Data, Sensor Data, Summary Data, and other Contextual Data mentioned in this disclosure), and/or any desirable data. Remote Monitor(s) can be selectively chosen to remotely monitor a Host based on a Host-initiated invitation process, such as those described in U.S. Patent Publication No. 2014/0184422 to Mensinger et al., which is incorporated herein by reference. Data accessible to the remote monitor device can be authorized according to a remote monitor authorization process, such as those described in U.S. Patent Publication No. 2014/0184422 to Mensinger et al.

As described, in some embodiments, a Host's CGM device can transfer the Host's data to a secure server. An authorized Remote Monitor can access the Host's data on the secure server. In some cases, if the CGM data is unavailable on the server, the authorized Remote Monitor can issue a command to request the Host's data from the CGM. For example, in some implementations the direct command request of the Host's data by the remote monitoring device can use near field communications (NFC) or other wireless protocol to enable communication between the Host's CGM electronics unit and the remote monitoring device.

A remote monitoring device and/or server can also receive data from other remote monitoring device(s). In some cases, a plurality of individuals can have particular roles (e.g., Caretakers, Social Associates, Strangers, Watchers, Assigned Remote Monitors, Universal Remote Monitors, and/or other roles) with respect to the Host. Ability to receive and/or transmit data between remote monitoring device(s) can allow for a level of coordinated role fulfillment that is difficult to achieve, or is unavailable with current technology, which may not have the level of interactivity, coordination, and/or integration of implementations described in this disclosure.

A remote monitoring device and/or server can also receive data from other device(s). For example, it may be desirable to receive information about a Remote Monitor to understand how the Remote Monitor may respond, behave, and/or react under certain conditions. By way of illustrative example, a Remote Monitor can be one of a plurality of Remote Monitors who fulfill the role of Caretaker to a Host. There can be a hierarchy of such Caretakers, which will be described in further detail later in this disclosure, where one or more Caretakers receive data, information, alerts, notifications, and/or other communications regarding a Host before other Caretakers. In some implementations, one or more classifications can be generated, where the classifications designate a hierarchy to provide communications based on notification rules to inform authorized remote monitoring devices about a Host's analyte state. In the case where a particular Caretaker receives data first, that Caretaker can be a Primary Caretaker. As an example, if that particular Primary Caretaker is under high stress as evidenced by blood pressure, pulse, temperature, and/or other measurements and/or data (e.g., analyte measurements, communications, Processed Data, Contextual Data, Health Data, System Data, Treatment Data, User Data, Sensor Data, Summary Data, and/or other data mentioned in this disclosure), that Primary Caretaker may not be in a position to adequately take care of a Host when the Host is in need. In some cases, that Primary Caretaker's remote monitoring device and/or a server can receive data indicative of high stress and/or determine (e.g., using a processor of the remote monitoring device and/or server) that other Caretakers and/or Remote Monitors should receive information first instead of that Primary Caretaker. The priority of which Remote Monitor (e.g., remote monitoring device) receives communication first can be determined based on a Remote Monitor's assigned classification.

Other data from other devices can be used to determine whether a change in classification of a remote monitoring device is warranted. These other devices can include, devices that measure data that may be relevant to a Remote Monitor's ability to fulfill a role with respect to a Host. Some non-limiting examples of other devices include sensor(s), mobile devices (e.g., tablets, cellphones, smartphones, e-readers, phablets, and the like), wearables (e.g., smart watches, smart rings, workout monitors, electrocardiographs, bioimpedance sensors, breathing monitors, sleep monitors, posture monitors, habit detectors, temperature trackers, fabrics embedded with sensors, moisture detectors, etc.), set-top boxes, internet streaming devices, gaming consoles, smart appliances, any device with access to the internet and/or any network protocol, computers (e.g., laptops, desktops, personal computers, etc.), medical devices, heart rate monitors, activity trackers, pulse oximeters, accelerometers, gyroscopes, speedometers, pedometers, blood pressure readers, pump data for administration of other drugs, continuous glucose monitors, drug sensors (e.g., breathalyzers and sensors configured to measure intoxication or presence of drugs), and/or any desirable device. In some cases, any of the aforementioned other device(s) may also be remote monitoring devices and/or host monitoring devices.

In Block 154, the received data from Block 152 can be processed. Block 154 can also receive other data from Blocks 156, 158. By way of illustrative example, a processor (e.g., a processor included in a remote monitoring device and/or server) can receive the data. Such processer can receive the data through wired and/or wireless connections, such as any wired and/or wireless connection described in this disclosure.

Such processor can be communicatively coupled to host monitoring device(s), remote monitoring device(s), server(s), and/or other device(s) so that data can be sent, received, and/or transmitted between them. Such sent data can include, any of the data described in this disclosure (e.g., analyte measurements, communications, Processed Data, Contextual Data, Health Data, System Data, Treatment Data, User Data, Sensor Data, Summary Data, and/or other data mentioned in this disclosure). Signals can also be sent, received, and/or transmitted between such processor and the aforementioned host monitoring device(s), remote monitoring device(s), server(s), and/or other devices(s), including any device described with respect to Blocks 152, 156, 158. Non-limiting examples of such signals include interrogative signals, status signals, synchronization signals, timer signals, data, and the like.

In some implementations, Block 154 can perform signal processing, pattern recognition, and/or any other analysis on the data received from Blocks 152, 156, 158. For example, such signal processing, pattern recognition, and/or any other analysis can be performed by a remote monitoring device and/or a server. In some cases, data can be generated based on the received data. By way of illustrative example, in the case where a remote monitoring device receives a communication regarding a Host based on the Host's glucose levels, Block 154 can process the communication and determine whether and how often to alert and/or notify a Remote Monitor based on predefined settings, such as predefined frequency of alerts, priority of alerts, availability of Remote Monitor, availability of other Remote Monitor(s), severity of notification, classification of Remote Monitor, position in hierarchy of classification of Remote Monitor, and/or other factors. Similarly, in some implementations, a server can receive a communication regarding a Host based on the Host's glucose level. Block 154 can then process the communication and determine whether and how often to alert and/or notify one or more Remote Monitors (e.g., using their remote monitoring devices) based on predefined settings, such as predefined frequency of alerts, priority of alerts, availability of Remote Monitor, availability of other Remote Monitor(s), severity of notification, classification of Remote Monitor, position in hierarchy of classification of Remote Monitor, and/or other factors.

In Block 156, the data (e.g., data from Blocks 152, 154, 158) can be displayed. For example, a display can be used, including any display described in this disclosure. In some cases, such display can be a component of and/or communicatively coupled to a remote monitoring device. In some cases, such display can be a component of and/or communicatively coupled to a server. In some implementations, a user interface can be communicatively coupled to the display, such as any user interface described in this disclosure. In this way, a user can input User Data related to the Host and/or Remote Monitor(s).

In some implementations, the display and/or user interface can display data from Blocks 152, 154, 158 directly or indirectly. Such data can include, data related to communications, analyte measurements, Processed Data Contextual Data, Health Data, System Data, Treatment Data, User Data, Summary Data, and Sensor Data, and/or other data received in Block 152, processed in Block 154, and/or transmitted in Block 158. In this way, if desirable, a user can input other information (e.g., any additional information), including, but not limited to, information in reaction to what is displayed on the display. This information can be sent to Block 154 for processing, including, but not limited to, the creation of Summary Data and Processed Data. In some implementations, the information can be sent directly to Block 158 for transmitting, or sent to Block 152 to inquire more data.

In Block 158, data can be transmitted. Such data can be any data aforementioned with respect to Blocks 152, 154, 156, and/or any data based on such data. A transmitter, receiver, and/or transceiver can be used for the transmittal. This transmitter, receiver, and/or transceiver can use a transmission protocol across any wired and/or wireless connection mentioned in this disclosure. In some implementations, such data can be transmitted to one or more remote monitoring device(s) either directly or through a network. Also, either directly or through a network, Block 158 can transmit data to other device(s), such as other sensor(s), host monitoring device(s), mobile devices (e.g., tablets, cellphones, smartphones, e-readers, phablets, and the like), wearables (e.g., smart watches, smart rings, workout monitors, electrocardiographs, bioimpedance sensors, breathing monitors, sleep monitors, posture monitors, habit detectors, temperature trackers, fabrics embedded with sensors, moisture detectors, etc.), medical devices, set-top boxes, internet streaming devices, gaming consoles, smart appliances, any device with access to the internet and/or any network protocol, computers (e.g., laptops, desktops, personal computers, etc.), and/or any desirable device. In some cases, any of the aforementioned other device(s) may also be remote monitoring devices and/or host monitoring devices.

Figure 2:
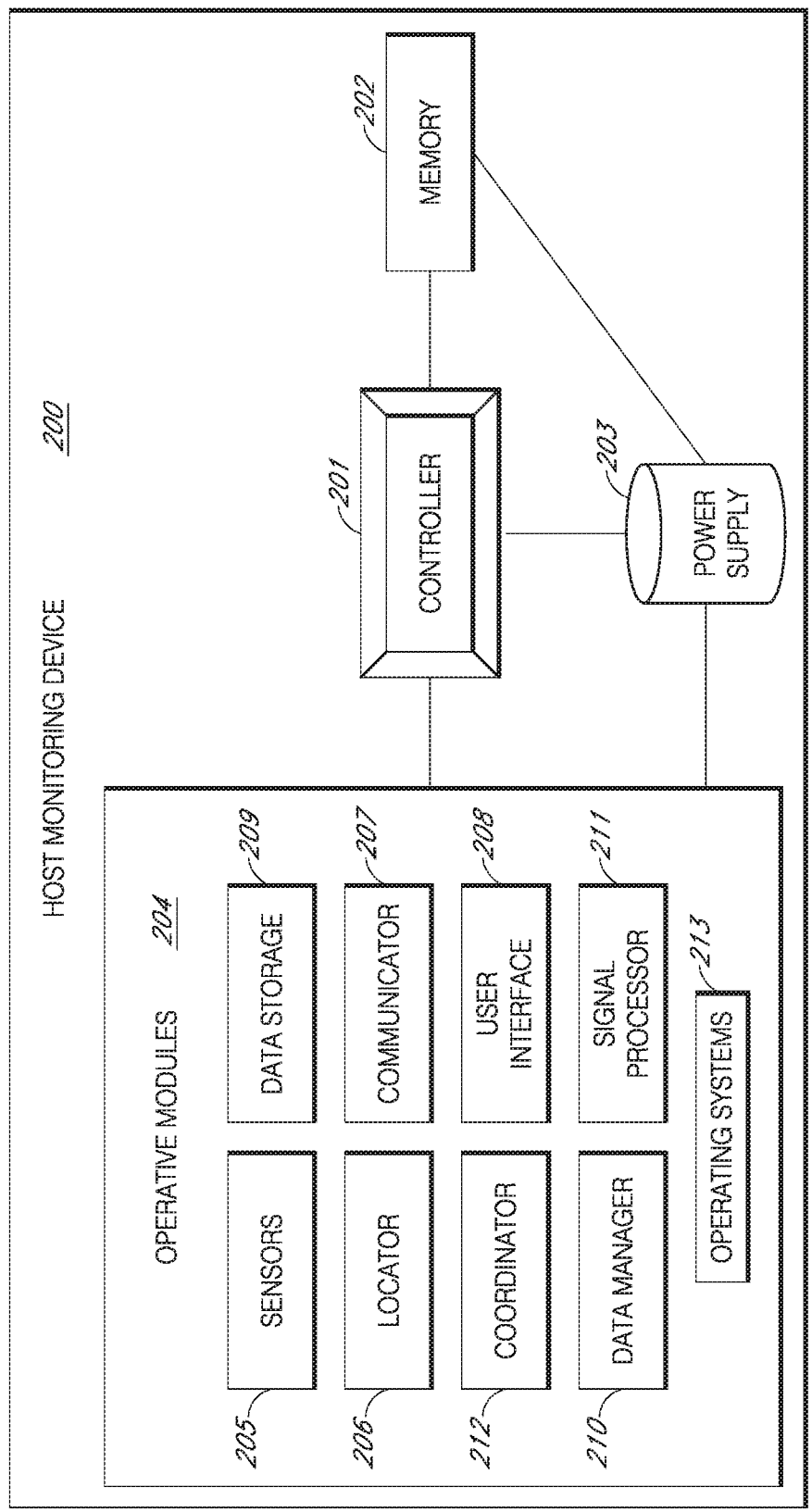
FIG. 2 illustrates a block diagram of an example host monitoring device.

FIG. 2 illustrates a block diagram of an example host monitoring device 200. Host Monitoring Device 200 can include Controller 201, Memory 202, Power Supply 203, and/or Operative Modules 204, each of which can be operatively and/or communicatively coupled to each other and each other's components and/or subcomponents. Controller 201 can control the various operations performed by Host Monitoring Device 200. In some implementations, Host Monitoring Device 200 can be configured to perform the example processes, methods, and/or systems, and/or substantially similarly processes, methods, and/or systems, illustrated in FIG. 1A.

Controller 201 can be operatively and/or communicatively coupled to Memory 202, which can include, volatile, non-volatile, read-only memory ("ROM"), and/or random access memory ("RAM"), and can provide instructions and data to Controller 201. A portion of Memory 202 can also include non-volatile random access memory ("NVRAM"). Controller 201 can perform logical and arithmetic operations based on program instructions stored within Memory 202. Controller 201 can include one or more processors (e.g., microprocessors) and other peripherals. The instructions in Memory 202 can be executable to implement the methods described herein. Operative Modules 204 can be coupled to Controller 201 to perform the various operations described herein. One or more, or none, of the modules in Operative Modules 204 can be included in some implementations. Throughout this disclosure, reference will be made to various controllers and/or processors. In some implementations, a single controller (e.g., Controller 201) can serve as the various controllers and/or processors described. In other implementations, different controllers and/or processors can be used. Controller 201 can send and/or receive signals, such as power signals, control signals, sensor signals, interrogatory signals, status signals, data signals, electrical signals and/or any other desirable signals, including discrete and analog signals. Controller 201 can coordinate and/or manage Operative Modules 204, and/or set timings (e.g., synchronously or asynchronously), turn on/off, control power budgets, receive/send network instructions and/or updates, update firmware, send interrogatory signals, receive and/or send statuses, and/or perform any operations for running features of Host Monitoring Device 200.

Operative Modules 204 can include various modules that perform functions for Host Monitoring Device 200. For example, such modules of Operative Modules 204 can include Sensors 205, Data Storage 209, Locator 206, Communicator 207, User Interface 208, Information Manager 210, and/or Signal Processor 211.

In some implementations, Sensors 205 can include apparatuses that can detect characteristics within and/or around a Host. Sensors 205 can be internal to Host Monitoring Device 200 or external, and/or have components that are partially internal and/or partially external. By way of illustrative example, sensors can include thermometers, analyte sensors (e.g., glucose sensors and/or continuous glucose monitoring sensors), health rate monitors, activity trackers, pulse oximeters, wearables (e.g., smart watches, smart rings, workout monitors, electrocardiographs, bioimpedance sensors, breathing monitors, sleep monitors, posture monitors, habit detectors, temperature trackers, fabrics embedded with sensors, moisture detectors, etc.), medical devices, drug sensors (e.g., breathalyzers and sensors configured to measure intoxication or presence of drugs), gyroscopes, speedometers, pedometers, blood pressure readers, medical device sensors, movement sensors, respirators, and/or any sensors desirable. Data and/or commands to/from Sensors 205 can be sent using Communicator 207.

In some implementations, Locator 206 can identify the location of Host Monitoring Device 200 and/or a Host. For example, Locator 206 can include GPS, Radio Frequency Identification ("RFID"), Global Navigation Satellite System ("GLONASS"), and/or any system that can identify location. In some implementations, Locator 206 can be positioned within a chassis of Host Monitoring Device 200. In other implementations, Locator 206 can be positioned on a Host, not within the chassis of Host Monitoring Device 200. Moreover, Locator 206 may include, or may be communicatively coupled to, transmitters and/or receivers capable of emitting signals that can be used to triangulate and/or otherwise derive the position of Host Monitoring Device 200. A controller, such as Controller 201, can perform such algorithms to calculate location based on emitted signals from Locator 206.

In some implementations, Communicator 207 can communicatively couple Host Monitoring Device 200, and/or any components therein (e.g., Operative Modules 204), to a network, computer, mobile device (e.g., tablets, cellphones, smartphones, e-readers, phablets, and the like), short-range receiver, long-range receiver, watch, remote, antenna, wearables (e.g., smart watches, smart rings, workout monitors, electrocardiographs, bioimpedance sensors, breathing monitors, sleep monitors, posture monitors, habit detectors, temperature trackers, fabrics embedded with sensors, moisture detectors, etc.), medical devices, set-top boxes, internet streaming devices, gaming consoles, smart appliances, any device with access to the internet and/or any network protocol, and/or any device desirable. Communicator 207 can include transmitters, receivers, transceivers, etc. Communicator 207 can be configured to send/receive over wired and/or wireless connections, such as any wired and/or wireless connection described in this disclosure.

Communicator 207 can be configured to send and receive signals including numbers, letters, alphanumeric characters, and/or symbols. In some cases, signals can be encrypted, using algorithms such as 128-bit or 256-bit keys and/or other encryption algorithms complying with standards such as the Advanced Encryption Standard ("AES"), RSA, Data Encryption Standard ("DES"), Triple DES, and the like. Communicator 207 can be configured to send and receive statuses, commands, and other data/information. For example, Communicator 207 can transmit statuses, commands, and/or data/information from Sensors 205, Data Storage 209, Locator 206, Communicator 207, User Interface 208, Information Manager 210, Signal Processer 211, Operating Systems 213, Controller 201, Power Supply 203, Memory 202, and/or any other component and/or subcomponent of Host Monitoring Device 200.

In some implementations, Communicator 207 can be configured to operate on a mobile ad hoc network ("MANET"). In some cases, Host Monitoring Device 200 can be part of a distributive network where information and/or data can be relayed, in whole or in parts) across other host monitoring devices, remote monitoring devices, and/or other devices. Advantageously, a MANET can allow additional robustness for the transfer of important data. Because it may already be desirable to send data to a plurality of devices, using a MANET can increase signal strength, robustness, and reliability, while decreasing energy use, interference, and infrastructural costs, especially when such devices are in close proximity of other devices. For example, such close proximity may be predetermined by hardware limitations of Communicators 207. In some implementations, close proximity can be based on standard ranges of wireless standard devices, such as between 0 and 1,045 square meters or the standard ranges (e.g., using any standard used in the art) as wireless standard devices are updated from time to time.

Data Storage 209 can be configured to temporarily and/or permanently store (e.g., record) data. Data Storage 209 can include storage devices that can store data using different mediums, such as electrical (e.g., semiconductors, floating-gate transistors, hard disks, flash memory, RAM, ROM, enterprise storage, cloud, distributive storage devices, etc.), optical storage (e.g., photographic, microform, holographic, optical disk, magneto-optical drives, 3D optical data storage, holographic data storage), chemicals (e.g., organics, proteins, synapses, receptors, chemical concentrations, etc.), thermodynamics (e.g., phase change materials, heat storage devices, etc.), photochemicals (e.g., films, etc.), mechanical (e.g., switches), magnetic storage (e.g., magnetic tape, wire, etc.), etc. Data Storage 209 can be configured to store any data desired, such as the data described with respect to FIGS. 1A-B, including data from analyte sensors, remote monitoring device(s), host monitoring device(s), and other device(s), communications, Contextual Data (e.g., time/amount/type of taken medicament, such as insulin, sulfonylureas, biguanids, meglitinides, thiazolidinediones, DPP-4 inhibitors, SGLT2 inhibitors, alpha-glucosidase inhibitors, bile acid sequestrants, and/or other drugs or treatments, time/amount/type of ingested food, such as carbohydrates, protein, dairy, fat, fruits, vegetables, candy, dessert, sugars, calories, quantities, preparations, etc., time/amount/type of exercise or activity undertaken, such as running, walking, sports, weight lifting, sitting, sleeping, idle, resting, etc., level of stress felt, such as acute, episodic acute, emotional, chronic, high stress, medium stress, low stress, no stress, anxiety, panic attack, etc., environment, such as weather, humidity, pressure, temperature, etc. and/or location, time of day, and/or other Contextual Data), Processed Data, Health Data, System Data, Treatment Data, User Data, Sensor Data, Summary Data, and/or other Data described in this disclosure, and/or patterns and/or combinations of any of the aforementioned. Data Storage 209 can also store any information based on data from any component of Host Monitoring Device 200, including Controller 201, Power Supply 203, and/or modules in Operative Modules 204. Some data can be inputted by User Interface 208 and subsequently stored.

Data Manager 210 can be configured to analyze and/or manage data in Data Storage 209, Memory 202, and/or any component of Host Monitoring Device 200 (e.g., Controller 201, Power Supply 203, and/or modules in Operative Modules 204). Operations that Data Manager 210 can use on such data include, but are not limited to, compression, decompression, sorting, categorizing, directing, optimizing, defragging, deleting, secure erasing, securing, manipulating, identifying, copying, pasting, write protecting (e.g., temporary write protection or permanent write protection), backing up, authenticating, etc. Advantageously, Data Manager 210 can identify the types and/or severity (e.g., the importance of) of communications by Host Monitoring Device 200. In some cases, such identification can allow Hosts to sort the information they receive, and determine the kinds and/or amounts of information that they desire to see. Data Manager 210 can have predetermined (e.g., programmed or user-defined) rules for allowing certain kinds and/or types of information to be shown (e.g., displayed using User Interface 208) to a Host. Similarly, Data Manager 210 can also be configured to manage what data Host Monitoring Device 200 shares to others, such as remote monitoring devices and other devices. Data Manager 210 can also perform error monitoring, error correction, and/or data validation, including identifying and/or fixing transmission-related errors, data formatting, device-related error codes, invalid data, duplicate data points, and/or other processes on the data.

User Interface 208 can be configured for a user to communicate with Host Monitoring Device 200. For example, User Interfaces 208 can include touch panels, buttons, keypads/keyboards, ports (e.g., USB, DVI, Display Port, E-Sata, Firewire, PS/2, Serial, VGA, SCSI, audio port, HDMI, PCMCIA ports, memory card ports (e.g., SD and miniSD), and/or ports for computer-readable medium), mouse, rollerballs, consoles, vibrators, audio transducers, and/or any interface for a user to input and/or receive data and/or commands, whether coupled wirelessly or through wires (including, any of the wireless or wired connections described in this disclosure). User Interface 208 can include a display, such as LCDs, LED displays, LED LCD displays, IPSs, cathode ray tubes, plasma displays, HD panels, 4K displays, retina displays, organic LED displays, touchscreens, surfaces, canvases, and/or any displays, televisions, monitors, panels, and/or devices known in the art for visual presentation.

Signal Processor 211 can be configured to process any data of Host Monitoring Device 200, including, as a non-limiting example, data stored in Data Storage 209 and/or managed by Data Manager 210. Signal Processor 211 can perform any analysis of data presented in this disclosure, as well as other analyses and/or processes. By way of illustrative example, Signal Processor 211 can determine patterns in analyte measurements, such as patterns in glucose level and other data (e.g., communications, Processed Data, Contextual Data, Health Data, System Data, Treatment Data, User Data, Sensor Data, Summary Data, and/or other data mentioned in this disclosure). Advantageously, the analysis of such patterns can allow predictive communications that can assist a Host and/or Remote Monitor(s) regarding Host care. By way of another illustrative example, Signal Processor 211 can analyze patterns in data from remote monitoring device(s) and/or other device(s). Where such data is based on characteristics (e.g., temporary or permanent) of a Remote Monitor, Signal Processor 211 can analyze patterns that can allow optimized communications that can accommodate Host and/or Remote Monitor interaction based on conditions of the Remote Monitor and/or Host.

Power Supply 203 can include one or more batteries, including, lithium, lithium ion, nickel-cadmium, nickel-metal hydride, nickel-hydrogen, carbon-zinc, silver-oxide, zinc-carbon, zinc-air, mercury oxide, alkaline, or any other type of battery known in the art. Certain batteries can be rechargeable, such as wirelessly (e.g., by a resonant circuit and/or a resonant tank circuit) and/or by plugging into an external power source. Power Supply 203 can also be any supplier of energy, including wall sockets and electronic devices that convert solar, wind, water, nuclear, hydrogen, gasoline, natural gas, fossil fuels, mechanical energy, steam, and/or any power source into electricity.

Operating System 213 can be configured to manage Memory 202, Controller 201, Power Supply 203, modules in Operative Modules 204, and/or any software, hardware and/or features of Host Monitoring Device 200. For example, Operating System 213 can include device drivers to manage hardware resources for Host Monitoring Device 200.

As previously mentioned, any of the aforementioned components of Host Monitoring Device 200 can be instantiated in software and/or hardware. For example, a module can be a piece of hardware or can be a module of code run on a computer.

Figure 3:
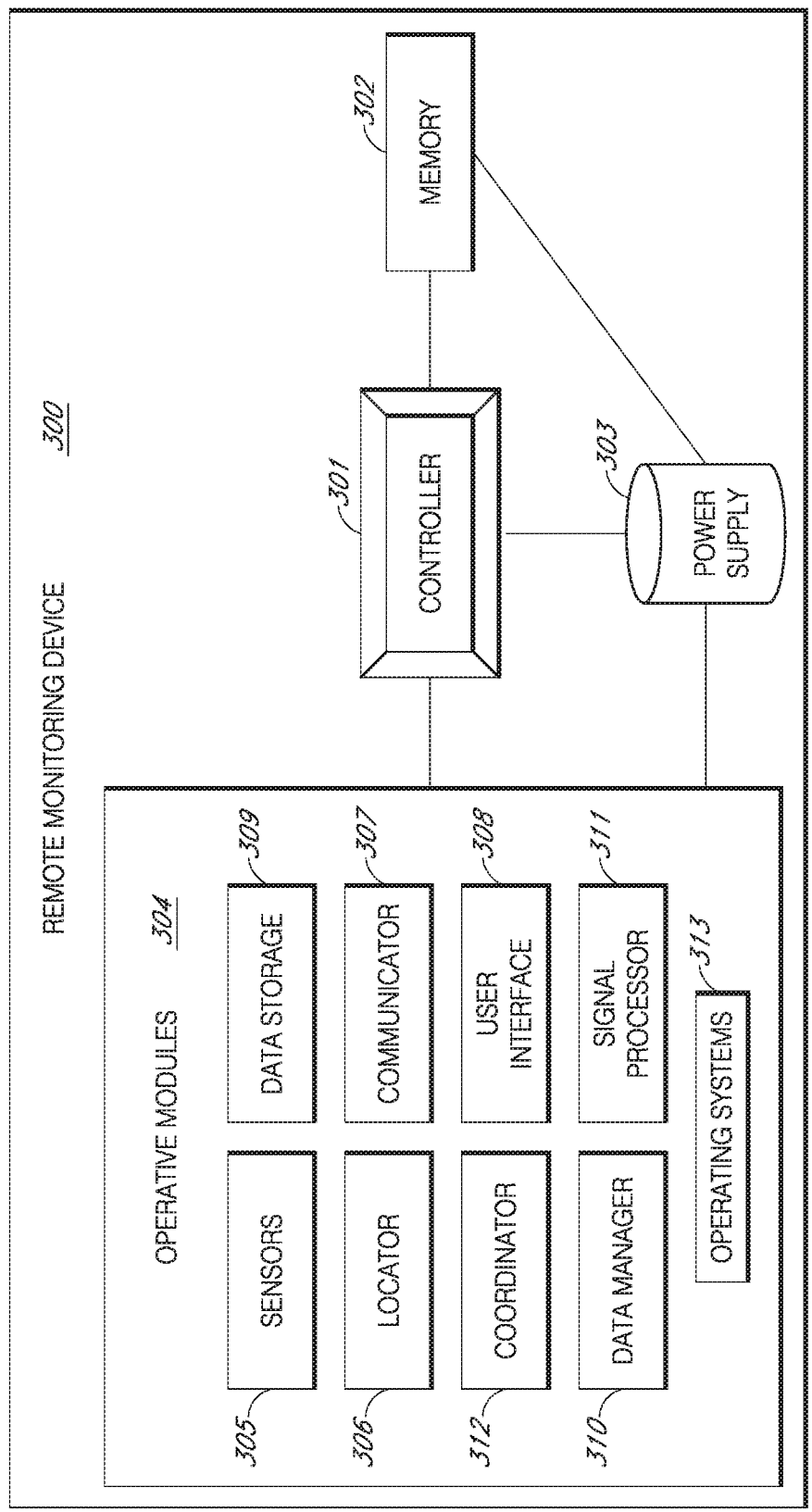
FIG. 3 illustrates a block diagram of an example remote monitoring device.

Similarly, FIG. 3 illustrates a functional block diagram of an example remote monitoring device. Remote Monitoring Device 300 can include Controller 301, Memory 302, Power Supply 303, and/or Operative Modules 304, each of which can be operatively and/or communicatively coupled to each other and each other's components and/or subcomponents. Controller 301 can control the various operations performed by Remote Monitoring Device 300. Like-labeled components of Remote Monitoring Device 300 can have analogous and/or substantially similar functionality as those of Host Monitoring Device 200, described with respect to FIG. 2. Some components will be re-described here. It should be noted that, in some implementations, host monitoring devices (e.g., Host Monitoring Device 200) can also serve as remote monitoring devices (e.g., Remote Monitoring Device 300) and vice versa. In some implementations, Remote Monitoring Device 300 can be configured to perform the example processes, methods, and/or systems, and/or substantially similarly processes, methods, and/or systems, illustrated in FIG. 1B.

Controller 301 can be operatively and/or communicatively coupled to Memory 302, which can include, volatile, non-volatile, ROM, and/or RAM, and can provide instructions and data to Controller 301. A portion of Memory 302 can also include NVRAM. Controller 301 can perform logical and arithmetic operations based on program instructions stored within Memory 302. Controller 301 can include one or more processors (e.g., microprocessors) and other peripherals. The instructions in Memory 302 can be executable to implement the methods described herein. Operative Modules 304 can be coupled to Controller 301 to perform the various operations described in this disclosure. One or more, or none, of the modules in Operative Modules 304 can be included in some implementations. Throughout this disclosure, reference will be made to various controllers and/or processors. In some implementations, a single controller (e.g., Controller 301) can serve as the various controllers and/or processors described. In other implementations, different controllers and/or processors can be used. Controller 301 can send and receive signals, such as power signals, control signals, sensor signals, interrogatory signals, status signals, data signals, electrical signals and/or any other desirable signals, including discrete and analog signals. Controller 301 can coordinate and/or manage Operative Modules 304, and/or set timings (e.g., synchronously or asynchronously), turn on/off, control power budgets, receive/send network instructions and/or updates, update firmware, send interrogatory signals, receive and/or send statuses, and/or perform any operations for running features of Remote Monitoring Device 300.

Operative Modules 304 can include various modules that perform functions for Remote Monitoring Device 300. For example, such modules of Operative Modules 304 can include Sensors 305, Data Storage 309, Locator 306, Communicator 307, User Interface 308, Information Manager 310, and/or Signal Processor 311.

In some implementations, Sensors 305 can include apparatuses that can detect characteristics within and/or around a Remote Monitor. Sensors 305 can be internal to Remote Monitoring Device 300 or external, and/or have components that are partially internal and/or partially external. By way of illustrative example, sensors can include thermometers, analyte sensors (e.g., glucose sensors and/or continuous glucose monitoring sensors), health rate monitors, activity trackers, pulse oximeters, wearables (e.g., smart watches, smart rings, workout monitors, electrocardiographs, bioimpedance sensors, breathing monitors, sleep monitors, posture monitors, habit detectors, temperature trackers, fabrics embedded with sensors, moisture detectors, etc.), medical devices, accelerometers, gyroscopes, speedometers, pedometers, blood pressure readers, pump data for administration of other drugs, drug sensors (e.g., breathalyzers and sensors configured to measure intoxication or presence of drugs), movement sensors, respirators, and/or any sensors desirable. Data and/or commands to/from Sensors 305 can be sent using Communication 307.

In some implementations, Locator 306 can identify the location of Remote Monitoring Device 300 and/or a Remote Monitor who is associated with Remote Monitoring Device 300. For example, Locator 306 can include GPS, RFID, GLONASS, and/or any system that can identify location. In some implementations, Locator 306 can be positioned within a chassis of Remote Monitoring Device 300. In other implementations, Locator 306 can be positioned on a Remote Monitor, not within a chassis of Remote Monitoring Device 300. Moreover, Locator 306 can include, or be communicatively coupled to, transmitters and/or receivers that can emit signals that can be used to triangulate and/or otherwise derive the position of Remote Monitoring Device 300. A controller, such as Controller 301, can perform such algorithms to calculate location based on emitted signals from Locator 306.

In some implementations, Communicator 307 can communicatively couple Remote Monitoring Device 300, and/or any components therein (e.g., Operative Modules 304), to a network, computer, mobile device (e.g., tablets, cellphones, smartphones, e-readers, phablets, and the like), short-range receiver, long-range receiver, watch, remote, antenna, wearables (e.g., smart watches, smart rings, workout monitors, electrocardiographs, bioimpedance sensors, breathing monitors, sleep monitors, posture monitors, habit detectors, temperature trackers, fabrics embedded with sensors, moisture detectors, etc.), medical devices, set-top boxes, internet streaming devices, gaming consoles, smart appliances, any device with access to the internet and/or any network protocol, computers and/or any device desirable. Communicator 307 can include transmitters, receivers, transceivers, etc. Communicator 307 can be configured to send/receive over wired and/or wireless connections, such as any wired and/or wireless connection described in this disclosure.

Communicator 307 can be configured to send and receive signals including numbers, letters, alphanumeric characters, and/or symbols. In some cases, signals can be encrypted, using algorithms such as 128-bit or 256-bit keys and/or other encryption algorithms complying with standards such as the AES, RSA, DES, Triple DES, and the like. Communicator 307 can be configured to send and receive statuses, commands, and other data/information. For example, Communicator 307 can transmit statuses, commands, and/or data/information from Sensors 305, Data Storage 309, Locator 306, Communicator 307, User Interface 308, Information Manager 310, Signal Processor 311, and/or Operating Systems 313. In some implementations, Communicator 307 can operate on a MANET substantially similar to Communicator 207.

Data Storage 309 can be configured to temporarily and/or permanently store (e.g., record) data. Data Storage 309 can include storage devices that can store data using different mediums, such as electrical (e.g., semiconductors, floating-gate transistors, hard disks, flash memory, RAM, ROM, enterprise storage, cloud, distributive storage devices, etc.), optical storage (e.g., photographic, microform, holographic optical disk, magneto-optical drives, 3D optical data storage, holographic data storage), chemicals (e.g., organics, proteins, synapses, receptors, chemical concentrations, etc.), thermodynamics (e.g., phase change materials, heat storage devices, etc.), photochemicals (e.g., films, etc.), mechanical (e.g., switches), magnetic storage (e.g., magnetic tape, wire, etc.), etc. Data Storage 309 can be configured to store any data desired, such as the data described with respect to FIGS. 1A-B and Data Storage 309. Advantageously, in certain implementations, Data Storage 309 can include data related to a Remote Monitor associated with Remote Monitoring Device 300 and/or other Remote Monitors. For example, data stored in Data Storage 309 can include classifications (e.g., hierarchical or lateral) regarding the relative role of Remote Monitors with respect to each other and with respect to a Host. Such data can be used by Remote Monitoring Device 300, Host Monitoring Device 200, and/or any other device to determine which remote monitoring device (e.g., which remote monitoring device associated with which Remote Monitor) should receive data first, second, third, etc., and which Remote Monitors are in position to effectively and/or efficiently assist and/or otherwise interact with a Host.

Data Manager 310 can be configured to analyze and/or manage data in Data Storage 309, Memory 302, and/or any component of Remote Monitoring Device 300 (e.g., Controller 301, Power Supply 303, and/or modules in Operative Modules 304). Operations that Data Manager 310 can use on such data include, but are not limited to, compression, decompression, sorting, categorizing, directing, optimizing, defragging, deleting, secure erasing, securing, manipulating, identifying, copying, pasting, write protecting (e.g., temporary write protection or permanent write protection), backing up, authenticating, etc. Advantageously, Data Manager 310 can identify the types and/or severity (e.g., the importance of) of notifications and alerts received by Remote Monitoring Device 300. In some cases, such identification can allow Remote Monitors to sort the information they receive, and determine the kinds and/or amounts of information that they desire to see. Data Manager 310 can have predetermined (e.g., programmed or user-defined) rules for allowing certain kinds and types of information to be shown (e.g., displayed using User Interface 308) to a Remote Monitor. Similarly, Data Manager 310 can also be configured to manage what data is shared by Remote Monitoring Device 300 to others, such as host monitoring devices and other devices. Data Manager 310 can also perform error monitoring, error correction, and/or data validation, including identifying and/or fixing transmission-related errors, data formatting, device-related error codes, invalid data, duplicate data points, and/or other processes on the data.

User Interface 308 can be configured for a user (e.g., a Remote Monitor and, in some cases, a Host) to communicate with Remote Monitoring Device 300. For example, User Interfaces 308 can include touch panels, buttons, keypads/keyboards, ports (e.g., USB, DVI, Display Port, E-Sata, Firewire, PS/2, Serial, VGA, SCSI, audio port, HDMI, PCMCIA ports, memory card ports (e.g., SD and miniSD), and/or ports for computer-readable medium), mouse, rollerballs, consoles, vibrators, audio transducers, and/or any interface for a user to input and/or receive data and/or commands, whether coupled wirelessly and/or through wires (including, any of the wireless and/or wired connections described in this disclosure). User Interface 308 can include a display, such as LCDs, LED displays, LED LCD displays, IPSs, cathode ray tubes, plasma displays, HD panels, 4K displays, retina displays, organic LED displays, touchscreens, surfaces, canvases, and/or any displays, televisions, monitors, panels, and/or devices known in the art for visual presentation.

Signal Processor 311 can be configured to process any data of Remote Monitoring Device 300, including, as a non-limiting example, any data stored in Data Storage 309 and/or managed by Data Manager 310. Signal Processor 311 can perform any analysis of data presented in this disclosure, as well as other analyses and/or processes. By way of illustrative example, Signal Processor 311 can determine patterns in analyte measurements, such as patterns in glucose level and other data (e.g., communications, Processed Data, Contextual Data, Health Data, System Data, Treatment Data, User Data, Sensor Data, Summary Data, and/or other data mentioned in this disclosure). Advantageously, the analysis of such patterns can allow predictive notifications that can assist a Host and/or Remote Monitor(s) regarding Host care. By way of another illustrative example, Signal Processor 311 can analyze patterns in data and/or information from host monitoring device(s) and/or other device(s). Where such data and/or information is based on characteristics (e.g., temporary or permanent) of a Remote Monitor, Signal Processor 311 can analyze patterns that can allow optimized communications that can accommodate Host and/or Remote Monitor interactions based on conditions and/or data of the Remote Monitor and/or Host.

Power Supply 303 can include any of the sources described with respect to Power Supply 203. Operating System 313 can be configured to manage Memory 302, Controller 301, Power Supply 303, modules in Operative Modules 304, and/or any software, hardware and/or features of Remote Monitoring Device 300. For example, Operating System 313 can include device drivers to manage hardware resources for Host Monitoring Device 300.

As previously mentioned, any of the aforementioned components of Remote Monitoring Device 300 can be instantiated in software and/or hardware. For example, a module can be a piece of hardware or can be a module of code run on a computer.

Figure 4:
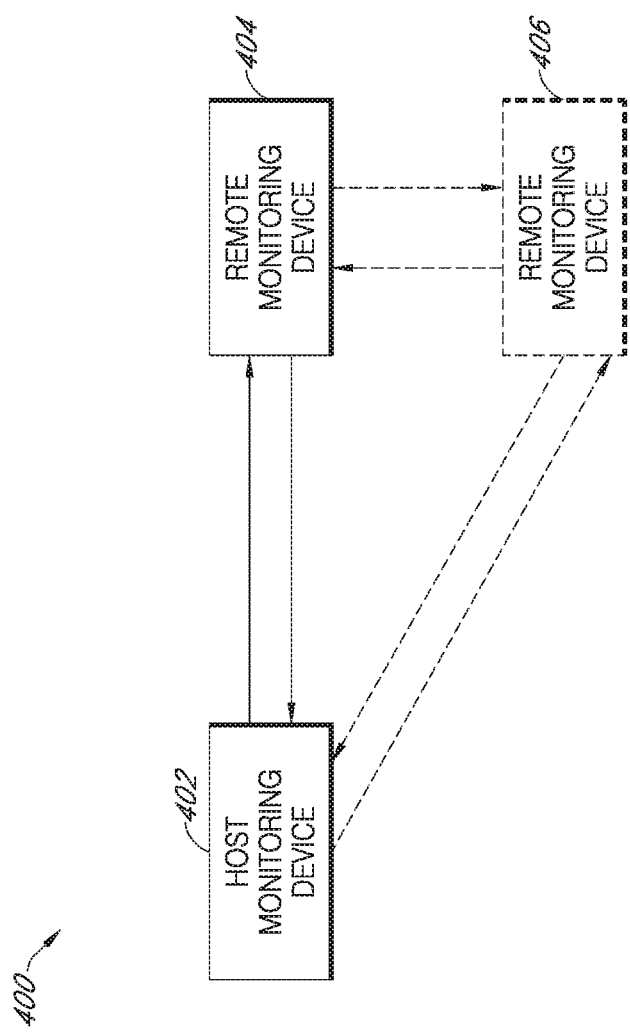
FIG. 4 illustrates a diagram of an example host monitoring device communicatively coupled to remote monitoring devices.

FIG. 4 illustrates a diagram of an example host monitoring device communicatively coupled to remote monitoring devices. Monitoring System 400 can include Host Monitoring Device 402 and Remote Monitoring Device 404. For example, Host Monitoring Device 402 can be configured substantially similar to Host Monitoring Device 200 and/or perform processes substantially similar to Process 100. Similarly, Remote Monitoring Device 404 can be configured substantially similar to Remote Monitoring Device 300 and/or perform processes substantially similar to Process 150. In some implementations, Host Monitoring Device 402 can be communicatively coupled to Remote Monitoring Device 404. Host Monitoring Device 402 can be associated with a Host, and Remote Monitoring Device 404 can be associated with a Remote Monitor. Host Monitoring Device 402 and Remote Monitoring Device 404 can be configured to send and receive communications (e.g., messages, notifications, alerts, interrogative signals, status signals, synchronization signals, timer signals, data, information, etc.) from each other.

In some implementations, Monitoring System 400 can also include Remote Monitoring Device 406, which can also be configured substantially similar to Remote Monitoring Device 300 and/or perform processes substantially similar to Process 150. Remote Monitoring Device 406 can be communicatively coupled to both Host Monitoring Device 402 and Remote Monitoring Device 404, where Host Monitoring Device 402 and Remote Monitoring Devices 404, 406 can be configured to send and/or receive communications (e.g., messages, notifications, alerts, interrogative signals, status signals, synchronization signals, timer signals, data, information, etc.) from each other.

Figure 5:
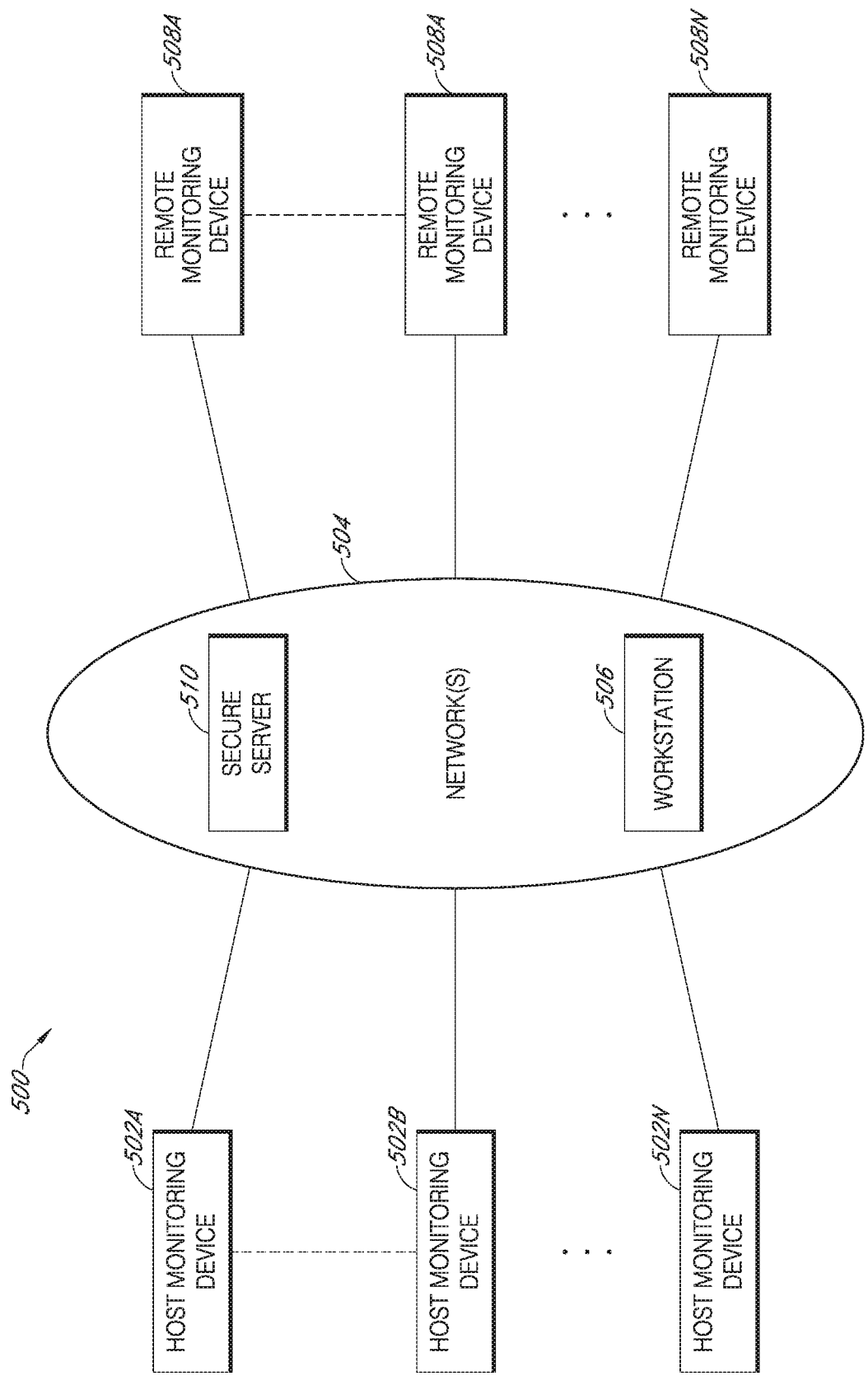
FIG. 5 illustrates an example extended system having a plurality of host monitoring devices and remote monitoring devices communicatively coupled through a network.

FIG. 5 illustrates an example extended system having a plurality of host monitoring devices and remote monitoring devices communicatively coupled through a network. Monitoring System 500 can include one or more of Host Monitoring Devices 502A-N, Remote Monitoring Devices 508A-N, and/or Network(s) 510. For example, Host Monitoring Devices 502A can be configured substantially similar to Host Monitoring Device 200 and/or perform processes substantially similar to Process 100. Similarly, Remote Monitoring Device 508A-N can be configured substantially similar to Remote Monitoring Device 300 and/or perform processes substantially similar to Process 150.

In some example implementations, Remote Monitoring Device 508A can receive communications for a single host monitoring system, such as Host Monitoring Device 502A, or a plurality of host monitoring systems, such as Host Monitoring Systems 502A-N. Furthermore, data can be generated by Secure Server 504 and then be sent to the one or more of Remote Monitoring Devices 508A-N and/or Host Monitoring Devices 502A-N. Secure Server 504 can be a server that can be configured to perform Processes 100, 150, and/or other processes.

In some implementations, Network(s) 510 can include a collection of hardware, software, services, and/or resources that can be invoked to instantiate a virtual machine, process, or other resource for a limited or defined duration, or an unlimited or undefined duration. Network(s) 510 can be communicatively or operatively coupled to a plurality of devices, systems, and/or servers, including devices and servers. In some implementations, Network(s) can include systems such as notification service, Short Message Service ("SMS"), wireless personal area networks ("WPANs"), wireless local area network ("WLAN"), wireless mesh networks, wireless metropolitan area networks, wireless wide area networks, global area networks, space networks, cellular networks (e.g., 2G, 4G, Long Term Evolution ("LTE"), 5G), mobile networks, local area network ("LAN"), star networks, ring networks, bus networks, and/or any other network. Network(s) 510 can include Secure Server 504 and Workstation 506.

In some implementations, there can be situations where it is desirable temporarily or permanently to coordinate care for Hosts. For example, Caretakers can be temporarily taking care of a plurality of Hosts in close proximity, and the care of one or more Host can be aided by data from other Hosts. In some cases, a plurality of host monitoring devices (e.g., Host Monitoring Devices 502A-N) can be in the same monitoring system and/or communicate with one another. For example, a host monitoring device, remote monitoring device, and/or secure server can take into account the location of other host monitoring devices in proximity to a particular host monitoring device. Such other host monitoring devices can be used to gather more information that could provide context to a particular host monitoring device. By way of illustrative example, in the case where Host Monitoring Device 502A and Host Monitoring Device 502B are in the vicinity (e.g., within 20 meters or any determined area) of each other. Host Monitoring Device 502A may not indicate that its Host is eating, but Host Monitoring Device 502B may show that its Host is eating. Host Monitoring Device 502B can send a communication to Host Monitoring Device 502A, Secure Server 504, and/or Remote Monitoring Devices 508A-N. In this scenario Host Monitoring Device 502A, Secure Server 504, and/or Remote Monitoring Devices 508A-N could find that there is an increased likelihood that the Host of Host Monitoring Device 502A is going to eat and/or can be impacted by a physical response due to the smell and/or sight of food, which could increase insulin levels and/or lower glucose levels of the Host of Host Monitoring Device 502A. Host Monitoring Device 502A can receive data based on the communication from Host Monitoring Device 502B. In some implementations, Host Monitoring Device 502A can then send communications (e.g., to Host Monitoring Devices 502B-N, Remote Monitoring Devices 508A-N, and/or Secure Server 504) indicating that there could be an event such as lowered glucose levels. In some implementations, Host Monitoring Device may, instead or in addition, enter data into a log indicating that Host Monitoring Device 502B indicated its Host was eating in the vicinity of Host Monitoring Device 502A.

One or more Remote Monitors can monitor the health of a plurality of Hosts. In an illustrative example, one or a few nurses in a school or a school district may be in charge of monitoring health and well-being of hundreds or thousands of students, where a percentage of the students may be diabetic patients. In some embodiments, a school nurse can be Remote Monitor and can remotely monitor multiple diabetic students from a remote monitoring device. This can also allow ease and speed of communication between the school nurse and teachers of diabetic students. The locator feature of host remote monitoring devices of diabetic students can allow the school nurse, teachers or school administrators to timely find an unresponsive child on school premises or during field trips. In some embodiments, the student patient (student Host(s)) can use a dedicated host monitoring device at school and leave the device at school outside school hours. The dedicated host monitoring device can pair with the student Host's transmitter when the student is at school and in range. The school nurse's remote monitoring device can monitor the student Host's sensor and other data as described herein with respect to Remote Monitor. Once school is over, the student Host patient can leave the dedicated school device in classroom or on school premises. Once the student Host arrives at home, and is in range with a remote monitoring device typically used by Remote Monitor(s) in the home such as the student Host's parents, the student Host's transmitter can then pair with such home remote monitoring devices. In some embodiments, the student Host's transmitter can be configured to be allowed to link to multiple devices.

In some embodiments, the classifications associated with a student Host's Remote Monitor(s) can be altered based on detecting the student Host's location and/or time of day. For example, upon detection that the student Host is at school, the school nurse remote monitoring device can be elevated to a higher priority classification and other remote monitoring devices, such as those in the student Host's home, can be relegated to a lower priority classification. Conversely, upon detecting that the student Host is at home, the remote monitoring device of the school nurse can be relegated to a lower priority classification and other the Remote Monitor(s), e.g., including the Remote Monitor(s) of the student Host's home, can be elevated to a higher priority classification. In some embodiments, one or more remote monitors may enjoy a permanent classification as to never miss any alarms or notifications.

As described, a school nurse could have a plurality of students with host monitoring devices that he/she is monitoring, e.g., as a Remote Monitor. For example, a first student could have Host Monitoring Device 502A and a second student could have Host Monitoring Device 502B. Information gathered from Host Monitoring Device 502B could have an impact on the health of the first student with Host Monitoring Device 502A. For example, emotional stress of the second student with Host Monitoring Device 502B could be measured using any device described in this disclosure, such as a heart rate monitor, smart watch, blood pressure monitor, etc. That measured data could be used as Actionable Data for the first student, where the stress of the second student could be indicative that the stress of the first student will increase. Accordingly, Host Monitoring Device 502B can send communications indicative of the emotional stress of the second student to one or more of Host Monitoring Device 502A, Secure Server 504, and/or Remote Monitoring Devices 508A-N. Host Monitoring Device 502A can receive data based on the communication from Host Monitoring Device 502B. In some implementations, Host Monitoring Device 502A can then send communications (e.g., to Host Monitoring Devices 502B-N, Remote Monitoring Devices 508A-N, and/or Secure Server 504) indicating that its Host could be under stress. In some implementations, Host Monitoring Device may, instead or in addition, enter data into a log indicating that Host Monitoring Device 502B indicated its Host was stressed in the vicinity of Host Monitoring Device 502A. For example, such contextual data sharing can empower the first student to positively intervene on behalf of the second student exhibiting the increased stress, as well as be self-aware on how the second student's emotional condition might affect him/herself. Also, for example, the contextual data benefits the school nurse to be aware and vigilant for how the stress situation of the second student might affect the other Hosts that he/she is remotely monitoring.

Embodiments described herein may be used to create a support or education community of patients and health care providers. Disposable CGMs can be provided to diabetic patients in community events, for example, a diabetes camp, where health care professionals can educate the interested members of the public and their loved ones on the available technologies described herein and offer a hands-on chance for reviewing the benefits thereof.

As another non-limiting example, in some cases the Host having Host Monitoring Device 502A may not have other devices that can measure data that can put that Host's analyte measurements into context (e.g., Processed Data, Contextual Data, Health Data, System Data, Treatment Data, User Data, Sensor Data, Summary Data, and/or other data mentioned in this disclosure). In some cases, Host Monitoring Device 502A can collect data from other host monitoring devices in its proximity to obtain such data. For example, the Host of Host Monitoring Device 502A has no other devices and the Host of Host Monitoring Device 502B has one or more other devices, such as a thermometer that can measure ambient temperature. Host Monitoring Device 502B can send communications indicative of the data measured by the thermometer to Host Monitoring Device 502A, Secure Server 504, and/or Remote Monitoring Devices 508A-N. Host Monitoring Device 502A can receive data based on the communications from Host Monitoring Device 502B. In some implementations, Host Monitoring Device 502A can then send communications (e.g., to Host Monitoring Devices 502B-N, Remote Monitoring Devices 508A-N, and/or Secure Server 504) indicating the temperature of the environment of the Host. In some implementations, Host Monitoring Device may, instead or in addition, enter data into a log indicating the temperature measured by Host Monitoring Device 502B in the vicinity of Host Monitoring Device 502A. In this illustrative example, a remote monitoring device (e.g., Remote Monitoring Device 508A-N) in the proximity of Host Monitoring Device 502A can be used instead or in addition to Host Monitoring Device 502B.

As another non-limiting example, where a Host associated with a first host monitoring device needs assistance, and his/her Remote Monitors are not available or responsive, having the ability to communicate with a second host monitoring device in the vicinity can give a greater likelihood of assistance because the Host associated with the second host monitoring device could be a diabetic with similar experiences. Accordingly, Host Monitoring Devices 502A-N can be operatively coupled to each other directly and/or through Network(s) 510.

In some implementations, Workstation 506 can be an access point such as devices, systems, and/or servers, including, but not limited to, computers, mobile devices, tablets, smart phones, cell phones, personal digital assistants, phablets, e-readers, smart watches, set-top boxes, internet streaming devices, gaming consoles, smart appliances, and/or any device with access to the internet and/or any network protocol. Workstation 506 can be used to access, read, generate, write, receive, and/or otherwise manipulate data and/or information accessible through Network(s) 510. Workstation 506 also can be used to perform system maintenance, updates, and/or optimizations.

Secure Server 504 can be a depository and/or processor of data from Host Monitoring Devices 502A-N, Remote Monitoring Devices 508A-N, Workstation 506, other devices (e.g., mobile devices (e.g., tablets, cellphones, smartphones, e-readers, phablets, and the like), wearables (e.g., smart watches, smart rings, workout monitors, electrocardiographs, bioimpedence sensors, breathing monitors, sleep monitors, posture monitors, habit detectors, temperature trackers, fabrics embedded with sensors, moisture detectors, etc.), set-top boxes, internet streaming devices, gaming consoles, smart appliances, any device with access to the internet and/or any network protocol, computers (e.g., laptops, desktops, personal computers, etc.), medical devices, heart rate monitors, activity trackers, pulse oximeters, accelerometers, gyroscopes, speedometers, pedometers, blood pressure readers, pump data for administration of other drugs, drug sensors (e.g., breathalyzers and sensors configured to measure intoxication or presence of drugs), continuous glucose monitors, and/or any desirable device), and/or any system connected to Network(s) 510 and/or Secure Server 504. Secure Server 504 can perform any function and/or operation that could be performed by host monitoring devices or remote monitoring devices (e.g., Process 100, Process 150, and/or any other method or process described in this disclosure), as well as other functions and operations. Likewise, any functionality herein ascribed to Secure Server 504 can also be performed by a host monitoring device or remote monitoring device. In some implementations Secure Server 504 can be software and/or hardware that requests and/or receives data from other devices or software. Secure Server 504 can include modules and/or other servers, including database servers, file servers, mail servers, print servers, web servers, application servers, etc. For example, Secure Server 504 can perform functions and/or operations substantially similar to Data Storages 209, 309, Data Managers 210, 310, Signal Processors 210, 310, and/or components of Operative Modules 204, 304. Secure Server 504 can also be communicatively and/or operatively coupled to any operative modules described in this disclosure, including, but not limited to, operative modules substantially similar to Operative Modules 204, 304, such as modules substantially similar to Locators 206, 306, Coordinators 212, 312, User Interfaces 208, 308, Communicators 207, 307, Sensors 205, 205, etc. Also, any of the functions and/or operations described with respect to Secure Server 504 can be performed by Data Storages 209, 309, Data Manager 210, 310, Signal Processors 210, 310, and/or components of Operative Modules 204, 304. In some implementations, Secure Server 504 can be replaced, and/or its functionality performed by, any other server, including an unsecure server.

In some implementations, Secure Server 504 can also provide a cloud-based data management framework that receives patient-related data from various devices, such as a medical device, a glucose meter, a continuous glucose monitor, a sensor system, a receiver, and/or other devices (e.g., a device providing food consumption, such as carbohydrates, consumed by a host or Remote Monitor, medicament delivery data, time of day, temperature sensors, exercise/activity sensors, and the like), including any device described in this disclosure. Furthermore, in some implementations, the cloud-based data management system can receive data programmatically with little (or no) intervention on the part of a user. The data received from devices, receivers, source systems, and the like can be in a variety of formats and can be structured or unstructured. For example, Secure Server 504 can receive raw sensor data from sensors (e.g., Sensors 205, 305, and sensors of other devices), which has been minimally processed or analyzed, and the received data can then be formatted, processed (e.g., analyzed), and/or stored in order to enable report generation by Secure Server 504. In addition to sensor data, the Secure Server 504 can also receive data from source systems, such as health care management systems, patient management systems, prescription management systems, electronic medical record systems, personal health record systems, and the like. Secure Server 504 can also receive any data described in this disclosure (e.g., analyte measurements, communications, Processed Data, Contextual Data, Health Data, System Data, Treatment Data, User Data, Sensor Data, Summary Data, and/or other data mentioned in this disclosure).

In some example implementations, Secure Server 504 can check received data for transmission-related errors, data formatting, device-related error codes, validity of the data, duplicate data points, and/or other aspects of the data. Moreover, if out-of-range data points or device errors are found, Secure Server 504 can identify those data points by, for example, flagging those data points, subsequently correcting the identified data points programmatically or by a system administrator, and storing the corrected data points. Moreover, Secure Server 504 can be configured by a user, such as a clinician, doctor, and the like, to perform additional data processing steps, such as correcting time of day, correcting the date, and/or analyzing data by specific cohorts, groups, and relationships (e.g., demographics, such as age, city, state, gender, ethnicity, Type I diabetes, Type II diabetes, age of diabetes diagnosis, lab results, prescription drugs being used, self-reported conditions of a patient (e.g., Host or Remote Monitor), diagnosed conditions of a patient (e.g., Host or Remote Monitor), responses to questions posed to a patient (e.g., Host or Remote Monitor), and/or any metadata representative of a patient (e.g., Host or Remote Monitor). Once Secure Server 504 performs initial data processing (e.g., checks, cleaning, and analysis), the processed and/or raw data can be stored at a repository operatively and/or communicatively coupled to the Secure Server 504, and/or stored within Secure Server 504 itself.

The processing at Secure Server 504 can also include associating metadata with the data received from the devices (e.g., Host Monitoring Devices 502A-N, Remote Monitoring Devices 508A-N, other devices, and/or any device disclosed in this disclosure), and/or sensors (e.g., Sensors 205, 305). Examples of metadata include patient information, keys used to encrypt the data, patient accelerometer data, location data (e.g., location of patient or location of patient's clinic), time of day, date, type of device used to generate associated sensor data, and the like. The patient information can include the patient's age, weight, sex, home address and/or any past health-related information, such as whether the patient has been diagnosed as a Type I or Type II diabetic, high-blood pressure, and/or as having any health condition. Secure Server 504 can include encryption of data. For example, Secure Server can use algorithms such as 128-bit or 256-bit keys and/or other encryption algorithms complying with standards such as the AES, RSA, DES, Triple DES, and the like.

The processing of Secure Server 504 can also include one or more of the following: analysis, such as determining one or more descriptive measurements; detecting or predicting events (e.g., a hypoglycemic, a hyperglycemic, and/or any other feature detected in the sensor data); applying pattern detectors to the received sensor data; and, generating reports based on received data. The descriptive measurements may include statistics (e.g., median, inner, and outer quartile ranges, mean, sum, standard deviation, and coefficients of variation). In some example implementations, Secure Server 504 can also associate metadata with the data received from the devices, sensors, source system, and/or receivers; determine one or more descriptive measurements, such as statistics (e.g., median, inner and outer quartile ranges, mean, sum, n, and standard deviation); generate reports including descriptive measurements; validate and/or verify the integrity of the received data from the devices, sensors, source system, and/or receivers; process received data based on metadata (e.g., to select certain patients, devices, conditions, diabetic types, and the like); and/or correlate received data from the devices, sensors, source system, and/or receivers so that the data can be compared and combined for processing including analysis. Moreover, the results of any processing performed by Secure Server 504 can be used to generate one or more reports, such as graphs, bar graphs, static charts, charts, and the like. Furthermore, the reports and other outputs generated by Secure Server 504 can be provided to Host Monitoring Devices 502A-N, Remote Monitoring Devices 508A-N, Workstation 506, any other device described in this disclosure, and/or any system connected to Network(s) 510 and/or Secure Server 504.

Secure Server 504 can be considered secure in the sense that it can keep private, patient identifiable information and/or restricts access to users registered and thus authorized to use Secure Server 504. For example, and without limitation Secure Server 504 can receive a request from a device (e.g., Host Monitoring Devices 502A-N, Remote Monitoring Devices 508A-N, Workstation 506, any other device described in this disclosure, and/or any system connected to Network(s) 510 and/or Secure Server 504) to perform an action (e.g., provide data, store data, analyze/process data, request a report, request configuration information, request registration, and the like). Before Secure Server 504 services the request, Secure Server 504 can process the request to determine whether the request is authorized and authenticated. For example, an authenticator and authorizer can determine whether a sender of a request is authorized by having a user provide a security credential (e.g., a user identifier, a password, a stored security token, and/or a verification identifier provided by text message, phone, or email) at a user interface presented on a device (e.g., Host Monitoring Devices 502A-N, Remote Monitoring Devices 508A-N, Workstation 506, any other device described in this disclosure, and/or any system connected to Network(s) 510 and/or Secure Server 504). Secure Server 504 can also consider the classification of the requester, if applicable. If authorized, authenticator and authorizer can authenticate the sender of the request to check whether a security credential associated with the sender of the request indicates that the sender is indeed permitted to access a specific resource at Secure Server 504 in order to perform the action, such as store (or upload) data at a repository, perform analyze/process data, request report generation, receive alerts, receive communications, and the like.

In some example implementations, Secure Server 504 can include a pattern detector to perform pattern detection on data, such as sensor data representative of glucose data, analytes, and/or other data (e.g., insulin pump data, carbohydrate consumption data, and the like). The pattern detector can detect the pattern and/or generate an output, which can be provided to a report generator at Secure Server 504 for generating a communication and/or display page to Host Monitoring Devices 502A-N, Remote Monitoring Devices 508A-N, Workstation 506, any other device described in this disclosure, and/or any system connected to Network(s) 510 and/or Secure Server 504.

Moreover, the pattern detector may detect patterns in data retrospectively for a predetermined time defined by Monitoring System 500 and/or a user. For example, the pattern detector can receive input data from a repository coupled to Secure Server 504, and the input data can include Sensor Data indicative of glucose concentration data, analytes, and/or other data (e.g., insulin pump data, carbohydrate consumption data, histograms and/or counts, data from a continuous glucose monitor (CGM data), time of day, amount of carbohydrates, other food related information, exercise, awake/sleep timer intervals, medications ingested, and the like). Moreover, the input data can include historical data obtained over a timeframe, such as 8 hours, 1 day, 2 days, 7 days, 30 days, and/or any other time period. For example, the input data may include counts representative of monitored analyte detection levels (e.g., glucose concentration levels) received and/or stored at Monitoring System 500 over a period covering a four-week timeframe.

To further illustrate the pattern detector, patterns can be recognized based on one or more predefined triggers (also referred to as criteria, rules, and filters). Furthermore, the one or more predefined triggers may be variable and adjustable based user input and/or programmatically based on one or more rules at Secure Server 504. And, some types of patterns may be selected, turned off and/or on, and/or modified by a user, a user's physician, and/or a user's guardian, although Monitoring System 500 can select, adjust, and/or otherwise modify triggers programmatically as well.

Some non-limiting examples of the types of relationships in the input data that can be considered a pattern are one or more of the following: a glucose level that exceeds a target glucose range (which may be defined by a user, a health care provider, Secure Server 504, Host Monitoring Devices 502A-N, Remote Monitoring Devices 508A-N, any device described in this disclosure, and/or a combination thereof); a glucose level that is below a target glucose range; a rapid change in glucose level from a low to a high (or vice versa); times of day when a low, a high, an at range, or rapid glucose level event occurs; days when a low, a high, an at range, and/or a rapid glucose level event occurs; a hyperglycemic pattern; a hypoglycemic pattern; patterns associated with a time of day or week; a weighted scoring for different patterns based on frequency, a sequence, and a severity; a custom sensitivity of a user; a transition from a hypoglycemic to hyperglycemic pattern; an amount of time spent in a severe event; a combination of glucose change and time information; and/or a pattern of high variability of glucose data. Such pattern recognition can be performed on any data described in this disclosure (e.g., analyte measurements, communications, Processed Data, Contextual Data, Health Data, System Data, Treatment Data, User Data, Sensor Data, Summary Data, and/or other data mentioned in this disclosure). Advantageously, more data types can provide context and further information on the health condition of the Host, as well as the Host's glucose level. Further, a pattern may be based on a combination of previous pattern data and a currently detected situation, whereby the combined information generates a predictive alert.

Hypoglycemic patterns by time of day may be detected based on events detected by Secure Server 504. For example, a pattern can be identified in situations where the user has low glucose concentrations around the same time in the day. Another type of pattern, which may be identified, is a "rebound high" situation. For example, a rebound high may be defined as a situation where a user overcorrects a hypoglycemic event by overly increasing glucose intake, thereby going into a hyperglycemic event. These events can be detected based on one or more predefined triggers.

To further illustrate examples of the patterns, basic patterns can be configured to allow a search for certain patterns in the data, such as values within range, high coefficient of variance, and the like. Each pattern can have one dimension, such as within range, with a separate pattern looking specifically for below range, another looking for low coefficient of variance, and the like. Each pattern can be statistically based and/or use standard descriptive statistics in the application of pattern matching. Each pattern can be assigned scores for various rules encoded with each pattern, such as is it positive, negative, how important an insight is, and the like. Each pattern can also be assigned a possible set of date ranges for which the pattern is applicable. For example, counting the number of times a high glucose value is followed by a low below range is a pattern that just applies to the full range. However, looking at high levels of variance can apply to a month, a week, a day, an intraday, every other hour, hourly, and combinations thereof. Each pattern can be assigned a minimally acceptable score before it can be considered for display or generation of an alert and/or notification message sent to one or more of Host Monitoring Devices 502A-N and/or Remote Monitoring Devices 508A-N. Each pattern (and any associated triggers/rules) may be processed for a set of data for a certain timeframe, and if the pattern is applied and meets certain minimal requirements, then the patterns are ranked according to significance. As such, the ranked patterns can each correspond to an alert and/or notification message sent to one or more of Host Monitoring Devices 502A-N and/or Remote Monitoring Devices 508A-N.

Connections can be established between one or more Remote Monitoring Devices 508A-N, either directly or through Network(s) 510, to provide additional layers of oversight into the operations of Host Monitoring Devices 502A-N and/or the care of Hosts associated with Host Monitoring Devices 502A-N. The connections to Remote Monitoring Devices 508A-N can be established based on invitations sent to Remote Monitoring Device 508A-N. These invitations can be sent with the consent of the respective Host Monitoring Devices 502A-N to be monitored and/or their associated Host. For example, Host Monitoring Device 502A and/or Remote Monitoring Device 508A can be requested to both accept invitations or to enter a code (e.g., a password, shared secret, and the like) in order to opt into Remote Monitoring System 500.

In some implementations, there can be various ways to send data and/or communications between Secure Server 504 and Remote Monitoring Devices 508A-N, Host Monitoring Devices 502A-N, and/or other devices. By way of illustrative example, Secure Server 504 can ping Remote Monitoring Device 508A (or any other Remote Monitoring Device 508B-N or Host Monitoring Device 502A-N) periodically (e.g., every 0.5, 1, 2, 3, 4, 5, 10, 15, 30, 45 and/or 60 minutes, or at any interval desirable, including any time between the aforementioned minutes). In some implementations, such as when Remote Monitoring Device 508A is a mobile device that runs a mobile application to monitor a Host, when the mobile application is open, it can request data (e.g., EGV data and/or any data described in this disclosure) from the server following the ping. However, when the mobile application is closed, it might not receive it in some cases. In such cases, there could be additional delays in receiving information, and/or information may not even be received, when the mobile application is later opened. To address such a situation, and/or where it is desirable, Secure Server 504 can send data (e.g., EGV data and/or any data described in this disclosure) in and/or with each ping. In this manner, whether Remote Monitoring Device 508A is asleep (e.g., idle) or awake (e.g., active), it can still receive current data.

In some implementations, Remote Monitoring Devices 508A-N, Host Monitoring Devices 502A-N, and/or other devices can receive real-time event information as a stream. In such cases, Remote Monitoring Devices 508A-N, Host Monitoring Devices 502A-N, and/or other devices can include a streaming component that can continuously or substantially continuously receive data regarding a Host.

In some implementations, the data generated by Secure Server 504 can be related to a page to be displayed at a user interface of Host Monitoring Device 502A-N and/or Remote Monitoring Device 508A-N. This page can include textual and/or a graphical indication of the status of the one or more Hosts being monitored, and/or textual and/or a graphical indication of the status of one or more Remote Monitors following a Host. Secure Server 504 can send the actual page that can be displayed, and/or send data for one or more of Host Monitoring Device 502A-N and/or Remote Monitoring Device 508A-N to generate such a page.

Figure 6:
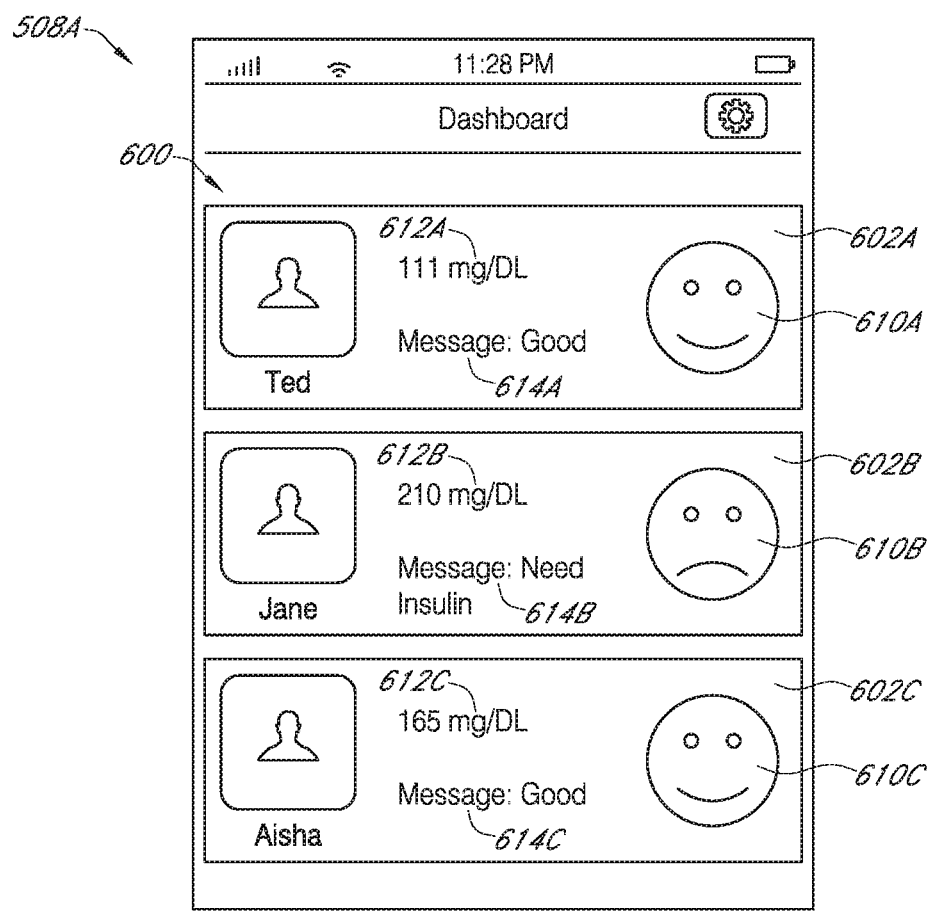
FIG. 6 illustrates an example page showing Host information that can be displayed on a remote monitoring device.

By way of illustrative example, a school nurse can have Remote Monitoring Device 508A, which can display a page depicting each of Host Monitoring Devices 502A-N that Remote Monitor 508A is monitoring. Each Host Monitoring Device 502A-N can be associated with a particular Host student who is associated with that host monitoring device. FIG. 6 illustrates an example page that can be displayed on a remote monitoring device in this example scenario. Page 600 can be displayed on Remote Monitoring Device 508A, which can be a smart phone and/or any remote monitoring device described in this disclosure. Page 600 can have the status information for each of the monitored students (e.g., Glucose Level 612A-C), the most recent notification message from each of the monitored students (e.g., Message 614A-C), an indication that the monitored student is within limits (e.g., Graphical Indication 610A,C), and/or an indication that the monitored student is not within limits (e.g., Graphical Indication 610B), and the like. For example, each student can be associated with a cell (e.g., a defined space on the page), such as Cells 602A-C. As such, the nurse can quickly view the user interface and see the status of each of the students being monitored. Graphical Indications 610A-C can be used to visually convey the overall status of each student in each student's cell. For example, a so-called "smiley" face icon can indicate the student's glucose levels (e.g., EGV) are within limits and a so-called "sad" face icon can indicate that student's glucose levels are of concern because they are above a threshold. Moreover, in some example implementations, Page 600 can be presented on a display (e.g., any display discussed in this disclosure), so that a selection using a user interface (e.g., any user interface described in this disclosure) of a cell, text, or graphical indication can result in additional information being displayed and/or provided to Remote Monitoring Device 508A. Although the previous example refers to glucose levels (e.g., EGV) and specific types of events, communications, and graphics, other types of events, communications, and/or graphics discussed herein may be used to convey the status of a Host.

In some implementations, selecting a cell of a monitored student (e.g., Cells 602A-C) can cause the Remote Monitoring Device 508A to access the Secure Server 504 and then receive additional data, such as one or more of current and prior glucose levels, patient information, and the like, and update the display page or transition to a new display page that displays information about the selected student in more detail (e.g., displaying a trend graph of the student's glucose level over the past three hours). Such data can also be stored locally on Remote Monitoring Device 508A. As another illustrative example, Page 600 can also be stored in memory on a server (e.g., Secure Server 504) and/or displayed on a display communicatively and/or operatively coupled to that server.

Figure 7A:
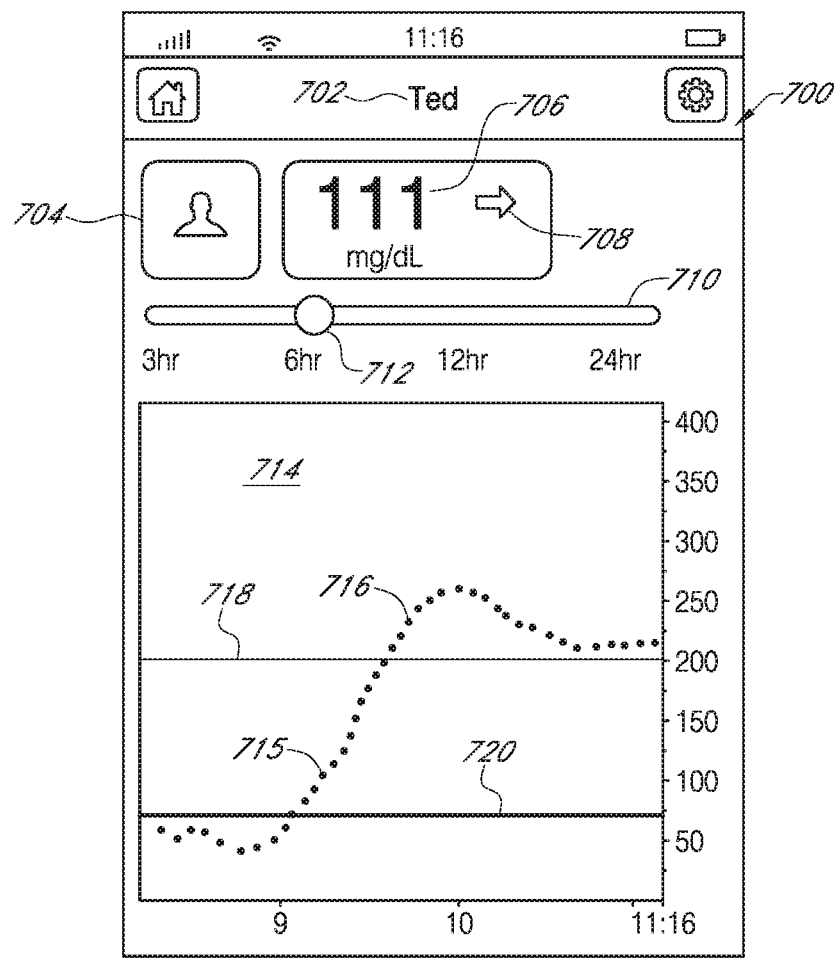
FIG. 7A illustrates an example display showing additional data regarding Host analyte measurements.

As a non-limiting example, FIG. 7A illustrates an example display showing additional data. When Cell 602A is selected, Page 700 can appear on Remote Monitoring Device 508A. In some cases, Page 700 can also be stored in memory on a server (e.g., Secure Server 504) and/or displayed on a display communicatively and/or operatively coupled to that server.

In some implementations, Page 700 can display Glucose Display 706 for Host 702. An image (e.g., picture, emoji, graphical representation, avatar, etc.) of Person 702 can appear as Image 704. Time Bar 710 can illustrate, and allow selection of, different windows of time for display in Display 714, which can display different points of measurements at different points in time (e.g., historical data) such as Glucose Measurements 715, 716. Display 714 can have axes that chart relevant information. For example, the y-axis can be glucose levels (e.g., EGV) in mg/dL, or other units, and the x-axis can be time. In this way, Display 714 can display historical data of a Host over time. Selected points in Display 714 can be displayed as Glucose Display 706. For example, Glucose Measurement 715 is displayed as illustrated in Glucose Display 706. Button 708, and similar buttons for navigation, can be used to display in Glucose Display 706 different points in Display 714. By hitting Button 708, later points can be displayed. By way of non-limiting example, each time Button 708 is hit, Glucose Display 706 can display the next glucose measurement in time (e.g., to the right). If Glucose Display 706 displays Glucose Measurement 715, pushing and/or holding a number of times (e.g., 1, 2, 3, 5, 11, and/or any other defined number) Button 708 can cause Glucose Display 706 to display Glucose Measurement 716. In some cases, the current glucose level can be displayed in Glucose Display 706.

Thresholds can be used for communications, in which the thresholds can be used to identify glucose measurements that when above or below those threshold, cause alerts, notifications, messages and/or other communications to be sent to one or more remote monitoring devices or other devices. These thresholds can be user configured or auto-populated, and typically coincide with the upper and lower bound of normal glucose levels. As a non-limiting example, Upper Threshold 718 can be a predetermined threshold, in which when glucose measurements (e.g., Glucose Measurement 716) fall above Upper Threshold 718, the Host for which those glucose measurements corresponds may have high glucose (e.g., hyperglycemia). In such a case, an alert, notification, message, and/or other communications can be sent to remote monitoring devices (e.g., Remote Monitoring Devices 508A-N), and/or displayed information on pages (e.g., Page 600) can be changed/updated (e.g., changing Graphical Indication 610A from a smiley face to a sad face). Lower Threshold 720 can be a predetermined threshold, in which when glucose measurements fall below Lower Threshold 720, the Host for which those glucose measurements corresponds may have low glucose (e.g., hypoglycemia). In such a case, an alert, notification, and/or other communications can be sent to remote monitoring devices (e.g., Remote Monitoring Devices 508A-N), and displayed information on pages (e.g., Page 600) can be changed/updated (e.g., changing Graphical Indication 610A from a smiley face to a sad face).

In some example implementations, pages (e.g., Page 600) can be configured as a so-called "dashboard" including dynamic content. For example, the icons for Hosts desiring the greatest care or attention (e.g., the Hosts with glycemic levels that are extremely high or low) can be arrange in the top row of page to allow the remote monitor to quickly ascertain the state of riskier Hosts. Although the previous arrangement described using the top row of the page to segregate some of the so-called riskier Host patients other segregation schemes can be used (e.g., different colors, intensities, and/or locations on the page). Furthermore, pages can be considered dynamic as Hosts desiring extra attention can change over time causing the page to depict different icons for different Hosts in the top row of the page, and/or any other indication. In some cases, some Hosts can be anonymous to some viewers (e.g., Hosts or Remote Monitors), where some or all of the identifying information of a Remote Monitor (e.g., name, serial number, etc.) can be not listed.

Figure 7B:
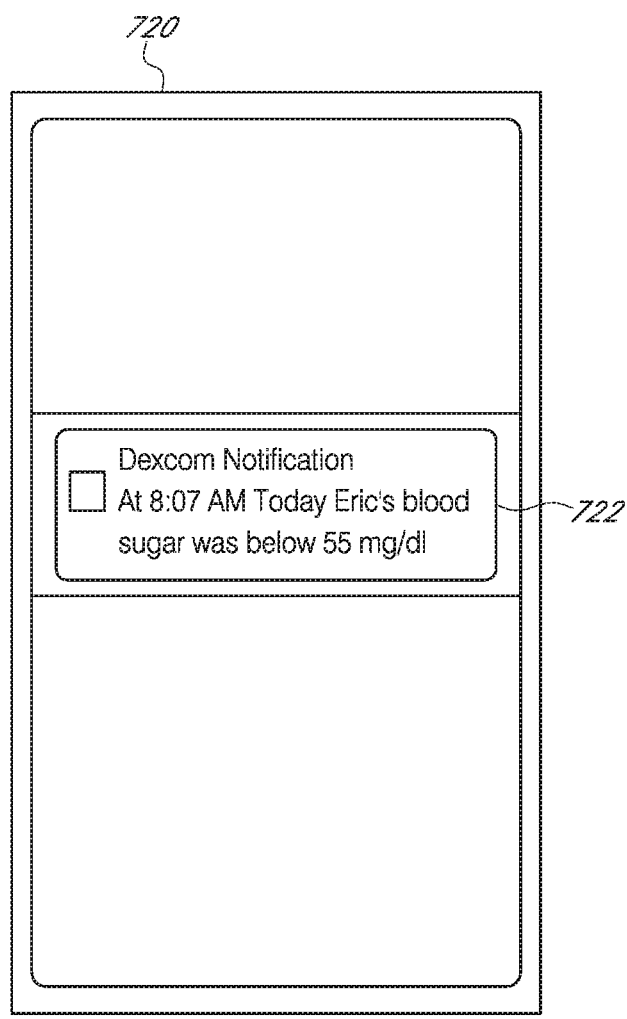
FIGS. 7B-C illustrate example communications that can be sent between a host monitoring device, remote monitoring device, and/or other devices.
Figure 7C:
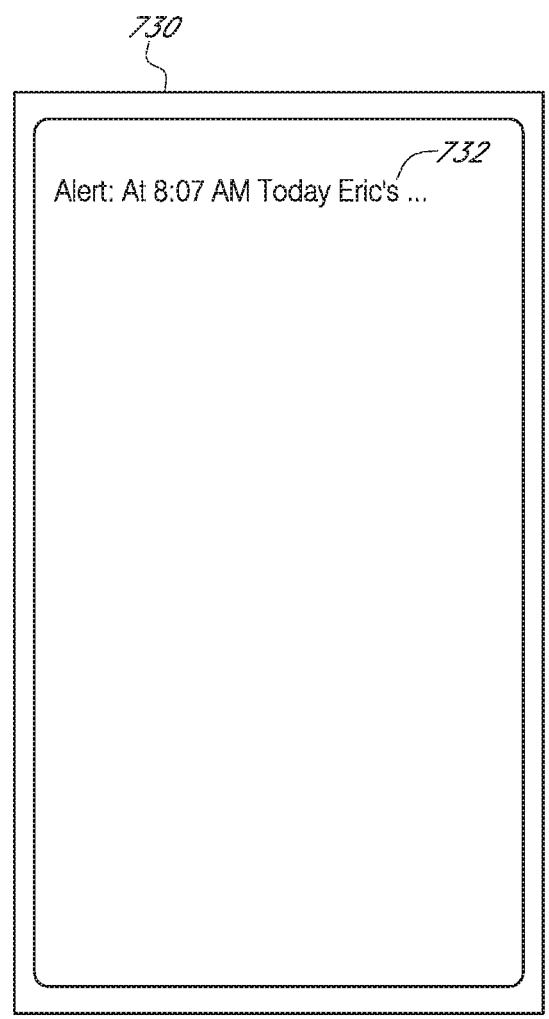

In some implementations, Remote Monitoring Device 508A-N can receive communications from Host Monitoring Device 502A-N. Such communications can, in addition to or in the alternative, be received and/or stored on Secure Server 504. FIGS. 7B-C illustrate example communications. Example Communication 722 can be presented on example Remote Monitoring Device 720, which can be substantially similar to any remote monitoring device described in this disclosure (e.g., Remote Monitoring Device 300). In some cases, Communication 722 can be received by a server (e.g., a server substantially similar to Secure Server 504), where Communication 722 is stored in memory on the server and/or displayed on a display operatively and/or communicatively coupled to the server. In some implementations, Remote Monitoring Device 720 and/or the server can include a touch screen as a user interface, where the touch screen is configured to display communications and graphics, and also configured to receive user (e.g., a Remote Monitor) inputs (e.g., responses). Notification 722 can appear as a window for user interaction when Remote Monitoring Device 720 and/or a server receive Notification 722. For example, a user interaction can include a Remote Monitor pressing a button on Remote Monitoring Device 300, touching the screen of Remote Monitoring Device 300 over an area associated with a portion of Notification 722, and/or activating (e.g., executing, opening, and the like) an application (e.g., program, mobile application, graphical user interface, user interface, etc.) at Remote Monitoring Device 720. In some implementations, Notification 722 can appear when another application (e.g., program, mobile application, graphical user interface, user interface, etc.) at Remote Monitoring Device 720 is actively being used. In such a scenario, Notification 722 can appear as a pop-up, tray symbol, audible signal, visual signal (e.g., light flash, turned-on light, brightened screen, etc.), vibration, and/or any other way of indicating that a notification has been received. There, a user interaction and/or response can include touching the screen over the area associated with a portion of Notification 722 to acknowledge receipt of Notification 722 before the user is allowed to resume the other application, although the user action can also preempt the other application and make the remote monitoring application the active application being viewed at Remote Monitoring Device 720. Moreover, the decision of whether to preempt the other application and/or resume the other application can be predetermined based on the severity level of the event, so that relatively more severe events can preempt the other application, while less severe events may not. In some implementations, Notification 722 can include time and/or location stamps for the Host, and/or time and/or location stamps for Remote Monitors.

FIG. 7C illustrates an example notification that may not request user interaction. Notification 732 can be presented on example Remote Monitoring Device 730, which can be substantially similar to any remote monitoring device described in this disclosure (e.g., Remote Monitoring Device 300). In some cases, Communication 732 can be received by a server (e.g., a server substantially similar to Secure Server 504), where Communication 732 is stored in memory on the server and/or displayed on a display operatively and/or communicatively coupled to the server. Notification 732 can be presented as a message and/or alert that appears in the user interface as an informational message that does not prompt intervention on the part of the user. Furthermore, when Notification 732 appears while another application is being used at Remote Monitoring Device 730, Notification 732 may not prompt the user (e.g., Remote Monitor) to acknowledge Notification 732, and/or even activate a remote monitoring application (which may be idle or inactive). In such cases, such lack of interruption can result in the continued use of the other application by the user. In some implementations, Notification 732 can include time and/or location stamps for the Host, and/or time and/or location stamps for Remote Monitors.

Other sorts of communications can be sent through communication channels. In some cases, with present technologies, Hosts and/or Remote Monitor(s) presently rely on outside communication channels to communicate with each other regarding the monitoring of a Host's health. Such outside communication channels can include phones, emails, texts, etc. In certain situations, using such outside communication channels may not only be inconvenient, but can also be unreliable for a variety of reasons outside the control of the health monitoring system. Such unreliability can also be platform specific, where certain devices have their own issues, compatibility problems, glitches, and/or other problems in communication. Accordingly, communications between Hosts and/or Remote Monitors (e.g., between a Host and a Remote Monitor, a Host and a Host, and/or a Remote Monitor and a Remote Monitor) and/or Secure Server 504 can include communications sent through Monitoring System 500. In some implementations, such communications can be sent in addition to or as an alternative to outside communication channels. Such communications can include user-entered data/messages and/or pre-populated data/messages that can be sent between one or more of Host Monitoring Devices 502A-N, Remote Monitoring Devices 508A-N, Network(s) 510, Secure Server 504, Workstation 506, and/or other devices. For example, such communications can appear as a pop-up and/or an inbox in software (e.g., a computer program or mobile application) run on Host Monitoring Devices 502A-N, Remote Monitoring Devices 508A-N, Network(s) 510, Secure Server 504, Workstation 506, and/or any other system described in this disclosure. In cases where glucose levels, Host and/or Remote Monitor data, and/or any process discussed in this disclosure are run through a software application on Host Monitoring Devices 502A-N, Remote Monitoring Devices 508A-N, Network(s) 510, Secure Server 504, Workstation 506, and/or other devices, communications can be sent via that same software application.

In some cases, such communications can be accumulated in one or more logs. Such logs can include communications from one or more persons (e.g., Hosts and/or Remote Monitors) and/or devices (e.g., Host Monitoring Devices 502A-N, Remote Monitoring Devices 508A-N, Network(s) 510, Secure Server 504, Workstation 506, and/or any other system described in this disclosure). These messages can be filtered and/or isolated for particular individuals or individual devices, and/or co-populated by a plurality of individuals and/or devices. In some cases, the contents of logs can be private to a particular device (e.g., one of Host Monitoring Devices 502A-N, Remote Monitoring Devices 508A-N, Network(s) 510, Secure Server 504, Workstation 506, and/or any other system described in this disclosure), and/or can be shared across a plurality of devices (e.g., a plurality of Host Monitoring Devices 502A-N, Remote Monitoring Devices 508A-N, Network(s) 510, Secure Server 504, Workstation 506, and/or any other system described in this disclosure). As a non-limiting example, a Host using Host Monitoring Device 502A can send a message (e.g., a communication) to one or more Remote Monitors using Remote Monitoring Devices 508A-N. Such a message can say, "I'm following my treatment" or other text. As another non-limiting example, a message (e.g., generated by a remote monitoring device, host monitoring device, or server) can be stored on Secure Server 504. Secure Server 504 can then send that message to another device, such as Remote Monitoring Devices 508A-N, Host Monitoring Devices 502A-N, Workstation 506, other servers, and/or other devices.

In some implementations, communications can be user-entered and/or prepopulated. For example, prepopulated messages can be based on patterns in analyte measurements and/or other data (e.g., communications, Processed Data, Contextual Data, Health Information, System Information, Treatment Information, User Data, Sensor Data, Summary Data, and/or other data mentioned in this disclosure). By way of illustrative example, Host Monitoring Device 502A can anticipate a lower glucose reading. From Contextual Data, such as an accelerometer and/or user-inputted data, Host Monitoring Device 502A can recognize that the Host is exercising. A prepopulated message may say to Remote Monitors, "I'm exercising," so that Remote Monitors know the context of the measurements. As another non-limiting example, a Host can select a prepopulated message out of a library of prepopulated messages. By way of illustration, a Host may send a message saying "I'm going to hang out with friends, but I'm being careful and have my insulin," to provide reassurance to Remote Monitors before the Host partakes in the activity. As another non-limiting example, prepopulated messages can generally say in a message what a Host will or will not do (e.g., treatment, activity, medicine, etc.).

A variety of communication tools can facilitate the flow of information between a Host and Remote Monitor(s) and increase the efficiency of conveying health information to positively affect the Host's health. Various techniques, as described herein, can be utilized to assist the Host and Remote Monitor(s) to better convey information, reduce errors, reduce monitor or host fatigue, save time and increase the passion and interest of all involved for engaging with the remote monitoring system.

For example, a smart keyboard can be utilized as a feature of the remote monitoring system. When interacting with the host remote monitoring device, or automatically, the smart keyboard can determine when a particular analyte condition (e.g., a low glucose condition) occurred or is present and generate a message to that effect. The messages can be kept short, friendly, colloquial and concise to convey information efficiently and without distraction (e.g., "Hey, I'm 60 and dropping"). On the Remote Monitor side, the smart keyboard feature can suggest or generate relevant responses of a similar character (e.g., "Did you treat?" or "How did you treat?"). Host responses can be logged as events as described herein. In some embodiments, the host monitoring device and the remote monitor can include a virtual assistance feature, for example in the form of a text bot. The virtual assistance can have access to relevant data and may be situationally aware. The virtual assistant can ask questions, offer decision support or suggestions to the Host or Remote Monitor(s) based on the information gathered, the underlying Host and/or Remote Monitor data and generate appropriate messages to be logged or transmitted between the Host and Remote Monitor(s).

In some cases, smart or dynamic sticker packs may be supported in the remote monitoring devices (of Host or Remote Monitors). Some Remote Monitors, as described herein, may utilize SMS text messages and emoji for communications with the Host. Sticker packs can utilize images to convey information more efficiently than text alone. Additionally, sticker packs may be interactive, allowing the Remote Monitors and Host to collaborate in a visually pleasing medium for building a health management or treatment strategy. In some embodiments, the remote monitoring devices of the Host and Remote Monitors can offer diabetes sticker packs for common issues and responses (e.g., low glucose, dropping or rising glucose values, need for ingesting carbs, waiting a predetermined time, emotional venting about the challenges of living with diabetes). Dynamic sticker packs can also be incorporated, for example via smart keyboards as described herein. Dynamic stickers can convey dynamic information about glucose level and its future trends. For example, one dynamic sticker can be a circle and an arrow on the perimeter of the circle, where a current glucose reading is displayed in the center of the circle and the location of the arrow on the perimeter of the circle can indicate a projection of a future direction of glucose values. Other dynamic stickers can be visuals conveying insulin on board (JOB) value, trend graphs or other visuals relevant to management of diabetes. To further simplify and facilitate efficient communication between the Host and Remote Monitors, relevant stickers or visuals based on present conditions can be offered to the Host and Remote Monitors. For example, when a low glucose value is detected, visuals or stickers relevant to the low glucose condition (e.g., a visual instructing consumption of carbs) can be presented in a convenient fashion for the Remote Monitor to choose to include in its communication with the Host. In a communication session, for example, via SMS, the Host and Remote Monitor can utilize visuals, dynamic visuals, stickers, text, emoji or other available communication tools to collaboratively build a treatment strategy.

In some embodiments, an application running on the remote monitoring devices can support wearable smart devices such as smart watches, smart glasses or similar devices to communicate rich notifications, allowing the Host and/or the Remote Monitor to quickly communicate without having to navigate or hunt for information through complicated menus. Intuitive graphical design interfaces can be used to deliver real-time or near real-time event sharing between the Host and Remote Monitor using rich notification techniques. For example, a dashboard view can provide quick glance overview of key health parameters important to diabetes patients (e.g., current glucose values, projected trends, charts, etc.). Rich notification techniques can be used, for example via a slide down menu on a smart wearable device (e.g., a smart watch), where dynamic notifications, such as current location of the Host or Remote Monitor, can be viewed. Frequently accessed menu options may also be integrated within a slide down application menu on a smart wearable device for efficient access. For example, the Remote Monitor can choose between options such as acknowledging notifications, calling the Host or texting the Host via the slide down application menu. As described herein, prepopulated and frequently used messages may be made available to the Host and Remote Monitors to select without having to type or dictate these messages (e.g., "Are you OK?" or "I took care of it."). Prepopulated text messages or graphics facilitate easy and efficient communication between all involved to better manage diabetes or other health issues.

A feature of the disclosed remote monitoring systems described herein is the real time or near real time sharing of Host data with Remote Monitors. Accordingly, communications between the Host and Remote Monitors can benefit from instant or near instant sharing of messages including suggestions and/or encouragements. For example, customized or personalized messages can be generated and presented to the Host and Remote Monitors to encourage healthy behavior and provide community and support as the Host and loved ones deal with the challenges of managing diabetes or other health conditions. The process can encourage other Remote Monitors (e.g., family members) who may be at risk to adopt healthy behavior and understand the challenges. As described, the customized or personalized messages may be short, friendly, colloquial and concise (e.g., "Your numbers look great today! Thanks, Dad."). Suboptimal results can also trigger alerts to Remote Monitors (e.g., health coaches, family members, health care professionals, etc.). In some embodiments, personalized dashboards maybe used to track and hold the Host accountable. Undesirable trends can trigger personalized "social"

alerts, video calls, voice calls, text messages, social media posts, etc. to influence Host's health trends in a healthy direction.

Figure 8:
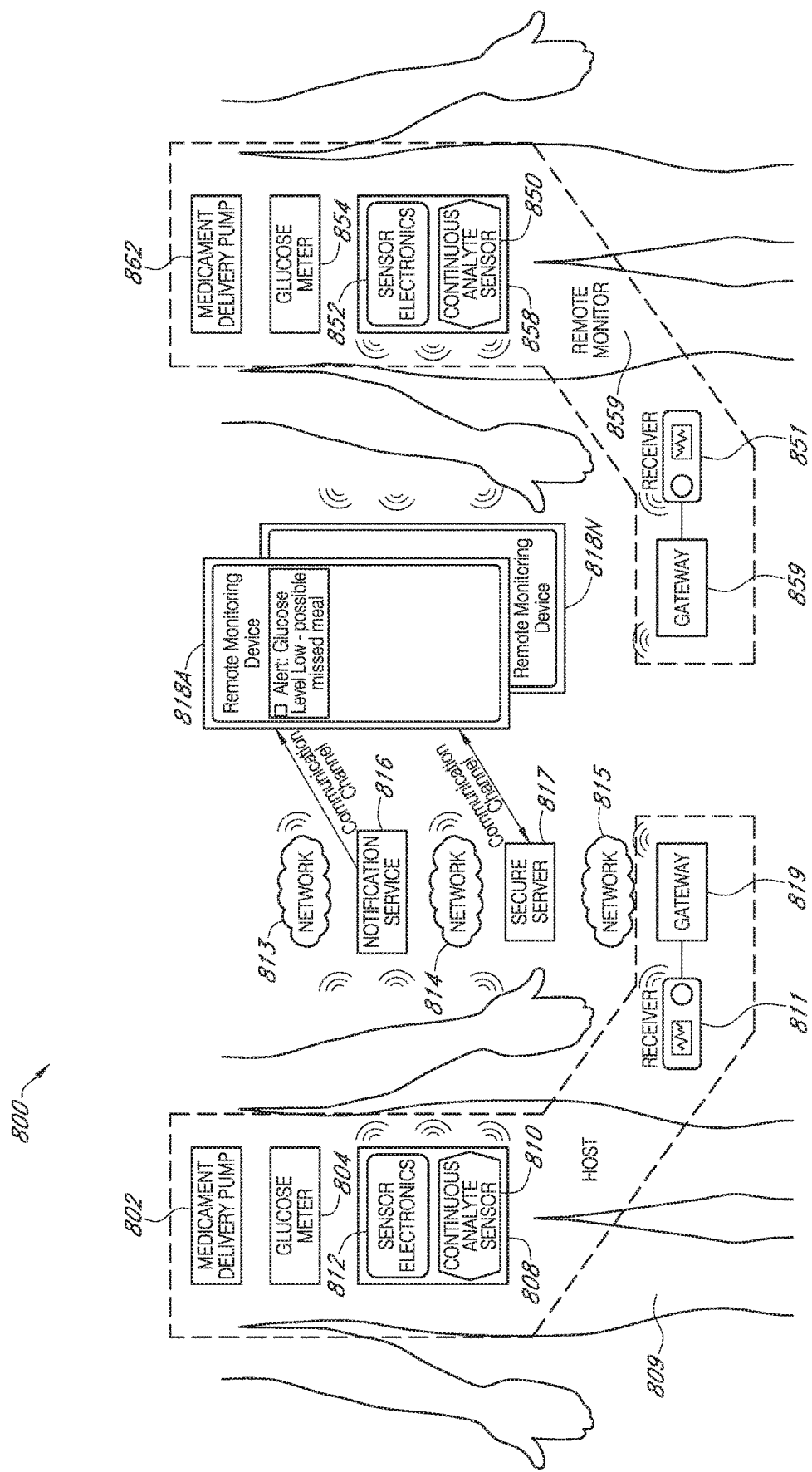
FIG. 8 illustrates a graphical depiction of an example system having a host monitoring device, a plurality of remote monitoring devices, a secure server, and networks.

FIG. 8 illustrates a graphical depiction of an example system having a host monitoring device, a plurality of remote monitoring devices, a server, and networks. Monitoring System 800 can include Host 809. Host 809 can have a plurality of devices. For example, Host 809 can have Medicament Delivery Pump 802, which can be configured to deliver a medicament such as insulin (e.g., a glucagon pump). Host 809 can also have Glucose Meter 804 (e.g., a blood finger stick meter), and/or any other device and/or sensor. Host 809 can also have Host Monitoring Device 808, which can include Sensor Electronics 812, Continuous Analyte Sensor 810, and/or any component substantially similar to Host Monitoring Device 200.

In some implementations, Host Monitoring Device 808 can communicatively couple (e.g., wirelessly, wired, and/or the like) with one or more devices, such as Receiver 811 and the like, presenting (and/or alerting) information, such as sensor information transmitted by Host Monitoring Device 808 for display at Receiver 811. Receiver 811 can be a separate component or integrated into Host Monitoring Device 808. Receiver 811 can include one or more interfaces, such as machine-to-machine interfaces and/or user interfaces. For example, such user interfaces can include a variety of interfaces, such as any of the interfaces described with respect to User Interface 208. The components that include the user interface may provide controls to interact with the user (e.g., the Host). One or more buttons can allow, for example toggle, menu selection, option selection, status selection, yes/no response to on-screen questions, a "turn off" function (e.g., for an alert), a "snooze" function (e.g., for an alert), a reset, and/or the like. A display (e.g., a LCD screen or any other display described in this disclosure) can provide the user with, for example, visual data output. An audio transducer (e.g., a speaker) can provide audible signals in response to triggering of certain alerts, such as present and/or predicted hyperglycemic and hypoglycemic conditions. In some example implementations, audible signals can be differentiated by tone, volume, duty cycle, pattern, duration, and/or the like. In some example implementations, the audible signal can be configured to be silenced (e.g., snoozed or turned off) by pressing one or more buttons of Receiver 811 and/or by signaling the Sensor Electronics 812 using a button or selection on Receiver 811. Receiver 811 can be communicatively and/or operatively coupled to Gateway 819, which can give network access to Receiver 811.

Medicament Delivery Pump 802, Glucose Meter 804, Host Monitoring Device 808, Receiver 811, and/or Gateway 819 can each be communicatively coupled to one or more networks, such as Networks 813, 814, 815. In some cases, there can be other modes of communication, such as notification services (e.g., Notification Service 816), which can be configured to transmit communications, such as notifications, alerts and/or other communications described in this disclosure. Capabilities of those other modes of communications can also be incorporated into Networks 813, 814, 815.

In example implementations, Secure Server 817 (which can be substantially similar to Secure Sever 504) can receive a communication (e.g., notification and/or message) from Notification Service 816, and/or otherwise (e.g., directly from Remote Monitoring Device 818A-N and/or Host Monitoring Device 808) that a remote monitoring device is out of service or otherwise unreachable, in which case, Secure Server 817 can resend the notification and/or message to a different remote monitoring device. By way of illustrative example, suppose there are Remote Monitoring Devices 818A-N. Remote Monitoring Device 818A had a malfunction and was unreachable. Secure Server 817 could resend any notification and/or message that was supposed to go to Remote Monitoring Device 818A to Remote Monitoring Device 818B. Similarly, where a device (e.g., Remote Monitoring Device 818A-N and/or Host Monitoring Device 808) is unable and/or unavailable to send a communication, Secure Server 817 can send such communication. For example, Remote Monitoring Device 818A could request a previous analyte measurement from Host Monitoring Device 808. However, in this example, Host Monitoring Device 808 could be temporarily unavailable (e.g., due to network and/or device issues). Secure Server 817 could have stored in memory Host Monitoring Device 808's previous analyte measurement and send it to Remote Monitoring Device 818A.

Secure Server 817 can use a delay for resending communications (e.g., notifications, alerts, messages, and/or any other communication described in this disclosure). Such a delay can be configured based on the severity and/or type of the event, and/or Secure Sever 817 can also include rules defining a predetermined quantity of unsuccessful resends (e.g., 1, 2, 3, 4, 5, 6, or more resends) before escalation to another remote monitoring device, a secondary/backup monitor, an emergency medical service, and the like. And, this predetermined quantity of unsuccessful resends can also be configured at Secure Server 817 to vary based on severity and/or type of the event and/or be user configured.

In some implementations, as described in this disclosure, additional information about a Remote Monitor can also be desirable in order to provide better care for a Host and/or to enhance relationships between Hosts and/or Remote Monitors. In some cases, a Remote Monitor in one system can even be a Host him/her self in the same system and/or another system. In some cases, the Remote Monitor may not be a Host per se, but provide data from his/her devices to a server, host monitoring device, and/or other devices. These other devices can provide context and/or allow a monitoring system to adaptively and/or contextually adjust communication settings (e.g., frequency, type, kind, etc.) and/or classifications based on such data from the Remote Monitor's devices.

Example Remote Monitor 859, who can be associated with one or more of Remote Monitoring Devices 818A-N can also have devices communicatively coupled to Remote Monitoring Devices 818A-N, Networks 813, 814, 815, Secure Server 817, Notification Service 816, Medicament Delivery Pump 802, Glucose Meter 804, Host Monitoring Device 808, and/or any device in Monitoring System 800. For example, Remote Monitor 859 can have Medicament Delivery Pump 862, which can be configured to deliver a medicament such as insulin (e.g., a glucagon pump). Remote Monitor 859 can also have Glucose Meter 854 (e.g., a blood finger stick meter), and/or any other device and/or sensor. Remote Monitor 859 can also have Device 858, which can include Sensor Electronics 852, Continuous Analyte Sensor 850. Remote Monitor 859 can also have other devices, such as health rate monitors, activity trackers, pulse oximeters, wearables (e.g., smart watches, smart rings, workout monitors, electrocardiographs, bioimpedance sensors, breathing monitors, sleep monitors, posture monitors, habit detectors, temperature trackers, fabrics embedded with sensors, moisture detectors, etc.), accelerometers, gyroscopes, speedometers, pedometers, blood pressure readers, pump data for administration of other drugs, drug sensors (e.g., breathalyzers and sensors configured to measure intoxication or presence of drugs), medical devices, and/or other devices that measure a characteristic of the Remote Monitor and/or is described in this disclosure.

Figure 9:
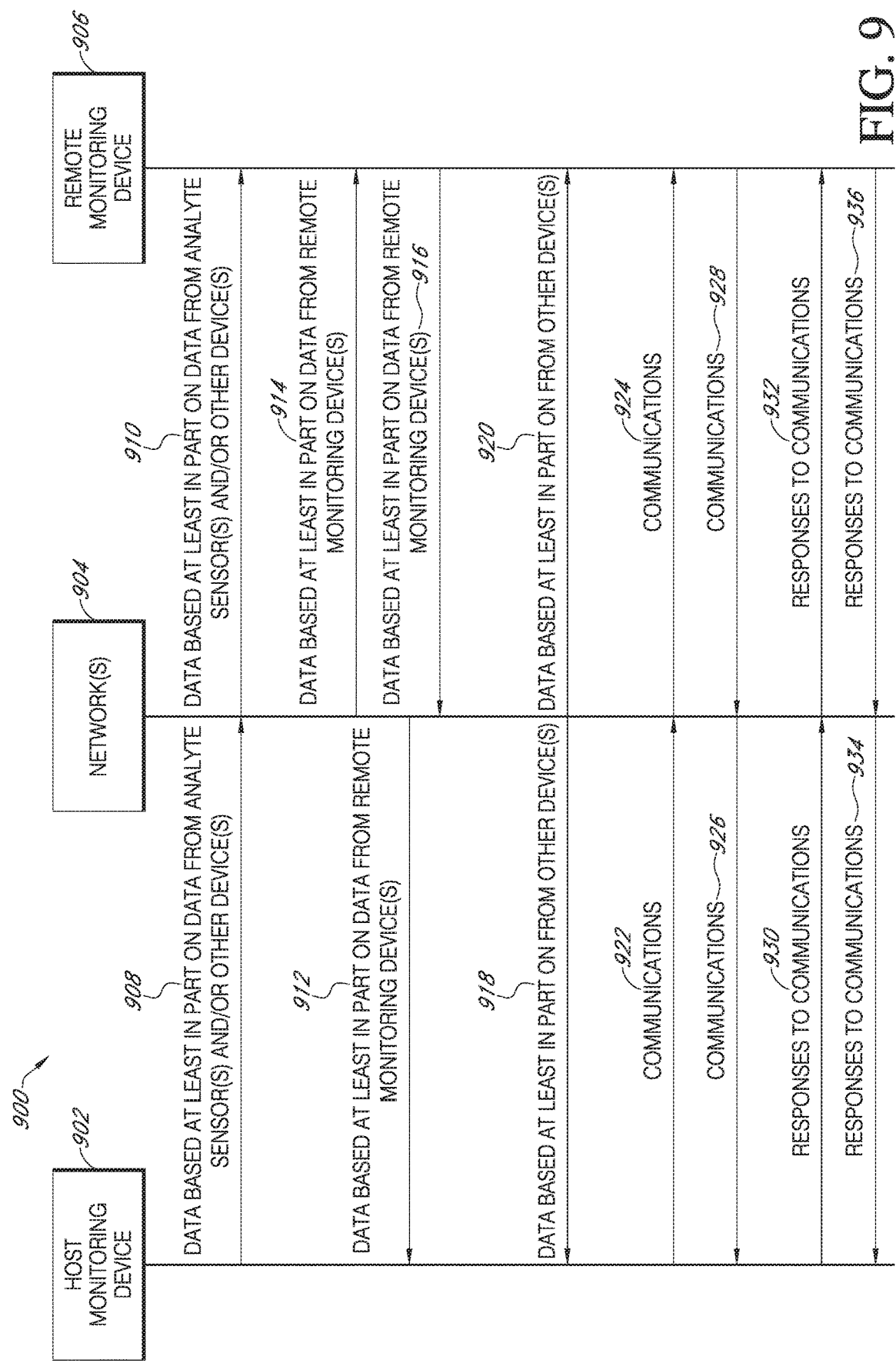
FIG. 9 illustrates a diagram showing example signals transmitted between a host monitoring device, network(s), and a remote monitoring device.

FIG. 9 illustrates a diagram showing example signals transmitted between a host monitoring device, network(s), and a remote monitoring device. Example Monitoring System 900 includes Host Monitoring Device 902, Network(s) 904, and Remote Monitoring Device 906. In some implementations, Host Monitoring Device 902 can be substantially similar to Host Monitoring Device 200 and/or any host monitoring device mentioned in this disclosure, and/or can be configured to perform processes similar to Process 100 and other processes described in this disclosure. Similarly, in some implementations, Remote Monitoring Device 906 can be substantially similar to Remote Monitoring Device 300 and/or any remote monitoring device mentioned in this disclosure, and/or can be configured to perform processes similar to Process 150 and other processes described in this disclosure. Communications (e.g., data, information, messages, notifications, alerts, responses, signals, etc.) can pass between Host Monitoring Device 902, Network(s) 904, and/or Remote Monitoring Device 906. Host Monitoring Device 902 and/or Remote Monitoring Device 906 can use communicators (e.g., communicators substantially similar to Communicators 207, 307) for such communications. Network(s) 904 can be substantially similar to Network(s) 510 and/or any network(s) described in this disclosure, and can also include a server (e.g., a server substantially similar to Secure Server 504 and/or any other server described in this disclosure) and/or a workstation (e.g., a workstation substantially similar to Workstation 506 and/or any other workstation described in this disclosure). Network(s) 904 can communicatively and/or operatively couple to a server (e.g., a secure server substantially similar to Secure Server 504) and/or a processor to process, relay, and/or store data and/or information it receives and/or sends.

In some cases, it can be desirable that signals are not immediately or substantially immediately (e.g., as quickly as the signal can be processed and/or sent) passed from Host Monitoring Device 902 to Remote Monitoring Device 906. For example, a Host associated with Host Monitoring Device 902 can sometimes address the subject of an alert to Remote Monitoring Device 906 relatively quickly and/or inconsequentially without involving the Remote Monitor associated with Remote Monitoring Device 906. By way of illustrative example, Host Monitoring Device 902 could send an alert that shows a low glucose level that could cause a Remote Monitor associated with Remote Monitoring Device 906 unwarranted concern and worry, and could suggest that the Host associated with Host Monitoring Device 902 could need immediate assistance. However, that Host may have already realized the issue and could immediately eat something to raise his/her glucose in response, making the low glucose level a non-issue. In such cases, it may be desirable to delay or prevent alarming notifications from going to Remote Monitoring Device 906 where such issues are already addressed.

As another example, a Host may not want to cause disruption or worry to Remote Monitors when an alert has been addressed and/or treated by the Host. For example, some alert settings may be programmed "conservatively," where an alert is more easily triggered by a glucose concentration measurement not within, but close to, upper or lower threshold glucose measurements, a duration of measurements threshold, or by a defined combination of measurement and duration. If the Host has addressed his/her situation, he/she may want to shield the Remote Monitors from being alerted to a situation under control/managed.

In some implementations, an intentional delay can be built into signal transmission between Host Monitoring Device 902, Network(s) 904, and/or Remote Monitoring Device 906. By way of illustration, Network(s) 904 can have a built-in delay (e.g., a delay stored in a server and/or other network hardware and/or software) where after signals are received by Network(s) 904 from Host Monitoring Device 902 and/or Remote Monitoring Device 906, Network(s) 904 does not immediately (and/or substantially immediately) send a corresponding communication. Rather, Network(s) 904 can delay a predetermined amount of time. Such predetermined amount of time can be set by a Host through Host Monitoring Device 902, a Remote Monitor through Remote Monitoring Device 906, factory programming, hardcoding, firmware and/or software, operators, Network(s) 904, and/or any way of adjusting an operational parameter. As non-limiting examples, such delays can be seconds (e.g., 0, 1, 5, 10, 15, 20, 25, 30, or more seconds, or any amount of time between the aforementioned seconds), minutes (e.g., 0, 1, 5, 10, 15, 20, 25, 30, or more minutes, or any amount of time between the aforementioned minutes), or hours (e.g., 0, 1, 5, 10, 15, 20, 25 or more hours, or any amount of time between the aforementioned hours). In some cases, different delays can be used for different events. In those cases, enough time can be given for a reasonable Host to respond. This amount of time can take into account context (e.g., Contextual data), patterns in Host or Remote Monitor behavior, time of day, and/or other factors. For example, after receiving from Host Monitoring Device 902 a low glucose measurement and an alert of such around lunch time, Network(s) 904 can delay 30 minutes to see if Host's glucose increases (e.g., by eating something). If no increase has occurred, Network(s) 904 can forward on a notification telling Remote Monitoring Device 906 that Host Monitoring Device 902 has a low glucose measurement and may need assistance. If an increase has occurred, Network(s) 904 can forward on the data, but not give an alert or say that the Host may need assistance.

As another non-limiting example, a Host can have a glucose level spike after dinner every day that reduces within an hour of the spike without consequence. By recognizing the daily pattern of that spike, Network(s) 904 can delay sending any notifications that would alert a Remote Monitor of the spike until more than an hour has passed and the glucose level has not reduced as it typically would.

In some implementations, the delay can be event-triggered instead of based on time. For example, Host Monitoring Device 902, Network(s) 904, and/or Remote Monitoring Device 906 can wait for a certain number of measurements with a determined characteristic (e.g., above or below a threshold) before sending a communication. By way of illustrative example, Host Monitoring Device 902 could have an analyte measurement below a lower threshold of analyte measurements. A communication based on this low measurement may not be sent immediately and/or substantially immediately. Instead, a Host Monitoring Device 902 can wait until five (5) (or any determined number of measurements) analyte measurements below the lower threshold have been measured, and if that event occurs, then send the communication. A similar process can be performed by a Remote Monitoring Device and/or Network(s) 904.

In some implementations, Network(s) 904, Host Monitoring Device 902 and/or Remote Monitoring Device 906 can have substantially similar delays. For example, Remote Monitoring Device 906 can delay sending a communication at the front end. Similarly, Remote Monitoring Device 906 can delay displaying a received communication at the back end. Network(s) 904, including a server, can hold onto communications before relaying them to Remote Monitoring Device 906 and/or Host Monitoring Device 902.

For example, the delay can be threshold-based where a host monitoring device (e.g., a host monitoring device substantially similar to the Host Monitoring Device 902, 502 or other) generates an alert for the Host when the Host's analyte level is determined to exceed a first threshold (e.g., a moderate threshold to generate an alert to the Host) but not a second threshold (e.g., an extreme threshold indicative of a dangerous analyte level). In such instances, for example, a server (e.g., a secure server substantially similar to Secure Server 504) may receive the alert from the Host Monitoring Device and/or may generate the alert based on the analyte data received by the server from the host monitoring device. The server will delay providing notifications to the remote monitoring devices pertaining to Host's analyte level exceeding the first threshold, for a predetermined amount of time. This may allow the Host to take action regarding his/her analyte level and can alleviate the need for having to provide the notification to the remote monitoring device(s). In such instances, the server can monitor the Host's response to the alert by monitoring the Host's analyte level after the alert. For example, if the Host's analyte level returns to a level that does not exceed the first threshold, then the server can close the alert and not generate any notifications to the remote monitoring device(s). If, for example, the Host's analyte level does not return to a level that does not exceed the first threshold (e.g., remains exceeding the first threshold), then the server can provide the notifications to the remote monitoring device(s) based on the notification rules associated with the respective remote monitoring device(s). In some implementations, for example, the server can send a communication to the Host to remind the Host to take an action associated with the analyte level or to prompt a response from the Host to acknowledge he/she is aware of the alert and/or is taking action to remedy the analyte level exceeding the first threshold. In such instances, for example, if the Host responds and confirms that action has been taken, then the server can continue the delay (e.g., within the predetermined period and/or provide an extension period of delay) and monitor the Host's monitoring the Host's analyte level to make sure it returns to a level not exceeding the threshold. If the analyte level does not return to a level not exceeding the threshold in the predetermined time period or extension period, the server can send a follow up communication (e.g., reminder or prompt for response) to the host monitoring device, and/or the server can remove the delay and reinitiate the process to notify the appropriate remote monitoring device(s). In this example, the system can keep non-urgent alerts private to the Host, which can avoid unnecessarily disturbing the Remote Monitors.

Host Monitoring Device 902 can generate Signal 908 and send Signal 908 (e.g., via a communicator such as Communicator 207) to Network(s) 904, which may also receive Signal 908 via a communicator substantially similar to Communicators 207, 307. Signal 908 can include data based on data from analyte sensor(s) and/or other device(s). For example, analyte sensor(s) can include glucose levels measured by a CGM and/or other sensor(s). The analyte sensor(s) or other device(s) can generate data including, Contextual Data (e.g., time/amount/type of medicament (e.g., insulin, sulfonylureas, biguanids, meglitinides, thiazolidinediones, DPP-4 inhibitors, SGLT2 inhibitors, alpha-glucosidase inhibitors, bile acid sequestrants, and/or other drugs or treatments) taken, time/amount/type of food (e.g., carbohydrates, protein, dairy, fat, fruits, vegetables, candy, dessert, sugars, calories, quantities, preparations, etc.) ingested, time/amount/type of exercise or activity undertaken (e.g., running, walking, sports, weight lifting, sitting, sleeping, idle, resting, etc.), level of stress felt (e.g., acute, episodic acute, emotional, chronic, high stress, medium stress, low stress, no stress, anxiety, panic attack, etc.), environment (e.g., weather, humidity, pressure, temperature, etc.) and/or location, time of day, and/or any other Contextual Data), Processed Data, Health Data, System Data, Treatment Data, User Data, Sensor Data, Summary Data, and/or any data described in this disclosure, and/or patterns and/or combinations of any of the aforementioned. Signal 908 can include such generated data, or data based on such generated data. Network(s) 904 can receive Signal 908 and store, relay, and/or process Signal 908.

Signal 910 can include data based on data from analyte sensor(s) and/or other device(s), such as data based on Signal 908 received by Network(s) 904. Remote Monitoring Device 906 can receive Signal 910 via a communicator.

In some cases, Signal 910, and other signals discussed with reference to FIG. 9, can be adaptive and/or contextual, in which certain events, measurements, and/or patterns of the foregoing allow for signals to be sent. For example, signals can be sent in response to measurements above or equal to a certain threshold, measurements below or equal to a certain threshold, determined amounts of oscillations, particular rates of change (e.g., fast rising or fast falling measurements), outliers, stability over a determined time (e.g., measurements falling within a defined range), activities (e.g., working out, eating, homework, walking, etc.), events (e.g., rock concert, movie, etc.), patterns in other data (e.g., in response to measurements of heart rate, temperature, acceleration, and/or any other data from any device described in this disclosure), and the like.

Remote Monitoring Device 906 can send Signal 916, which can include data based on data from Remote Monitoring Device 906. Such data from Remote Monitoring Device 906 can include data about the Remote Monitor including, but not limited to, data based on data from analyte sensor(s) and/or other device(s). For example, analyte sensor(s) can include glucose levels measured by a CGM and/or other sensor(s). The analyte sensor(s) and/or other device(s) can generate data including, Contextual Data (e.g., time/amount/type of medicament (e.g., insulin, sulfonylureas, biguanids, meglitinides, thiazolidinediones, DPP-4 inhibitors, SGLT2 inhibitors, alpha-glucosidase inhibitors, bile acid sequestrants, and/or other drugs or treatments) taken, time/amount/type of food (e.g., carbohydrates, protein, dairy, fat, fruits, vegetables, candy, dessert, sugars, calories, quantities, preparations, etc.) ingested, time/amount/type of exercise or activity undertaken (e.g., running, walking, sports, weight lifting, sitting, sleeping, idle, resting, etc.), level of stress felt (e.g., acute, episodic acute, emotional, chronic, high stress, medium stress, low stress, no stress, anxiety, panic attack, etc.), environment (e.g., weather, humidity, pressure, temperature, etc.) and/or location, time of day, and/or any other Contextual Data), Processed Data, Health Data, System Data, Treatment Data, Summary Data, Sensor Data, and/or any data described in this disclosure, and/or patterns and/or combinations of any of the aforementioned. Similarly, Network(s) 904 can receive data based on data from each of the respective other remote monitoring device(s). Accordingly Network(s) 904 can receive Signal 908 and/or data from any other remote monitoring device(s), and store, relay, and/or process Signal 908 and/or data from any other remote monitoring device(s).

Network(s) 904 can then send Signal 912 to Host Monitoring Device 902. Signal 912 can include data based on data from remote monitoring device(s), such as Remote Monitoring Device 906 and/or any other remote monitoring device. Similarly, Network(s) 904 can send Signal 914 to Remote Monitoring Device 906, where Signal 914 can include data based on data from other remote monitoring device(s).

Hosts associated with Host Monitoring Device 902 and Remote Monitors associated with Remote Monitoring Device 906 each can have one or more other device(s) that can be communicatively coupled (e.g., via communicators substantially similar to Communicators 207, 307) directly to Host Monitoring Device 902 and/or Remote Monitoring Device 906, respectively, and/or coupled to Network(s) 904. In the case where those other device(s) are coupled to Network(s) 904 (and/or may or may not be coupled to Host Monitoring Device 902 and/or Remote Monitoring Device 906 directly), those devices can send data to Network(s) 904, including, Contextual Data (e.g., time/amount/type of medicament (e.g., insulin, sulfonylureas, biguanids, meglitinides, thiazolidinediones, DPP-4 inhibitors, SGLT2 inhibitors, alpha-glucosidase inhibitors, bile acid sequestrants, and/or other drugs or treatments) taken, time/amount/type of food (e.g., carbohydrates, protein, dairy, fat, fruits, vegetables, candy, dessert, sugars, calories, quantities, preparations, etc.) ingested, time/amount/type of exercise or activity undertaken (e.g., running, walking, sports, weight lifting, sitting, sleeping, idle, resting, etc.), level of stress felt (e.g., acute, episodic acute, emotional, chronic, high stress, medium stress, low stress, no stress, anxiety, panic attack, etc.), environment (e.g., weather, humidity, pressure, temperature, etc.) and/or location, time of day, and/or other Contextual Data), Processed Data, Health Data, System Data, Treatment Data, User Data, Sensor Data, Summary Data, and/or any data described in this disclosure, and/or patterns and/or combinations of any of the aforementioned. Network(s) 904 can receive such data from those device(s) and/or store, relay, and/or process that data. Network(s) 904 can then send Signal 918 to Host Monitoring Device 902. Signal 918 can include data based on data from those other device(s). Similarly, Network(s) 904 can send Signal 920 to Remote Monitoring Device 906, where Signal 920 can include data based on data from those other device(s).

As mentioned in this disclosure, in some implementations, communications (e.g., notifications, messages, alerts, and/or any communications described in this disclosure, including but not limited to communications discussed with reference to FIG. 7B-C and FIG. 14D) can be sent between one or more of Host Monitoring Device 902, Network(s) 904, and/or Remote Monitoring Device 906 using communicators (e.g., communicators substantially similar to Communicators 207, 307). Where such communications are between Host Monitoring Device 902 and Remote Monitoring Device 906, such communications can be sent directly between them and/or through Network(s) 904. For example, Signal 922 can include communications from Host Monitoring Device 902 sent to Network(s) 904. Network(s) can receive, store, relay, and/or process Signal 922 and/or other communications (e.g., from host monitoring devices and/or other devices), and send Signal 924 to Remote Monitoring Device 906, where Signal 924 is based on the communications received by Network(s) 904. Similarly, Signal 928 can include communications from Remote Monitoring Device 906 sent to Network(s) 904. Network(s) 904 can receive, store, relay, and/or process Signal 928 and/or other communications (e.g., from remote monitoring devices and/or other devices) and/or send Signal 926 to Host Monitoring Device 902, where Signal 926 is based on the communications received by Network(s) 904.

Based on the reception of communications, Host Monitoring Device 902, Remote Monitoring Device 906, and/or other devices can send responses to communications, such as messages, acknowledgements, notifications, alerts, dismissals, feedback, error messages, etc. For example, Host Monitoring Device 902 can send Signal 930 to Network(s) 904, where Signal 930 is a response to a communication received by Host Monitoring Device 902. Network(s) 904 can receive, store, relay and/or process Signal 930 and/or other responses to communications (e.g., from host monitoring devices and/or other devices), and send Signal 932 to Remote Monitoring Device 906, where Signal 930 is based on the responses to communications received by Network(s) 904. Similarly, Signal 936 can include responses to communications from Remote Monitoring Device 906 sent to Network(s) 904. Network(s) 904 can receive, store, relay, and/or process Signal 936 and/or other responses to communications (e.g., from remote monitoring devices and/or other devices) and/or send Signal 934 to Host Monitoring Device 902, where Signal 934 is based on the responses to communications received by Network(s) 904.

Figure 10:
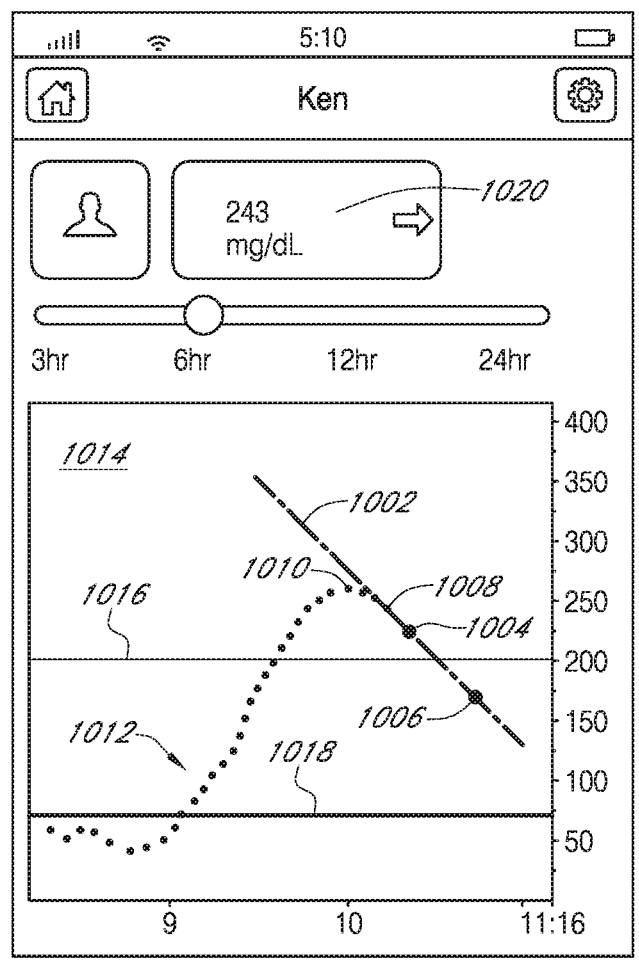
FIG. 10 illustrates a predictive calculation based at least in part on measured data of a Host.

FIG. 10 illustrates a predictive calculation based on measured data of a Host. In some cases, a Remote Monitor and/or Host can desire to not only know analyte measurements that have already occurred, but also future projections and/or predictions of analyte measurements. Such capability can allow Hosts and/or Remote Monitors to prepare for the future and/or allow for present planning of treatment. In the case of diabetes, a CGM can collect data and a host monitoring device, remote monitoring, server, and/or other device can perform a predictive calculation.

In some implementations a host monitoring device (e.g., substantially similar to Host Monitoring Device 200 and/or perform processes substantially similar to Process 100), remote monitoring device (substantially similar to Remote Monitoring Device 300 and/or perform processes substantially similar to Process 150), servers (e.g., Secure Server 504), and/or other device can display a graph, such as Graph 1012 in Display 1014. Graph 1012 can include discrete measurements that are displayed as points on Graph 1012, such as Points 1008, 1010. In some implementations, the host monitoring device, remote monitoring device, and/or other device can display Graph 1012 as a continuous curve in which the displaying device receives a continuous (e.g., analog) or substantially continuous stream of points, and/or interpolates between discrete points. Such interpolation can be performed by the host monitoring device, remote monitoring device, server, and/or other device.

In some implementations, points in Graph 1012 can be selected for further information. For example, Point 1010 can be selected to display its value (e.g., the EGV associated with Point 1010). That value can be displayed in Display 1020. Other information can be displayed in the display as well. For example, Processed Data, Contextual Data, Health Data, System Data, Treatment Data, User Data, Sensor Data, Summary Data, communications, and/or any data described in this disclosure can be displayed in Display 1020 or elsewhere on the display of a remote monitoring device, host monitoring device, and/or other device.

Display 1014 can include determined thresholds for Graph 1012. Such thresholds can be indicative of a measuring event that will trigger an action. Such thresholds can be determined and/or inputted by a Host, Remote Monitor, health practitioner, or others. As a non-limiting example, where Graph 1012 includes glucose measurements, and each point (e.g., Points 1008, 1010) is indicative of a glucose concentration, thresholds can indicate the values of measurements that trigger an alert, alarm, communication, or other event. Lower Threshold 1018 can be a lower threshold in which measurements at or below the determined value of the threshold (e.g., glucose concentration) trigger the alert, alarm, communication, and/or other event. Similarly, Upper Threshold 1016 can be an upper threshold where measurements at or above the determined value of the threshold trigger the alert, alarm, communication, and/or other event.

Display 1014 can show predictive measurements, such as Predictive Points 1004, 1006. Such points can be extrapolated from Graph 1012 using extrapolation that takes into account one or more points (e.g., measurements of an analyte such as glucose concentration) of Graph 1012. Such extrapolation techniques can include linear extrapolation, polynomial extrapolation, conic extrapolation, French curve extrapolation, forecasting, multigrid methods, predictive intervals, regression analysis, Richardson extrapolation, trend estimation, domain analysis, and/or any other extrapolation technique known in the art. Such predictive measurements can be shown in Display 1014 or calculated and displayed as number values or otherwise.

In some implementations, additional outputs and/or determinations can be displayed in Display 1014. For example, rate of change, treatment suggestions, and/or future projections can be displayed. Line 1002 is a non-limiting example of a rate of change displayed in Display 1014. Line 1002 illustrates the rate of change at Point 1008. Line 1002 can be used to predict future values, such as Predictive Points 1004, 1006, which can be projected along Line 1002 as possible future measurements. Advantageously, in this example, Line 1002 shows a downward trend in the Host's glucose concentration. Using Line 1002 and/or Predictive Points 1004, 1006, a Host and/or Remote Monitor viewing Display 1014 can anticipate that the Host's glucose level will return to normal levels, and also see the approximate time in which that may happen. In some implementations, a curve can be fitted to Graph 1012, and predictive points estimated by the curve. Example curve fitting techniques include least squares and other known algorithms.

Additional signal processing can be performed on Graph 1012 as well. There can be additional, illuminating information that can be extracted from analyte measurements such as glucose levels. For example, such information can include the amount of oscillation in measurements, the number of times thresholds are crossed, comparisons to other curves, removal of outliers, and/or other desired information. Such can be measured and/or displayed as desired. Such signal processing can be performed using Fourier Transform, convolution, correlation, auto correlation, cross-correlation, covariance, etc. In some implementation, signal processing can include outlier and/or malfunction detection. Such can be detected and/or controlled through noise filters, correlation, auto calibration, and/or other techniques.

In some cases, it can be desirable to get more information about the context in which a measurement was taken. Such context can allow a Host and/or Remote Monitor to better understand the measurement and possible future treatments. In some implementations, each point (e.g., Points 1008, 1010) can be selectable to bring up an additional screen that gives more information about the context of that point. In some cases, such information can include data such as communications, Processed Data, Contextual Data, Health Data, System Data, Treatment Data, User Data, Sensor Data, Summary Data, and/or any data described in this disclosure, as well as data based on the aforementioned.

Figure 11:
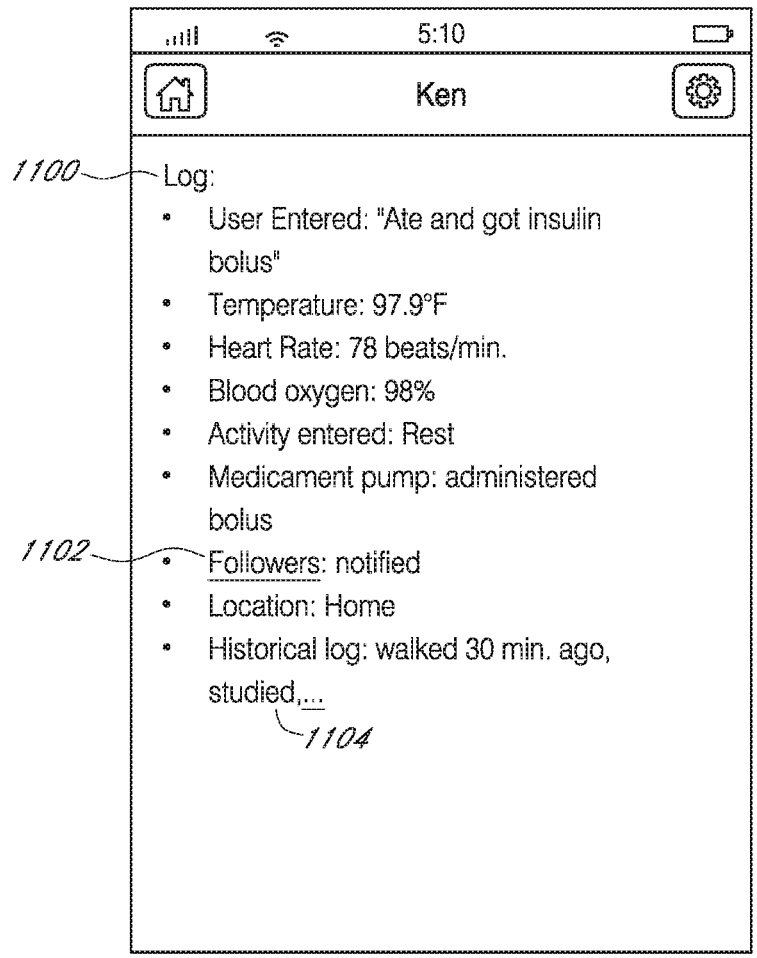
FIG. 11 illustrates an example log that can be displayed for a data point on the graph of FIG. 10.

FIG. 11 illustrates an example log that can be displayed for a data point on the graph of FIG. 10. For example, selecting Point 1010 in FIG. 10 could cause the display to show Log 1100. By way of illustrative example, Log 1100 can show details such as user entered information (e.g., "Ate and got insulin bolus"), temperature, heart rate, blood oxygen level, activities entered, statuses/logs of other devices (e.g., medicament pump), locations, information about Remote Monitors, and/or historical logs. In some cases, additional information and/or data can be displayed by selecting any of the aforementioned (e.g., selecting the words with a touch on a touch screen, a mouse on a monitor, etc.). Such additional information can include historical data, notes, details about the measuring sensors (e.g., model, make, status, operational parameters, settings (e.g., adjustable or non-adjustable)), and the like. For example, historical logs can be more information about the aforementioned or other data (e.g., analyte measurements, communications, Processed Data, Contextual Data, Health Data, System Data, Treatment Data, User Data, Sensor Data, Summary Data, and/or any data described in this disclosure, as well as data based on the aforementioned) that can be used to provide more context of a particular measurement. By selecting historical logs, an additional screen can appear providing a log with information about past measurements. In some implementations, Detail 1102 can be a link that when selected can show additional information about Remote Monitors. For example, an additional display can provide details about a Host's Remote Monitors. Similarly, in some implementations, Detail 1104 can be a link that when selected can show additional historical data logs detailing data collected (e.g., analyte measurements, communications, Processed Data, Contextual Data, Health Data, System Data, Treatment Data, User Data, Sensor Data, Summary Data, and/or any data described in this disclosure, as well as data based on the aforementioned). For example, Detail 1104 can open a display that shows Retrospective Data that chronicles activities of a Host entered (e.g., by a Host, Remote Monitor, and/or other user) and/or automatically detected by a host monitoring device and/or server.

By way of illustrative example, Log 1100 can be displayed on the display of a host monitoring device (e.g., a host monitoring device substantially similar to Host Monitoring Device 200 and/or perform processes substantially similar to Process 100). In such a case, Log 1100 can show information related to a Host using that host monitoring device. As a result, Log 1100 can give Host information about his/her own activities and therapies to put measurements into context. For example, a Host may be viewing Display 1014 as illustrated in FIG. 10 and/or desire more information about a particular point.

By way of illustrative example, Log 1100 can be displayed on the display of a remote monitoring device (e.g., a remote monitoring device substantially similar to Remote Monitoring Device 300 and/or perform processes substantially similar to Process 150). A Remote Monitor can view Log 1100 in order to give context to Host information. For example, a Remote Monitor may be viewing Display 1014 as illustrated in FIG. 10 and desire more information about a particular point.

As another non-limiting example, Log 1100 can be a log stored (e.g., in memory and/or any other data storage described in this disclosure) on a server (e.g., a secure server substantially similar to Secure Server 504). Such a log can be viewed on a display communicatively coupled to the server, and/or on remote monitoring devices and/or host monitoring devices communicatively coupled to the server.

Figure 12:
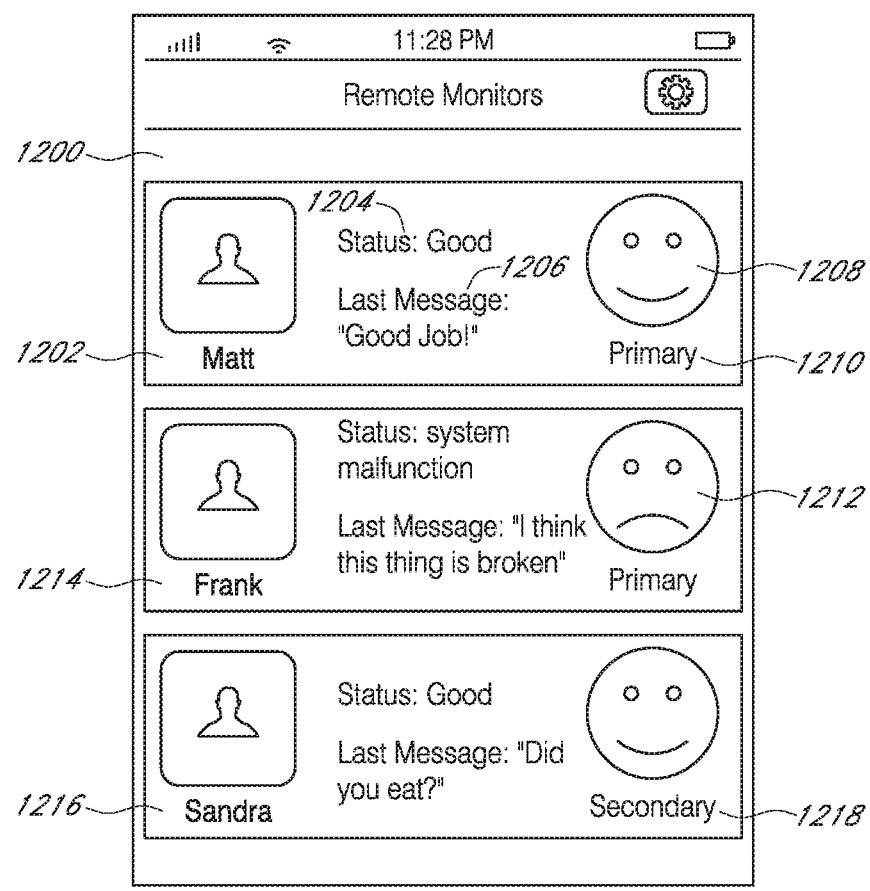
FIG. 12 illustrates an example page showing information about Remote Monitors.

FIG. 12 illustrates an example page showing information about Remote Monitors. Page 1200 can be displayed on a host monitoring device, remote monitoring device, and/or other device described in this disclosure. In some implementations, Page 1200 can be stored on a server and/or displayed on a display operatively and/or communicatively coupled to the server. Page 1200 can include cells, such as Cells 1202, 1214, 1216, which can each correspond to different Remote Monitors. Each cell can display information about the Remote Monitors, including their names, statuses (e.g., Status 1204), messages they have sent (e.g., Message Display 1206), classifications (e.g., Classifications 1210, 1218), and/or graphical indications of their statuses (e.g., Graphical Indication 1208, which can indicate the overall status of a Remote Monitor). In some implementations, a user can select the cells of Remote Monitors to see more information about the Remote Monitors (e.g., communications, analyte measurements, Processed Data, Contextual Data, Health Data, System Data, Treatment Data, User Data, Sensor Data, Summary Data, and/or any data described in this disclosure, as well as data based on the aforementioned). Such information can be pulled from a remote monitoring device, host monitoring device, server, other device, and/or any other system described in this disclosure. Advantageously, Page 1200 allows a viewer (e.g., Host and/or Remote Monitor) to quickly view a user interface to see the status and/or relationship of Remote Monitors. Although the example illustrated in FIG. 12 refers to glucose levels and specific types of messages and icons, other types of events, messages, and icons discussed herein may be used to convey the status of a host.

In the case where a Host is viewing Page 1200 on a host monitoring device, Page 1200 can give the Host information about his/her Remote Monitor(s). Such information can be desirable in order for the Host to see the status and/or relevant information about each of his/her Remote Monitors. In the case where a Remote Monitor is viewing Page 1200 on a remote monitoring device, Page 1200 can give the Remote Monitor information about other Remote Monitors so that care for a Host can be coordinated. In some cases, some Remote Monitors can be anonymous to some viewers (e.g., Hosts or Remote Monitors), where some or all of the identifying information of a Remote Monitor (e.g., name, serial number, etc.) can be not listed. As another non-limiting example, Page 1200 can be stored (e.g., in memory or any other data storage described in this disclosure) on a server (e.g., a secure server substantially similar to Secure Server 504). Such a page can be viewed on a display communicatively coupled to the server or on remote monitoring devices and/or host monitoring devices communicatively coupled to the server.

In some cases, it can be desirable for a Host and/or Remote Monitor to compare measurements to other data, such as historical data measurements. In some cases, a display on a host monitoring device, remote monitoring device, and/or other device can show such historical data measurements as numbers, graphs, or otherwise. In some cases, such historical data can be presented and/or overlaid with current and/or recent measurements. In some cases, such historical data can be displayed non-graphically, such as a table of numbers, lists, logs, etc.

FIGS. 13A-D illustrate historical Host data overlays that can be viewed with Host data. One or more overlays can be used to serve as comparisons on how a Host behaved in similar, and/or substantially similar, circumstances, and how the Host's analyte measurements (e.g., glucose levels) reacted. Similarities can be determined by comparisons. For example, historical data can be stored in memory, analyzed, and/or displayed in a remote monitoring device (e.g., Remote Monitoring Device 300), host monitoring device (e.g., Host Monitoring Device 200), server (e.g., Secure Server 504), and/or any other device described in this disclosure. By way of illustrative example, Displays 1314, 1324, 1334, 1344 can be displayed on a remote monitoring device so that a Remote Monitor can view and/or analyze measurements of a Host in which the Remote Monitor is interested. As another non-limiting example, a Host may view Displays 1314, 1324, 1334, 1344 on a host monitoring device in order to view and/or analyze his/her own measurements. As another non-limiting example, Displays 1314, 1324, 1334, 1344 and/or the data/information contained within can be stored in memory on a server, and/or displayed on a display communicatively and/or operatively coupled to that server. In some cases, that server can transmit Displays 1314, 1324, 1334, 1344 to a host monitoring device, remote monitoring device, and/or any device described in this disclosure.

Comparison methods between current and/or recent measurements to that historical data can be used. Such comparison methods can include, without limitation correlation, cross-correlation, pattern recognition, curve fitting, statistical analysis, and/or other techniques for comparison. In some cases, one or more parameters of the measurements can be compared to historical data, such as zero crossing, averages, variances, residuals, standard deviations, maximums, minimums, range, mode, rate of change, etc. Other statistical methods can also be performed, including p-tests, t-tests, Chi Square, etc.

In some cases, a Host and/or Remote Monitor can select measurements in overlays and/or historical data sets and be able to see the context in which those measurements were taken (e.g., by viewing a log such as Log 1100 illustrated in FIG. 11 and/or any other way of displaying any data discussed in this disclosure). Such context can allow the Host and/or Remote Monitors to learn from previous experiences and understand what treatments, or set of circumstances, allowed for good outcomes or bad outcomes. In some implementations, selections can be made on the display of, and/or communicatively and/or operatively coupled to, a host monitoring device, server, and/or remote monitoring device.

Figure 13A:
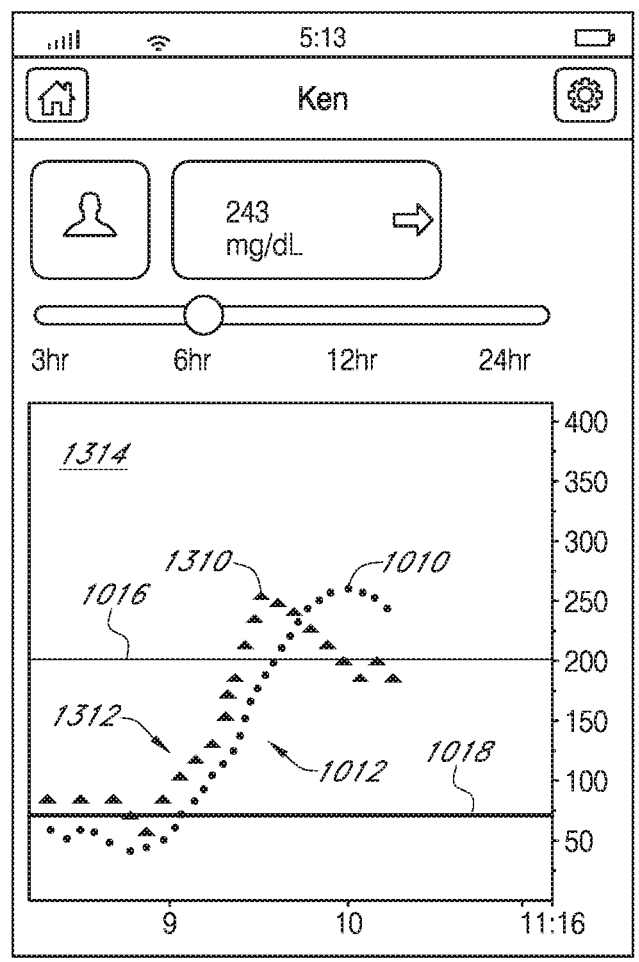
FIGS. 13A-D illustrate historical Host data overlays that can be viewed with Host data.

In some cases, it may be desirable for a Host and/or Remote Monitor to see a comparable situation where the Host's analyte measurements, such as glucose levels, had a similar pattern, and/or to see what the outcome was. It should be understood that similar displays, functionality, systems, and/or methods in FIGS. 13A-D can also be applied to a Remote Monitor where analyte measurements of a Remote Monitor are displayed. In the case of glucose levels, FIG. 13A illustrates an example comparative case where a Host had a substantially similarly high glucose reading but ended up returning to a normal range relatively quickly. Display 1314 includes Graph 1012, Point 1010, Upper Threshold 1016, and Lower Threshold 1018, as were described with reference to FIG. 10. Graph 1312 includes historical data with a similar pattern to Graph 1012, in which the glucose levels of the historical data initially rise to a substantially similar high point as Graph 1012, but then decreases below Upper Threshold 1016 back into a normal range.

Graph 1312 can be identified by pattern recognition. By way of illustrative example, a host monitoring device, remote monitoring device, server, other device, and/or any device discussed in this disclosure could look at one or more factors/criteria such as the maximum, the minimum, the time, and the rate of change (e.g., the slope or derivative), approximate equation for the curve, and/or other similarities to identify Graph 1312 as being similar to Graph 1012. By way of illustrative example, Point 1010 of Graph 1012 and Point 1310 of Graph 1312, which are both maximums over the range of measurements, have substantially similar values. Similarly, the rising slopes (e.g., the measurements as shown in Display 1314 of Graphs 1012, 1312 between Upper Threshold 1016 and Lower Threshold 1018) are substantially similar. These graphs also appear around the same time and over the same length of time. Based on one or more of these factors, a host monitoring device, remote monitoring device, server, other device, and/or any device described in this disclosure can also look at other measurements in a database of historical measurements to identify which measurement sets are similar and could be of interest. In some cases, a scoring method can be used to determine which measurement sets have the most similarities, such as computing a percentage similarity of each factor and computing an overall metric that is based on those percentages (e.g., in some cases an average of the percentages can be used). In some cases, a user can select criteria (e.g., maximum, minimum, time, and rate of change, approximate equation for the curve, and/or other factors) in which to search for comparable data. For example, a user (e.g., Host and/or Remote Monitor) can select options that allow it to look for a pattern where measurements had a substantially similar high point. That user can also search based on dates and times. In some cases, measurements from a different point in time can be transposed and/or overlaid onto a present graph (or the measurements can be viewed in a non-graphical representation) to see similarities between those measurements and recent measurements.

In some cases, a Host and/or Remote Monitor can desire to view historical data measurements that had a poor outcome for the Host. For example, a Host and/or Remote Monitor can be interested in seeing a situation where the Host had a hyperglycemic reaction as a point to compare recent measurements.

Figure 13B:
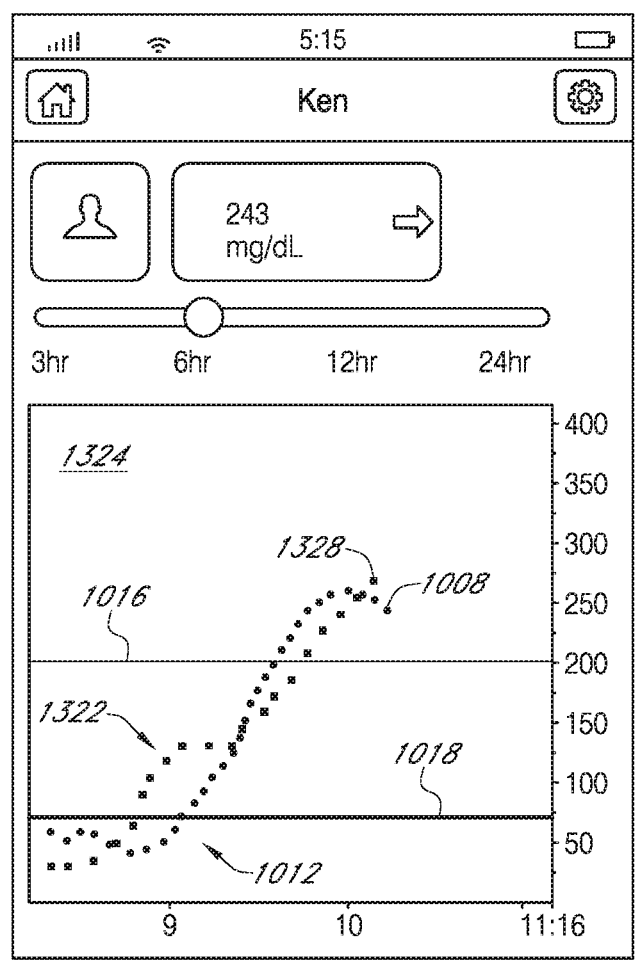

FIG. 13B illustrates a comparative case where the Host was not able to control glucose levels and went into a hyperglycemic state. Display 1324 shows Graph 1012 and Graph 1322. While Graph 1012 rises and then turns downward towards Point 1008, Graph 1322 continues to rise to Point 1328. In some cases, by comparing Graph 1322 and Graph 1012, and/or any logs and/or other data giving the measurements of Graph 1322 and/or Graph 1012 context, a Host and/or Remote Monitor can learn why the Host's glucose level kept going up in Graph 1322 and what can be done to prevent the same thing from happening.

Figure 13C:
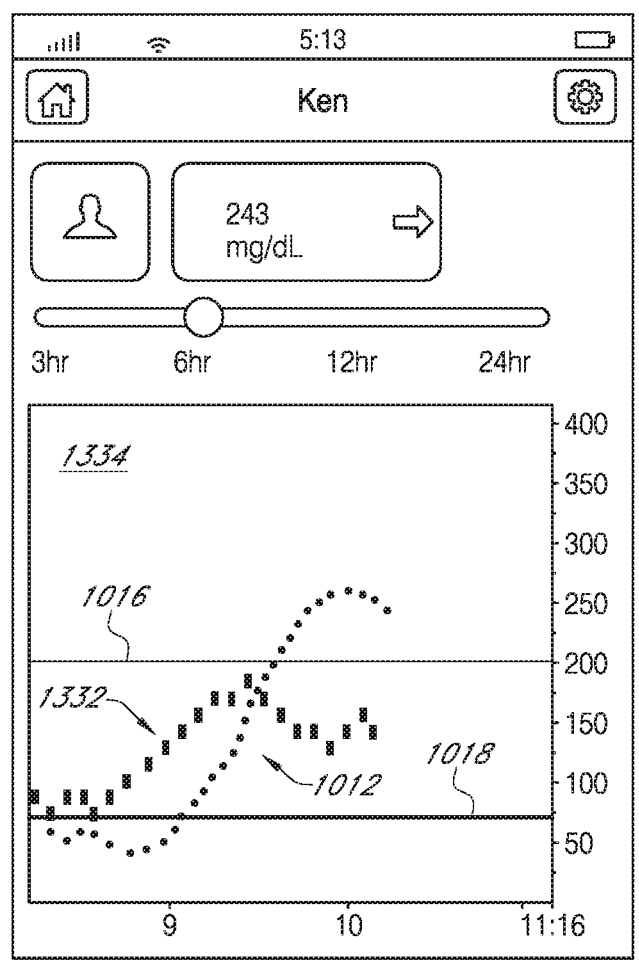

FIG. 13C illustrates a comparative case where the Host was able to keep glucose levels within the predefined range. Display 1334 again displays Graph 1012. Display 1334 also displays Graph 1332, which reflects a situation where the Host maintained his/her glucose measurements between Upper Threshold 1016 and Lower Threshold 1018. In some cases, by comparing Graph 1332 and Graph 1012, and any logs or other data giving the measurements of Graph 1332 and Graph 1012 context, a Host, Remote Monitor, and/or processor (e.g., a processor of a host monitoring device, remote monitoring device, and/or server using pattern recognition) can learn why the Host's glucose level stayed within Upper Threshold 1016 and Lower Threshold 1018 in Graph 1332, and what can be done to control glucose levels in the future.

Figure 13D:
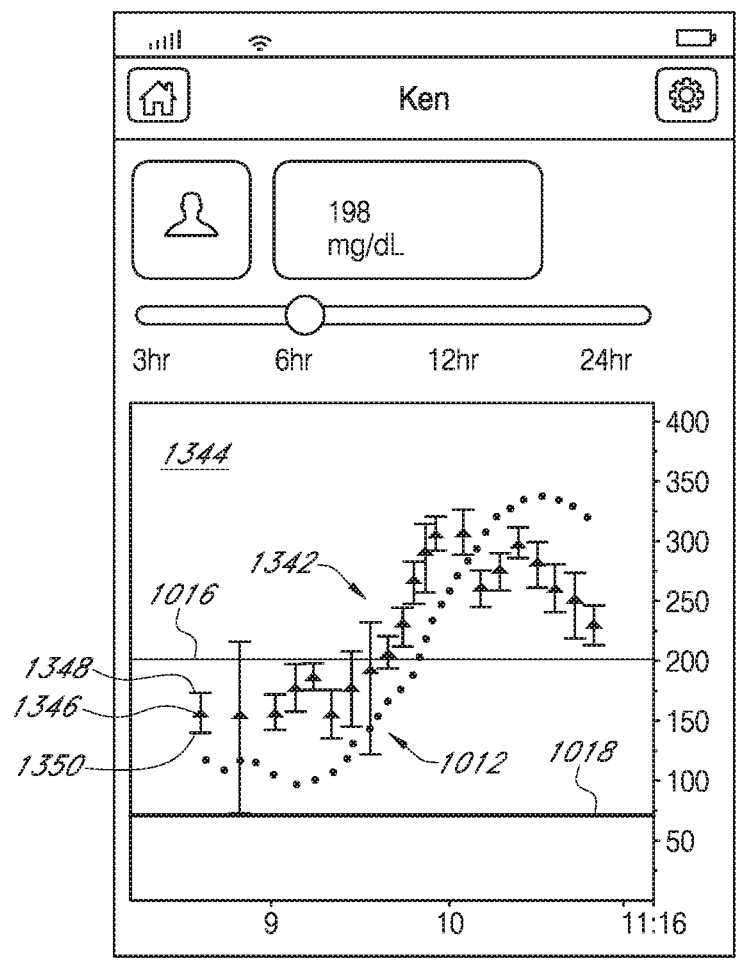

FIG. 13D illustrates a curve of average values in similar circumstances, where a confidence interval is also displayed. In some cases, it may be desirable to view other kinds of statistics and/or parameters for comparison. For example, a Host's average glucose measurements at a determined time of day (and/or range of times), during determined activities, in determined ranges, during determined events (e.g., eating), and/or using any characteristics desired can be viewed. Display 1344 again displays Graph 1012. Display 1344 can also display Graph 1342, which can include average glucose measurements of the Host in similar time periods. Other statistics can also be displayed in addition or in the alternative to averages, such as variances, standard deviations, confidence intervals, maximums, minimums, range, mode, rate of change, etc. Graph 1342 also includes confidence intervals. By way of illustrative example, Graph 1342 includes Point 1346, which can be an average over a determined period of time. Graph 1342 can also display 95% percent confidence interval with Upper Bound 1348 and Lower Bound 1350 around Point 1346, allowing for further understanding of a Host's measurements.

Furthermore, in some implementations, a Host and/or Remote Monitor may not be interested in recent measurements at all, and/or desire to reflect on previous, historical occurrences. As such, using similar comparisons and factors as described above, with respect to any of FIGS. 13A-D, a remote monitoring device (e.g., Remote Monitoring Device 300), host monitoring device (e.g., Host Monitoring Device 200), server (e.g., Secure Server 504), and/or any other device described in this disclosure can view two or more historical measurement sets.

In some cases, it may be desirable for Hosts and/or Remote Monitors to be able to adaptively and contextually modify what kinds of communications can be sent between Hosts and Remote Monitors. By allowing such modification, monitoring systems can enhance Host and Remote Monitor relationships and assist in allowing the right amount and kinds of information (e.g., not too much or too little) to transfer from a Host to each of his/her Remote Monitors.

A remote monitoring device (e.g., Remote Monitoring Device 300), host monitoring device (e.g., Host Monitoring Device 200), server (e.g., Secure Server 504), and/or any other device described in this disclosure can provide adaptive and/or contextual communication of a Host based on a Host's activities, measurements, and/or other data (e.g., analyte measurements, communications, Processed Data, Contextual Data, Health Data, System Data, Treatment Data, User Data, Sensor Data, and/or any data described in this disclosure). Similarly, such adaptive and/or contextual communication can be based on a Remote Monitor's activities, classification, and/or other data (e.g., analyte measurements, communications, Processed Data, Contextual Data, Health Data, System Data, Treatment Data, User Data, Sensor Data, and/or any data described in this disclosure), and/or patterns in such data.

FIGS. 14A-D illustrate example interactions of different classifications of Remote Monitors. While FIGS. 14A-D reference Remote Monitors (e.g., Remote Monitors 1410, 1412, 1414, 1416) and a Host, it should be understood that each Remote Monitor has a remote monitoring device and each Host has a host monitoring device. A remote monitoring device can be substantially similar to Remote Monitoring Device 300 and/or perform processes substantially similar to Process 150. A host monitoring device can be configured substantially similar to the Host Monitoring Device 200 and/or can perform processes substantially similar to Process 100. Such remote monitoring devices and host monitoring device can send and/or receive communications, determine classifications, and/or operate based on classifications as will be described. Classifications can be stored in memory in one or more of the host monitoring devices, remote monitoring devices, servers, and/or other devices. Similarly, classifications can be determined, for example, by a processor of a host monitoring device, remote monitoring device, server, and/or other devices. For example, a remote monitoring device can determine its own classification and store it in memory. The remote monitoring device can also store in memory the classification of other remote monitoring devices. Advantageously, this can allow the remote monitoring device to know how to communicate (e.g., with notifications, alerts, messages, data, and/or any other communications in this disclosure) with other remote monitoring devices and/or its relative role as compared to other remote monitoring devices in its monitoring system. Similarly, a host monitoring device and/or a server (e.g., secure server) can store in memory the classifications of one or more or all of its Remote Monitors. Advantageously, for example, this can allow the host monitoring device to know the relative relationship the Host has with the Remote Monitors in its system, and/or send communications based on classifications and permissions attributed to Remote Monitors. Also, in some implementations, a server (e.g., a secure server) can store the classifications of the Remote Monitors in order to direct communications to the relevant Remote Monitors. In this way, the server can act as an intelligent central hub(s) that can direct communication traffic in the remote monitoring system by, for example, storing, receiving and/or sending.

In some embodiments, each classification is associated with a set of permissions, which can determine what data a remote monitoring device corresponding to a classification is authorized to access. The set of permissions can be pre-selected and/or modifiable by Host for each remote monitoring device.

Figure 14A:
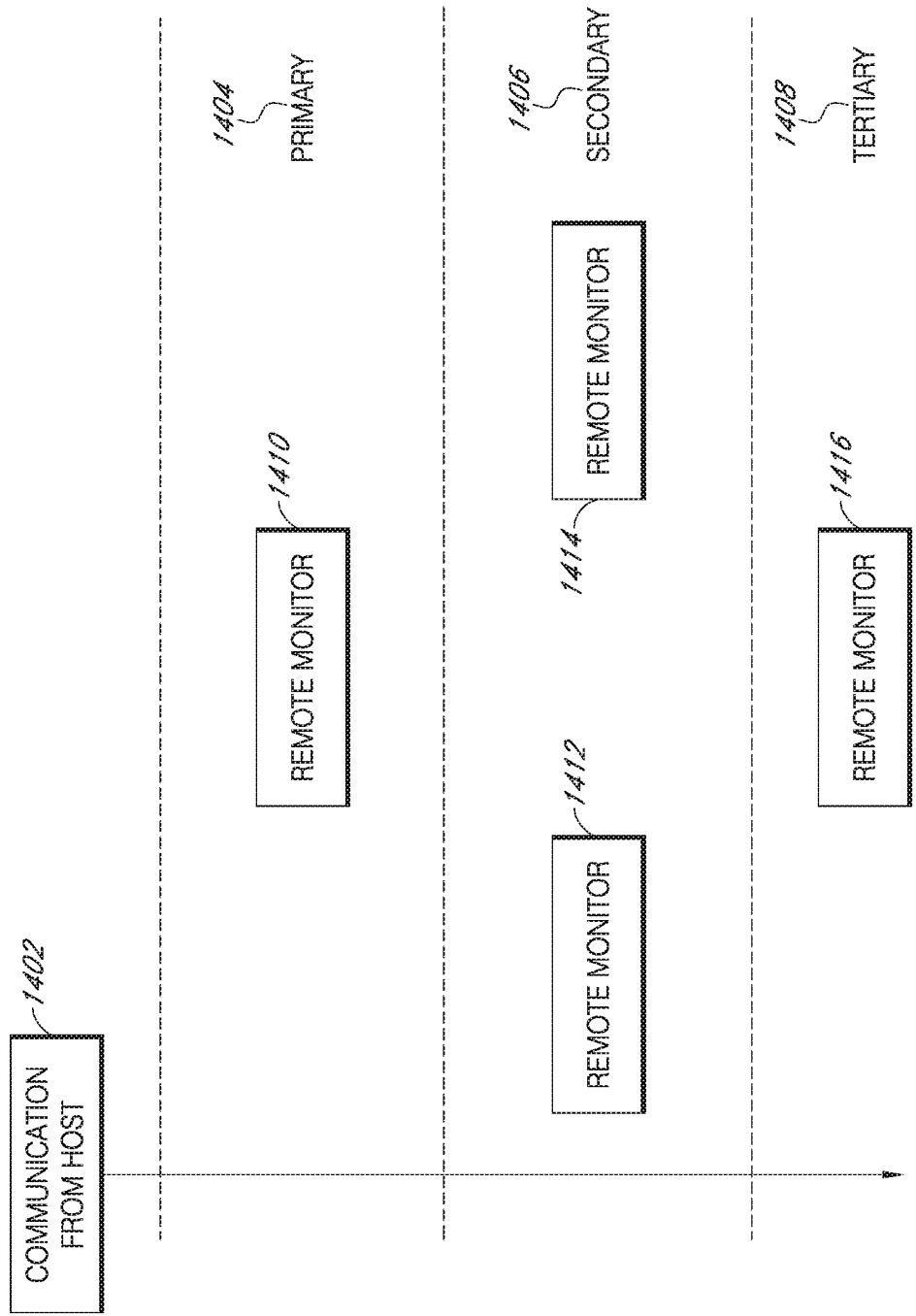
FIGS. 14A-D illustrate example interactions of different classifications of Remote Monitors.

FIG. 14A illustrates that, in some cases, monitoring systems can have classifications that create a hierarchical structure where communications from a Host first go to higher classified Remote Monitors before passing to lower classified Remote Monitors. In some embodiments, the lower classified Remote Monitors can have greater restrictions to the permissible data that they can access compared to the higher classified Remote Monitors. In some cases, the lower classified Remote Monitors can have more restrictive notification rules compared with higher classified Remote Monitors. Having such classifications can allow some Remote Monitors not to be inundated with information that they do not desire to see and/or would not be helpful for them to see. Also, as described herein, Remote Monitors may not desire to see alerts when they have already been addressed.

In some cases, Remote Monitors can be assigned classifications based on one or more of the following: proximity between a host device and a remote monitoring device, a characteristic of the user of the remote monitoring device communicated to a secure server managing the remote monitoring system, a relationship between the user of the remote monitoring device and Host, and/or a behavior of a remote monitoring device.

For example, in the case where Remote Monitors 1410, 1412, 1414, 1416 are all Caretakers of a Host. Remote Monitors 1410, 1412, 1414, 1416 can be divided into Primary Classification 1404, Secondary Classification 1406, and Tertiary Classification 1408 of the Caretaker classification. As illustrated, Remote Monitor 1410 is in Primary Classification 1404. Remote Monitors 1412, 1414 are in Secondary Classification 1406. And Remote Monitor 1416 is in Tertiary Classification 1408. In some cases Primary Classification 1404, Secondary Classification 1406, and Tertiary Classification 1408 can define relative roles with respect to Remote Monitors and the Host. More classifications can be made to further define roles (e.g., quaternary, quinary, senary, and so forth, or any other name or designation desired). For example, Remote Monitors in Primary Classification 1404 can be the persons directly taking care of a Host. By way of illustrative example, where a Host is a child, Caretakers in Primary Classification 1404 can be the child's parent in close proximity. Such Caretaker Remote Monitors in Primary Classification 1404 can be the ones presently and/or actively taking care of the child. The Host child can also have other Caretakers. For example, Caretaker Remote Monitors in Secondary Classification 1406 can be the child's other parent or grandparent who are not in close proximity. These Caretaker Remote Monitors in Secondary Classification 1406 can have an interest in the Host (e.g., when Host is a child) and would take care of the Host in his/her presence, but are presently away. These Caretaker Remote Monitors in Secondary Classification 1406 can be interested in what is happening with Host, but may not be in a position to assist Host unless the Caretaker in Primary Classification 1404 did not or was unable to respond to an emergency. Accordingly, these Caretaker Remote Monitors in Secondary Classification 1406 may not need all the communications. Accordingly, Remote Monitors of Secondary Classification 1406 may have more restrictive notification rules compared with Remote Monitors of the Primary Classification 1404. Similarly, Caretaker Remote Monitors in Tertiary Classification can be even further removed, such as an aunt or uncle who have an interest in the child Host, but would desire to step in if Caretaker Remote Monitors in Primary Classification 1404 and Secondary Classification 1406 did not or were unable, or if there was an emergency.

In some embodiments, Remote Monitors can be assigned to one or more classifications generated and managed at a server as described herein. The classifications may include varying notification rules. The server can receive the location of a remote monitoring device and modify the classification of a remote monitoring device based on a predefined proximity from a host device. In some embodiments, the modification of classification may include relegating a remote monitor from a higher privilege/priority classification to a lower privilege/priority classification based on proximity.

In some embodiments, the classification may be relegated from a higher privilege/priority classification to a lower privilege/priority classification based on status or availability of the user of a remote monitoring device.

Other roles of classifications can be defined as desired by Hosts, Remote Monitors, Administrators, practitioners, operators, etc. Primary Classification 1404, Secondary Classification 1406, Tertiary 1408, and any other classification can apply to other roles, and not just Caretakers. For example, substantially similar hierarchies can be applied to Social Associates, Strangers, Watchers, Assigned Remote Monitors, Universal Remote Monitors, and/or any other Remote Monitor described in this disclosure.

As a result of the hierarchy, not all communications from a Host's host monitoring device, such as Communication 1402, may go to remote monitoring devices of all Remote Monitors (e.g., Remote Monitors 1410, 1412, 1414, 1416). For example, a remote monitoring device may not send all communications to the remote monitoring devices in its remote monitoring system. As another non-limiting example, a host monitoring device can send a communication to a server, and the server may not direct the communication to all remote monitoring devices in the monitoring system.

By way of illustrative example, Communication 1402 can first go to a remote monitoring device of Remote Monitor 1410 in Primary Classification 1404. In the case where the contents of Communication 1402 can be addressed by Remote Monitor 1410, Communication 1402 may not go to remote monitoring devices of Remote Monitors (Remote Monitors 1412, 1414, 1416) or may be altered before being sent.

For example, Communication 1402 can be an alert message, stating that Host's glucose level is low. Communication 1402 can be sent to a remote monitoring device of Remote Monitor 1410 in Primary Classification 1404. The Remote Monitor 1410 can address the alert by making sure Host eats an appropriate food. As a result of Remote Monitor's actions, it may not be desirable to further alert Remote Monitors 1412, 1414, 1416 and/or send the same alert to their remote monitoring devices.

In some implementations a remote monitoring device (e.g., Remote Monitoring Device 300), host monitoring device (e.g., Host Monitoring Device 200), server (e.g., Secure Server 504), and/or other devices described in this disclosure can have a delay before transmitting alerts or notifications (e.g., 30 minutes or other desirable delay as described herein). If the reason for which Communication 1402 is to be sent has been addressed, the alert may not be sent to remote monitoring devices of one or more of Remote Monitors 1412, 1414, 1416. For example, no alert may be sent at all, or a lower level alert and/or notification stating the issue and/or that the issue has been addressed can be sent. Whether or not an issue has been addressed can be determined from Host input (e.g., Host indicating a meal has been taken), analyte measurements, Processed Data, communications from Host or Remote Monitor, Contextual Data, Health Data, System Data, Treatment Data, User Data, Sensor Data, Summary Data, and/or other data as described herein.

In some implementations, Remote Monitor 1410, after receiving Communication 1402 with a remote monitoring device, can prevent Communication 1402 from being sent to one or more of Remote Monitors 1410, 1412, 1414, 1416 (e.g., at their remote monitoring devices) by acknowledging Communication 1402, sending a message, and/or any other form of communication indicative of Remote Monitor 1410 seeing Communication 1402 and/or addressing the situation. In some cases, such acknowledgment, sending a message, and/or any other form of communication can be in the form of a response inputted by the Remote Monitor on a user interface that displays Communication 1402. In such cases, a host monitoring device may not send Communication 1402 to one or more of Remote Monitors 1410, 1412, 1414, 1416. In other situations, Remote Monitor 1410 can select a response to Communication 1402 that sends Communication 1402 to one or more of Remote Monitors 1410, 1412, 1414, 1416. For example, there could be a response that allows Remote Monitor 1410 to select one or more Remote Monitors 1410, 1412, 1414, 1416 to receive the message. As another non-limiting example, Remote Monitor 1410 can send an ignore or "I'm busy" response (e.g., by selecting an option in a pulldown menu and/or hitting an on-screen button in a display). Communication 1402 can then cascade (e.g., be sent) to the remote monitoring devices of the next classification in the hierarchy, which can be Remote Monitors in Secondary Classification 1406 in this case.

In some cases, where Remote Monitor 1410 has not addressed a situation, has not acknowledged Communication 1402, and/or a delay has expired, Communication 1402 can be sent in whole or in part to other Remote Monitors. A host monitoring device, server, and/or other device described in this disclosure can perform such sending. By way of illustration, in the example hierarchical structure illustrated in FIG. 14A, Communication 1402 may then be sent (e.g., from a host monitoring device) to Remote Monitors 1412, 1414 because they are in the next classification in the hierarchy, Secondary Classification 1406.

In some implementations, the same process just described can filter down throughout the classifications. For example, remote monitoring devices of Remote Monitors 1412, 1414 in Secondary Classification 1406 can receive a communication (e.g., Communication 1402 or a communication based on Communication 1402 after Remote Monitor 1410 has seen it). If one or more of Remote Monitors 1412, 1414 address a situation within a delay period, then the same alert may not be sent to remote monitoring devices of Remote Monitors in Tertiary Classification 1408, such as Remote Monitor 1416. In some implementations, one or more Remote Monitors 1412, 1414, after receiving the communication, can prevent that communication from being sent to Remote Monitor 1416 by acknowledging that communication, sending a message, and/or any other form of communication indicative of one or more of Remote Monitors 1412, 1414 seeing the communication and/or addressing the situation. In some cases, such acknowledgment, sending a message, and/or any other form of communication can be in the form of a response inputted by the Remote Monitor on a user interface that displays the communication. In some cases, where Remote Monitors 1412, 1414 have not addressed a situation, have not acknowledged the communication, and/or a delay has expired, the communication (e.g., Communication 1402 and/or a communication based on Communication 1402 after Remote Monitor 1410 has seen it) can be sent in whole or in part to remote monitoring devices of Remote Monitors in Tertiary Classification 1408. A host monitoring device, server, and/or any other device described in this disclosure can perform such sending. The aforementioned pattern can continue for more classifications. It should be noted that in some implementations, one or more classifications may not contain a Remote Monitor. In such a case, messages can be sent to Remote Monitors based on their relative classifications, not their absolute. For example, if there are no Remote Monitors in Primary Classification 1404, Communication 1402 can first be sent to Remote Monitors in Secondary Classification 1406 and so forth. In some cases, a processor (e.g., a processor of a host monitoring device, remote monitoring device, server, and/or any other device described in this disclosure) can assign classifications so that classifications are filled from primary on down with no empty classifications.

In some implementations, it can be desirable for Remote Monitors to change classifications dynamically in order to account for Remote Monitor and/or Host conditions and Remote Monitor's ability to assist a Host.

Figure 14B:
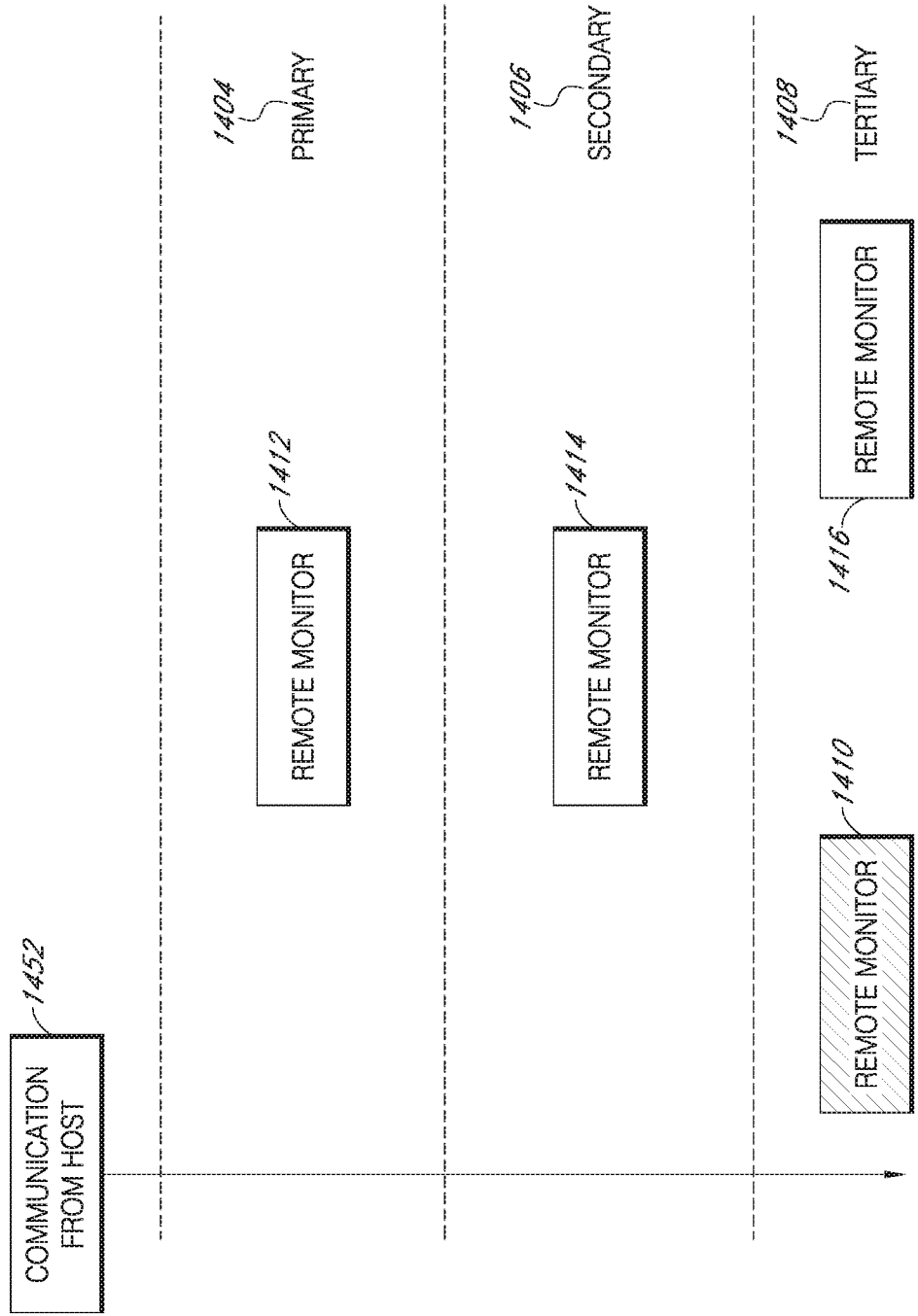

FIG. 14B illustrates that classifications can be dynamic, where the classification of a Remote Monitor can be based on Host and/or Remote Monitor preferences and/or data acquired on a Remote Monitor. For example, Remote Monitor 1410 was illustrated as part of the Primary Classification in FIG. 14A, but is shown as in Tertiary Classification 1408 in FIG. 14B. Similarly, Remote Monitor 1412 was previously in Secondary Classification 1406, but is now illustrated in Primary Classification 1404. Such changes can dynamically occur based on factors such as location of the Remote Monitor and/or Host, data about the Host and/or Remote Monitor (e.g., analyte measurements, communications, Processed Data, Contextual Data, Health Data, System Data, Treatment Data, User Data, Sensor Data, Summary Data, and/or any data described in this disclosure), preferences (e.g., preferences and/or desires of Hosts, Remote Monitors, practitioners, and/or any other person), frequency and/or quality of communication responses, and/or any other factor or criteria desirable. These dynamic changes can be analyzed and/or processed a remote monitoring device (e.g., Remote Monitoring Device 300), host monitoring device (e.g., Host Monitoring Device 200), server (e.g., Secure Server 504), and other devices. In some cases, changes in classifications can be made automatically. In some cases, changes in classifications may first be detected, and then prompted on a remote monitoring device and/or host monitoring device. If such change in classification is approved by the user of the prompted remote monitoring device and/or host monitoring device (e.g., by a Host and/or Remote Monitor responding and/or clicking an approve button), then the change can be made. If such change in classification is declined by the user of the prompted remote monitoring device and/or host monitoring device (e.g., by a Host and/or Remote Monitor responding and/or clicking a decline button), then the change may not be made. Changes in classifications can be made in memory of a host monitoring device, remote monitoring device, server, and/or any other device described in this disclosure.

For example, a Remote Monitor can change classifications based on location, such as proximity of Remote Monitors and/or Hosts. Remote Monitor 1410 could have been in Primary Classification 1404 when Remote Monitor 1410 was in close proximity (e.g., between 0 and 1,045 square meters and/or within a suitable range to see, hear, and/or otherwise take care of a Host and/or the closest Remote Monitor to the Host). However, when Remote Monitor 1410 is not in close proximity, Remote Monitor 1410 may be a different classification, such as Tertiary Classification 1408. Other factors can be considered in addition or in the alternative to proximity. As another non-limiting example, the availability of a Remote Monitor can be taken into account in determining classification. Data (e.g., analyte measurements, communications, Processed Data, Contextual Data, Health Data, System Data, Treatment Data, User Data, Sensor Data, Summary Data, and/or any data described in this disclosure) can be indicative of availability. For example, where a Remote Monitor is wearing a GCM, if the Remote Monitor has a hyperglycemic or hypoglycemic condition (or otherwise determined glucose conditions that are not desirable), then that Remote Monitor may not be in a position to be available to assist a Host. Other health-related factors indicative of a Remote Monitor's availability include, high/low heart rate, high/low temperatures, sleep (e.g., as determined by a sleep monitor or accelerometer), high levels of anxiety, high/low blood pressure, high/low ratings on a worry scale, etc.

Dynamic changes of Remote Monitor classification can happen by consideration of the aforementioned factors by a remote monitoring device (e.g., Remote Monitoring Device 300), host monitoring device (e.g., Host Monitoring Device 200), server (e.g., Secure Server 504), and/or any other device described in this disclosure. In some cases, changes can be user-inputted, such as by a Host and/or Remote Monitor assigning Remote Monitors to classifications.

Figure 14C:
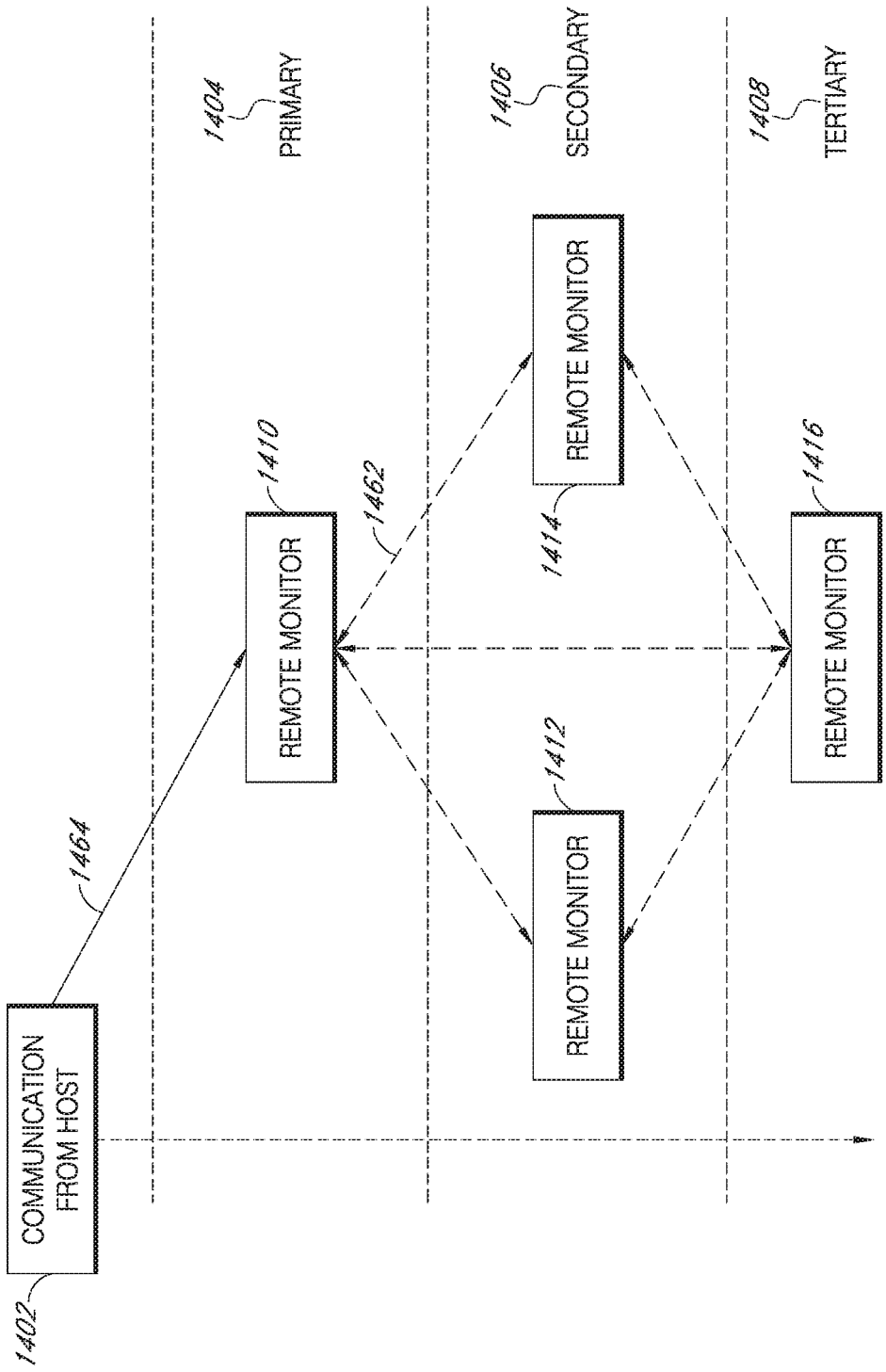

FIG. 14C illustrates an example where Remote Monitors (e.g., using remote monitoring devices), can communicate with each other and/or exchange data and/or information. In some cases, communications from a Host can be relayed between Remote Monitors at their remote monitoring devices. In some cases, each remote monitoring device can store in memory its classification and the classifications of one or more remote monitoring devices in its monitoring system. Advantageously, such storage can allow each remote monitoring device to determine what communications to send to other remote monitoring device, and/or what communications to display. In some implementations, a server (e.g., Secure Server 504) can store the classifications and/or synchronize (e.g., send updates) to the remote monitoring devices so that they have updated information on the classifications of other remote monitoring devices in their monitoring system.

By way of illustrative example, Communication 1464 can be sent to Remote Monitor 1410, who for illustrative purposes, can be in Primary Classification 1404. As described with reference to FIG. 14A, Remote Monitor 1410 can take actions such as addressing the contents of Communication 1464 (e.g., addressing the issue of which Communication 1464 is about), acknowledging Communication 1464, sending a message, and/or any other form of communication. In such cases, acknowledgments, sending of messages, and/or any other form of communications can be in the form of a response inputted by the Remote Monitor on a user interface. Where such action is taken, Communication 1464 may not be relayed to Remote Monitors 1412, 1414, 1416. Instead, no communication can be sent, or another communication (e.g., an alert, notification, message, or other communication) can be generated by Remote Monitor 1410 (e.g., using a remote monitoring) to send to other Remote Monitors, such as Remote Monitors 1412, 1414 in Secondary Classification 1406. Such other communication can be based on the classes of one or more of Remote Monitor 1410, 1412, 1414, 1416, Communication 1464, the actions taken by Remote Monitor 1410, responses by Remote Monitor 1410, and/or other data and/or information. For example, where Remote Monitor 1410 took actions that address the content of Communication 1464 (e.g., where Communication 1464 was an alert stating low glucose and Remote Monitor 1410 feeding Host), communications to Remote Monitors 1412, 1414 can be notifications that say Host's glucose was low and Remote Monitor 1410 addressed it. Such notification can be displayed on a user interface of the remote monitoring devices of Remote Monitors 1412, 1414. In the case where Remote Monitor 1410 does not take actions to address Communication 1464 and/or a delay has expired, Communication 1464 may automatically pass to one or more of Remote Monitors 1412, 1414, 1416. A similar interaction can occur between Remote Monitors 1412, 1414, where unaddressed communications pass to Remote Monitors 1416, or where the communications are addressed, no communication is sent or another communication is sent from remote monitoring devices of Remote Monitors 1412, 1414. Such other communication can be based on the classes of one or more of Remote Monitor 1410, 1412, 1414, 1416, Communication 1464, responses to communications, the communication received by Remote Monitors 1412, 1414, the actions taken by Remote Monitors 1412, 1414, and/or other data and/or information.

In other situations, Remote Monitors can select to send Communication 1464 or other communications to one or more other Remote Monitors. For example, there can be a response to Communication 1464 and/or other communications that allows Remote Monitor 1410 to select one or more other Remote Monitors to receive the message. In some cases, a Remote Monitor can send an ignore or "I'm busy" response, and the communication can cascade (e.g., be sent) to the next classification in the hierarchy and/or other classifications. In some cases, permissible communications can cascade to other Remote Monitors who would not have otherwise received that information.

Furthermore, each of Remote Monitors 1410, 1412, 1414, 1416 can communicate with one another using communication channels between their remote monitoring devices, such as Channel 1462. Such communication can enable a higher level of coordination and care of a Host from Remote Monitors. For example, Remote Monitors 1412, 1414, 1416 can communicate with Remote Monitor 1410, who can be in Primary Classification 1404, to give Remote Monitor 1410 feedback, requests, directions, data, etc. Moreover, Remote Monitor 1410 can give Remote Monitors 1412, 1414, 1416 updates, information, requests, feedback, directions, data etc. In some implementations, Communication 1402, which can be sent from a host monitoring device, can also be sent to one or more of Remote Monitors 1412, 1414, 1416.

In addition, or in the alternative, in some implementations, the same communication can be sent and/or relayed to a plurality of Remote Monitors. However, the remote monitoring devices of the plurality of Remote Monitors can have different displays in response to the communication based on the classification of the receiving Remote Monitor. For example, a remote monitoring device of a Remote Monitor in Primary Classification 1404 can receive a communication and display substantially all of the communication including a data measurement and an alert, whereas a remote monitoring device of a Remote Monitor in Secondary Classification 1406 may only display a data measurement.

Figure 14D:
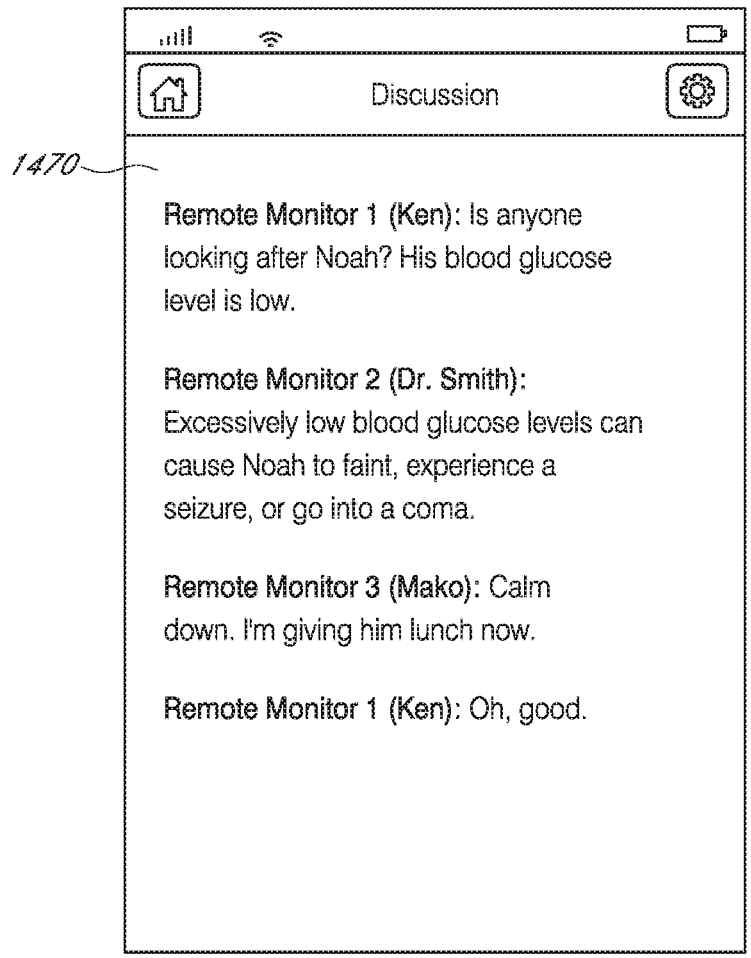

FIG. 14D illustrates an example discussion chain between Remote Monitors, in which the Remote Monitors can share information about a Host and/or any other information the Remote Monitors want to share and/or discuss. Discussion chains (e.g., logs) can be restricted or open based on individual Remote Monitors, classifications of Remote Monitors, urgency, proximity of the Host and/or Remote Monitors, etc. Remote Monitors can be identified (e.g., by name, remote monitoring device serial number, nickname, classification, etc.) or anonymous. Discussion 1470 shows a plurality of Remote Monitors discussing a Hosts' glucose measurements. Each Remote Monitor can see the other's messages, which can allow them to coordinate care. However, in some implementations, only some Remote Monitors may see some messages, and only other Remote Monitors may see other messages. Discussion 1470 can be displayed on a remote monitoring device (e.g., Remote Monitoring Device 300), host monitoring device (e.g., Host Monitoring Device 200), server (e.g., Secure Server 504), and/or any other device described in this disclosure. Advantageously, a remote monitoring device can view Discussion 1470 to see what its Remote Monitors are discussing and/or other Remote Monitors are discussing. Similarly, a host monitoring device can view Discussion 1470 in order to see what its Remote Monitors are discussing. A server can store Discussion 1470 in memory and/or display Discussion 1470 on a display communicatively and/or operatively coupled to the server. In some implementations, the server can coordinate and/or compile the communications into Discussion 1470.

In some implementations, the monitoring system can include a server and a plurality of remote monitoring devices. The plurality of remote monitoring devices can each have a classification. Each of the plurality of remote monitoring devices can be configured to send communications to the server. The server can be configured to create a log (e.g., Discussion 1470) containing a subset of the communications between the plurality of remote monitoring devices and the server. The creation of the log can be based on the classification of the communicating remote monitoring device. The server can then send the log to the remote monitoring devices whose communications are included in the log. In some implementations, the server can also send the log to a host monitoring device. In some implementations, the communications from one or more remote monitoring devices can be restricted out of the log.

Figure 15:
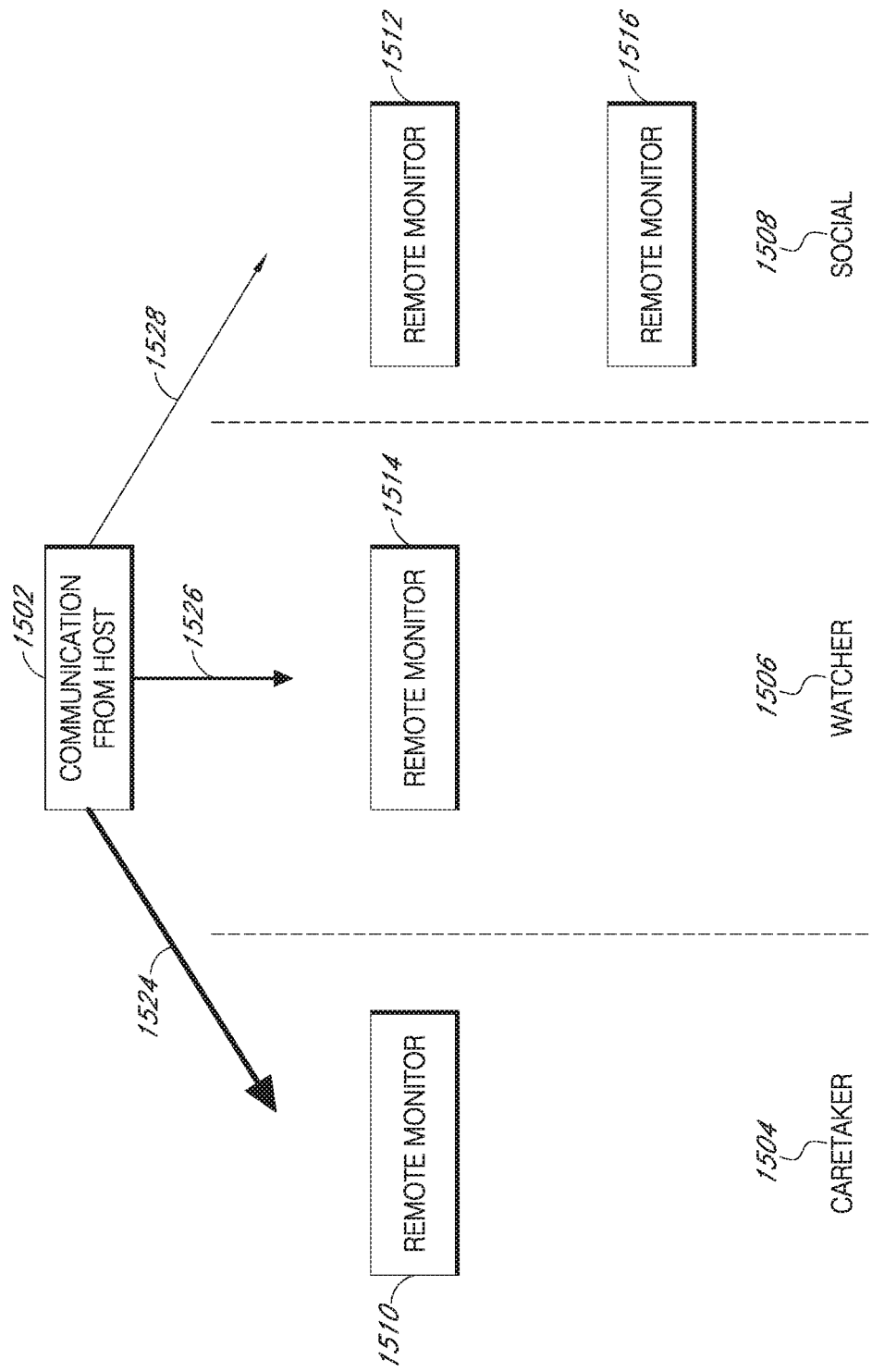
FIG. 15 illustrates an example classification of Remote Monitors where different classifications of Remote Monitors receive different amounts and/or different kinds of data.

FIG. 15 illustrates an example classification of Remote Monitors where different classifications of Remote Monitors receive different amounts and/or different kinds of data. Whereas FIG. 14A-C showed hierarchical stratification of classes, FIG. 15 illustrates lateral stratification. Classifications can have both hierarchical (or vertical) and lateral stratification (e.g., Watchers, Caretakers, Social Associates, etc. can have Primary, Secondary, Tertiary, etc. classifications). In lateral stratification, the different classes (e.g., Caretakers, Social Associates, Strangers, Watchers, Assigned Remote Monitors, Universal Remote Monitors, etc.) receive different kinds and different amounts of data. Such classifications can also be stored in memory and/or determined by a remote monitoring device, host monitoring device, server, and/or any other device described in this disclosure.

In some embodiments, the server may provide a message informative of an event associated with the analyte state of a Host to a Remote Monitor having a higher privilege/priority classification. If the Remote Monitor fails to provide an acknowledgement response to the message, within a predetermined time period, the server can relegate the Remote Monitor's classification to a different, for example, a lower privilege/priority classification. In some embodiments, the server may send a plurality of messages informative of an event associated with the analyte state of Host. The relegating can occur after a predetermined number of instances of lack of acknowledgement from Remote Monitor.

In addition, the server may elevate the classification of the Remote Monitor to a different classification, for example, from a lower privilege/priority to a higher one based on receipt of acknowledgement response from the Remote Monitor, within a predetermined period of time. In some embodiments, when a plurality of messages informative of Host state has been sent, the elevating can occur after receipt of a predetermined number of instances of acknowledgement responses.

In some cases, the server can provide an alert informative of an event associated with the analyte state of the host to a first remote monitoring device in a first classification, based on the notification rules associated with the first classification. The server can receive a response from the first remote monitoring device indicative of inability or unavailability of a Remote Monitor to react to the alert. Alternatively, the sever may detect a lack of response from the first remote monitoring device within a predetermined time period after providing the alert. The server can provide the alert to a second monitoring device. In some embodiments, the server may send the alert to a second remote monitoring device when the Remote Monitor associated with the first remote monitoring device indicates an ability to react to the alert. In some embodiments, the classification of the second remote monitoring device can be elevated after receiving an acknowledgement within a predetermined time after providing the alert to the second monitoring device. In some embodiments, the classification of a first remote monitoring device can be relegated to a lower privilege/priority classification based on lack of response or receiving of a message indicating inability or unavailability of the Remote Monitor associated with the first remote monitoring device.

In some embodiments, the notification rules associated with a given classification may be overridden before providing an alert to a second remote monitoring device, where the classification may otherwise not allow for delivery or receipt of the alert. The overriding may also occur based on the severity factor of the information associated with the alert.

Remote Monitor 1510, who can be in Caregiver Classification 1504, can receive with a remote monitoring device Communication 1524. Communication 1524 can include notifications, messages, and/or alerts regarding a Host's analyte measurements (e.g., glucose level) and/or data based on other data (e.g., Processed Data, Contextual Data, Health Data, System Data, Treatment Data, User Data, Sensor Data, Summary Data, and/or any data described in this disclosure). A high degree of communication can be helpful to Remote Monitor 1510 as a Caretaker.

Remote Monitor 1514 can be in Watcher Classification 1506. As a Watcher, Remote Monitor 1514 may have less responsibility as to the Host than a Caretaker, and may not desire as much communications. As such Communication 1526 can contain less information, and may not contain the detail that a Caretaker may desire. Communications can also be sent to a remote monitoring device of Remote Monitor 1514 less frequently.

Remote Monitors 1512, 1516 can be in Social Classification 1508. As Social Associates, Remote Monitors 1512, 1516 may have little to no responsibility for the Host, and may not desire much communication at all besides high-level data. As such Communication 1528 can contain even less information than Communication 1526, and may not contain the detail that a Caretaker or Watcher may desire. Communications can also be sent to remote monitoring devices of Remote Monitors 1512, 1516 less frequently.

In some implementations, communications can be relayed between Remote Monitors in different classifications (e.g., Caretaker Classification 1504, Watcher Classification 1506, and Social Classification 1508) where a remote monitoring device of a first Remote Monitor in a first class receives a communication, and then sends a different communication to a remote monitoring device of a second Remote Monitor in a second class. In some cases, the different communication can include less data and/or information. For example, if the first Remote Monitor is a Caretaker and the second Remote Monitor is a Social Associate, the Social Associate may desire less information than the Caretaker. Such different communication can be based on the communication of the first class, the classes of the first and second Remote Monitors, actions of the first Remote Monitor, and/or any other criteria desired. By way of illustrative example, Remote Monitor 1510 can receive at a remote monitoring device Communication 1524, which can contain a low glucose measurement and an alert. As a Caretaker, Remote Monitor 1510 can then feed the Host. Remote Monitor 1510's remote monitoring device can then generate a communication to send to a remote monitoring device of Remote Monitor 1514, who is in Watcher Classification 1506, that says the Host's low glucose measurement and that Remote Monitor 1510 fed the Host. Since Remote Monitor 1514 may desire less information than a Caretaker, Remote Monitor 1514 may receive less information, such as a log update and/or a low priority notification. Had Remote Monitor 1514 been in Caretaker Classification 1504, he/she may have received more information, such as a message and/or a higher priority notification.

In some embodiments, a first Remote Monitor in one classification can send a request to elevate a second Remote Monitor to a higher privilege/priority classification. In some embodiment, the elevating occurs after the second Remote Monitor has indicated acceptance of the higher privileges and duties associated with the higher classification.

In some implementations, a communication can be sent and/or relayed to a plurality of Remote Monitors. However, the remote monitoring devices of the plurality of Remote Monitors can have different displays in response to the communication based on the classification of the receiving Remote Monitor. For example, a Caretaker can receive a communication and display substantially all of the communication including a data measurement and an alert, whereas a remote monitoring device of a Social Associate may only display a data measurement.

In some cases, it can be desirable to have a way to assign a classification to each Remote Monitor. In some implementations, a user interface can allow a Host and/or Remote Monitor to assign a classification to a Remote Monitor, and/or allow a Host and/or Remote Monitor to customize the communications and/or other data received by a particular Remote Monitor. The notification rules can define circumstances to send a message to a respective remote monitoring device informative of an event associated with the analyte state of the Host. The notification rules can be modifiable by the authorized remote monitoring devices within the scope of a set of permissions to the data associated with the respective remote monitoring device.

In some embodiments, the permissible data can include (i) retrospective sensor data, (ii) real time sensor data, and (iii) a trend in the rate of change of the analyte state of the host, as well as other types of data described herein.

FIGS. 16A-D illustrate an example display allowing the selection of a classification for a Remote Monitor and configuration of other settings. The display can be displayed on a host monitoring device that is followed by remote monitoring devices. In some cases, the contents of the display can be stored on a server (e.g., Secure Server 504). In some implementations, the classification of Remote Monitor can be selected and preferences automatically filled in. In addition or in the alternative, for each individual Remote Monitor, a Host, Remote Monitor, Administrator (e.g., adult caretaker of a child host, such as a parent/guardian or health care provider), and/or other user can define the frequency of communications, rights, and/or privileges of that Remote Monitor.

In some cases, it may be desirable to be able to quickly configure any Remote Monitor, including newly added Remote Monitors. Pull-down Menu 1602 can be used to select from the group of predefined classifications/classes, and/or any classification described in this disclosure (e.g., Caretakers, Social Associates, Strangers, Watchers, Assigned Remote Monitors, Universal Remote Monitors, and/or any other role, and/or their hierarchical classification, including Primary, Secondary, Tertiary, and the like). The Pull-down Menu 1602 can also be used to define any user-defined class as desired. If such is selected, the frequency of communications, rights, and/or privileges of a Remote Monitor can be predefined in one or more sets of permissions and/or in one or more sets of notification rules.

In some cases, a particular Remote Monitor can be restricted in the classifications/classes that he/she can choose. In a non-limiting example, a Remote Monitor may be presented with the display of FIG. 16A on his/her remote monitoring device, and/or wish to be a Primary Caretaker. However, if the Host and/or an Administrator has restricted that Remote Monitor from being a Primary Caretaker, then the Caretaker may only be presented with available choices based on the restriction, such as "Secondary Caretaker" and/or "Tertiary Caretaker" or the like, on the Pull-down Menu 1602.

In some cases, a Remote Monitor, Host, and/or other user may desire to define (e.g., customize) the settings for a particular individual. Returning to FIG. 16A, as a non-limiting example, such Remote Monitor, Host, Administrator, and/or other user can use a user interface to define such settings. For example, Cell 1604 can define how the Remote Monitor receives Urgent Low Alerts (e.g., urgent alerts when a Host's glucose level is low). Such Urgent Low Alerts can be toggled on/off using Slide 1606. The Remote Monitor, Host, and/or other user can set Threshold 1608, in which, when glucose measurements of the Host with a host monitoring device are less than or equal to Threshold 1608, an alert can occur. Alert Type 1610 can be used to set how an alert occurs, such as a sound, vibration, flashing light, etc.

Similarly, Cell 1612 can define how the Remote Monitor receives Low Alerts (e.g., alerts when a Host's glucose level is low). Such Low Alerts can be toggled on/off using Slide 1614. The Remote Monitor, Host, and/or other user can set Threshold 1616, in which, when glucose measurements of the Host with a host monitoring device (e.g., a host monitoring device that can be substantially similar to Host Monitoring Device 300 and/or any other device described in this disclosure) are less than or equal to Threshold 1616, an alert can occur. Other thresholds can be set, such as Threshold 1618, which can give a duration of measurements (e.g., greater than or equal to Threshold 1618) that can set off a Low Alert. Threshold 1620 can be used to set an amount of snooze before re-alerting.

Similarly, Cell 1622 can define how the Remote Monitor receives High Alerts (e.g., alerts when a Host's glucose level is high). Such High Alerts can be toggled on/off using Slide 1624. The Remote Monitor, Host, and/or other user can set Threshold 1626, in which, when glucose measurements of the Host with a host monitoring device are greater than or equal to Threshold 1626, an alert can occur. Other thresholds can be set, such as Threshold 1628, which can give a duration of measurements (e.g., greater than or equal to Threshold 1628) that can set off a High Alert. Threshold 1630 can be used to set an amount of snooze before re-alerting. Alert Type 1632 can be used to set how an alert occurs, such as a sound, vibration, flashing light, etc.

Similarly, Cell 1634 can define how the Remote Monitor receives alerts when no data has been transmitted. Such No Data Alerts can be toggled on/off using Slide 1636. The Remote Monitor, Host, and/or other user can set Threshold 1638, in which, if no data has been received for a duration greater than or equal to Threshold 1638, an alert is sent. Alert Type 1640 can be used to set how an alert occurs, such as a sound, vibration, flashing light, etc. Other types of alerts can be set as desired.

Figure 16A:
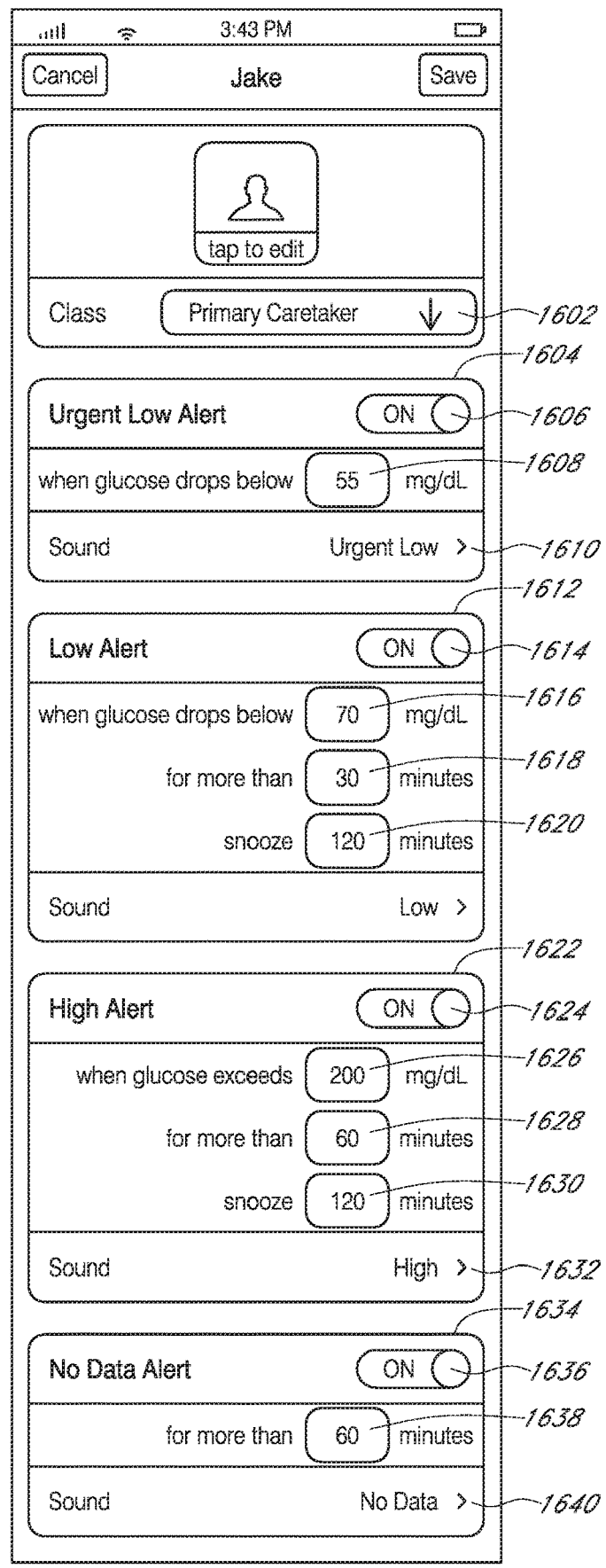
FIGS. 16A-D illustrate an example display allowing the selection of a classification for a Remote Monitor and configuration of other settings.
Figure 16B:
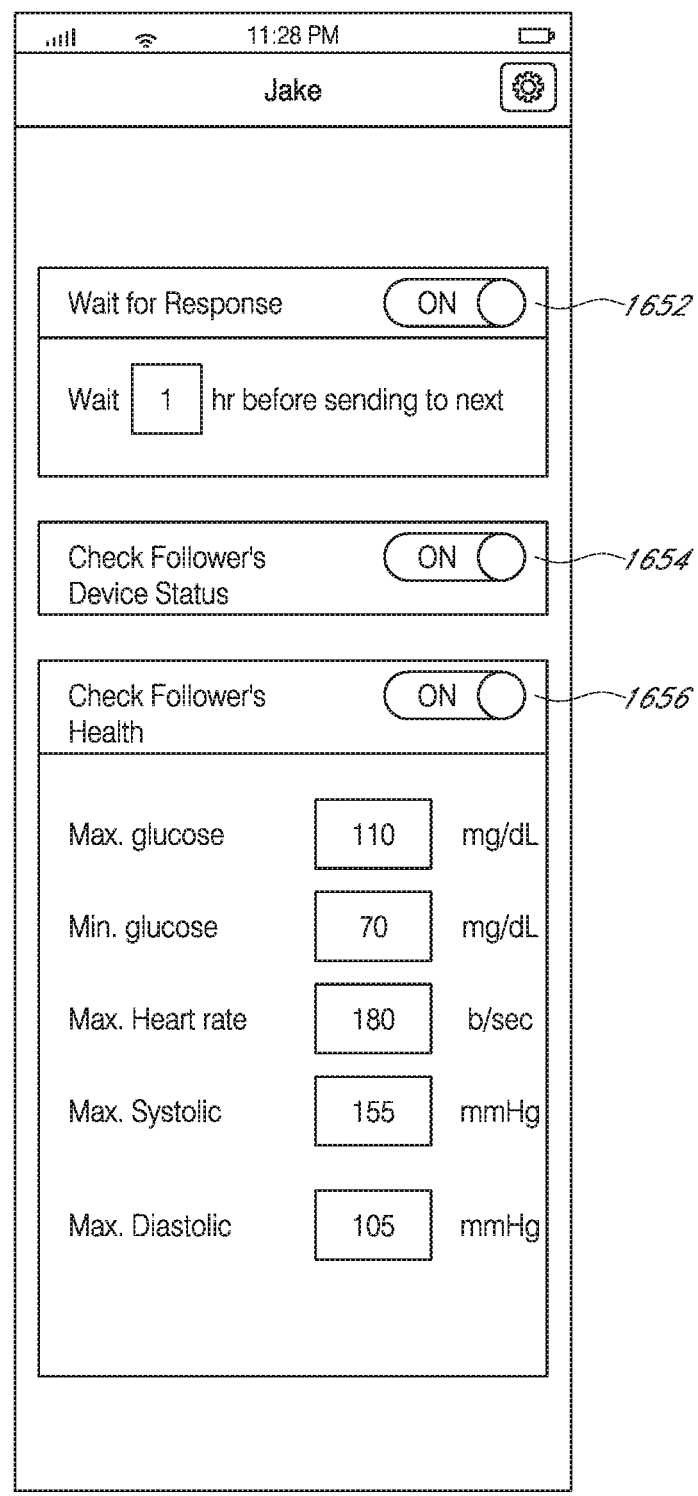

Other rights, privileges, and/or other settings can be also configured for the Remote Monitor. FIG. 16B illustrates more options. Cell 1652 can be used to set the wait for response (e.g., delay) for a Remote Monitor. Cell 1654 can be used to set whether the Remote Monitor's remote monitoring device status (e.g., whether or not it is functioning properly by looking at System Data) will be taken into account in communicating. Cell 1656 can set whether a Remote Monitor's health characteristics (e.g., based on analyte measurements or other data, including communications, Processed Data, Contextual Data, Health Data, System Data, Treatment Data, User Data, Sensor Data, Summary Data, and/or any data described in this disclosure) will be taken into account for communications, and any thresholds to consider when considering whether or not to communicate to a Remote Monitor. For example, a Remote Monitor may not receive communications if his/her glucose measurements falls outside of a defined range (e.g., defined by minimum and maximum values), his/her heart rate is greater than or equal to a defined threshold, and/or his/her blood pressure is over a defined threshold. A Host and/or Remote Monitor can similarly set parameters for other health characteristics in which a Remote Monitor will and/or will not get communications. In some embodiments, the classification of Remote Monitor may be modified from a high to low or vice versa, based on that Remote Monitor's health characteristics relative to other Remote Monitors.

Figure 16C:
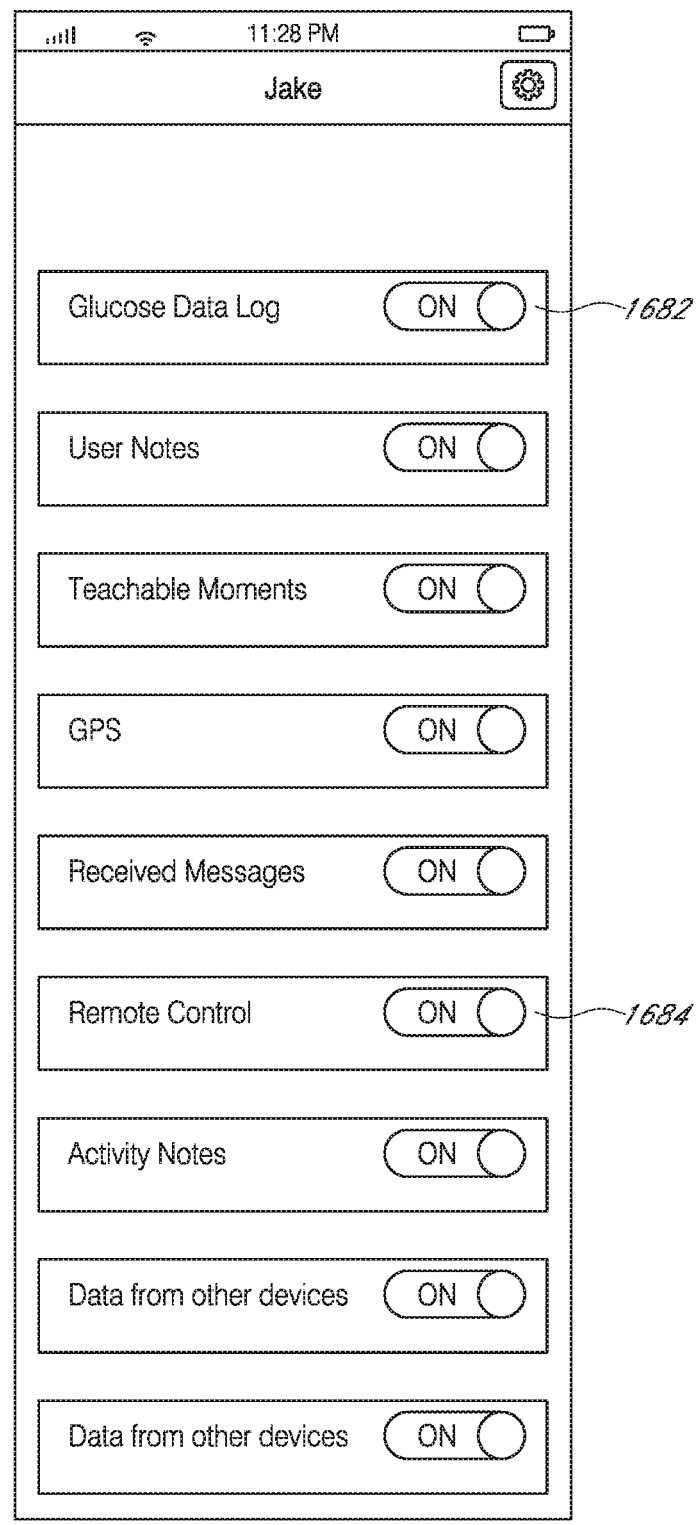

FIG. 16C illustrates more options. Other rights and/or privileges can be set for a Remote Monitor, such as Cell 1682, which can allow or disallow a Remote Monitor from viewing logs (e.g., Log 1100) associated with glucose measurements. Such may be desirable because certain types of Remote Monitors (e.g., Caretakers) may be highly active and desire to have access to more information, such as insulin intake, activity, location of the Host, location of the Remote Monitors, and other data. Examples of other data can include: analyte measurements, Processed Data, Contextual Data, Health Data, System Data, Treatment Data, User Data, Sensor Data, Summary Data, and/or any data described in this disclosure). The Host and/or Remote Monitor can toggle the viewing of each on/off for each Remote Monitor.

Another non-limiting example is Cell 1684, which allows a Remote Monitor, Host, and/or other user to toggle on/off Remote Control. In some implementations, a remote monitoring device can control a Host's treatment. Such control can include calibrating the host monitoring device or other devices (e.g., insulin administration using a medicament delivery pump). In some cases, for maintaining security, other authorizations (e.g., in addition or in the alternative to toggling on) can be used to allow the remote control of the remote monitoring device. For example, a Remote Monitor may need to authenticate himself or herself using a thumbprint, biometric sensor, password, passcode, authentication key, private/public passcode combination, etc. before the Remote Monitor can take remote control. As another non-limiting example, a Remote Monitor can be given control only in situations where he/she is in close proximity to the Host, where proximity (e.g., within 1000 square meters or other determined ranges) can be determined based on locators of the host monitoring device and remote monitoring device. In some implementations, authentication can occur when another remote monitoring device, the host monitoring device, and/or another device (e.g., any device described in this disclosure) verifies and/or approves the remote control. For example, a communication can go to another remote monitoring device and that Remote Monitor can approve the remote control. In some cases, the approval communication may be sent in select cases, such as if the Remote Monitor taking remote control wants to do something that is atypical or not something the programming of a host monitoring device and/or device would normally do (e.g., not following a bolus calculator recommendation).

In some cases, it may also be desirable for a Host to take remote control of a remote monitoring device. Such control can include calibrating the remote monitoring device or other devices (e.g., insulin administration using a medicament delivery pump). Similar authentication and/or security can be built into such remote control as was described for remote control of a host monitoring device.

In some implementations, remote control can include approval. For example, a Host may desire to perform an action (e.g., administer insulin and/or other mendicants). The Host can indicate (e.g., using a message, selecting from a pulldown menu, hitting a button, etc.) that he/she is going to perform such action, and/or such can be automatically detected by the host monitoring device based on various received data as described herein. A host monitoring device can send a communication to the remote monitoring device requesting approval for an intended action. For example, a child may want to administer insulin. The host monitoring device can detect that the child's insulin levels are low and that child is trying to administer insulin. The host monitoring device can send a message and/or notification to the remote monitoring device indicating that the child would like to administer insulin. The child's parent using the remote monitoring device, who may also be classified as Primary Caretaker, can then approve or disapprove the administration using the remote monitoring device. For example, the message and/or notification can come with options (e.g., buttons, pulldown menu, check boxes, etc.), including "Approve" or "Disapprove," that the parent can select on a user interface.

In some cases, a Remote Monitor, Host, and/or other user can customize settings for a classification, which can then be selected. For example, the alerts settings for a classification can be set, and then that classification with those settings can be assigned to a Remote Monitor using Pull-down Menu 1602. In some implementations, different classifications and/or Remote Monitors can be notified differently based on the urgency of a Host's condition.

In some implementations, setting the frequency of communications, rights, and/or privileges of Remote Monitors can be restricted, in which only some users have an ability to adjust those settings. For example, a Host (e.g., adult host) and/or an Administrator (e.g., adult caretaker of a child host, a parent/guardian or health care provider) can be provided complete control over the communications, rights, and/or privileges to be shared with his/her Remote Monitor(s). Advantageously, an Administrator can control in some cases when the Host is not competent to adequately manage the system (e.g., when Host is too young, too old, too busy, lacks the awareness and/or ability, has mental challenges, is injured, is diseased, etc.). Whether a Host and/or Administrator controls, such controls can be set on a user interface of a display of the host monitoring device (e.g., such as the example shown in FIG. 12). As a result, other users (e.g., users who are not the Host and/or an Administrator) may not be able to control at least some aspects and/or functionalities of communications, rights, and/or privileges for themselves and/or other users. In some implementations, various controls can be placed on customizable settings. For example, for the aforementioned other users (e.g., users who are not the Host and/or Administrator), settings may not be configurable, may be limited in valid values, and/or may have only selectable options from a predetermined list of options. In some cases, a Host and/or Administrator can override any customizations made by a Remote Monitor and/or otherwise.

Figure 16D:
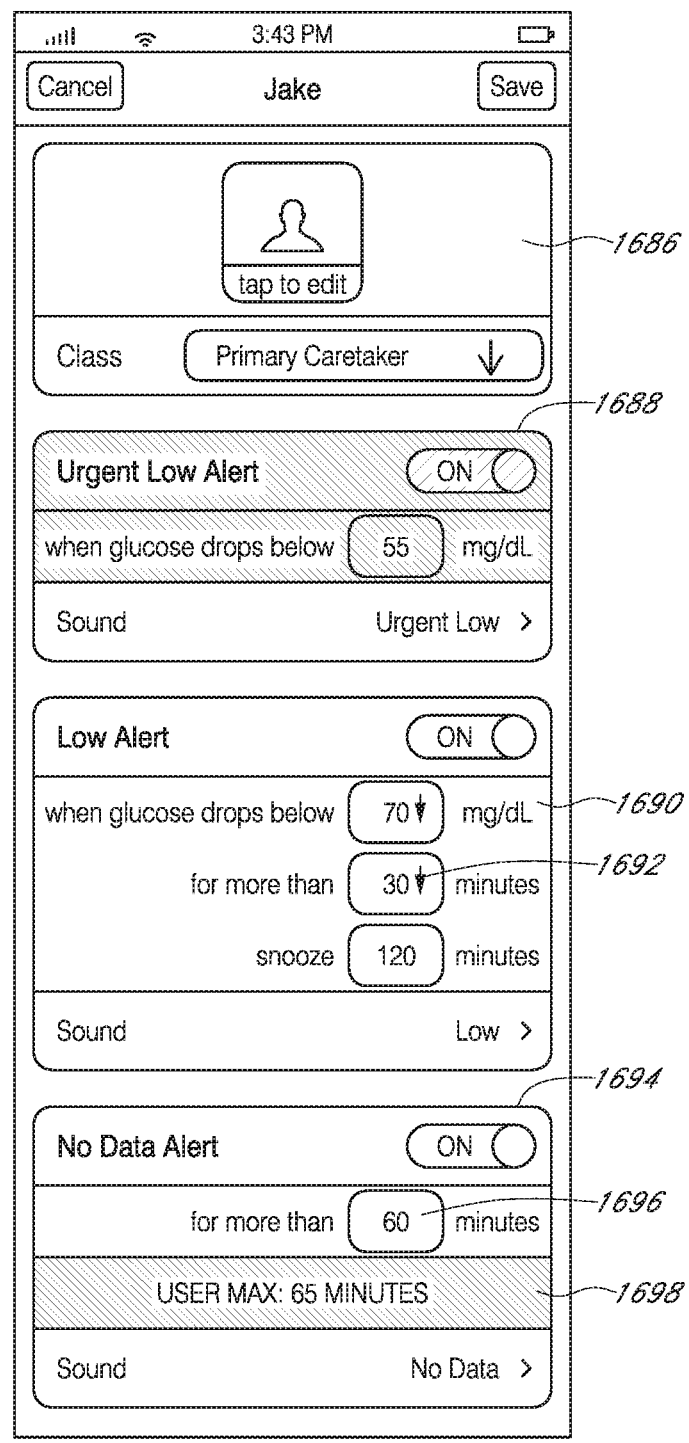

FIG. 16D illustrates an example display where customizations may be restricted by a Host, Administrator, and/or any other user with control to restrict. Display 1686 can be displayed on a remote monitoring device that can be substantially similar to Remote Monitoring Device 300 and/or any other device described in this disclosure. Display 1686 can also be displayed on a host monitoring device and/or any other device described in this disclosure. Contents of Display 1686 can be stored on a server (e.g., Secure Server 504). For example, when Display 1686 is displayed on a remote monitoring device and/or viewed by a Remote Monitor, Cell 1688 can illustrate an example where settings cannot be changed by the Remote Monitor. The Remote Monitor using Display 1686 cannot modify options in Cell 1688 (e.g., Remote Monitor cannot toggle on/off Urgent Low Alerts and/or set the glucose thresholds). Cell 1690 illustrates restricted options of a Remote Monitor from a selection of predetermined options. For example, Pulldown Menu 1692 can display predetermined options from which the Remote Monitor can select values to populate the field. Cell 1694 shows an example where the Remote Monitor can have some ability to customize, but such ability is restricted. For example, the Remote Monitor can enter a value into Threshold 1696. However, the value entered as Threshold 1696 has an upper limitation, where the Remote Monitor cannot enter a value above the upper limitation. For example, Restriction 1698 indicates that the maximum is 65 minutes.

Figure 17A:
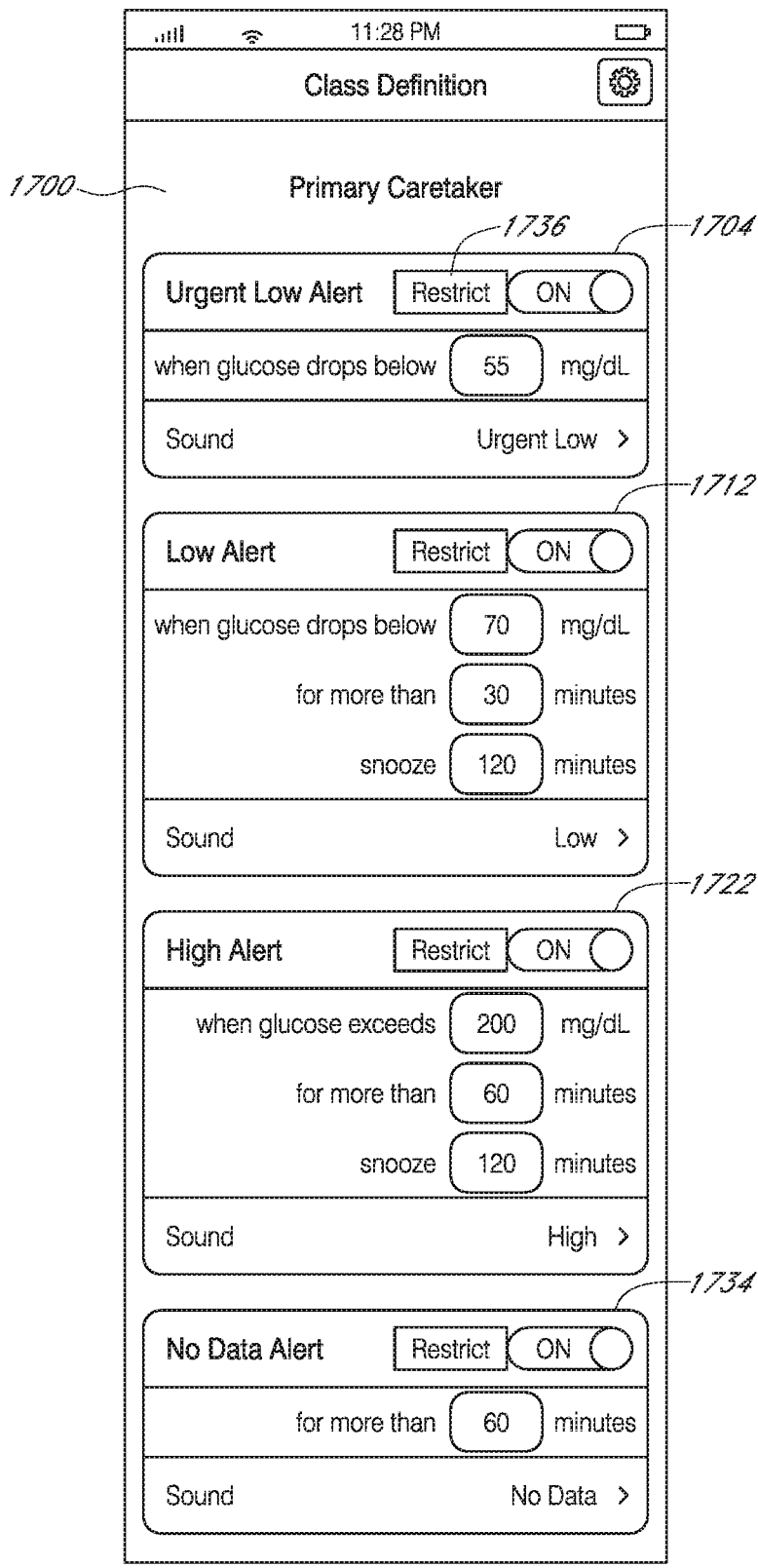
FIGS. 17A-D illustrate example customizable features of a Remote Monitor classification definition.
Figure 17B:
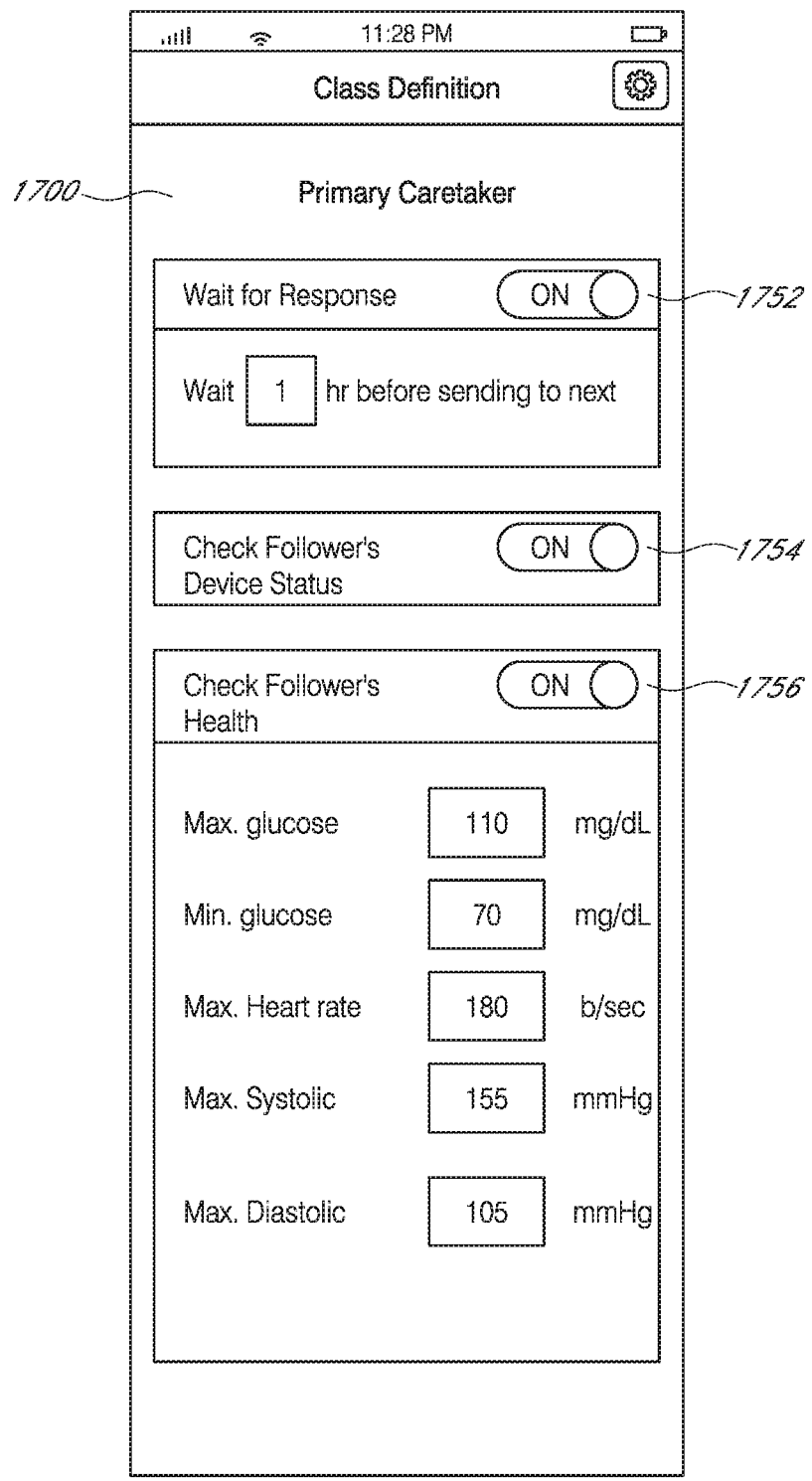
Figure 17C:
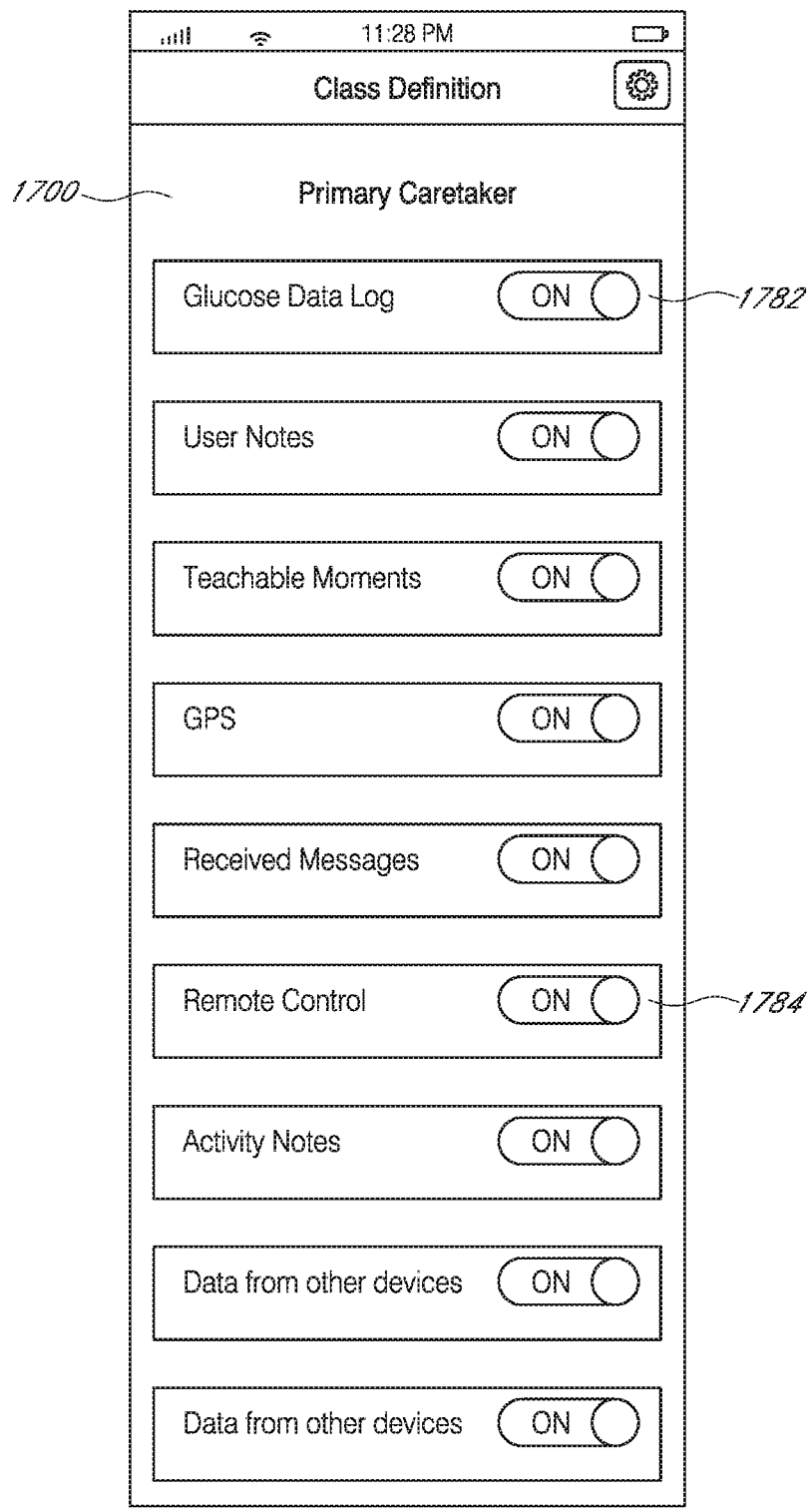

FIGS. 17A-D illustrate example customizable features of a Remote Monitor classification definition. FIG. 17A illustrates communications settings that can be set for an example Remote Monitor classification/class. Such settings can be predefined or customized by a Remote Monitor, Host, and/or other user. Settings 1700 can allow communications to be set for an example Primary Remote Monitor class. Any other classification described in this disclosure can similarly be configured. For example, alert settings can be set using Cells 1704, 1712, 1722, 1734 which can be substantially similar to Cells 1604, 1612, 1622, 1634, respectively. Cells 1752, 1754, 1756, 1782, 1784 can be substantially similar to Cells 1652, 1654, 1656, 1682, 1684 as well. These settings, ones made, can affect all Remote Monitors of a classification. In some cases, individual remote monitoring devices can have little or no ability to modify their own settings (and/or the settings of any other remote monitoring device and/or other devices described in this disclosure). In such cases, the settings for each individual remote monitoring device can be established by class definition settings and/or by individual settings made by the Host and/or Administrator. In some implementations, remote monitoring devices may have at least some freedom to adjust one or more settings in their communications, rights, and/or privileges, and/or the communications, rights, and/or privileges of other remote monitoring devices and/or other devices described in this disclosure.

In some implementations, the predefined settings of remote monitors can be initially set based on how active Remote Monitors are in predefined classes. For example, Primary Caretakers (in their respective classifications) generally, can get more alerts and/or information than other Remote Monitors. Moderately active Remote Monitors, such as Tertiary Caretakers, may desire fewer alerts and/or information. Low active Remote Monitors, such as Social Associates, may desire even fewer alerts and/or information.

Figure 17D:
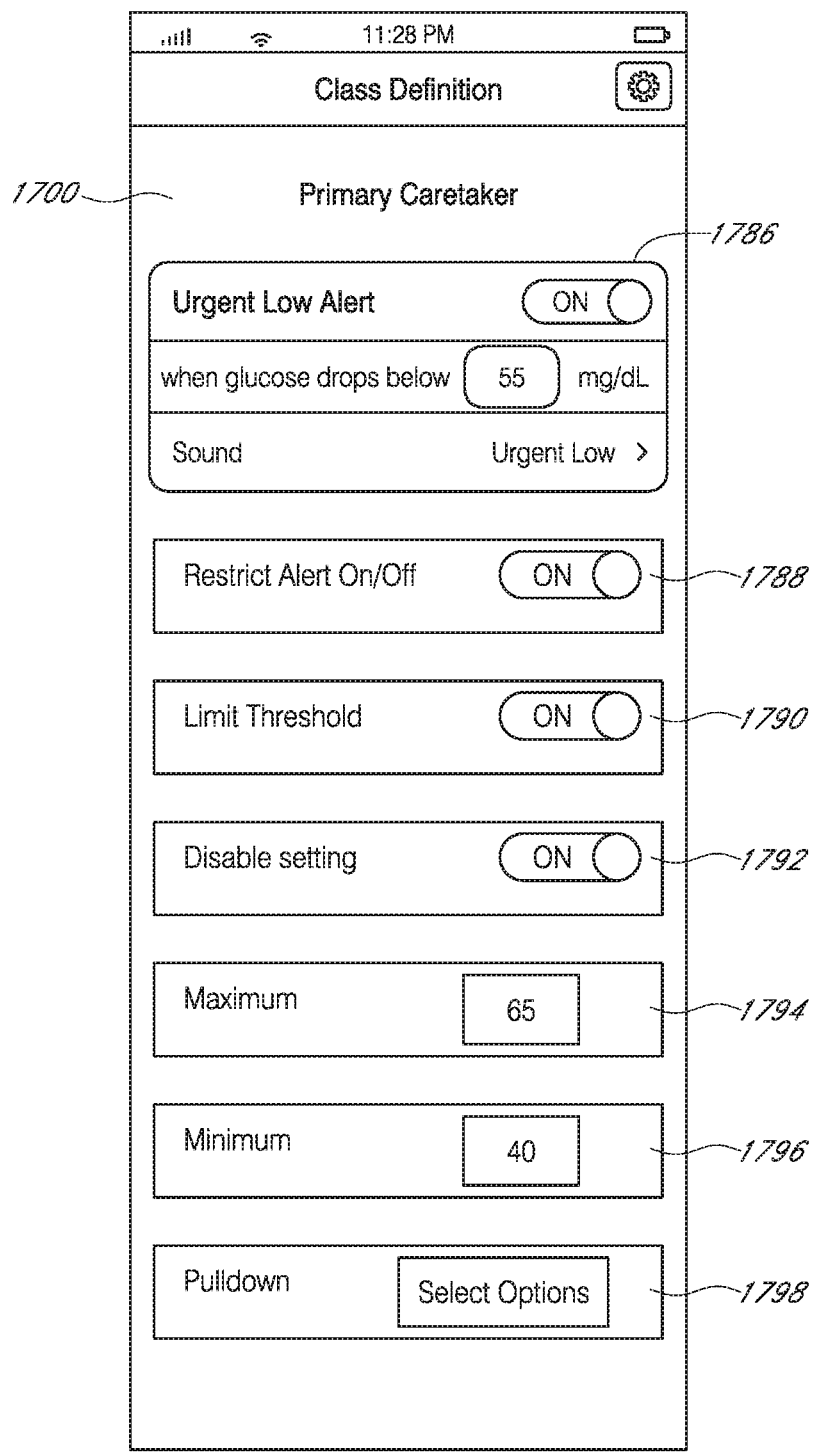

As previously described, a Host and/or Administrator can restrict the ability of some users (e.g., Remote Monitors and/or other users desired to be restricted) to customize settings. By way of illustrative example, a Host using a host monitoring device can restrict one or more settings. For example, referring to FIG. 17A there can be restrict buttons, such as Restrict Button 1736, that the Host can select when viewing Settings 1700. Restrict Button 1736 can present a Host with various options to restrict how a Remote Monitor can configure a setting in his/her remote monitoring device. FIG. 17D illustrates an example interface that could pop up to allow the Host to configure how a Remote Monitor can be restricted. The interface can be displayed on a host monitoring device. In some implementations, the interface can be stored in memory on a server (e.g., Secure Server 504) and/or displayed on a display communicatively and/or operatively coupled to the server. Cell 1786 can display the cell that is to be configured for the Remote Monitor (e.g., to view on the Remote Monitor's remote monitoring device), which in this illustration is the Urgent Low Alert cell. Cell 1788 can present the option of toggling on/off a Remote Monitor's ability to toggle on/off the Urgent Low Alerts on his/her remote monitoring device. Cell 1790 can allow the Host to toggle on/off limits to threshold that a Remote Monitor can enter into his/her Urgent Low Alert cell as viewed on his/her remote monitoring device, in which the threshold can indicate the glucose measurement below which an Urgent Low Alert is sent to the Remote Monitor's remote monitoring device. Cell 1792 can allow the Host to disable a Remote Monitor's ability to enter a threshold at all, and/or lock the threshold value to the Host's determined value. Cell 1794 can allow the Host to set a maximum value for the threshold that the Remote Monitor can enter. Cell 1796 can allow the Host to set a minimum value for the threshold that the Remote Monitor can enter. In some cases, the Host can set a range of values for the threshold (e.g., upper thresholds or lower thresholds) where a Remote Monitor can adjust the threshold within the range to trigger communications. In some implementations, thresholds can be set for other characteristics, such as any category of data described herein. Cell 1798 can allow a Host to define options for a Remote Monitor to choose from when setting the threshold for Urgent Low Alerts (e.g., via a pulldown menu and/or by prompting Remote Monitor).

Figure 18A:
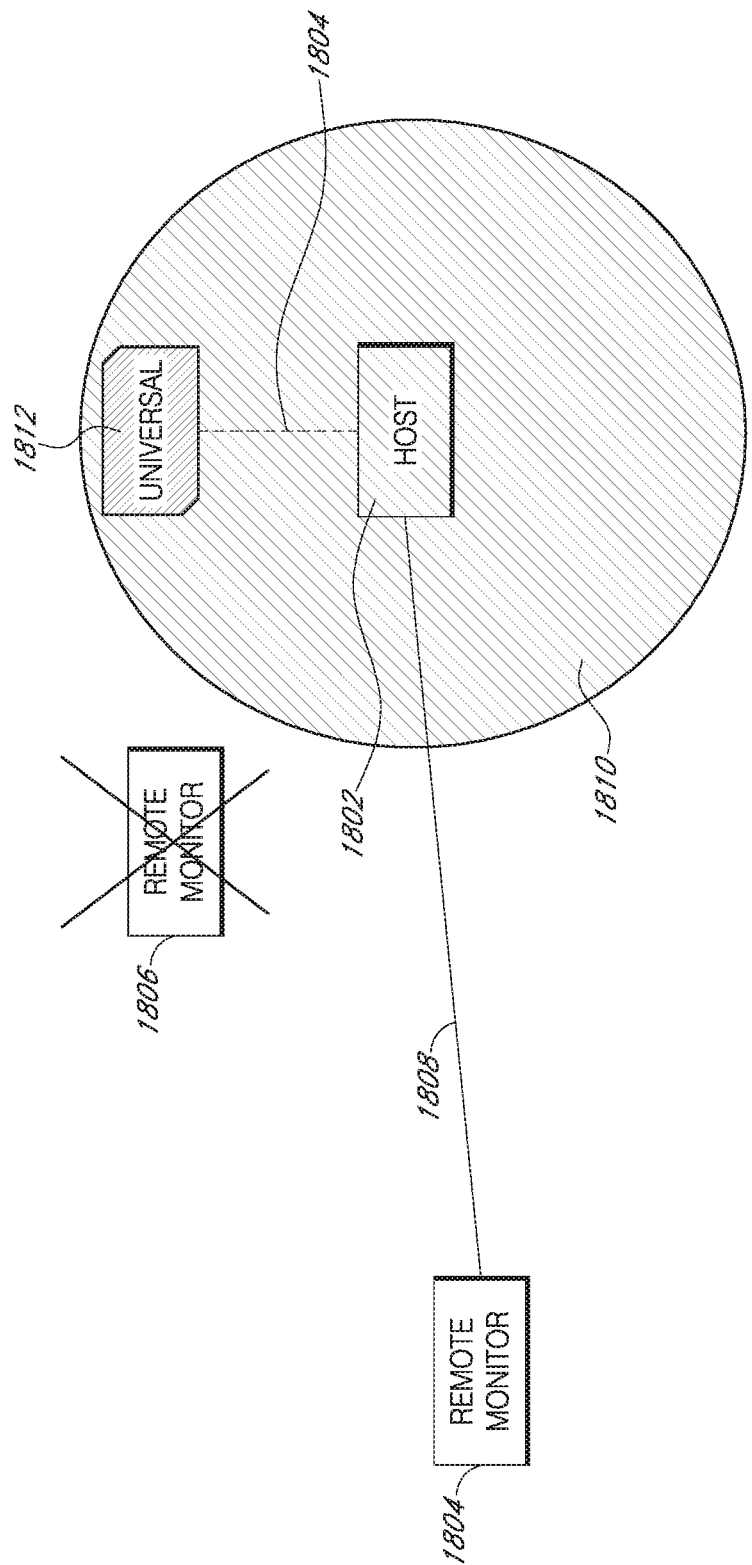
FIG. 18A illustrates an example where a Host communicates with a Universal Remote Monitor in close proximity for assistance.

FIG. 18A illustrates an example where a Host communicates with a Universal Remote Monitor in close proximity for assistance. In some implementations, upon determining an inability of Remote Monitors to react to an alert informative of a dangerous event associated with the analyte state of Host, a server, handling the remote monitor operations, can assign a Universal Remote Monitor in close proximity to Host for obtaining assistance. For example, Host 1802 can have a host monitoring device that is followed by remote monitoring devices as described herein. A first remote monitoring device can be associated with Remote Monitor 1806, and a second remote monitoring device can be associated with Remote Monitor 1804. At a time when Host 1802 desires assistance, Remote Monitor 1806 may be unavailable or unable to assist. In some cases, Remote Monitor 1806 may not receive communications from Host 1802's host monitoring device. In some cases, Remote Monitor 1806 can send a response indicating it is unavailable. Remote Monitor 1804 may be available and can send and/or receive communications via Channel 1808. However, Remote Monitor 1804 may be too far away to provide timely assistance. In such a case, Host 1802's host monitoring device can search for a Universal Remote Monitor within Area 1810, which can be a predefined area (e.g., 1000 square feet) and/or a predefined distance, typically (and/or contextually) defined with a proximity close enough to timely help Host 1802. For example, for a severe hyperglycemic response, the proximity may be within a few feet. As another non-limiting example, for a low, but not critically low, glucose reading, the proximity may be within a five minute travel distance (e.g., by car, bike, walking, running, etc.). In some cases, proximity can be as close as the closest Universal Remote Monitor. In Area 1810, Universal Remote Monitor 1812 can be in a position to assist. In some cases, notifying Universal Remote Monitor 1812 can be reserved for high priority emergencies.

In some embodiments, a server handling remote monitoring operations (e.g., Secure Server 504), can receive location information of the Host-designated remote monitoring devices and Host's device. The server can determine the ability or inability of each of Host-designated selected remote monitoring devices to react to an alert informative of a dangerous event associated with the analyte state of the Host based on a proximity of a Host-designated remote monitoring device to the Host's device within a predetermined distance. The predetermined distance can be set or derived as described above. Upon determining an inability of all of Host-designated remote monitoring devices to react to an alert, the server can assign a universal remote monitoring device not among Host-designated remote monitoring devices. The server, as part of the assigning process can generate a set of notifications rules pertaining to circumstances to send a message to the universal remote monitoring device informative of the dangerous event associated with the analyte state of the Host.

By way of illustrative example, Host 1802 can be attending a new school across the country from his/her Remote Monitors (e.g., Remote Monitors 1804, 1806). Host 1802's glucose level could drop to a low value, as measured by a host monitoring device. Universal Remote Monitor 1812 could be another student who also attends the school and is in close proximity within Area 1810. In this situation, Universal Remote Monitor 1812 could receive a communication (e.g., an alert) to help. In some cases, Universal Remote Monitor 1812, and/or any other Universal Remote Monitor, may need to pass a pre-approval process to become a Universal Remote Monitor. Such pre-approval process can include a background check, attending classes, and/or obtaining certain knowledge about helping diabetics and/or persons with health conditions. In some cases, a Universal Remote Monitor 1812 can become a Universal Remote Monitor based on characteristics and/or expertise of Host 1802 and/or Universal Remote Monitor 1812. For example, Universal Remote Monitor 1812 could be a medical professional with expertise in assisting diabetics. As another non-limiting example, Host 1802 could prefer a Universal Remote Monitor of the same gender as Host 1802. In some implementations, communications to Universal Remote Monitor 1812 can be anonymous and/or limited. For example, Universal Remote Monitor 1812 may only be able to see a defined subset of data about Host 1802. Such subset of data can be based on the kinds of data Universal Remote Monitor 1812 would use to help Host 1802. In some cases, Hosts can be identified (e.g., by name, remote monitoring device serial number, nickname, classification, etc.) or be anonymous to Universal Remote Monitor 1812. As another non-limiting example, a communication channel between Universal Remote Monitor 1812 and one or more of Host 1802's Remote Monitors (e.g., Remote Monitor 1804) could be opened so that Universal Remote Monitor 1812 could communicate with one or more of those Remote Monitors.

Such communication can include the transmission of data that can assist Universal Remote Monitor 1812 in helping Host 1802.

In some embodiments, as part of assigning a Universal Remote Monitor, the server assigns authorization to the Universal Remote Monitor for accessing Host's data. The scope of the authorization can be determined based on what data may be of use to the Universal Remote Monitor (and/or the characteristics or relationship between the Universal Remote Monitor and Host). In some embodiments, the authorization may be for a temporary time frame. In some embodiments, Host 1802 may be prompted to accept or decline the assignment of Universal Remote Monitor 1812. Host 1802 can also determine the duration of the temporary time frame. In some implementations, the server, handing the remote monitor operations (e.g., Secure Sever 510), can revoke the assignment of Universal Remote Monitor 1812 if a Host-designated Remote Monitor is detected to be available and able to assist Host 1802. Revoking the assignment can include removing authorization of access previously granted to Universal Remote Monitor 1812. The data made available to Universal Remote Monitor 1812 can include one or more of (i) retrospective sensor data, (ii) real time sensor data, (iii) a trend in the rate of change of the analyte state of Host 1802 or other data as described herein. In some implementations, the analyte state includes the glucose level.

Proximity can have other implications. Remote Monitors may not only want to know (e.g., be alerted) when a Host has an alert-worthy situation, but also may desire to know where the Host is presently located so that the Remote Monitor can take direct and/or indirect action to assist the Host. For example, a host monitoring device can send location data of the Host: (1) when a communication is generated (e.g., the recorded location data of the host associated with the CGM data that triggered an alert), and/or (2) after the communication is triggered (e.g., in case the Host is on the move, or has changed locations since an alert). The location data can be received by a remote monitoring device, server, and/or any other device described in this disclosure. In some cases, a Remote Monitor's classification (e.g., hierarchical or lateral) can dynamically change based on proximity. Such changes can be user customized (e.g., designated) or automatically changed based on predefined class definitions. The changes can be stored in memory and/or processed by a remote monitoring device, host monitoring device, server, and/or any other device described in this disclosure.

Figure 18B:
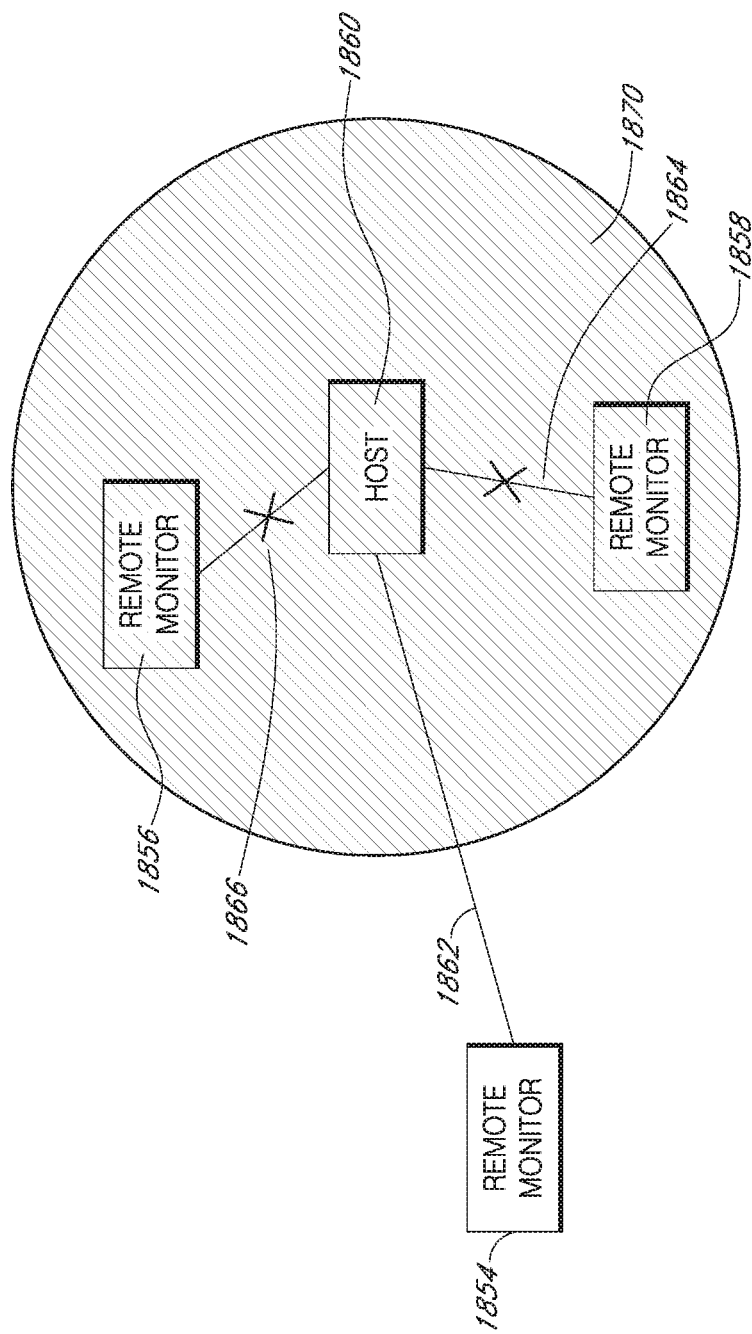
FIG. 18B illustrates an example where communications can be suppressed based on proximity.

In some cases, proximity can cause a host monitoring device to temporarily disable or enable alerts. FIG. 18B illustrates an example where communications can be suppressed based on proximity. By way of illustrative example, when Remote Monitor is able to receive communications from a Host's host monitoring device and/or other devices, one issue that can occur is duplicative communication. When Remote Monitor is nearby a Host (e.g., in the same room), communications may be triggered between Host and Remote Monitor in such a way that the same underlying communication can generate one or more simultaneous alarms, notifications or warnings between two or more devices. Such duplicity can cause frustration, irritation, and/or annoyance.

In some implementation, a remote monitoring device (e.g., Remote Monitoring Device 300), host monitoring device (e.g., Host Monitoring Device 200), server (e.g., Secure Server 504), and/or any other device described in this disclosure can detect duplicative communications and delay and/or suppress communications sent to one or more devices. In some cases, such detection can be based on location, pattern of communications, and/or responses by Remote Monitors and/or Hosts (e.g., repeated ignoring of communications, any feedback indicative of over/under communication, and/or user inputted changes to communication settings). In some cases, only certain kinds of communications may be suppressed. For example, a remote monitoring device, host monitoring device, server, and/or any other device described in this disclosure may suppress all alerts except urgent alerts.

For example, Host 1860 can be in Area 1870 with Remote Monitors 1856, 1858 and may desire to suppress and/or delay communications. As a result, remote monitoring devices of Remote Monitors 1856, 1858 and/or the host monitoring device of Host 1860 can suppress Communication Channels 1866, 1864. Such suppression can prevent communications from being sent and/or can turn off one or more sounds, vibrations, flashes, and/or other indicators of communication. In some implementations, this suppression can be ordered from the host monitoring device. For example, the host monitoring device of Host 1860 can detect that the remote monitoring devices of Remote Monitors 1856, 1558 are within Area 1870 and not send communications to those remote monitoring devices. In some implementations, suppression can occur by remote monitoring devices. For example, remote monitoring devices of Remote Monitor 1856 and/or 1858 may detect whether they are within Area 1870, and decline to receive communications from the host monitoring device of Host 1860 when in Area 1870. As another example, remote monitoring devices of Remote Monitors 1856 and/or 1858 can receive communications from a host monitoring device of Host 1860 when within Area 1870, but not display such communications. In some implementations, suppression can be handled by a server. The server can receive the locations of each host monitoring device and/or remote monitoring device and not relay messages from host monitoring devices to remote monitoring devices when such remote monitoring devices are within Area 1870 of the host monitoring device.

In some embodiments, the server handling the remote monitoring operations (e.g., Secure Server 504), can process an alert informative of a dangerous event associated with the analyte state of Host 1860. The processed alert can be within a set of notification rules associated with at least one of the authorized remote monitoring devices (e.g., remote monitoring devices 1854, 1856 and 1858). The server can receive an instruction to suppress sending the message associated with the alert one or more of the authorized remote monitoring devices. The server then can suppress the sending of the message one or more of the authorized remote monitoring devices.

In some embodiments, the dangerous event includes the analyte state of Host 1860 exceeding a predetermined analyte concentration threshold or a predetermined rate of concentration change threshold. In some implementations, processing the alert includes receiving alert data from the host monitoring device of Host 1869. The alert data can be generated at one or both of the host monitoring device of Host 1860 or a sensor electronics device in communication with the continuous analyte sensor of Host 1860. In some implementations, the server can generate the alert by processing the data to determine if the analyte state exceeds a predetermined analyte concentration threshold or a predetermined rate of concentration change threshold. In some implementations a second predetermined analyte concentration threshold lower than the predetermined analyte concentration threshold can be defined. A second predetermined rate of concentration change threshold lower than the predetermined rate of concentration change threshold can also be defined. In the implementations defining these second thresholds, prior to suppressing a message, the analyte data can be processed to determine whether the analyte state exceeds these second thresholds. If the analyte state has exceeded the second thresholds, the instruction to suppress is overridden and the message is sent to at least one of the authorized remote monitoring devices after a predetermined delay.

Communications can be delayed, where the communications are not sent and/or displayed until after a determined amount of time (e.g., 0, 5, 10, 15, 20, 30, 60 minutes or any number of minutes desirable including any number of minutes between any of the aforementioned). In some cases, delays can be cued to events, such as where communications are delayed from being sent or displayed until a user wakes a device. As has been described in this disclosure, delays can be handled by remote monitoring devices, host monitoring devices, servers, and/or any other device in this disclosure. In some implementations, when the communications are delayed, the server can override an instruction to suppress the communication. In some cases, there can be other Remote Monitors, such as Remote Monitor 1854, who are not in Area 1870 and who have communication channels such as Communication Channel 1862. Such Remote Monitors may continue to have communications unimpeded.

Detection of whether Remote Monitors and Hosts are within a defined proximity can be accomplished using locators (e.g., Locators 206, 306) in remote monitoring devices, host monitoring devices, and/or any device in this disclosure. For example, GPS can be used. As another non-limiting example, when a remote monitoring device receives an alert, it can start a Bluetooth or iBeacons scan for Host 1860's host monitoring device or other devices. If the remote monitoring device detects the host monitoring device and/or other devices (e.g., within 30 feet for a Bluetooth detection), the remote monitoring device can examine the Received Signal Strength Indicator ("RSSI") to determine how close (e.g., far, near, very near) it is to the host monitoring device and/or other device. When the remote monitoring device determines it is near or very near the Host, the remote monitoring device can delay received communications (e.g., alerts) for a determined amount of time (e.g., one or two minutes) to give the Host a chance to respond. If the Host does respond within the determined amount of time, then the alert would not sound on the remote monitoring device.

In some cases, it may be desirable for a Remote Monitor to receive more communications when in close proximity because the Remote Monitor can be of more help when in close proximity. In such cases, the aforementioned proximity detection can be used to increase alerts. In some cases, proximity can be used in conjunction with pattern recognition, such as any pattern recognition described in this disclosure, to determine whether more or fewer communications are desirable.

Figure 19:
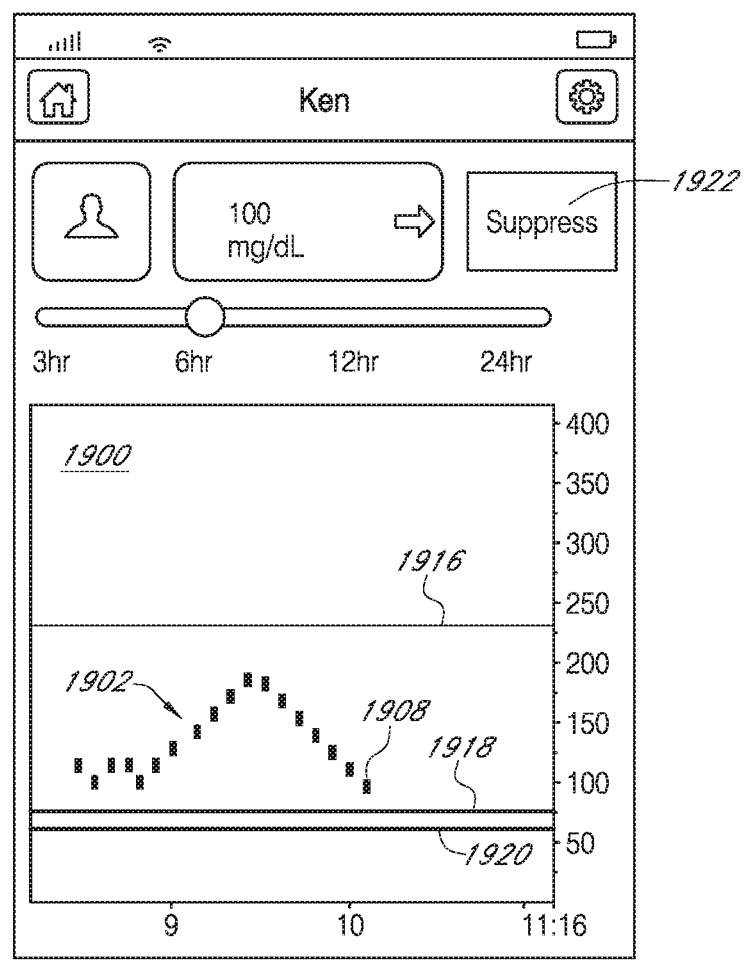
FIG. 19 illustrates an example situation where a Host can preempt a communication before it is sent to a Remote Monitor.

FIG. 19 illustrates an example situation where a Host can preempt a communication before it is sent to a Remote Monitor. For example, a Host may preempt a communication when the Host knows an event will happen and/or is addressing the event. Communications, such as alarms, typically lack the context for why they are triggered. Many, if not most, alarms are not caused in emergency situations because the context of the alarm (e.g., the situational factors of the Host) is typically under the Host's control. For example, a Host may have missed a meal and/or eaten later than scheduled, undergone previously unplanned physical activity, and/or been under unusual, excessive stress. Host may be aware of and/or is capable of remedying these issues. For example, a Host can ingest or take a prescribed medicine (e.g., bolus insulin), modify behavior, eat extra snacks and/or meals to make-up for missed or late meal, take additional rest to account for extra physical activity, engage in relaxation (e.g., by doing yoga, meditation, watching TV, etc.) to compensate for excessive stress. Yet, Host's Remote Monitor(s) may not be aware of Host's awareness and/or his/her actions to attend to the situation. Therefore, increasing the amount of informational context associated with the alert would be beneficial to both Remote Monitor(s) and Host. Remote Monitors will be provided with peace of mind, knowing that Host is responding appropriately to remedy the situation. In addition, Host will be relieved of the responsibility or obligation to explain to Remote Monitor(s) why the alert was triggered.

In some cases, if a Host and/or Remote Monitor sees that the Host's glucose level is dropping and/or trending downwards, he/she might want to send out alerts, notifications, and/or other communications as soon as possible rather than wait until the glucose level falls below a lower threshold (e.g., Lower Threshold 1918). Or, Host might want to send these alerts or notifications before the glucose level rises above an upper threshold (e.g., Upper Threshold 1916). In some cases, Host can notify Remote Monitors preemptively that a situation has been taken care of and/or give other contextual information that can help Remote Monitor understand future alerts, alarms, and/or communications sent by the host monitoring device. In some cases, such communications can include user populated and/or prepopulated messages. Based on predicted values, historical communication patterns, and/or other data described in this disclosure, a host monitoring device can send prepopulated communications to Remote Monitors' remote monitoring devices indicating that a Host will be fine. In some implementations, a server (e.g., Secure Server 504) can send the communications. The server can detect patterns in Host data (e.g., whether Host is exercising, under stress, etc.) and send prepopulated messages to remote monitoring devices.

As another non-limiting example, a Host and/or Remote Monitor may want to send a communication early. For example, if there are some future risks that a Host and/or Remote Monitor wants to make known to other Remote Monitors, there can be a button that a Host and/or Remote Monitor can press. In some implementations, a Host and/or Remote Monitor can otherwise use a user interface to send communications to one or more Remote Monitors. In some cases, such communications can be prepopulated based on pattern recognition. For example, a host monitoring device can, at Point 1908, recognize that a Host's glucose level will fall below Lower Threshold 1918. Based on predicted values, historical communication patterns, and/or other data described in this disclosure, a host monitoring device can send prepopulated communications to Remote Monitors' remote monitoring devices indicating that Host may need assistance.

In some cases, it can also be desirable for a Host to temporarily disable communications, increase delays, change thresholds, etc. The Host may do so, for example, to avoid causing concern to Remote Monitors when the situation is already going to be taken care of by the Host and/or a Caretaker. The Host can also temporarily disable communications for other reasons, such as not wanting to show others an expected jump in glucose for privacy reasons. As another example, certain events can cause expected jumps in glucose values (e.g., health or stress events). By being able to temporarily disable and/or limit communications, a Host may avoid judgment from his/her Remote Monitors for predictable and/or embarrassing high blood sugar levels. Temporarily disabling communications can be performed by a host monitoring device, remote monitoring device, server, and/or any other device described in this disclosure. For example, a host monitoring device can temporarily disable communications by temporarily not sending communications. As another non-limiting example, a remote monitoring device can temporarily disable communications by temporarily not receiving communications and/or displaying communications. As another non-limiting example, a server can temporarily disable communications by temporarily not relaying communications (e.g., between host monitoring devices and/or remote monitoring devices) and/or by temporarily not displaying communications on displays coupled to the server.

As an illustrative example, Display 1900 can be displayed on a host monitoring device. Display 1900 can include Graph 1902, which can include analyte measurements such as glucose levels (e.g., EGV). Display 1900 can also include Upper Threshold 1916 and Lower Threshold 1918. At Point 1908, a Host can notice that his/her glucose levels are trending downwards and may believe that measurements will fall below Lower Threshold 1918. This can cause an alarm, notification, and/or other communications to be sent to one or more remote monitoring devices. Not desiring for such alarms, notifications, and/or other communications to be sent, the Host can suppress those messages by selecting an option in the display, such as Suppress Button 1922. In some implementations, pulling up a different display/page can allow suppression (e.g., selecting Point 1908 and/or opening up a log can present an option for suppression). When Suppress Button 1922 is selected, measurements falling below Lower Threshold 1918 may not cause an alarm, notification, and/or other communications to be sent from the host monitoring device to remote monitoring devices. In some implementations, such communications can be modified and/or delayed.

In some cases, for safety reasons and/or otherwise, when a Host suppresses a communication, a new threshold can be set, in which, if the Host exceeds the new threshold in the case of a new upper threshold, or goes below the new threshold in the case of a new lower threshold, an alert, notification, and/or other communication can be sent. Having such new threshold can protect a Host against unexpected and/or unanticipated effects that can be dangerous. For example, after glucose level surpassing Point 1908, if Host hits Suppress Button 1922 to prevent alarms, notifications, and/or other communications to be sent to remote monitoring devices, a new lower threshold can be set, such as New Lower Threshold 1920. If glucose values fall below New Lower Threshold 1920, alerts, notifications, and/or other communications can be sent to remote monitoring devices. In some implementations, determining whether a new upper threshold and/or a new lower threshold should be set can include a predictive calculation as described in this disclosure. When a future point is projected to be below Lower Threshold 1918, a new lower threshold (e.g., New Lower Threshold 1920) can be used. When a future point is projected to be above Upper Threshold 1916, a new upper threshold can be used.

In some cases, suppression may only last for a determined number of measurements and/or a determined amount of time before the suppression is turned off. For example, at Point 1908, a host monitoring device may be configured to suppress only the next 10 (or whatever number desired) measurements before communications are sent as usual. As another non-limiting example, communications may only be suppressed for 5 minutes (or other desired time) before being sent as usual. In some implementations, suppression can be turned off using pattern recognition. For example, at Point 1908, a user may suppress communications. Using any method described in this disclosure, a host monitoring device may detect when the Host's glucose levels go down and then rebound back up, and may turn off suppression on the rebound.

As another non-limiting example, a host monitoring device and/or remote monitoring device can increase or shorten a delay of a communication to be sent to a Remote Monitor depending upon Host and/or Remote Monitor action (e.g., treatment). The host monitoring device and/or remote monitoring device can manage the increase or shortening of a delay of a communication based on the type of communication, specific data within the communication, and/or other parameters to provide time to receive feedback from Host/Remote Monitor about Host/Remote Monitor action (e.g., treatment). In some cases, a host monitoring device and/or remote monitoring device can increase delays if a Host and/or Remote Monitor manually logs that a treatment has been performed. Similarly, that delay can be decreased if the Host and/or Remote Monitors fails to acknowledge a communication and/or condition, and/or fail to act upon them.

In some cases, instead of preemption disabling (e.g., suppressing) communications, other communications can be sent. For example, instead of an alert, a notification can be sent saying the Host's glucose measurement and/or that it is being taken care of. As another non-limiting example, instead of an alert, an entry in a log of glucose measurements can be made. In some implementations, preemption can be handled from a remote monitoring device where Remote Monitors preempt communications from being sent to one or more Remote Monitors (including themselves).

In some implementations, suppression can be done automatically through pattern recognition. A remote monitoring device (e.g., Remote Monitoring Device 300), host monitoring device (e.g., Host Monitoring Device 200), server (e.g., Secure Server 504), and/or any other device described in this disclosure can recognize patterns in Host and/or Remote Monitor data in order to identify correlations with suppressed communications. In this way, communications can be preempted automatically when a pattern reoccurs. For example, suppose a Host typically has a low glucose reading around 11:30 AM before lunch. However, typically, the Host eats lunch soon thereafter and the low glucose reading is not an issue. A remote monitoring device (e.g., Remote Monitoring Device 300), host monitoring device (e.g., Host Monitoring Device 200), server (e.g., Secure Server 504), and/or any other device described in this disclosure can suppress any alerts, notifications, and/or communications, or modify those alerts, notifications and/or communications, based on that pattern of behavior.

In some cases, Remote Monitors not only want to know (e.g., be alerted, notified, and/or communicated to) when a Host has an alert-worthy situation, but Host's may also want to know if the Remote Monitor is actively following the Host's condition. In some circumstances, knowing when and/or how often Remote Monitors view a Host's communications can allow Hosts, Remote Monitors, and/or other users to better gauge how to set permissions and/or communications settings for individual Remote Monitors based on what communications were sent to a Remote Monitor's remote monitoring device, and/or whether (and/or how) such communications were acknowledged by the Remote Monitor. Furthermore, affirmation that a Remote Monitor is viewing communications and/or data can encourage Hosts to use features and/or continue certain activities and/or treatments.

In some implementations, a remote monitoring device (e.g., Remote Monitoring Device 300), host monitoring device (e.g., Host Monitoring Device 200), server (e.g., Secure Server 504), and/or any other device described in this disclosure can track a Remote Monitor's response behavior to communications, and/or provide overall monitoring of Host's shared data. In some implementations, a host monitoring device and/or remote monitoring device can display a log/report showing the tracked behavior to the Hosts and/or Remote Monitors. Such a log/report can also be stored in memory on a server and/or displayed on a display communicatively and/or operatively coupled to the server.

Figure 20:
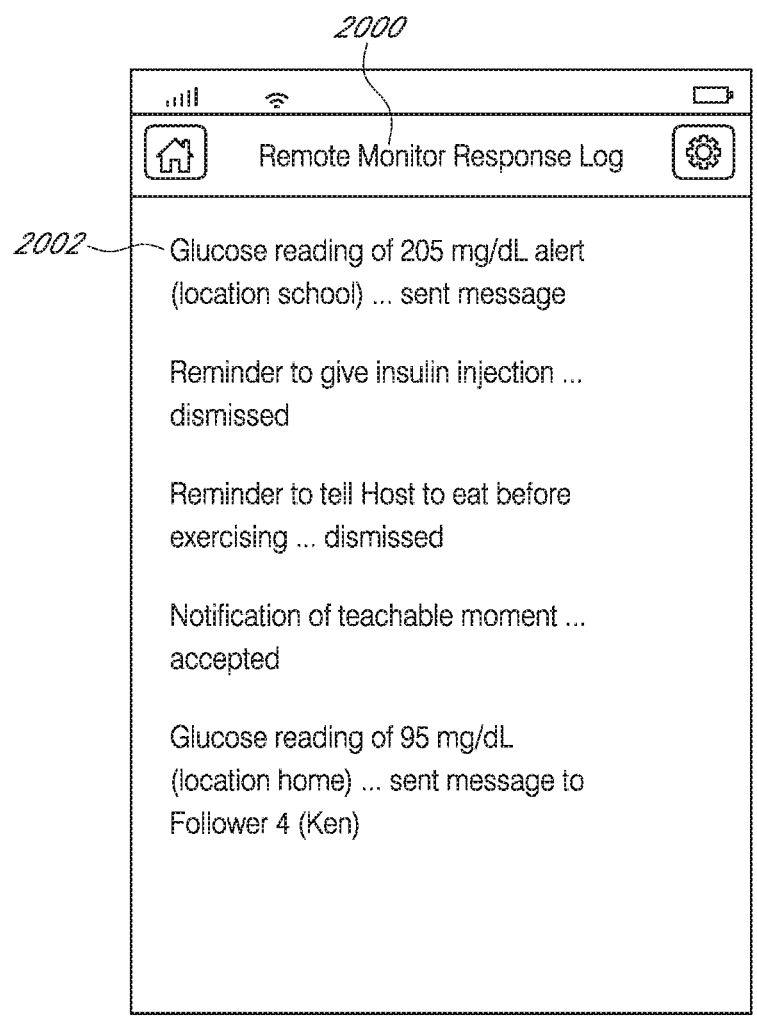
FIG. 20 illustrates an example Remote Monitor Response Log showing how a Remote Monitor responded to communications.

FIG. 20 illustrates an example Remote Monitor Response Log showing how a Remote Monitor responded to communications. Remote Monitor Response Log 2000 can be stored in memory and/or displayed on a remote monitoring device (e.g., Remote Monitoring Device 300), host monitoring device (e.g., Host Monitoring Device 200), and/or any other device described in this disclosure. In some cases, a server (e.g., Secure Server 504) can store Log 2000 in memory and/or display Log 2000 on a display communicatively and/or operatively coupled to the server. Remote Monitor Response Log 2000 can include entries such as Entry 2002. These entries can state a communication received by a Remote Monitor and/or that Remote Monitor's response. For example, Entry 2002 can state that Remote Monitor received an alert stating the Host had a glucose reading of 205 mg/dL at school. Entry 2002 can also state what the Remote Monitor did, which as illustrated, shows the Remote Monitor sent a message in response. In some implementations, clicking on text such as "sent message" can allow a viewer to see the text of the message and/or other related data and logs.

Remote Monitor Reponses Log 2000 can allow a viewer to see what kinds of communications a Remote Monitor received and/or the Remote Monitor's responses to such messages. In some cases, this can allow the viewer to manually examine the communications and/or responses, and/or act accordingly. Such actions can include changing the settings and/or permissions of the Remote Monitor (e.g., adjusting frequency of communications, rights, and/or privileges of a Remote Monitor, such as by using settings as discussed with reference to FIGS. 16A-D and/or FIGS. 17A-D).

In some implementations, a remote monitoring device (e.g., Remote Monitoring Device 300), host monitoring device (e.g., Host Monitoring Device 200), server (e.g., Secure Server 504), and/or any other device described in this disclosure can perform pattern recognition and/or adjust settings (e.g., frequency of communications, rights, and/or privileges of a Remote Monitor) and/or give automatic responses based on learned behavior from historical Host/Remote Monitor actions. As an illustrative example, a remote monitoring device can examine a Remote Monitor's communication-response behavior and determine that a Remote Monitor always sends messages after receiving a low alert. The remote monitoring device can then create prepopulated messages and/or make suggested responses for the Remote Monitor when the Remote Monitor receives a low alert. As another example, when a Remote Monitor always ignores low alerts, a host monitoring device can stop sending that Remote Monitor's remote monitoring device low alerts. In some cases, a Remote Monitor's classification can change based on the Remote Monitor's responsiveness. As an illustrative example, a Primary Caretaker who is unresponsive may be moved down to a Secondary Caretaker. The recognition of unresponsiveness and/or movement of the Primary Caretaker to Secondary Caretaker can be performed by host monitoring devices, remote monitoring devices, servers, and/or other devices. In some cases, when a Remote Monitor is not responsive to certain communications, such communications can be sent to another Remote Monitor.

In some cases, it may be desirable for a host monitoring device and/or remote monitoring device to include the ability to self-monitor its components. Such can allow malfunctions and/or hardware/software problems to be detected before they interfere with health monitoring.

In some implementations, such self-monitoring can be accomplished by using components of host monitoring devices and/or remote monitoring devices to monitor other components in that same device. For example, a microphone can detect if the speaker is functioning, an accelerometer can detect if the vibrator motor is functioning, or an optical sensor can detect optical data to monitor the display. Such self-monitoring can be included in System Data. In some implementations, a test sequence can be run to test one or more components of a host monitoring device and/or remote monitoring device. Such test sequence can be initiated by the respective host monitoring device and/or remote monitoring device, and/or other host monitoring devices and/or remote monitoring devices in the monitoring network. In some cases, a server can initiate the test sequence on one or more of the host monitoring devices and/or remote monitoring devices in the monitoring system.

In some implementations, a remote monitoring device can receive self-monitored data about a host monitoring device. The remote monitoring device can receive the self-monitored data to display to the Remote Monitor. This self-monitored data can give the Remote Monitor peace of mind that the host monitoring device is properly functioning, which may be indicative of whether the Host is able to receive an alarm. If failures are found, diagnostics can identify where the problem might be and determine whether the failures are clinically risky. For example, if speakers of a host monitoring device are not working, it could be clinically risky because a Host may not receive communications such as alerts and alarms. In some cases, communications regarding a failing or muted host monitoring device may be escalated because Host may not be able to see and/or hear clinically important alarms. Examples of escalation can include: alerts to Remote Monitors escalating faster, fewer delays, changes in kind of alert, alerting different Remote Monitors and alerting Remote Monitors of a different classification, alerting Universal Remote Monitors, etc.

In the case of remote monitoring device failure, for example, as indicated by self-monitoring data, the Remote Monitor's classification can be altered. For example, if the Remote Monitor with a failing remote monitoring device was the Primary Caretaker, a different Remote Monitor could become a Primary Caretaker, and the Remote Monitor with the failing remote monitoring device could be reclassified.

In some cases, the remote monitoring device, such as a Remote Monitor's smartphone operating a remote monitoring software application (e.g., "remote monitoring app"), may be set up and/or used by the Remote Monitor with a low volume setting or a mute option such that the respective Remote Monitor may miss alarms and/or notifications about the Host's analyte state sent to the remote monitoring device. Such settings can be detected and overridden to reliably deliver such alarms and/or notifications to Remote Monitor.

In some implementations, remote monitoring app can include a method for overriding a low volume setting, mute or other non-disturb mode set by the Remote Monitor on his/her remote monitoring device. For users' mobile computing devices that include appropriate vibration hardware to create a vibrate action (such as smartphones) and do not disturb (DND) modes on their operating systems, the remote monitoring app can be configured to override the mute switch or DND modes set by the Remote Monitor on their smartphone, such as phone calls, texts, notifications, or other alerts, to reliably alert the Remote Monitor of the Host's analyte condition in a manner that respects the Remote Monitor's desire to be uninterrupted, and therefore reduce alert fatigue. Illustratively, it is necessary that a Host reacts appropriately to certain states or circumstances associated with the Host's medical condition. Using the remote monitoring systems and methods in accordance with the disclosed embodiments, a Remote Monitor can supplement or augment the Host's management of his/her medical condition by checking on the Host, particularly when the Host's state is in alert. Therefore, it is important that the Remote Monitor also receive the alarms pertaining to the Host's medical condition (e.g., analyte levels and trend) to promptly and properly react to their condition. However, Remote Monitors must balance their responsibility as a remote monitor of a Host with the numerous interruptions of life, which often occur on the same remote monitoring device as the remote monitoring app, i.e., the smartphone, tablet and/or smart wearable device. Thus, in some embodiments, the remote monitoring app provides an intelligent alert process to deliver the Host's analyte-related alerts when Remote Monitor's remote monitoring device is set to mute, low volume, and/or DND mode. For example, the intelligent alert process is implemented automatically by the remote monitoring app, so that setup by the Remote Monitor is not required.

EXAMPLES

In some embodiments of the present technology (example 1), a method for remote monitoring of a subject's health data by authorized monitors includes receiving, at a secure server, data associated with an analyte state of a host that is provided by a host device operable to receive sensor data generated by a continuous analyte sensor worn by the host, in which one or more remote monitoring devices are authorized by the secure server to access permissible data of the received data stored on the secure server based on a set of permissions pre-selected and modifiable by the host for each remote monitoring device, in which the permissions are associated with what data is available to a remote monitoring device once authorized; generating, at the server, a plurality of classifications including a first classification and a second classification of the remote monitoring devices authorized to access permissible data, in which a classification of the remote monitoring devices designates a hierarchy to provide communications based on notifications rules to inform an authorized remote monitoring device about the host's analyte state; and assigning, at the server, each of the remote monitoring devices to one of the plurality of classifications, in which the second classification includes one or both of (i) greater restrictions to the permissible data than that of the first classification, and (ii) more restrictive notification rules than the first classification.

Example 2 includes the method of example 1, in which assignment of the remote monitoring device to the first and second classifications is based on one or more of locations of the host device and the remote monitoring devices, a characteristic of a user of the remote monitoring device communicated to the server by the user's remote monitoring device, a relationship between the user of the remote monitoring device and the host, or a behavior of a remote monitoring device.

Example 3 includes the method of example 1, in which assignment of the remote monitoring device to the first and second classifications is based at least in part on locations of the host device and the remote monitoring devices.

Example 4 includes the method of examples 2 or 3, further including receiving, at the server, the locations of the host device and the remote monitoring devices; relegating, by the server, a remote monitoring device from the first classification to the second classification when the remote monitoring device exceeds a predetermined proximity from the host device.

Example 5 includes the method of example 1, in which assignment of the remote monitoring device to the first and second classifications is based at least in part on one or more characteristics of the users of the remote monitoring devices.

Example 6 includes the method of examples 2 or 5, in which the characteristics include health data associated with the user of the remote monitoring device collected by one or more of a continuous glucose monitor, a heart rate monitor, or other health monitoring device.

Example 7 includes the method of examples 2 or 5, in which the characteristics include an activity status associated with the user of the remote monitoring device including an available status, a busy status, or a sleep status.

Example 8 includes the method of example 1, in which assignment of the remote monitoring device to the first and second classifications is based at least in part on a relationship of the remote monitor user and the host.

Example 9 includes the method of examples 2 or 8, in which the first classification includes the remote monitor user being a primary caretaker of the host, and the second classification includes the remote monitor user being one or more of a primary caretaker, an assigned watcher of the host, a friend of the host, or a family member of the host.

Example 10 includes the method of example 1, in which assignment of the remote monitoring device to the first and second classifications is based at least in part on a behavior of a remote monitoring device.

Example 11 includes the method of example 2 or 10, further including providing, by the server, a message informative of an event associated with the analyte state of the host to a first remote monitoring device assigned to the first classification; and relegating, by the server, the first remote monitoring device from the first classification to the second classification based at least in part on a lack of acknowledgment by the first remote monitoring device within a predetermined time period after the providing the message.

Example 12 includes the method of example 11, in which the providing includes providing a plurality of messages informative of a plurality of respective events to the first monitoring device over a duration of time, and the relegating is based on the lack of acknowledgment of the first monitoring device to a predetermined number of instances of the plurality of the provided messages.

Example 13 includes the method of examples 2 or 10, further including providing, by the server, a message informative of an event associated with the analyte state of the host to a first remote monitoring device assigned to the second classification; and elevating, by the server, the first remote monitoring device from the second classification to the first classification based at least in part on acknowledgment by the first remote monitoring device within a predetermined time period after the providing the message.

Example 14 includes the method of example 13, in which the providing includes providing a plurality of messages informative of a plurality of respective events to the first monitoring device over a duration of time, and the elevating is based at least in part on the acknowledgment of the first monitoring device to a predetermined number of instances of the plurality of the provided messages.

Example 15 includes the method of examples 1 or 2, in which the plurality of classifications includes a third classification of the remote monitoring devices authorized to access permissible data, in which the third classification includes one or both of (i) greater restrictions to the permissible data than that of the first classification or the second classification or both, and (ii) more restrictive notification rules than the first classification or the second classification or both.

Example 16 includes the method of example 1, in which the authorized remote monitoring devices include a first remote monitoring device operated by a first remote monitor user and a second remote monitoring device operated by a second remote monitor user, in which the first remote monitoring device is assigned to the first classification, and the second remote monitoring device is assigned to the second classification.

Example 17 includes the method of example 16, in which the first and second remote monitoring devices are in wireless communication with each other.

Example 18 includes the method of examples 16 or 17, further including receiving, at the server, a request from the first monitoring device to elevate the second remote monitoring device to the first classification; and elevating, by the server, the second remote monitoring device from the second classification to the first classification after acceptance of the request.

Example 19 includes the method of example 18, further including prior to the elevating, accepting, by the server, the request based on an established awareness by the second remote monitoring device to accept privileges and duties associated with the first classification.

Example 20 includes the method of example 16, further including providing, by the server, an alert informative of an event associated with the analyte state of the host to the first remote monitoring device based on the notification rules associated with the first classification; receiving, at the server, a response from the first remote monitoring device indicative of inability to react to the alert or a lack of response from the first remote monitoring device within a predetermined time period after the providing the alert; and responsive to the receiving the response from the first remote monitoring device, providing, by the server, the alert to the second remote monitoring device.

Example 21 includes the method of example 20, further including receiving, at the server, a response from the second remote monitoring device indicative of ability to react to the alert.

Example 22 includes the method of example 21, further including elevating, by the server, the second remote monitoring device from the second classification to the first classification based at least in part on acknowledgment by the second remote monitoring device within the predetermined time duration after the providing the alert.

Example 23 includes the method of example 20, further including relegating, by the server, the first remote monitoring device from the first classification to the second classification based on the response indicative of inability or the lack of response.

Example 24 includes the method of example 20, in which the alert includes information outside of the notification rules associated with the second classification; and the method further includes, prior to the providing the alert to the second remote monitoring device, overriding, by the server, the notification rules associated with the second classification for the alert to be provided to the second remote monitoring device based on a severity factor of the information associated with the alert.

Example 25 includes the method of examples 1-24, in which the analyte state includes glucose level.

Example 26 includes the method of examples 1-25, in which the notification rules define circumstances to send a message to a respective remote monitoring device informative of an event associated with the analyte state of the host, and in which the notification rules are modifiable by the authorized remote monitoring devices within a scope of the set of permissions to the data associated with the respective remote monitoring device.

Example 27 includes the method of examples 1-25, in which the permissible data includes (i) retrospective sensor data, (ii) real time sensor data, and (iii) a trend in the rate of change of the analyte state of the host.

In some embodiments of the present technology (example 28), a method for remote monitoring of a subject's health data by authorized monitors includes receiving, at a secure server, data associated with an analyte state of a host that is provided by a host device operable to receive sensor data generated by a continuous analyte sensor worn by the host, in which a plurality of remote monitoring devices are authorized by the secure server to access permissible data of the received data stored on the secure server based on a set of permissions pre-selected and modifiable by the host for each remote monitoring device, in which the permissions are associated with what data is available to a remote monitoring device once authorized; providing, by the server, an alert informative of an event associated with the analyte state of the host to selected remote monitoring devices based on notification rules that define circumstances to send the alert to a respective remote monitoring device, in which the notification rules are modifiable by the authorized remote monitoring devices within a scope of the set of permissions to the data associated with the respective remote monitoring device; receiving, at the server, a response from one or more of the selected remote monitoring device; and processing, by the server, the received response to determine the ability or inability of the selected remote monitoring device corresponding to the received response to react to the alert.

Example 29 includes the method of example 28, in which the receiving includes a plurality of responses corresponding from a plurality of the selected remote monitoring devices, in which the received responses are indicative of at least one of the selected remote monitoring devices having the ability to react to the alert.

Example 30 includes the method of example 29, further including providing, by the server, a message to the selected remote monitors indicating that the at least one of the selected remote monitoring devices has indicated the ability to react to the alert.

Example 31 includes the method of example 30, in which the providing the message includes providing a log of the received responses by the selected remote monitors.

Example 32 includes the method of examples 28, 29, 30 or 31, further including generating, at the server, a plurality of classifications including a first classification and a second classification of the remote monitoring devices authorized to access permissible data, in which a classification of the remote monitoring devices designates a hierarchy to provide communications based on the notifications rules; and assigning, at the server, each of the remote monitoring devices to one of the plurality of classifications, in which the second classification includes one or both of (i) greater restrictions to the permissible data than that of the first classification, and (ii) more restrictive notification rules than the first classification.

Example 33 includes the method of examples 28-32, in which the permissible data includes (i) retrospective sensor data, (ii) real time sensor data, and (iii) a trend in the rate of change of the analyte state of the host.

Example 34 includes the method of examples 28-33, in which the analyte state includes glucose level.

In some embodiments of the present technology (example 35), a method for remote monitoring of a subject's health data by authorized monitors includes receiving, at a secure server, data associated with an analyte state of a host that is provided by a host device operable to receive sensor data generated by a continuous analyte sensor worn by the host, in which a plurality of host-designated remote monitoring devices are authorized by the secure server to access permissible data of the received data stored on the secure server based on a set of permissions pre-selected and modifiable by the host for each host-designated remote monitoring device, in which the permissions are associated with what data is available to a remote monitoring device once authorized; receiving, by the server, location information of the host-designated remote monitoring devices and the host device; determining, by the server, the ability or inability of each of the host-designated selected remote monitoring devices to react to an alert informative of a dangerous event associated with the analyte state of the host based on a proximity of a host-designated selected remote monitoring device to the host device within a predetermined distance; upon the determining the inability of all of the host-designated selected remote monitoring devices to react to an alert, assigning, by the server, a universal remote monitoring device not among the host-designated selected remote monitoring devices, in which the assigning includes generating a set of notifications rules pertaining to circumstances to send a message to the universal remote monitoring device informative of the dangerous event associated with the analyte state of the host.

Example 36 includes the method of example 35, in which the assigning the universal remote monitoring device to at least some of the data associated with the analyte state of the host includes authorization to access the at least some of the data for a temporary time frame.

Example 37 includes the method of examples 35 or 36, further including providing, by the server, a communication to the host device informative of assignment of the universal remote monitoring device and prompting the host device to accept or decline the assignment.

Example 38 includes the method of example 37, receiving, at the server, a response communication by the host device with an acceptance or declination of the assignment.

Example 39 includes the method of example 38, in which the temporary time frame is determined by the host device.

Example 40 includes the method of example 35, further including upon the determining the ability of at least one of the host-designated selected remote monitoring devices to react to an alert, revoking, by the server, assignment of the universal remote monitoring device, in which the revoking includes removing access of the universal remote monitoring device to at least some of the data associated with the analyte state of the host.

Example 41 includes the method of examples 35-40, in which the notification rules are within a scope of the set of permissions to the data associated with the host-designated remote monitoring devices.

Example 42 includes the method of examples 35-40, in which the data includes one or more of (i) retrospective sensor data, (ii) real time sensor data, or (iii) a trend in the rate of change of the analyte state of the host.

Example 43 includes the method of example 35-42, in which the analyte state includes glucose level.

In some embodiments of the present technology (example 44), a method for remote monitoring of a subject's health data by authorized monitors includes receiving, at a secure server, data associated with an analyte state of a host that is provided by a host device operable to receive sensor data generated by a continuous analyte sensor worn by the host, in which one or more remote monitoring devices are authorized by the secure server to access permissible data of the received data stored on the secure server based on a set of permissions pre-selected and modifiable by the host for each remote monitoring device, in which the permissions are associated with what data is available to a remote monitoring device once authorized, and in which the one or more remote monitoring devices are assigned notification rules that define circumstances to send a message to a respective remote monitoring device informative of an event associated with the analyte state of the host, in which the notification rules are modifiable by the authorized remote monitoring devices within a scope of the set of permissions to the data associated with the respective remote monitoring device; processing, by the server, an alert informative of a dangerous event associated with the analyte state of the host, in which the processed alert is within a set of notification rules associated with at least one of the authorized remote monitoring devices; receiving, by the server, an instruction to suppress sending the message associated with the alert to the at least one of the authorized remote monitoring devices; and suppressing, by the server, the sending of the message to the at least one of the authorized remote monitoring devices.

Example 45 includes the method of example 44, in which the dangerous event includes the analyte state of the host exceeding a predetermined analyte concentration threshold or a predetermined rate of concentration change threshold.

Example 46 includes the method of example 44, in which the processing the alert includes receiving alert data from the host device, in which the alert data is generated at one or both of the host device or a sensor electronics device in communication with the continuous analyte sensor.

Example 47 includes the method of example 44, in which the processing the alert includes generating, by the server, the alert by processing the data to determine if the analyte state exceeds the predetermined analyte concentration threshold or the predetermined rate of concentration change threshold.

Example 48 includes the method of example 44, further including sending the message associated with the alert to the at least one of the authorized remote monitoring devices after a predetermined delay.

Example 49 includes the method of example 48, in which the sending the message includes overriding, by the server, the received instruction to suppress.

Example 50 includes the method of example 44, further including prior to the suppressing, processing the data to determine if the analyte state exceeds a second predetermined analyte concentration threshold lower than the predetermined analyte concentration threshold or a second predetermined rate of concentration change threshold lower than the predetermined rate of concentration change threshold, in which, if the analyte state exceeds the second predetermined analyte concentration threshold or the second predetermined rate of concentration change threshold, sending the message associated with the alert to the at least one of the authorized remote monitoring devices after a predetermined delay, in which the sending includes overriding the received instruction to suppress.

Example 51 includes the method of examples 44-50, in which the permissible data includes (i) retrospective sensor data, (ii) real time sensor data, and (iii) a trend in the rate of change of the analyte state of the host.

Example 52 includes the method of examples 44-51, in which the analyte state includes glucose level.

In some embodiments of the present technology (example 53), a method for remote monitoring of a subject's health data by authorized monitors includes receiving, at a secure server, data associated with an analyte state of a host that is provided by a host device operable to receive sensor data generated by a continuous analyte sensor worn by the host, in which one or more remote monitoring devices are authorized by the secure server to access permissible data of the received data stored on the secure server based on a set of permissions pre-selected and modifiable by the host for each remote monitoring device, in which the permissions are associated with what data is available to a remote monitoring device once authorized; providing, by the server, a notification informative of an event associated with the analyte state of the host to selected remote monitoring devices based on notification rules that define circumstances to send the notification to a respective remote monitoring device, in which the notification rules are modifiable by the authorized remote monitoring devices within a scope of the set of permissions to the data associated with the respective remote monitoring device; and providing, by the server, contextual information with the notification, the contextual information including a time, an amount, and/or a type of (i) a medicament taken by the host, (ii) a food or drink ingested by the host, (iii) an exercise or activity undertaken by the host, (iv) a level of stress experienced by the host, or (v) an environmental condition experienced by the host, or a combination of (i)-(vi) thereof.

Example 54 includes the method of example 53, in which the exercise or activity undertaken by the host includes one or more of running, walking, swimming, skiing or snowboarding, skateboarding, biking, weight lifting, sitting, resting, or sleeping.

Example 55 includes the method of example 53, in which the level of stress experienced by the host includes one or more of acute or episodic acute stress, chronic stress, high stress, medium stress, low stress, no stress, anxiety, emotional stress, or panic attack.

Example 56 includes the method of example 53, in which the environmental condition experienced by the host includes one or more of weather, humidity, pressure, temperature, scenery, location, or situation including at work, at school, or on break or vacation.

Example 57 includes the method of example 53, in which the notification includes an alert informative of a dangerous event associated with the analyte state of the host.

Example 58 includes the method of example 53, further including generating, at the server, a plurality of classifications including a first classification and a second classification of the remote monitoring devices authorized to access permissible data, in which a classification of the remote monitoring devices designates a hierarchy to provide communications based on the notifications rules; and assigning, at the server, each of the remote monitoring devices to one of the plurality of classifications, in which the second classification includes one or both of (i) greater restrictions to the permissible data than that of the first classification, and (ii) more restrictive notification rules than the first classification.

Example 59 includes the method of example 58, further including prior to the providing contextual information with the notification, determining, by the server, an assigned classification of the respective remote monitoring device to receive the notification; and if the respective remote monitoring device is assigned to the first classification, then providing the contextual information with the notification, and if the respective remote monitoring device is assigned to the second classification, then not providing the contextual information with the notification or providing a limited amount of the contextual information with the notification.

Example 60 includes the method of example 59, in which the limited amount of the contextual information is based on a predetermined categorization determined by the host device.

Example 61 includes the method of example 53, further including receiving, at the server, a response from at least one of the remote monitoring devices, in which the received response includes contextual data of a remote monitor user operating the respective remote monitoring device, the contextual data including a time, an amount, and/or a type of (i) an activity undertaken by the remote monitor user, (ii) a level of stress experienced by the remote monitor user, or (iii) an environmental condition experienced by the remote monitor user, or a combination of (i)-(iii) thereof.

Example 62 includes the method of example 61, further including processing, by the server, the received response to determine the ability or inability of the at least one remote monitoring device to react to an alert based on the contextual data.

Example 63 includes the method of example 62, in which, when the contextual data includes an activity, level of stress, or environmental condition of the remote monitor user indicative of the inability to react to an alert, the method further includes providing, by the server, a communication to the host device including at least some of the contextual data of the received response.

Example 64 includes the method of example 62, in which, when the contextual data includes an activity, level of stress, or environmental condition of the remote monitor user indicative of the inability to react to an alert, the method further includes providing, by the server, a communication to other remote monitoring devices indicating that the at least one remote monitoring device is unable to react to alerts.

Example 65 includes the method of examples 53-64, in which the permissible data includes (i) retrospective sensor data, (ii) real time sensor data, and (iii) a trend in the rate of change of the analyte state of the host.

Example 66 includes the method of examples 53-65, in which the analyte state includes glucose level.

Example 67 includes a continuous analyte sensor system including a continuous analyte sensor device worn by the host including the continuous analyte sensor to detect signals associated with an analyte of the host, and a sensor electronics module to perform at least some processing of the signals to generate sensor data and transmitting the sensor data to the host device; a non-transitory computer program product at least partially stored on the host device and including instructions that, when executed by a processor of the host device, causes the processor to perform at least some processing of the sensor data to produce the data associated with the analyte state of the host; and the secure server in communication with the host device to perform the method of any of the aforementioned examples 1-66.

In some implementations, a computing system that has components including a central processing unit ("CPU"), input/output ("I/O") components, storage, and memory can be used to execute the monitoring system, or specific components and/or subcomponents of the monitoring system. The executable code modules of the monitoring system can be stored in the memory of the computing system and/or on other types of non-transitory computer-readable storage media. In some implementations, monitoring system can be configured differently than described above.

Each of the processes, methods, and algorithms described in the preceding sections can be embodied in, and fully or partially automated by, code modules executed by one or more computers, computer processors, or machines configured to execute computer instructions. The code modules can be stored on any type of non-transitory computer-readable medium or tangible computer storage device, such as hard drives, solid state memory, optical disc, and/or the like. The systems and modules can also be transmitted as generated data signals (e.g., as part of a carrier wave or other analog or digital propagated signal) on a variety of computer-readable transmission mediums, including wireless-based and wired/cable-based mediums, and can take a variety of forms (e.g., as part of a single or multiplexed analog signal, or as multiple discrete digital packets or frames). The processes and algorithms can be implemented partially or wholly in application-specific circuitry. The results of the disclosed processes and process steps can be stored, persistently or otherwise, in any type of non-transitory.

The various features and processes described above can be used independently of one another, or can be combined in various ways. All possible combinations and sub-combinations are intended to fall within the scope of this disclosure. In addition, certain method or process blocks can be omitted in some implementations. The methods and processes described herein are also not limited to any particular sequence, and the blocks or states relating thereto can be performed in other sequences that are appropriate. For example, described tasks or events can be performed in an order other than that specifically disclosed, or multiple can be combined in a single block or state. The example tasks or events can be performed in serial, in parallel, or in some other manner. Tasks or events can be added to or removed from the disclosed example implementations. The example systems and components described herein can be configured differently than described. For example, elements can be added to, removed from, or rearranged compared to the disclosed example implementations.

Conditional language used herein, such as, among others, "can," "could," "might," "may," "e.g.," and the like, is not generally intended to imply that features, elements and/or steps are required for one or more implementations or that one or more implementations necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is otherwise understood with the context as used in general to convey that an item, term, etc. can be either X, Y or Z. Thus, such conjunctive language is not generally intended to imply that certain implementations require at least one of X, at least one of Y and at least one of Z to each be present. The terms "about" or "approximate" and the like are synonymous and are used to indicate that the value modified by the term has an understood range associated with it, where the range can be ±20%, ±15%, ±10%, ±5%, or ±1%. The term "substantially" is used to indicate that a result (e.g., measurement value) is close to a targeted value, where close can mean, for example, the result is within 80% of the value, within 90% of the value, within 95% of the value, or within 99% of the value. Also, as used herein "defined" can include "predefined" and/or otherwise determined values, conditions, thresholds, measurements, and the like.

While certain example implementations have been described, these implementations have been presented by way of example only, and are not intended to limit the scope of the inventions disclosed herein. Thus, nothing in the foregoing description is intended to imply that any particular feature, characteristic, step, module, or block is necessary or indispensable. Indeed, the methods and systems described herein can be embodied in a variety of other forms; furthermore, various omissions, substitutions and changes in the form of the methods and systems described herein can be made without departing from the spirit of the inventions disclosed herein.

What is claimed is:

1. A method for remote monitoring of a subject's health data by authorized monitors, comprising:
   receiving, at a secure server, data associated with an analyte state of a host from a host device operable to receive sensor data from a transcutaneous continuous analyte sensor worn by the host;
   identifying at least two remote monitoring devices authorized to receive a notification of an event associated with the analyte state of the host based on notification rules that define circumstances under which the notification should be sent to a respective remote monitoring device of the at least two remote monitoring devices, wherein the at least two remote monitoring devices are authorized by the secure server to access permissible data of the received data based on a set of permissions for each of the at least two remote monitoring devices, wherein the set of permissions indicate what portion of the received data is permissible data for each of the at least two authorized remote monitoring devices, and wherein the set of permissions for each of the at least two remote monitoring devices is different;
   receiving, at the secure server, contextual data associated with each remote monitor user operating a respective remote monitoring device of the at least two remote monitoring devices, the contextual data indicating at least one of a time, an amount, or a type of at least one of (i) a level of stress experienced by each remote monitor user determined based on one or more of blood pressure, pulse, body temperature, or heart rate data measured by a device associated with each remote monitor user, wherein the level of stress is one of acute, episodic acute, emotional, chronic, high stress, medium stress, low stress, no stress, anxiety, or panic attack, or (ii) an environmental condition experienced by each remote monitor user including at least one of weather, humidity, pressure, or temperature, wherein each remote monitor user is not the host;

processing, at the secure server, the contextual data associated with the remote monitor user operating one of the at least two remote monitoring devices to determine an ability or inability of the remote monitor user operating the one of the at least two remote monitoring devices to react to the notification wherein if the remote monitor user operating the one of the at least two remote monitoring devices is determined to be able to react to the notification, then:

generating, at the secure server, the notification based on the received data, wherein a content of the notification is modified based on the set of permissions for the one of the at least two remote monitoring devices and the contextual data associated with the remote monitor user operating the one of the at least two remote monitoring devices; and providing, by the secure server, the notification to the one of the at least two remote monitoring devices, wherein the notification includes the permissible data for the one of the at least two remote monitoring devices;

wherein if the remote monitor user operating the one of the at least two remote monitoring devices is determined to be unable to react to the notification, then:

generating, at the secure server, the notification based on the received data, wherein the content of the notification is modified based on the set of permissions for another one of the at least two remote monitoring devices and the contextual data associated with the remote monitor user operating the another one of the at least two remote monitoring devices; and providing, by the secure server, the notification to the another one of the at least two remote monitoring devices, wherein the notification includes the permissible data for the another one of the at least two remote monitoring devices.

2. The method of claim 1, wherein the notification includes an alert informative of the analyte state of the host exceeding a predetermined analyte concentration threshold or a predetermined rate of concentration change threshold.

3. The method of claim 1, wherein the method further includes:

providing, at the secure server, a communication to the another one of the at least two remote monitoring devices indicating that the one of the at least two remote monitoring devices is unable to react to alerts.

4. The method of claim 1, wherein the permissible data includes (i) retrospective sensor data, (ii) real time sensor data, and (iii) a trend in the rate of change of the analyte state of the host.

5. The method of claim 1, wherein the analyte state includes a glucose level.

6. The method of claim 1, further comprising:
determining that the notification should be modified based on the contextual information;
modifying the notification; and
providing the modified notification to the one of the at least two remote monitoring devices or the another one of the at least two remote monitoring devices in addition to or in lieu of the notification.

7. The method of claim 1, further comprising providing, at the secure server, contextual information relating to the host with the notification, the contextual information relating to the host including a time, an amount, and/or a type of (i) a medicament taken by the host, (ii) a food or a drink ingested by the host, (iii) an exercise or an activity undertaken by the host, (iv) a level of stress experienced by the host, or (v) an environmental condition experienced by the host, or a combination of (i)-(v) thereof.

8. The method of claim 1, further comprising generating, at the secure server, a plurality of classifications based on the set of permissions, the plurality of classifications including a first classification and a second classification of the at least two remote monitoring devices authorized to access permissible data, wherein classifications of the at least two remote monitoring devices designate a hierarchy to provide communications based on the notification rules.

9. The method of claim 8, further comprising assigning, at the secure server, each of the at least two remote monitoring devices to one of the plurality of classifications, wherein the second classification includes one or both of (i) greater restrictions to the permissible data than that of the first classification, and (ii) more restrictive notification rules than the first classification, wherein a classification of the one of the at least two remote monitoring devices indicates that the one of the at least two remote monitoring devices is authorized to access the permissible data of the received data.

10. The method of claim 9, further comprising modifying the classification of the one of the at least two remote monitoring devices or the another one of the at least two remote monitoring devices based on the contextual data associated with the remote monitor user operating the one of the at least two remote monitoring devices or the another one of the at least two remote monitoring devices.

11. A continuous analyte sensor system, comprising:
a continuous analyte sensor device worn by a host comprising a transcutaneous continuous analyte sensor to detect signals associated with an analyte state of the host, and a sensor electronics module to perform at least some processing of the signals to generate sensor data and to transmit the sensor data to a host device associated with the host;
the host device, comprising:
a memory storing executable instructions;
a processor in data communication with the memory and configured to execute instructions to perform at least some processing of the sensor data received from the sensor electronics module to produce data associated with an analyte state of the host; and
a secure server in communication with the host device configured to:
receive the data associated with the analyte state of the host from the host device, wherein the host device receives the data from the transcutaneous continuous analyte sensor;
identify at least two remote monitoring devices authorized to receive a notification of an event associated with the analyte state of the host based on notification rules that define circumstances under which the notification should be sent to a respective remote monitoring device of the at least two remote monitoring devices, wherein the at least two remote monitoring devices are authorized by the secure server to access permissible data of the received data based on a set of permissions for each of the at least two remote monitoring devices, wherein the set of permissions indicate what portion of the received data is permissible data for each of the at least two authorized remote monitoring devices, and wherein the set of permissions for each of the at least two remote monitoring devices is different;

receive contextual data associated with each remote monitor user operating a respective remote monitoring device of the at least two remote monitoring devices, the contextual data indicating at least one of a time, an amount, or a type of at least one of (i) a level of stress experienced by each remote monitor user determined based on one or more of blood pressure, pulse, body temperature, or heart rate data measured by a device associated with each remote monitor user, wherein the level of stress is one of acute, episodic acute, emotional, chronic, high stress, medium stress, low stress, no stress, anxiety, or panic attack, or (ii) an environmental condition experienced by each remote monitor user including at least one of weather, humidity, pressure, or temperature, wherein each remote monitor user is not the host;

process the contextual data associated with the remote monitor user operating one of the at least two remote monitoring devices to determine an ability or inability of the remote monitor user operating the one of the at least two remote monitoring devices to react to the notification, wherein if the remote monitor user operating the one of the at least two remote monitoring devices is determined to be able to react to the notification, then:
generate the notification based on the received data, wherein a content of the notification is modified based on the set of permissions for the one of the at least two remote monitoring devices and the contextual data associated with the remote monitor user operating the one of the at least two remote monitoring devices; and
provide the notification to the one of the at least two remote monitoring devices, wherein the notification includes the permissible data for the one of the at least two remote monitoring devices;

wherein if the remote monitor user operating the one of the at least two remote monitoring devices is determined to be unable to react to the notification, then:
generate the notification based on the received data, wherein the content of the notification is modified based on the set of permissions for another one of the at least two remote monitoring devices and the contextual data associated with the remote monitor user operating the another one of the at least two remote monitoring devices; and
provide the notification to the another one of the at least two remote monitoring devices, wherein the notification includes the permissible data for the another one of the at least two remote monitoring devices.

* * * * *